US009732083B2

(12) United States Patent
Bensen et al.

(10) Patent No.: US 9,732,083 B2
(45) Date of Patent: Aug. 15, 2017

(54) TRICYCLIC GYRASE INHIBITORS

(75) Inventors: Daniel Bensen, Carlsbad, CA (US); Zhiyong Chen, San Diego, CA (US); John Finn, Encinitas, CA (US); Thanh To Lam, San Diego, CA (US); Suk Joong Lee, San Diego, CA (US); Xiaoming Li, San Diego, CA (US); Douglas W. Phillipson, Del Mar, CA (US); Leslie William Tari, San Diego, CA (US); Michael Trzoss, San Diego, CA (US); Junhu Zhang, San Diego, CA (US); Felice C. Lightstone, Fremont, CA (US); Toan B. Nguyen, San Ramon, CA (US); Sergio E. Wong, San Jose, CA (US); Paul Aristoff, Dexter, MI (US); Michael Jung, Los Angeles, CA (US)

(73) Assignees: MERCK SHARP & DOHME CORP., New York, NY (US); LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 290 days.

(21) Appl. No.: 13/496,188

(22) PCT Filed: Mar. 14, 2012

(86) PCT No.: PCT/US2012/029104

§ 371 (c)(1),
(2), (4) Date: Mar. 14, 2012

(87) PCT Pub. No.: WO2012/125746

PCT Pub. Date: Sep. 20, 2012

(65) Prior Publication Data

US 2012/0238751 A1 Sep. 20, 2012

Related U.S. Application Data

(60) Provisional application No. 61/453,011, filed on Mar. 15, 2011.

(51) Int. Cl.
*C07D 487/04* (2006.01)
*C07D 487/14* (2006.01)

(52) U.S. Cl.
CPC ......... *C07D 487/04* (2013.01); *C07D 487/14* (2013.01)

(58) Field of Classification Search
CPC .................................................... C07D 487/04
See application file for complete search history.

(56) References Cited

U.S. PATENT DOCUMENTS 5,795,986 A 8/1998 Bundy et al.
6,147,085 A 11/2000 Horvath et al.
2005/0227992 A1* 10/2005 Hurley et al. ........... 514/252.16
2008/0051414 A1 2/2008 Hurley et al.
2009/0082374 A1 3/2009 Gangjee
2009/0099165 A1 4/2009 Hurley et al.
2009/0143399 A1* 6/2009 Hurley et al. ........... 514/252.16

FOREIGN PATENT DOCUMENTS

| | | |
|---|---|---|
| EP | 1749822 A1 | 2/2007 |
| IN | 157280 A1 | 2/1986 |
| JP | 2000038350 | 2/2000 |
| JP | 2006036762 | 2/2006 |
| JP | 2007169216 | 7/2007 |
| WO | WO 93/20078 A1 | 10/1993 |
| WO | WO 96/26941 A1 | 9/1996 |
| WO | WO 98/29397 A1 | 7/1998 |
| WO | WO 98/42708 A2 | 10/1998 |
| WO | WO 99/06024 A1 | 2/1999 |
| WO | WO 99/51598 A1 | 10/1999 |
| WO | WO 9951600 A1 | 10/1999 |
| WO | WO 00/66585 A1 | 11/2000 |
| WO | WO 02/40016 A2 | 5/2002 |
| WO | WO 03/037898 A1 | 5/2003 |
| WO | WO 03/057149 A2 | 7/2003 |
| WO | WO 03/062443 A2 | 7/2003 |
| WO | WO 2004/058764 A1 * | 7/2004 |
| WO | WO 2004/058767 A1 | 7/2004 |
| WO | WO 2005/037825 A2 | 4/2005 |
| WO | WO 2006/001511 A1 | 1/2006 |
| WO | WO 2006/116733 A2 | 11/2006 |
| WO | WO 2007/025090 A2 | 3/2007 |
| WO | WO 2008/007113 A2 | 1/2008 |
| WO | WO 2008/055233 A1 | 5/2008 |
| WO | WO 2009/004329 A1 | 1/2009 |

(Continued)

OTHER PUBLICATIONS

Bratt, J., et al. "Polyhalogenoaromatic Compounds. Part 41. Photochemical Dehalogenation and Arylation Reactions of Polyhalogenoaromatic and Polyhalogenoheteroaromatic Compounds." J.C.S. Perkin I. (Published Jan. 1, 1980), pp. 648-656.*
Han, H.K. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Chalcogens. Available at: <http://web.archive.org/web/20090312103521/http://www.angelo.edu/faculty/kboudrea/periodic/periodic_main6.htm >. Published on Web: Mar. 12, 2009.*
Thornber, et al. "Isosterism and Molecular Modification in Drug Design." pp. 563-580.*
Andrus et al., "Neuroprotective effects of the novel brain-penetrating pyrrolopyrimidine antioxidants U-101033E and U-104067F against post-ischemic degeneration of nigrostriatal neurons", Journal of Neuroscience Research (1997), 47(6):650-654.

(Continued)

*Primary Examiner* — Noble Jarrell
*Assistant Examiner* — John S Kenyon
(74) *Attorney, Agent, or Firm* — Fox Rothschild LLP

(57) ABSTRACT

Disclosed herein are compounds having the structure of Formula I and pharmaceutically suitable salts, esters, and prodrugs thereof that are useful as antibacterially effective tricyclic gyrase inhibitors.
Related pharmaceutical compositions, uses and methods of making the compounds are also contemplated.

5 Claims, 3 Drawing Sheets

(56) References Cited

FOREIGN PATENT DOCUMENTS

| | | | |
|---|---|---|---|
| WO | WO 2009/091476 | A1 | 7/2009 |
| WO | WO 2010/006032 | A1 | 1/2010 |
| WO | WO 2011/056739 | A1 | 5/2011 |

OTHER PUBLICATIONS

Bundy et al., "Synthesis of 2,4-diaminopyrrolo[2,3-d]pyrimidines via thermal Fischer indolization. Pyrazole formation with ytterbium triflate catalysis", Journal of Heterocyclic Chemistry (2000), 37(6):1471-1477.

Bundy et al., "Synthesis of Novel 2,4-Diaminopyrrolo[2,3-d]pyrimidines with Antioxidant, Neuroprotective, and Antiasthma Activity", Journal of Medicinal Chemistry (1995), 38(21):4161-3.

Bundy et al., "Synthesis of 2,4-Di-l-pyrrolidinyl-9H-pyrimido[4,5-b]indoles, Including Antiasthma Clinical Candidate", Organic Process Research & Development (2001), 5(2):144-151.

Chin et al., "Preclinical evaluation of anti-inflammatory activities of the novel pyrrolopyrimidine PNU-142731A, a potential treatment for asthma", Journal of Pharmacology and Experimental Therapeutics (1999), 290(1):188-195.

Davarani et al., Electro-organic synthesis of new pyrimidine and uracil derivatives, Journal of Heterocyclic Chemistry (2010), 47(1):40-45.

Dent, Gordon , "PNU142731A Pharmacia", Current Opinion in Investigational Drugs (PharmaPress Ltd.) (2000), 1 (4):449-451.

Dotzauer et al., "Synthesis of medicinally interesting 2,4-diamino-9H-pyrimido[4,5-b]indol-6-ols via extension of the Nenitzescu reaction", Synlett (2004), (6):1039-1043.

Dotzauer et al., "2,4-Diamino-9H-pyrimido[4,5-b]indo1-5-ols: Synthesis, in vitro cytotoxic activity, and QSAR investigations", Bioorganic & Medicinal Chemistry (2006),14(21):7282-7292.

Easter, John A., "Synthesis of isotopically labeled 1-[(2,4-di-1-pyrrolidiny1-9H-pyrimido[4,5-b]indo1-9-yl)acetyl]pyrrolidine monohydrochloride, PNU-142731a, an orally active antiasthma agent", Isotope Production and Applications in the 21st Century, Proceedings of the International Conference on Isotopes, 3rd, Vancouver, BC, Canada, Sep. 6-10, 1999 (2000):345-346.

Easter et al., "Synthesis of several isotopically labeled pyrrolo [1 ,3-d]pyrimidine analogs", Journal of Labelled Compounds & Radiopharmaceuticals (2001), 44(11):797-810.

Epps et al., "The preparation of dipalmitoyllecithin bilayers as probed by the fluorescent pyrrolopyrimidine, U-104067", Chemistry and Physics of Lipids (1997), 86(2):121-133.

Glushkov, R. G., "Synthesis of indolo[2,3-d]pyrimidines", Khimiko-Farmatsevticheskii Zhurnal (1967), 1 (9):25-32.

Hall et al., "Pyrrolopyrimidines: novel brain-penetrating antioxidants with neuroprotective activity in brain injury and ischemia models", Journal of Pharmacology and Experimental Therapeutics (1997), 281 (2):895-904.

Higashin et al., " Triazolo[4,5-d]pyrimidines. VII. The photochemical transformation of 3-phenyl-3H-1 ,2,3-triazolo[4,5-d]pyrimidines into 9H-pyrimido[4,5-b]indoles", Heterocycles (1981),15(1):483-487.

International Search Report and Written Opinion dated May 11, 2012 issued in PCT/US2012/029104 filed Mar. 14, 2012.

Lapachev et al., 4-Aminouracils and pyrimido[4,5-b]indolediones from 4-azidouracils, Monatshefte fuer Chemie (1988), 119(1):97-102.

Lipton et al. "Four generations of pyrrolopyrimidines", ACS Symposium Series (2002), 817(From Bench to Pilot Plant), 101-112.

Mauragis et al., "Evaluation and Rapid Scale-Up of the Synthesis of the Pyrrolopyrimidines U-101033E and U-104067F", Organic Process Research & Development (1997), 1(1):39-44.

Monge et al., "New 4-amino-7,8-dimethoxy-5H-pyrimido[5,4-b]indole derivatives: synthesis and studies as inhibitors of phosphodiesterases", Archiv der Pharmazie (Weinheim, Germany) (1993), 326(11):879-885.

Nogimori et al., A new class of propylthiouracil analogs: comparison of 5'-deiodinase inhibition and antithyroid activity, Endocrinology (1986), 118(4):1598-604.

Oostveen et al., "Neuroprotective efficacy and mechanisms of novel pyrrolopyrimidine lipid peroxidation inhibitors in the gerbil forebrain ischemia model", Journal of Cerebral Blood Flow and Metabolism (1998), 18(5):539-547.

Rauscher et al., "Effects of new antioxidant compounds PNU-104067F and PNU-74389G on antioxidant defense in normal and diabetic rats", Journal of Biochemical and Molecular Toxicology (2000), 14(4):189-194.

Sethy et al., "Neuroprotective effects of the pyrrolopyrimidine U-104067F in 3-acetylpyridine-treated rats", Experimental Neurology (1996), 140(1):79-83.

Smith et al., "Two novel pyrrolopyrimidine lipid peroxidation inhibitors U-101 033E and U-104067F protect facial motor neurons following neonatal axotomy", Experimental Neurology (1996), 141(2):304-309.

Stolle et al, "The preparation of isotopically labeled 2,4,6-trisubstituted pyrimidines", Synthesis and Applications of Isotopically Labelled Compounds, Proceedings of the International Symposium, 7th, Dresden, Germany, Jun. 18-22, 2000 (2001), 272-275.

Venugopalan et al., "Synthesis of 6,7-dimethoxypyrimido[4,5-b]indoles as potential antihypertensive agents", Journal of Heterocyclic Chemistry (1988), 25(6):1633-9.

Warner et al., "Identification of a lead small-molecule inhibitor of the Aurora kinases using a structure-assisted, fragmentbased approach", [Erratum to document cited in CA145:388697], Molecular Cancer Therapeutics (2006), 5(12):3312.

Wright, G. E., 9H-Pyrimido[4,5-b]indole-2,4-diones. The acid-catalyzed cyclization of 6-(phenylhydrazino)uracils, Journal of Heterocyclic Chemistry (1976), 13(3):539-44.

Wright et al., Acid-catalyzed rearrangements of 6-(p-tolylhydrazino)-2-thiouracil, Journal of Heterocyclic Chemistry (1979), 16(2):401-2.

First Examination Report issued in New Zealand Patent Application No. 614983 dated Jun. 5, 2014.

Bratt, J. et al., Polyhalogenoaromatic Compounds. Part 41 .I Photochemical Dehalogenation, Journal of the Chemical Society, Perkin Transactions 1, 1980, pp. 648-565, 1.

Davarani, S. S. H., et al., 2-Substituted 4H-[1,3]thiazolo[3,2-a][1,3,5]triazine-4-thiones: Synthesis, Crystal Structure, and Antifungal Activity, Journal of Hetericyclic Chemistry, 2010, pp. 40-45, 47(1).

Lapachev, V. V., et al., 4-Aminouracils and pyrimido[4,5-b]indolediones from 4-azidouracils, Organische Chemie Und Biochemie, 1988, pp. 97-102, 119(1).

Mallory, F. B., et al., Photocyclization of Stilbenes and Related Molecules, Organic Reactions, 1984, pp. 1-456, 30(1).

Niogimori, T., et al., A New Class of Propylthiouracil Analogs: Comparison of 5'-Deiodinase Inhibition and Antithyroid Activity, Endocrinology, 1986, pp. 1598-1605, 118(4).

Wright, G. E., 9H-Pyrimido[4,5-B]Indole-2,4-Diones—Acid-Catalyzed Cyclization of 6-(Phenylhydrazino)Uracils, Journal of Heterocyclic Chemistry, 1976, pp. 539-44, 13(3).

Wright, G. E., et al, Acid-Catalyzed Rearrangements of 6-(P-Tolyhydrazino)-2-Thiouracil, Journal of Heterocyclic Chemistry, 1979, pp. 401-402, 16(2).

* cited by examiner

A = 7.0 − 10.5 Å
B = 6.0 − 9.0 Å
C = 3.5 − 6.0 Å
D = 5.0 − 7.5 Å

TRICYCLIC GYRASE INHIBITORS

CROSS-REFERENCE TO RELATED APPLICATIONS

This application is a U.S. national phase under 35 U.S.C. §371 of International Application No. PCT/US12/29104, entitled "TRICYCLIC GYRASE INHIBITORS", filed Mar. 14, 2012, which claims priority under 35 U.S.C. §119(e) to U.S. Provisional Application No. 61/453,011 filed Mar. 15, 2011. The contents of each of these applications are incorporated herein by reference in their entireties.

STATEMENT REGARDING FEDERALLY SPONSORED R&D

This claimed invention was made with government support under Contract No. HHSN272200800042C awarded by the National Institute of Allergy and Infectious Diseases. The government has certain rights in the invention.

PARTIES OF JOINT RESEARCH AGREEMENT

The claimed invention was made pursuant to a joint research agreement between Trius Therapeutics, Inc. and Lawrence Livermore National Security, LLC under its United States Department of Energy Contract No. TC02128.0.

BACKGROUND

Field

The present disclosure relates to the field of medicinal chemistry and in particular to compounds, and pharmaceutical compositions thereof, that are useful as antibiotics. Particularly, tricyclic gyrase compounds inhibit DNA Gyrase B (GyrB) and Topoisomerase IV (ParE) enzymes. Related methods of treating bacterial infections and methods of making the compounds using novel intermediates are also contemplated.

Description of the Related Art

Bacterial infections pose a continuing medical problem because anti-bacterial drugs eventually engender resistance in the bacteria on which they are used. Consequently, a need exists for new drugs with efficacy against pathogenic bacteria for use in the therapy and prophylaxis of bacterial infections.

One target for development of anti-bacterial drugs has been DNA Gyrase B (GyrB) and Topoisomerase IV (ParE) enzymes necessary for DNA replication. Gyrase inhibitors have been disclosed in RE40,245, which is hereby incorporated by reference in its entirety.

The GyrB enzymatic pocket has been characterized in detail in Wigley, D. B. et al., Nature, 351(6328), 624-629, 1991. See also, Tsai F T, et al., *The high-resolution crystal structure of a 24-kDa gyrase B fragment from E. coli complexed with one of the most potent coumarin inhibitors, clorobiocin*, Proteins. 1997 May; 28(1):41-52.

The ParE enzymatic pocket has been characterized in detail in Bellon, S., et al. *Crystal structures of Escherichia coli topoisomerase IV ParE subunit (24 and 43 kilodaltons): a single residue dictates differencesin novobiocin potency against topoisomerase IV and DNA gyrase*, Antimicrob. Agents Chemother. 48: 1856-1864 (2004). These references are hereby incorporated by reference in their entirety.

In contrast, patent publications naming Hurley et al. as inventors, are directed to protein kinase inhibitors that are useful for protein kinase-mediated diseases and conditions such as cancer. See, e.g., US 2008/0051414, US 2009/0143399, and US 2009/0099165.

SUMMARY

Tricyclic gyrase compounds of Formula I inhibit DNA Gyrase B (GyrB) and Topoisomerase IV (ParE) enzymes. The compound of Formula I has the structure Formula I

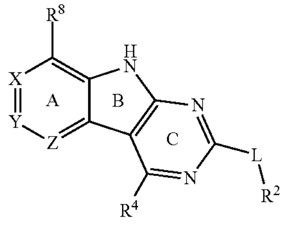

Pharmaceutically suitable salts, esters, and prodrugs thereof are also contemplated. The variables in Formula I follow.

L can be O or S.

$R^8$ can be H or an interacting substituent having a length of about 1 Å to about 5 Å from the carbon attachment point on the A Ring to the terminal atom in $R^8$ and a width of about 3.3 Å or less.

X, Y and Z can be independently selected from the group consisting of N, $CR^X$, $CR^Y$, and $CR^Z$, provided that no more than two of X, Y and Z are N. $R^X$ can be H or an interacting substituent having a length of about 1 Å to about 2 Å from the carbon in $CR^X$ to the terminal atom in $R^X$. $R^Y$ can be H or an interacting substituent having a length of about 1 Å to about 3 Å from the carbon in $CR^Y$ to the terminal atom in $R^Y$. $R^Z$ can be H or an interacting substituent having a length of about 1 Å to about 2 Å from the carbon in $CR^Z$ to the terminal atom in $R^Z$.

$R^2$ can be a 6-membered aryl or heteroaryl ring containing 0-3 O, S, or N heteroatoms, optionally substituted with 0-3 noninterfering substituents, wherein 2 adjacent noninterfering substituents on $R^2$ can form one or more fused rings with the 6-membered aryl or heteroaryl ring. In some aspects, the 6-membered aryl or heteroaryl ring of $R^2$ has a CH at the positions immediately adjacent the position where $R^2$ attaches to L.

$R^4$ can be:

- H;
- an optionally substituted $OR^a$;
- an optionally substituted secondary or tertiary amine attached to the C Ring through the secondary or tertiary amine N; or
- an optionally substituted 5-10 membered unsaturated cyclic or heterocyclic residue containing 0-3N, O or S heteroatoms.

The optional substituent can be 0-3 noninterfering substituents. $R^a$ can be a 5-6 membered aryl or heteroaryl containing 0-3O, S, or N heteroatoms optionally substituted with 0-3 noninterfering substituents. In some aspects, $R^4$ substituent does not project greater than about 3 Å below the plane of the A, B and C Rings toward the GyrB/ParE binding pocket floor in the bound conformation. In addition, in some aspects, $R^4$ does not sterically interfere with $R^2$ or Z when the compound is in the bound conformation. Methods of using the compound to treat antibacterial infections and methods of making the compounds using novel intermediates are also contemplated.

These and other related aspects are set forth in more detail below.

DETAILED DESCRIPTION

Figure 1:
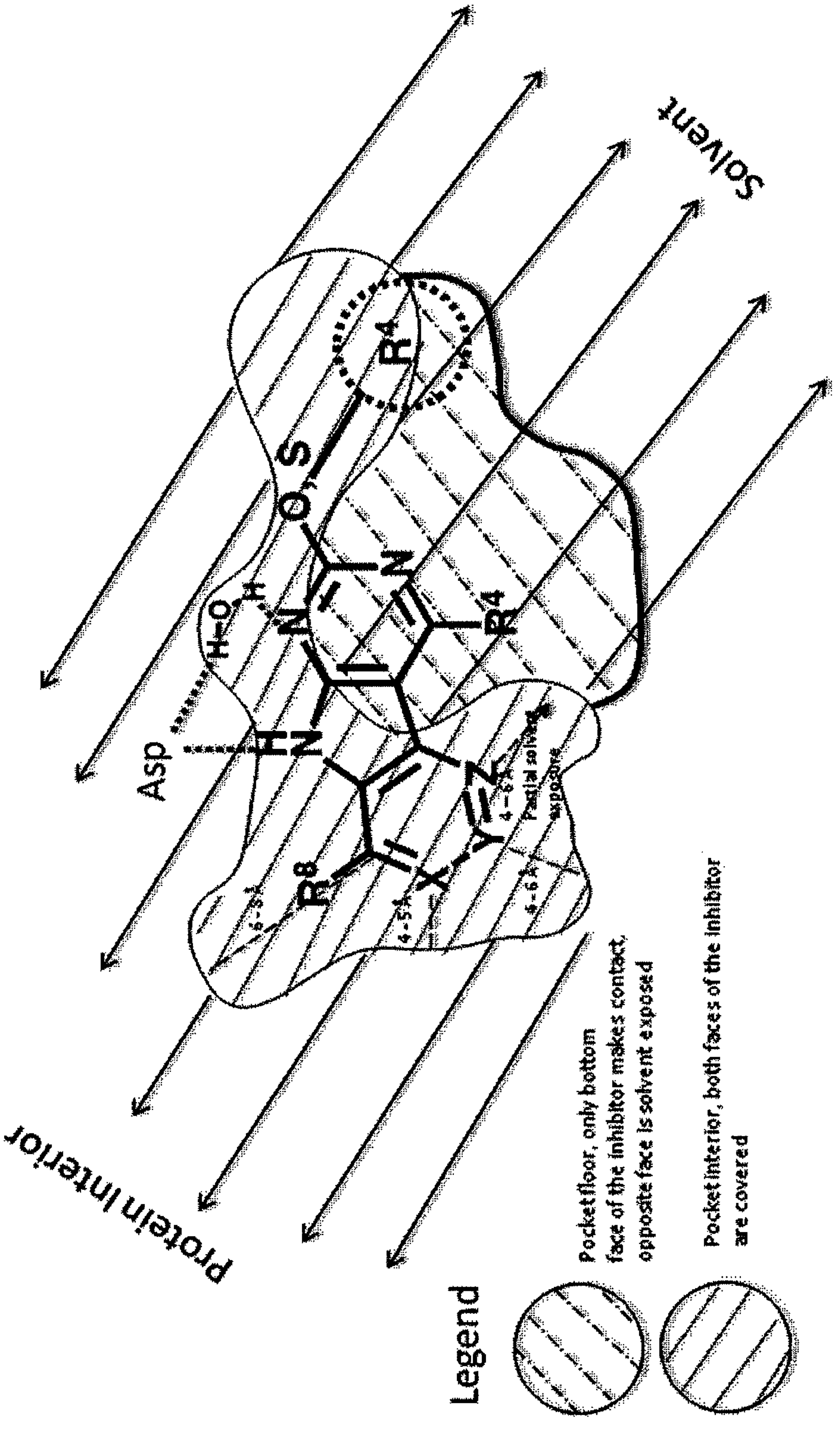
FIG. 1 illustrates a schematic representation of the receptor constraints on the compound, particularly, the binding modes of the tricyclic inhibitors to the GyrB/ParE active-site pocket (from crystallographic data). The measurements provided for the lengths are measured from atom center of the A Ring member to the atom center of the nearest non-hydrogen atom on the active site pocket. The figure indicates a length of about 6 Å to about 8 Å from the C atom attached to $R^8$ to the atom on the active site pocket; about 4 Å to about 5 Å from the A Ring atom of X to the atom on the active site pocket; about 4 Å to about 6 Å from the A Ring atom of Y to the atom on the active site pocket; and about 4 Å to about 6 Å from the A Ring atom of Z to the atom on the active site pocket. The relative positions of the $R^8$, $R^4$, and cyclic $R^2$ substituents are shown. The approximate shape of a cross-section of a representative GyrB/ParE active-site pocket in and above the plane of the tricyclic scaffold (i.e., the A, B and C Rings) is shown. The hatched area having unbroken lines depicts regions of the inhibitor that are covered on both surfaces by the active-site pocket. In addition, the approximate shape of a cross-section of a representative GyrB/ParE active-site pocket below the plane of the tricyclic scaffold is shown. The hatched area having dashed lines depict regions of the inhibitor that make contact with the floor surface of the active-site pocket, while the plane above the tricyclic ring system is solvent exposed. The approximate position of the conserved substrate-binding Asp side-chain and structural water molecule are shown in FIG. 1, along with the constellation of potential hydrogen-bonds (depicted as dotted lines) observed between the tricyclic scaffold and the Asp and water. The solvent exposed and solvent sheltered faces of the active-site pocket are highlighted. The solvent refers to the in vivo surroundings of GyrB/ParE active site as part of a protein, which generally includes an aqueous environment in which the protein is situated within a cell. Also, the $R^4$ moiety in some aspects does not project atoms greater than about 3 Å below the plane of the tricyclic ring system towards the GyrB/ParE binding pocket floor in the bound state.

Certain aspects of the compounds of Formula I are elaborated below. In Formula I above, L is a linker that bridges $R^2$ to the C Ring. L may be O or S. In some aspects, L is O. In some aspects, L is S.

As used herein, the term "aryl" refers to optionally-substituted monocyclic and fused bicyclic hydrocarbyl moiety. Any monocyclic or fused ring bicyclic system which has the characteristics of aromaticity in terms of electron distribution throughout the ring system is included in this definition. Typically, the ring systems contain 5-12 ring member atoms. "Heteroaryl" refers to optionally-substituted aromatic monocyclic and fused bicyclic heterocycles containing one or more heteroatoms selected from N, O and S. The inclusion of a heteroatom permits inclusion of 5-membered rings as well as 6-membered rings.

As used herein, the term "alkyl," include straight- and branched-chain and cyclic monovalent substituents. Examples include methyl, ethyl, propyl, isopropyl, and cyclopropyl. Where indicated, the alkyl substituents may contain 1-10C (1 to 10 carbon atoms) such as 1-3C, 1-6C, or 1-8C.

As used herein, "hydrocarbyl residue" refers to a residue which contains only carbon and hydrogen. The hydrocarbyl residue may be saturated or unsaturated, aliphatic or aromatic, straight-chain, branched-chain, or cyclic including a single ring, a fused ring system, a bridge ring system, or a spiro ring system, or a combination hydrocarbyl groups. The hydrocarbyl residue, when so stated however, may contain heteroatoms over and above the carbon and hydrogen members of the substituent residue. Thus, when specifically noted as containing such heteroatoms, the hydrocarbyl residue may also contain heteroatoms such as O, S or N within the "backbone" of the hydrocarbyl residue. A hydrocarbyl group may include a combination hydrocarbyl containing moieties such as a heterocyclic group, linked to a heteroalkyl containing a combination of a straight chain alkyl and a cycloalkyl group.

As used herein, "cyclic residue" refers to a cyclic hydrocarbyl residue, which contains only carbon and hydrogen. The cyclic residue, when so stated however, may contain heteroatoms over and above the carbon and hydrogen members of the substituent residue. Thus, when specifically noted as containing such heteroatoms, the heterocyclic residue may also contain heteroatoms such as O, S or N within the "backbone" of the cyclic residue. In some aspects, when so stated, the cyclic residue is a cycloaliphatic or cycloheteroaliphatic residue. A saturated cycloaliphatic or saturated cycloheteroaliphatic residue refers to a ring containing saturated bonds between each ring member.

As used herein, "unsaturated cyclic residue" refers to an at least partially unsaturated or aromatic cyclic hydrocarbyl residue, which contains only carbon and hydrogen. The unsaturated cyclic residue, when so stated however, may contain heteroatoms over and above the carbon and hydrogen members of the substituent residue. Thus, when specifically noted as containing such heteroatoms, the unsaturated heterocyclic residue may also contain heteroatoms such as O, S or N within the "backbone" of the unsaturated cyclic residue.

The term "members" or "membered" in the context of heterocyclic and heteroaryl groups refers to the total atoms, carbon and heteroatoms N, O and/or S, which form the ring. Thus, an example of a 6-membered saturated cycloheteroaliphatic ring is piperidine and an example of a 6-membered heteroaryl ring is pyridine.

The bound conformation refers to the conformation (i.e., the spatial arrangement of atoms) the tricyclic gyrase compound would assume if it was bound to the GyrB/ParE active-site pocket in the enzyme's interior. In use, the compound may interact with the active site pocket and inhibit the ATPase activity. When the compound is bound to the GyrB/ParE active-site pocket, some substituents interact with certain amino acids and thus the substituents' ability to rotate freely about a bond is constrained. Thus, more useful measurements may be made to determine distances relevant for determining the dimensions of proper substituents. When indicated, measurements are based on the relative positions of substituents on the compound while hypothetically bound to the GyrB/ParE active-site pocket. References to the bound conformation with respect to the compound should not be interpreted as literally encompassing the GyrB/ParE active-site pocket in combination with the compound. The bound conformation is characterized via measurements derived from the three dimensional structure from x-ray crystallographic data on the inhibitor complexed with a protein construct that typically encompasses the 24 or 46 kDa ATP-binding domain of one or more representative bacterial GyrB or ParE orthologs. Given the high degree of sequence identity between GyrB and ParE enzymes in most pathogenic organisms of interest, structural information derived from a protein ortholog from any pathogen of clinical relevance should be sufficient to describe the bound conformation. Briefly, crystallographic structures are generated using the following methods: Proteins of interest (e.g., *E. faecalis* GyrB, *E. coli* GyrB, *F. tularensis* ParE or *E. coli* ParE) are generated in a standard *E. coli* expression system. The open reading frames are cloned into an expression plasmid (e.g., pET28a), and expressed in and appropriate *E. coli* expression strain (e.g., BL21 (DE3)). For crystallography the 24 kDa and 46 kDa ATP binding domains are cloned with a C(His)$_6$ tag to aid purification by metal affinity chromatography. This robust chromatography step typically yields greater than 80% pure protein. Polishing steps including ion exchange and size exclusion chromatography, are performed as needed until satisfactory (>95%) purity is achieved. Once purified protein is available, complexes of GyrB or ParE and the inhibitor molecule of interest are generated by mixing a stoichiometric excess of the inhibitor of interest with the recombinant protein target in solution and crystallizing the complex using established crystallization methods (typically vapor diffusion, as described in Drenth J. (1999) In Principles of protein x-ray crystallography. 2$^{nd}$ ed. Springer, New York). Once crystallized, x-ray diffraction data are collected on single crystals of the protein-inhibitor complexes using monochromatic x-rays generated by a rotating anode or synchrotron radiation source. X-ray data processing, analysis and subsequent structure solution and refinement are carried out using well established computational methods (reviewed in Drenth J. (1999) In Principles of protein x-ray crystallography. 2$^{nd}$ ed. Springer, New York).

Interacting substituents on the compound that interact with the GyrB/ParE active-site pocket include those substituents that would be located within the protein's interior when the compound is in the bound conformation. Interactions of interacting substituents generally include hydrophobic interactions (which favor the apposition of lipophilic surfaces on the inhibitor and active-site pocket), and electrostatic interactions such as Van der Waals, dipole-dipole, coulombic interactions or hydrogen-bonding between atoms on the compound and atoms in the GyrB/ParE active-site pocket. For example, $R^8$, $R^X$, $R^Y$, and $R^Z$ interact with various portions of the protein's interior. If $R^8$, $R^X$, $R^Y$, or $R^Z$ is $NH_2$ or NHR (where R is, for example, a small alkyl group), the H atom(s) on the nitrogen may interact with electronegative atoms, such as nitrogen or oxygen, proximally located in the GyrB/ParE active-site pocket to which the compound may bind. When $R^8$, $R^X$, $R^Y$, and $R^Z$ are non-polar (e.g., a methyl group), the interacting substituent may also electrostatically interact with an atom in the protein's interior via Van der Waals interactions, and desolvate complementary lipophilic surfaces in the active-site pocket to form favorable hydrophobic interactions. Additionally, in some aspects, the shape and size of the active-site may place restrictions on the dimensions of compound's substituents that would be sterically compatible with the active-site pocket.

Where indicated, the dimensions of a substituent may be provided and are associated with the dimensions of the pocket in which the compound would be situated if in a bound conformation. For example, the length of a substituent may be given based on its distance from the atom on the tricyclic scaffold to the substituent's atom that is positioned farthest from the tricyclic scaffold, i.e., the terminal atom. The distance is measured based on the center of a first atom such as a C on the tricyclic scaffold, to the center of the terminal atom. The distance is measured from point to point in a straight line regardless of the fact that the bonds in the substituent are not linearly aligned, such as an ethyl or OH substituent.

The width of the $R^8$ substituent may be understood with respect to the dimension of the active site pocket in which $R^8$ resides ($R^8$ pocket), and with respect to the $R^8$ substituent when it adopts a conformation in the $R^8$ pocket, when the compound in the bound conformation. The $R^8$ substituent generally projects into the $R^8$ pocket along an axis that projects through the C atom on the A Ring that is attached to $R^8$, and the C atom on the same ring in the meta position that shares a common C atom with the B ring when the compound is in bound conformation. The width of the $R^8$ substituent refers to the width at its widest point measured from atom center to atom center that are farthest apart approximately perpendicularly about such an axis, when the compound is in the bound conformation. Thus, the $R^8$ substituent may be able to adopt a conformation, when the compound is in the bound conformation, having a width that does not exceed about 3.3 Å. For example, the NHMe moiety on $R^8$ has a width of approximately 2.8 Å. This width is derived by summing the distance of atom center of a methyl proton oriented trans to the N—H proton perpendicularly from the axis described above, with the distance of the center of the N—H proton perpendicularly from the same axis. Further, the width of a cyclopropyl substituent would be approximately 3.1 Å, measured as the distance between the centers of protons on adjacent carbon atoms on opposite faces of the cyclopropyl ring.

$R^8$ may be H or an interacting substituent having a length of about 1 Å to about 5 Å from the carbon attachment point on the A Ring to the terminal atom in $R^8$ and a width of about 3.3 Å or less. The length of $R^8$ is appropriate for the length from the tricyclic scaffold carbon to the active site pocket based on crystallographic data, which is about 6 Å to about 8 Å as shown in FIG. 1. In some aspects, $R^8$ is H, Cl, F, Br, $NH_2$, OH, 1-3C alkyl, amino-1-3C alkyl, aminocyclopropyl, $OCH_3$, $OCH_2CH_3$, cyclopropyl, $CH_2$cyclopropyl, $CH_2Cl$, $CH_2F$, $CHF_2$, $CF_3$, $CH_2CH_2F$, $CH_2CHF_2$, $CH_2CF_3$, $NHNH_2$, NHOH, $NHNHCH_3$, $NHOCH_3$, $NHCD_3$, $SCH_3$, or NHCOH, where D is deuterium. In some aspects, $R^8$ is H, Cl, F, Br, $NH_2$, 1-3C alkyl, amino-1-3C alkyl, aminocyclopropyl, $OCH_3$, $OCH_2CH_3$, cyclopropyl, $CH_2$cyclopropyl, $CH_2Cl$, $CHCl_2$, $CH_2F$, $CHF_2$, $CF_3$, $CH_2CH_2F$, $CH_2CHF_2$, $CH_2CF_3$, $NHNH_2$, NHOH, $NHNHCH_3$, $NHOCH_3$, $NHCD_3$, $SCH_3$, or NHCOH. For instance, $R^8$ may be H, $CH_3$, $CH_2CH_3$, Cl, $OCH_3$, $NHCD_3$, $NHCH_3$, $NHCH_2CH_3$, or $NH_2$, such as $NHCH_3$.

X, Y and Z may be independently selected from the group consisting of N, $CR^X$, $CR^Y$, and $CR^Z$, provided that no more than two of X, Y and Z are N. $R^X$ may be H or is an interacting substituent having a length of about 1 Å to about 2 Å from the carbon in $CR^X$ to the terminal atom in $R^X$. $R^Y$ may be H or an interacting substituent having a length of about 1 Å to about 3 Å from the carbon in $CR^Y$ to the terminal atom in $R^Y$. For example, $R^Y$ would not be a methoxy substituent because a methoxy substituent is longer than 3 Å. $R^Z$ may be H or is an interacting substituent having a length of about 1 Å to about 2 Å from the carbon in $CR^Z$ to the terminal atom in $R^Z$. These lengths of $CR^X$, $CR^Y$, and $CR^Z$ are appropriate in comparison to the lengths from the tricyclic scaffold carbon to the active site pocket based on crystallographic data shown in FIG. 1. In some aspects, X, Y and Z are $CR^X$, $CR^Y$, and $CR^Z$ respectively. $R^X$ may be H, $CH_3$, Cl, Br, or F, such as H or F. $R^Y$ may be H, $CH_3$, $CHF_2$, $CF_3$, CN, $CH_2CH_3$, Cl, Br, or F, such as H, F, Cl, or $CF_3$. $R^Z$ may be H, $CH_3$, Cl, Br, or F, such as H, $CH_3$ or F.

Without being bound by theory, $R^2$ may be useful for conferring selectivity and potency against eukaryotic ATP binding proteins, such as kinases and HSP90. Thus, one of the compounds' benefits includes avoiding toxicity due to off target binding, such as to a kinase, due in part to $R^2$'s selectivity as part of the compound. Generally, in some aspects, the compounds are not potent inhibitors for eukaryotic kinases. In some aspects, $R^2$ is a 6-membered aryl or heteroaryl ring containing 0-3 O, S, or N heteroatoms, optionally substituted with 0-3 noninterfering substituents, wherein 2 adjacent noninterfering substituents on $R^2$ may form one or more fused rings with the 6-membered aryl or heteroaryl ring. For example, $R^2$ may be an optionally substituted 6-membered aryl or heteroaryl ring containing 0-3 O, S, or N heteroatoms such as optionally substituted pyrimidinyl, phenyl, or pyridyl. In some aspects, $R^2$ is a heteroaryl ring such as 6-membered heteroaryl. In some aspects, $R^2$ may be attached to L through a carbon atom in the 6-membered aryl or heteroaryl ring. Without being bound by theory, solvent sheltered faces of the GyrB/ParE active-site pockets may restrict the size of substituents on the compound proximal those solvent sheltered faces. Thus, with respect to $R^2$, the 6-membered aryl or heteroaryl ring may contain a CH at the ring positions immediately adjacent the position where $R^2$ attaches to L. In some aspects, there is no N on the 6-membered aryl or heteroaryl ring of $R^2$ at the ring positions immediately adjacent the ring position where $R^2$ attaches to L.

Figure 2:
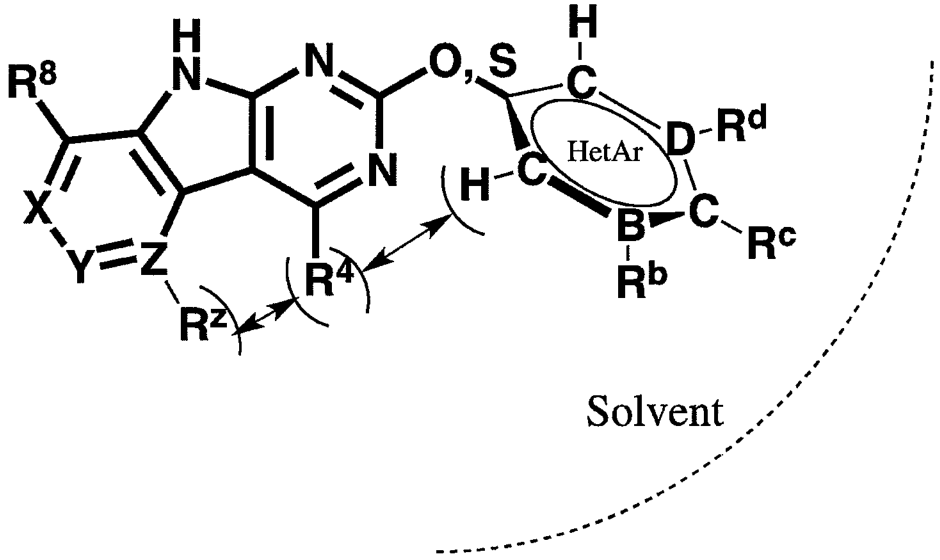
FIG. 2 illustrates a schematic representation of the intramolecular constraints on the compound wherein $R^2$ is a 6-membered ring. Specifically, the molecular geometry and the conformations of R-groups necessary to allow binding of tricyclic inhibitors to the GyrB/ParE active-site pockets constrain the size and composition of substituents at certain positions on the inhibitor scaffold. This figure illustrates regions of potential steric interference between the $R^4$ substituent and the $R^2$ or $R^Z$ substituent in the bound conformation.
Figure 3:
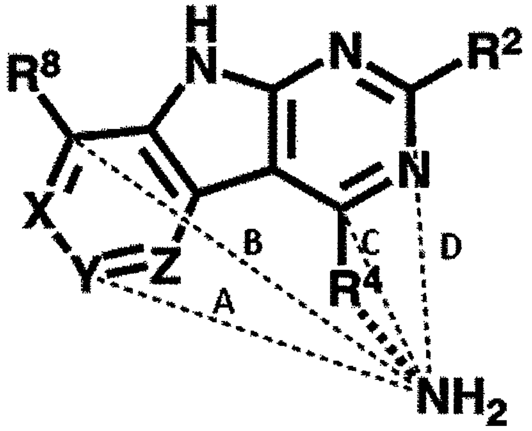
FIG. 3 illustrates an example of relative positions of a primary amine that is encompassed within $R^4$ when bound to GyrB/ParE. This illustration also applies to a secondary amine, which is not shown in FIG. 3. The volume occupied by the $R^4$ amine with respect to the tricyclic scaffold across the amines was determined using a four point trilateration procedure based on distances between the $R^4$ amine and four different atoms on the tricyclic scaffold from 17 different crystal structures of complexes of *E. faecalis* GyrB with tricyclic inhibitors containing a diverse set of $R^4$ amines comprising a secondary or tertiary amine attached to the C Ring through the secondary or tertiary amine N and a primary or secondary amine that is not attached to the C Ring. The relative position of the primary (or secondary, not shown) amine would be above the plane of the tricyclic scaffold, to avoid impinging the floor of the active site.

FIG. 2 illustrates $R^2$ as an optionally substituted 6-membered heteroaryl ring, although the positioning of the substituents also applies to a 6-membered aryl ring. In this illustration, A and E are C. $R^b$ and $R^c$ face the solvent in the bound conformation, and thus the substituents at this position may be varied and may include prodrugs. Cyclization between $R^b$ and $R^c$ may be permitted. $R^d$ is partially solvent exposed, and cyclization between $R^c$ and $R^d$ (for example, with an H-bond acceptor in the $R^d$ position) may be permitted. Large substituents such as large branched groups at $R^d$ may collide with the outer rim of the pocket.

In some aspects, the optionally substituted 6-membered aryl or heteroaryl ring of $R^2$ in combination with the one or more fused rings formed from optional substituents may be selected from the group consisting of optionally substituted indolyl, azaindolyl, pyrimidopyridyl, quinazolinyl, quinoxalinyl, naphthyridinyl, purinyl, imidizopyridinyl, furopyridinyl, isoindolylinyl, benzodioxinyl, dihydrobenzodioxinyl, benzothiazolyl, pyrrolopyridinyl, dihydropyrrolopyridinyl, benzoimidazolyl, imidazopyridinyl, dihydroimidazopyridinyl, tetrahydroisoindolyl, chromenyl, benzthiophene, benztriazolyl, benzfuranyl, benzoxadiazolyl, indazolyl, quinolinyl, isoquinolinyl, indoline, azaindolinyl, or

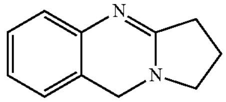

.

Solvent exposed faces of the GyrB/ParE active-site pockets allow portions of the compound to be exposed to a solvent environment when in use as illustrated in FIG. 1. In some aspects, noninterfering substituents may be water soluble to afford compatibility with an aqueous solvent environment. Proportions of the substituents in the direction of a potential solvent environment are not critical but one skilled in the art would understand that sterically unhindered substituents are useful. Thus, proportions of the solvent-exposed substituents may be diverse.

In contrast to an "interfering substituent," certain positions of the molecule may be described as permitting "noninterfering substituents." This terminology is used because the substituents in these positions generally speaking are less relevant to the activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound of Formula I to inhibit bacterial growth of at least one type of bacterium qualitatively intact. For example, the noninterfering substituent would leave the ability of the compound to provide antibacterial efficacy based on a minimum inhibitory concentration (MIC) of less than 32 µg/ml, or based on inhibition of ATPase activity of DNA Gyrase B (GyrB) or Topoisomerase IV (ParE) of less than 10 nm. Thus, the substituent may alter the degree of inhibition based on MIC or ATPase activity. However, as long as the compound of Formula I retains the ability to inhibit bacterial/ATPase activity, the substituent will be classified as "noninterfering." A number of assays for determining the MIC or the ability of any compound to inhibit ATPase activity of DNA Gyrase B (GyrB) or Topoisomerase IV (ParE) are available in the art, and some are exemplified in the Examples below. For instance, a coupled spectrophotometric assay, in which the enzyme-dependent release of inorganic phosphate from ATP hydrolysis is measured, determines the inhibitor activity of an arbitrarily chosen compound during incubation with GyrB or ParE upon the addition of ATP. The features related to the molecule's activity are tightly defined. The positions which are occupied by "noninterfering substituents" can be substituted by conventional moieties as is understood in the art. It is irrelevant to test the outer limits of such substitutions. The relevant features of the compounds are those set forth with particularity herein.

$R^2$ may have 0-3 noninterfering substituents on the 6-membered aryl or heteroaryl ring. For instance, $R^2$ may have a substituent selected from the group consisting of OH, $CO_2H$, CN, $NH_2$, Br, Cl, F, $SO_3H$, $SO_2NH_2$, $SO_2CH_3$, $SOCH_3$, NHOH, $NHOCH_3$, and $NO_2$. $R^2$ may also have a substituent that is an optionally substituted C1-15 hydrocarbyl residue containing 0-5 O, S, or N heteroatoms, optionally substituted with OH, CN, =O, $NH_2$, NHOH, =NOH, $=NNH_2$, $=NOCH_3$, Br, F, Cl, $SO_3H$, or $NO_2$. Substitutions may be on a carbon atom or a heteroatom thus permitting groups such as S=O. In cases where the heteroaryl contains a pyridine ring, the nitrogen atom may be oxidized to a pyridine N-oxide; thus, an OH substituent may be in the form of an oxide, thus for example, permitting a pyridyl having an N-oxide wherein the N is a ring heteroatom.

The C1-15 hydrocarbyl residue containing 0-5 O, S, or N heteroatoms may include a combination of hydrocarbyl groups such as a combination of aliphatic rings or chains and aromatic rings linked together.

In some aspects, two adjacent noninterfering substituents on $R^2$ form one or more fused rings. For example, the combination of the one or more fused rings with the 6-membered aryl or heteroaryl ring of $R^2$ contains 5-15 members, and 0-5 O, S, or N heteroatoms, optionally substituted, such as with OH, =O, CN, $NH_2$, Br, F, or Cl.

The optional substituents may occupy all positions of the $R^2$ ring structure that are not adjacent the linker such as one position, 1-2 positions, or 1-3 positions. In some aspects, one position is optionally substituted. These substituents may be optionally substituted with substituents similar to those listed. Of course, some substituents, such as halo, are not further substituted, as known to one skilled in the art.

In some aspects, $R^2$ may be pyrimidinyl or pyridinyl optionally substituted with $CH(OH)CH_3$, $C(OH)(CH_3)_2$, $OCH_3$, CN, $CH_3$, $CH_2CH_3$, O-cyclopropyl, $SCH_3$, Br, Cl, F, or $NH_2$.

The noninterfering substituents on $R^2$'s 6-membered aryl or heteroaryl ring that may be solvent exposed in the bound conformation may include large substituents such as prodrugs.

In some aspects $R^2$ may be selected from the substituents in the following Chart 1.

Chart 1

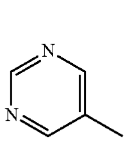
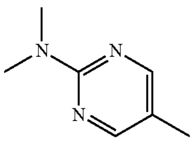
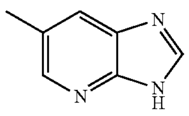
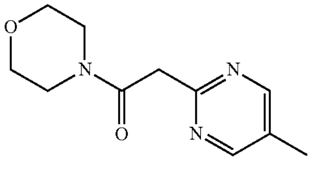
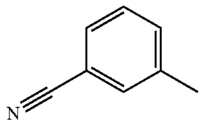

-continued

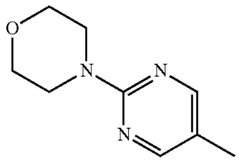
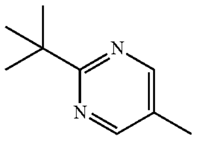
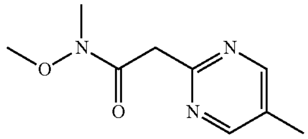
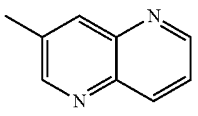
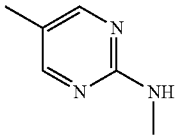
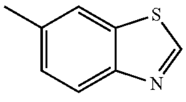
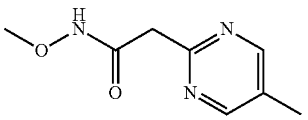
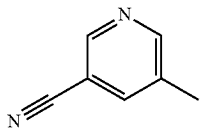
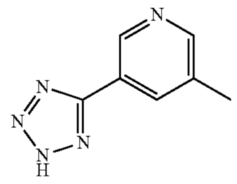
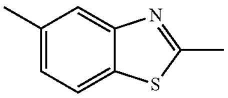
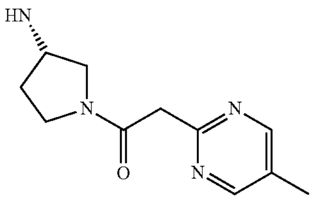
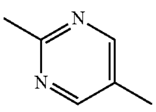
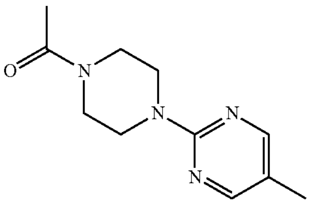
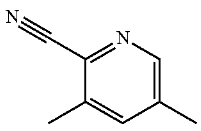
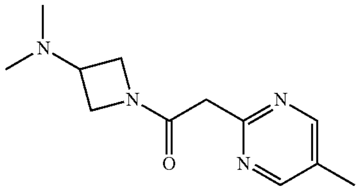
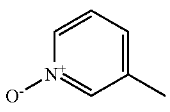
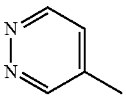
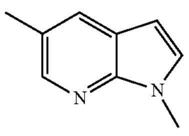
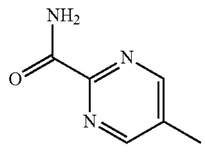
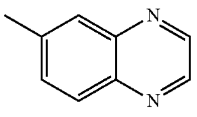
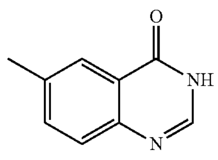

-continued
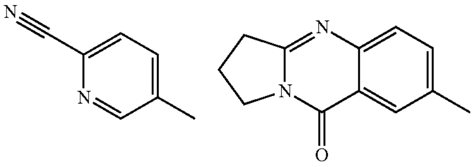
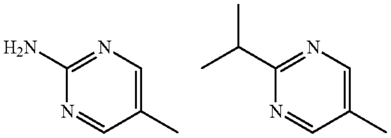
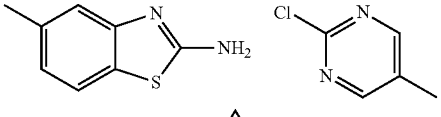
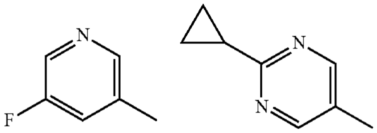
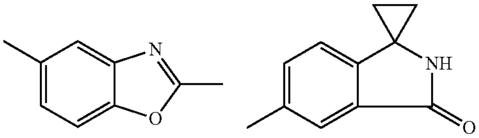
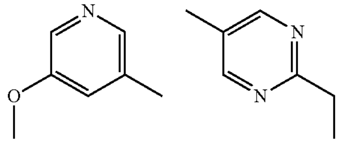
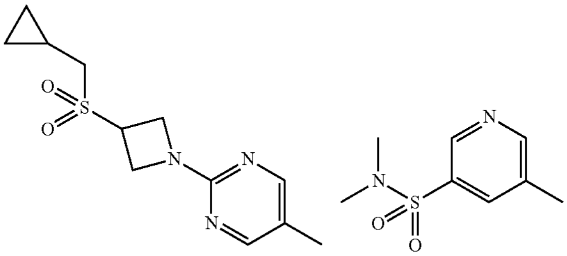
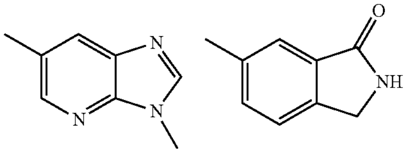
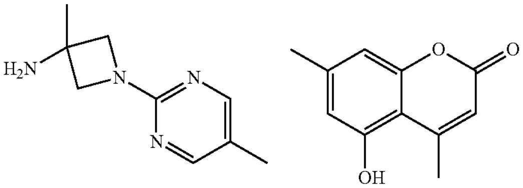
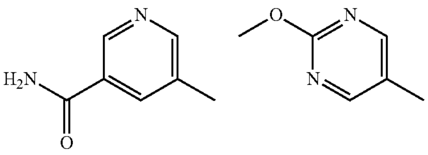
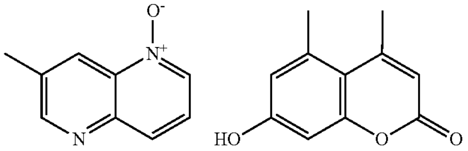
-continued
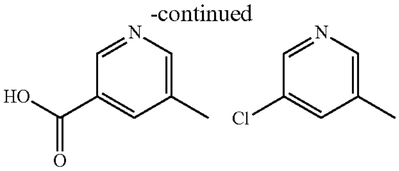
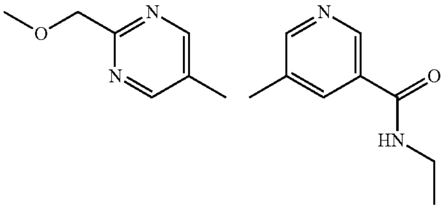
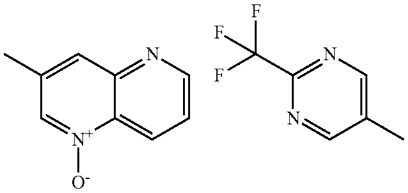
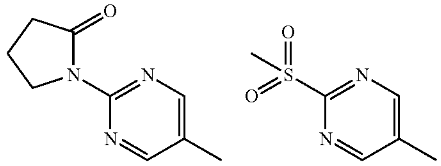
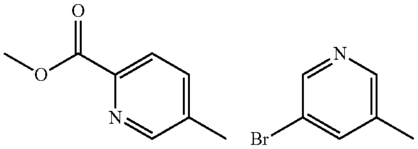
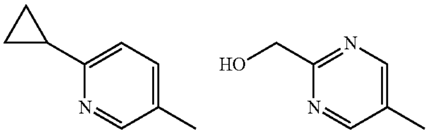
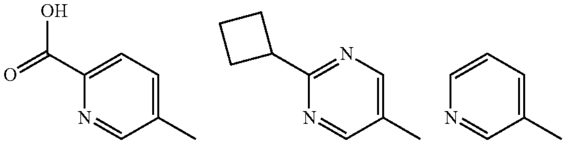
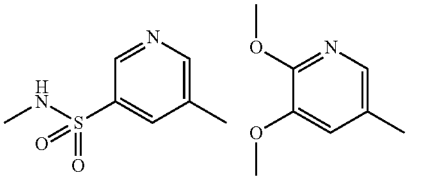
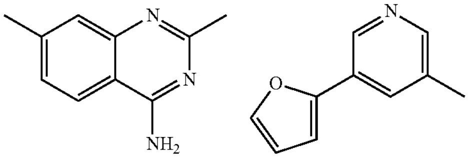
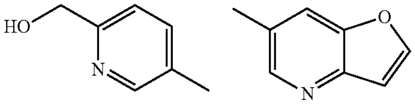
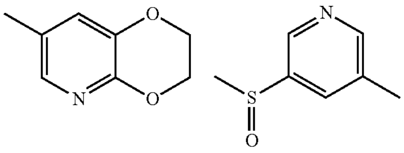

-continued
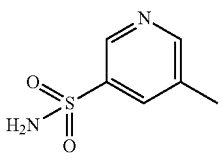
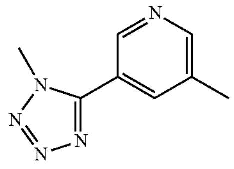
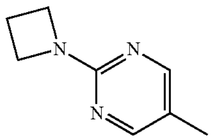
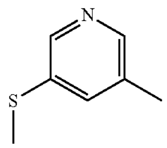
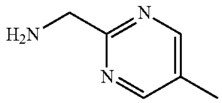
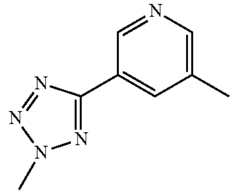
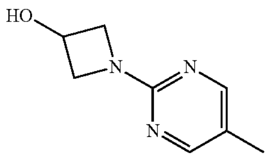
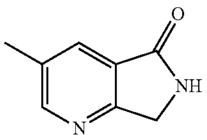
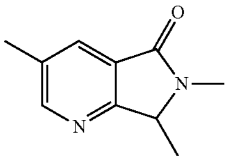
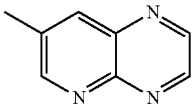
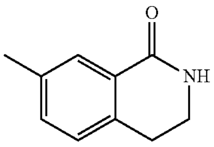
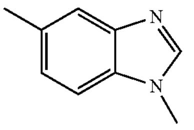
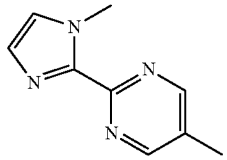
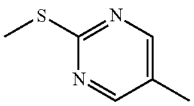
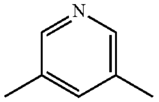
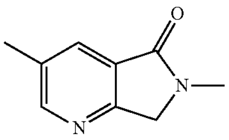
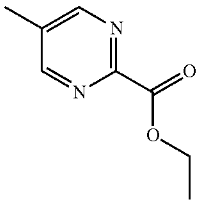
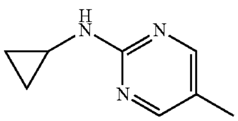
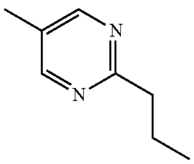
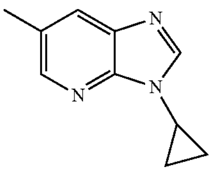
-continued
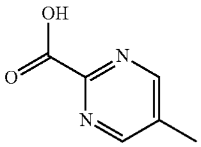
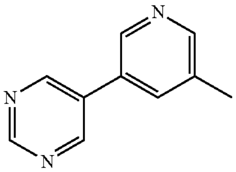
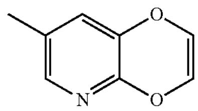
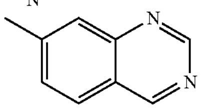
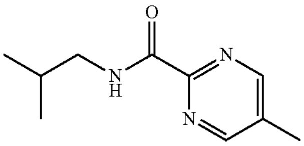
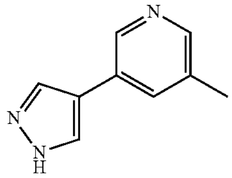
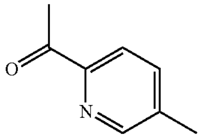
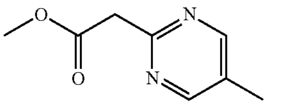
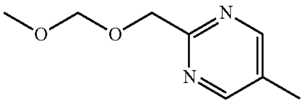
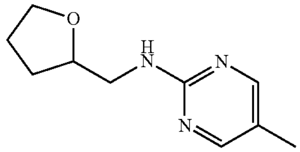
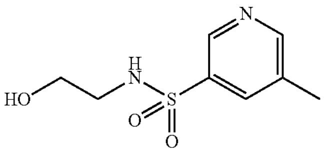
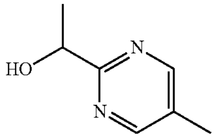
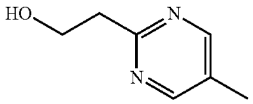
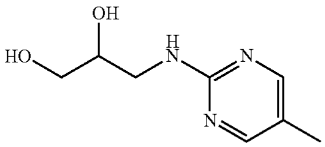
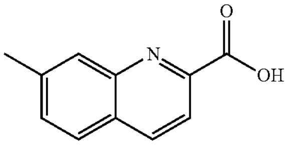
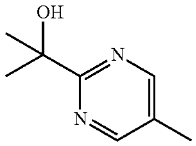
In some aspects $R^2$ may be selected from the substituents in the following Chart 2.
Chart 2
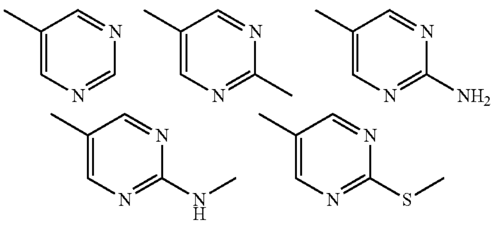

-continued
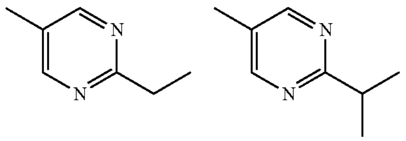
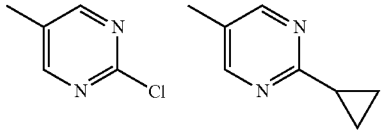
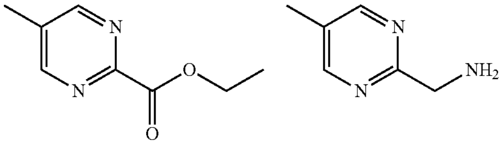
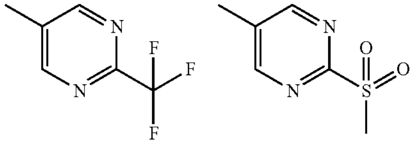
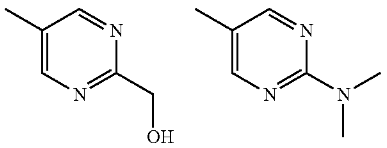
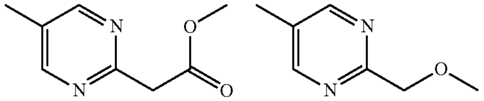
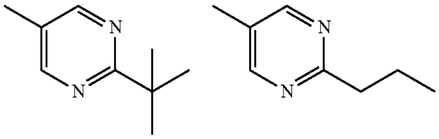
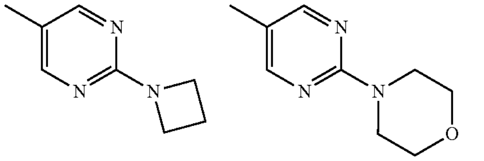
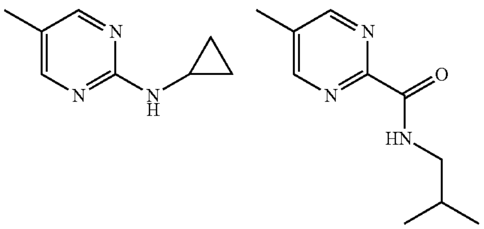
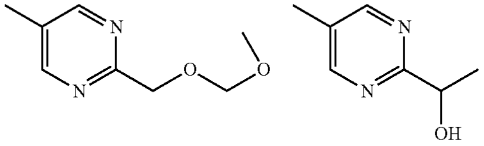
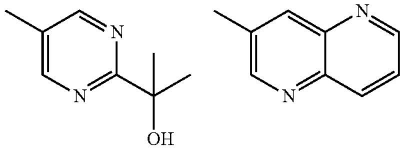
-continued
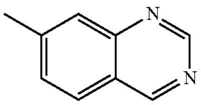
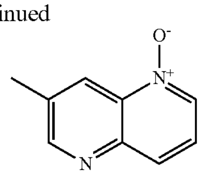
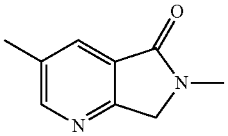
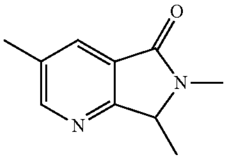
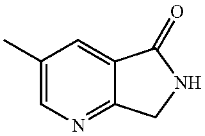
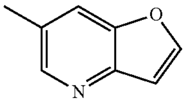
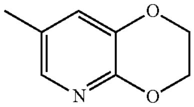
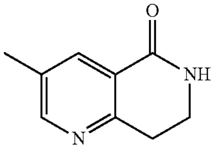
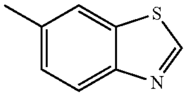
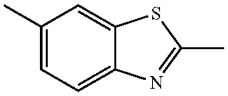
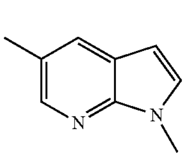
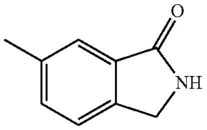
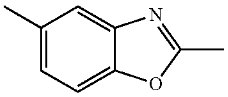
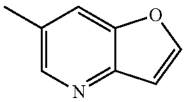
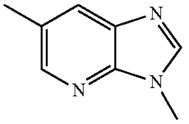
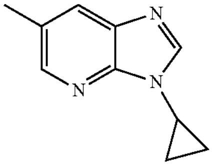
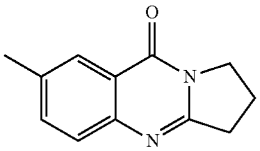
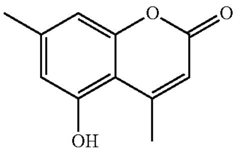
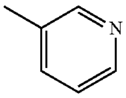
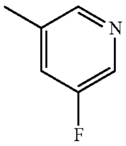
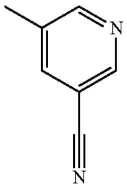
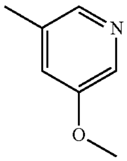
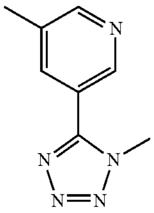
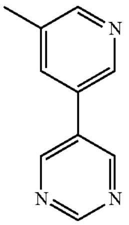
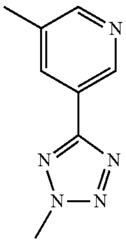
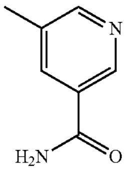

-continued

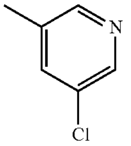
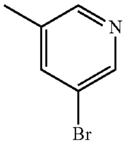
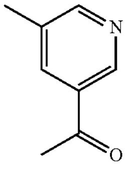
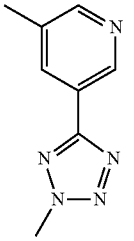
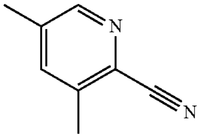
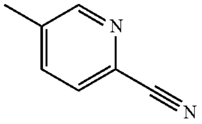
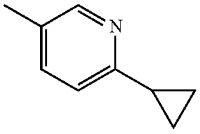
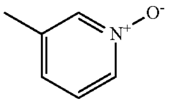
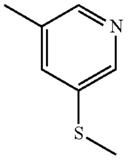
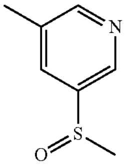

FIGS. 1 and 2 show that the compound is solvent exposed in the bound conformation along the $R^4$ bond axis and in a 0-90° counterclockwise sweep from the $R^4$ bond axis. Choices for prodrugs and substituents on $R^4$, therefore, may be varied. In selecting the $R^4$ substituent, in some aspects the $R^4$ groups do not sterically interfere with $R^2$ or Z groups in the bound conformation, which is illustrated in FIG. 2. A skilled artisan would understand that to avoid steric interference, atoms on $R^4$ should not approach atoms on $R^2$ or $R^Z$ (in the bound conformation) such that the interatomic distances of the closest atoms are less than the sums of their Van der Waals radii.

In addition, in some aspects, the $R^4$ substituent does not project greater than about 3 Å below the plane of the A, B and C Rings toward the GyrB/ParE binding pocket in the bound conformation. "Toward the GyrB/ParE binding floor pocket" refers to not projecting greater than about 3 Å below the plane within about 5-6 bonds from the point of attachment of $R^4$ to the scaffold. Thus, portions of $R^4$ that extend greater than about 5-6 bonds away from the point of attachment of $R^4$ to the C Ring may project greater than about 3 Å below the plane of the A, B and C Rings as these portions are not constrained by the floor of the GyrB/ParE binding pocket.

The distance is defined as the perpendicular distance from the plane aligned with atom centers of the tricyclic scaffold to the center of the most distal atom (from the plane) on the $R^4$ substituent in the bound conformation.

In some aspects, $R^4$ may be H.

In some aspects, $R^4$ may also be an optionally substituted $OR^a$; wherein $R^a$ is a 5-6 membered aryl or heteroaryl containing 0-3 O, S, or N heteroatoms optionally substituted with 0-3 noninterfering substituents. In some aspects, the ring positions adjacent the position where O attaches to $R^a$, may be substituted with small substituents such as those having 2 atoms in the backbone, such as $OCH_3$, $CH_3$, $CH_2CH_3$, OH, $NH_2$, F, Cl, Br, I, or NO. In the remaining positions, substituents can be larger and diverse as substituents in these positions are solvent exposed in the bound conformation. In some aspects, $R^a$ is an optionally substituted pyrimidinyl or pyridinyl, such as unsubstituted pyrimidinyl or pyrimidinyl substituted with $CH_3$ or $NH_2$. In some aspects, $OR^a$ is one of the following substituents in Chart 3.

Chart 3

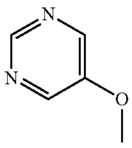
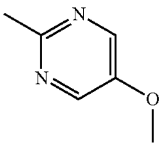
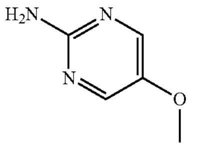

In some aspects, $R^4$ may be an optionally substituted secondary or tertiary amine attached to the C Ring through the secondary or tertiary amine N. "Secondary amine" refers to an N-containing substituent that contains one H attached to the secondary amine N when the substituent is attached to the remainder of the molecule. "Tertiary amine" refers to an N-containing substituent that contains no H attached to the tertiary amine N when the substituent is attached to the remainder of the molecule.

When $R^4$ is the optionally substituted secondary or tertiary amine attached to the C Ring through the secondary or tertiary amine N, $R^4$ may further comprise a primary or secondary amine, wherein the primary or secondary amine is not directly attached to the C Ring. "Primary amine" refers to an amine group that contains two H atoms attached to the primary amine N when attached to the remainder of the substituent. With respect to the "secondary amine" that is not directly attached to the C Ring, in this instance, the secondary amine refers to an amine group that contains one H atom attached to the secondary amine N when attached to the remainder of the substituent. The primary or secondary amine that is not directly attached to the C Ring may be positioned in the compound in the bound conformation wherein:

a) the distance between the C or N atom of Y and the primary or secondary amine N is about 7 Å to about 10.5 Å;
b) the distance between the C atom to which $R^8$ is attached and the primary or secondary amine N is about 6 Å to about 9 Å;
c) the distance between the C atom to which $R^4$ is attached and the primary or secondary amine N is about 3.5 Å to about 6 Å; and
d) the distance between the C atom to which $R^2$ is attached and the primary or secondary amine N is about 5 Å to about 7.5 Å.

"Not directly attached to the C Ring" with regard to the primary or secondary amine refers to the lack of a bond joining the primary or secondary amine to the C Ring.

In some aspects, $R^4$ may be an optionally substituted tertiary amine that is an optionally substituted 4-14 membered saturated cycloheteroaliphatic tertiary amine ring system containing 1-3N atoms, 0-3 O atoms and 0-1 S atoms; and wherein the 4-14 membered saturated cycloheteroaliphatic ring system is a single ring, a fused ring system, a bridge ring system, or a spiro ring system.

In some aspects, $R^4$ may be the optionally substituted tertiary amine attached to the C ring through the tertiary amine N, wherein the optionally substituted tertiary amine contains at least one additional N separated from the tertiary amine N by 2-3 atoms. The atoms separating the N's need not be located in the same ring. For example, one atom separating the N's may be in a ring and the second atom may be found in a substituent, or both atoms separating the N's may be in the backbone in, or a substituent on, the same or different rings.

In some aspects, the optionally substituted secondary or tertiary amine of $R^4$ is one of the following substituents in Chart 4.

Chart 4

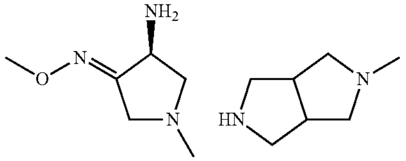
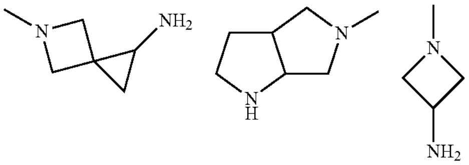
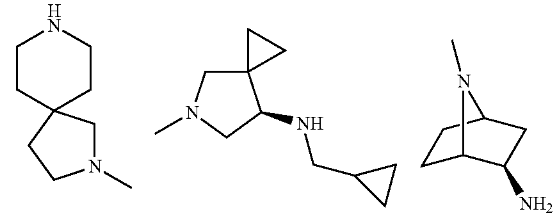
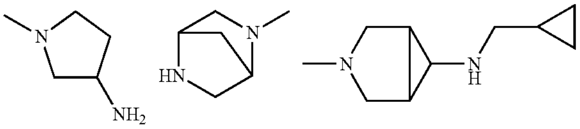
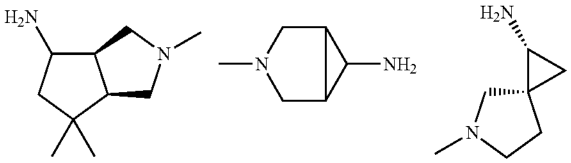
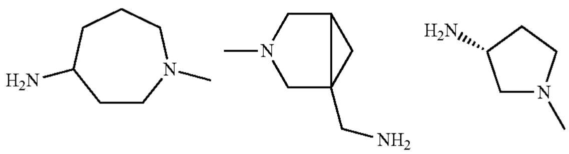
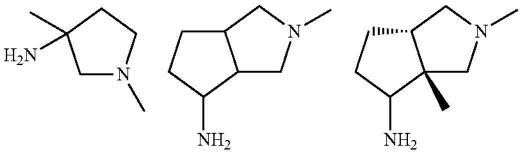
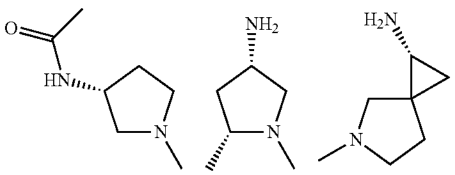

-continued

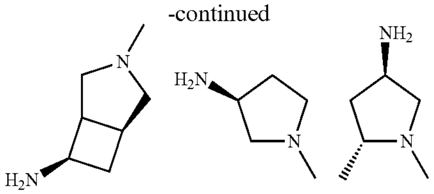
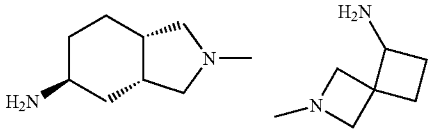
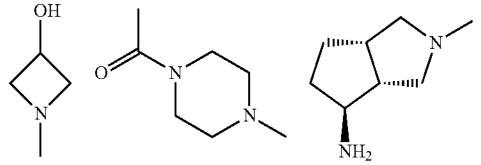
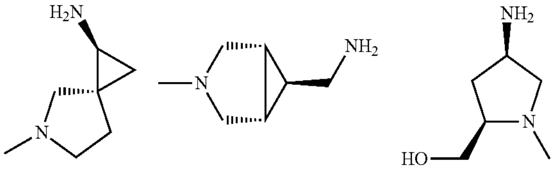
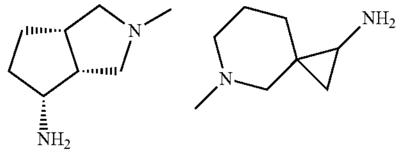
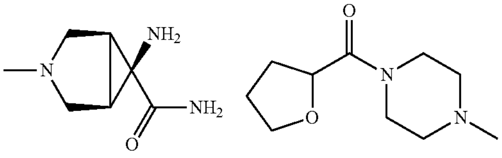
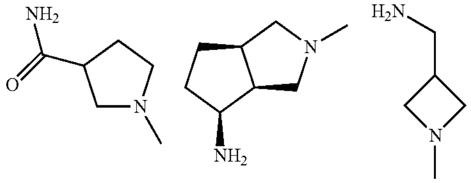
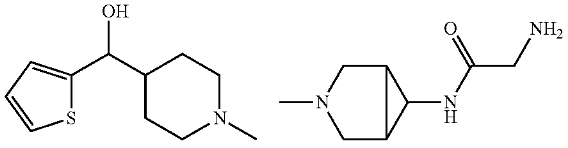
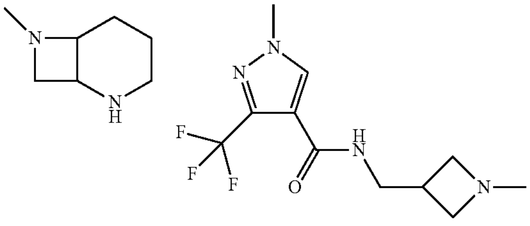
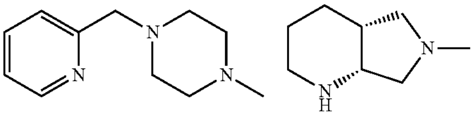
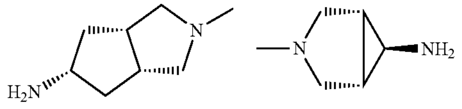

-continued
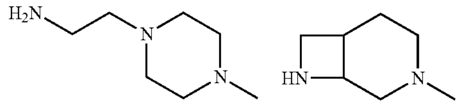
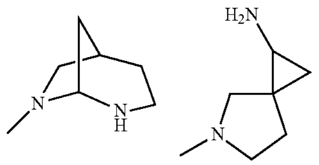
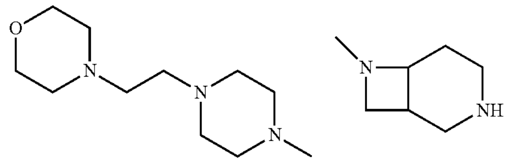
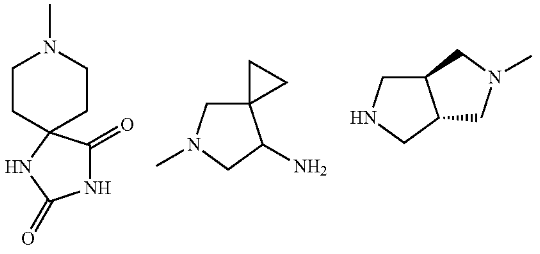
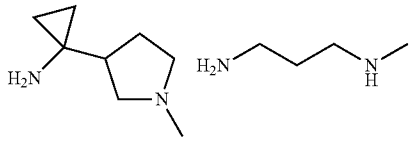
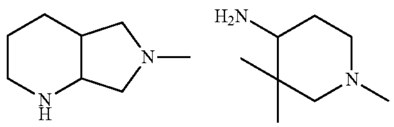
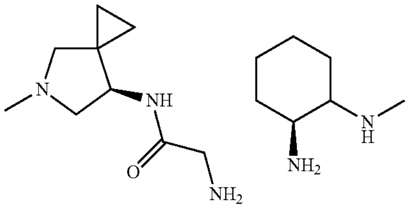
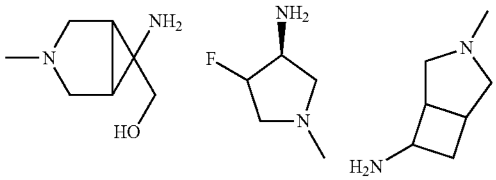
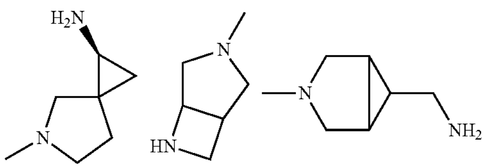
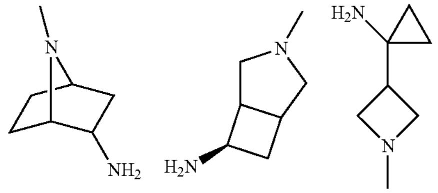
-continued
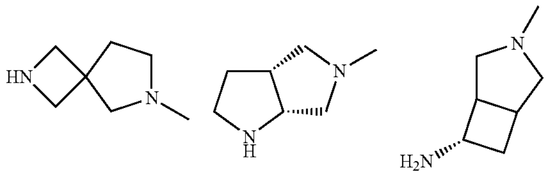
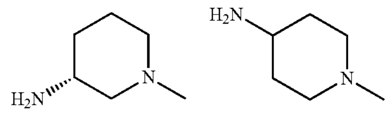
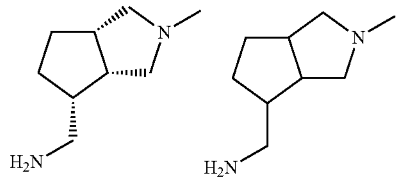
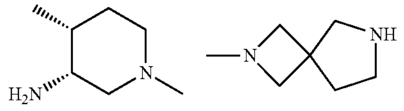
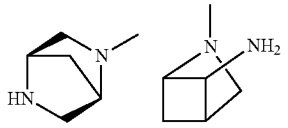
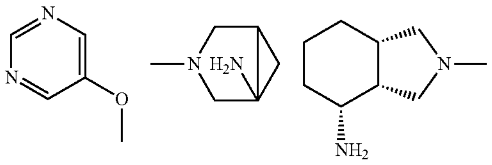
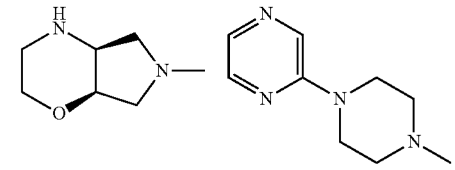
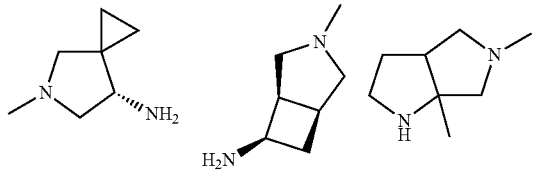
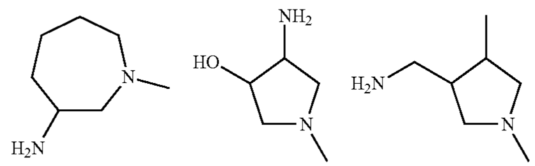
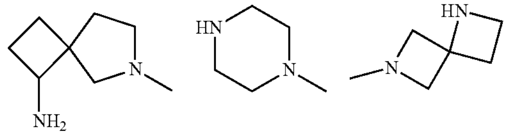
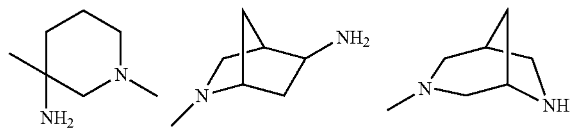

-continued
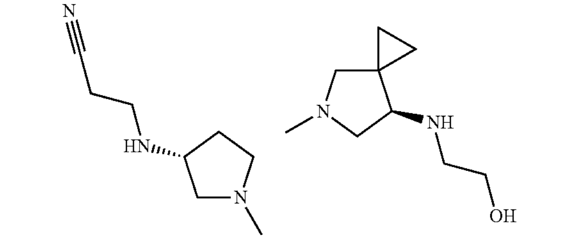
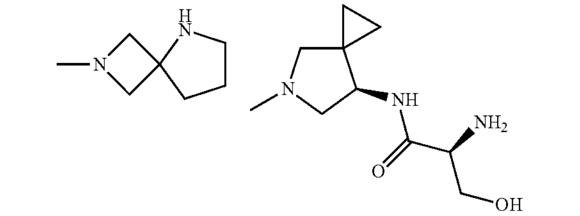
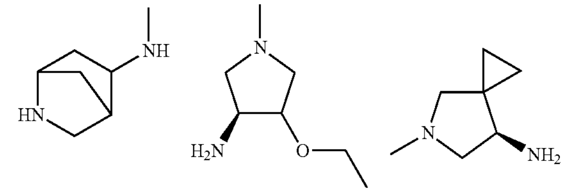
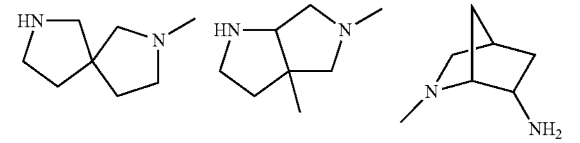
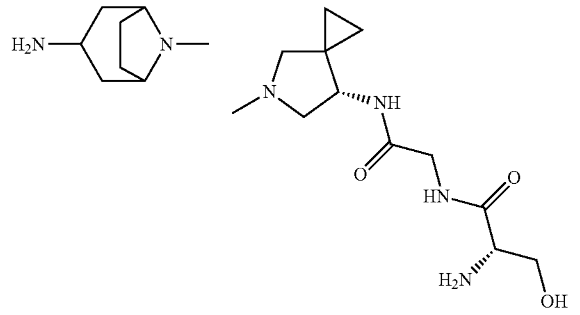
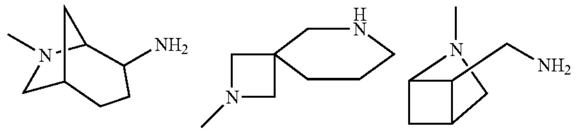
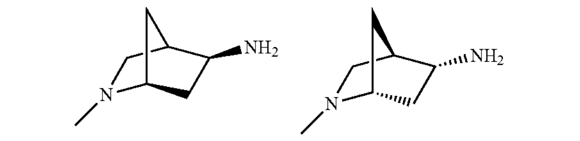
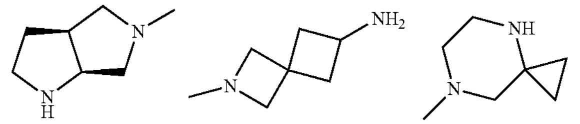
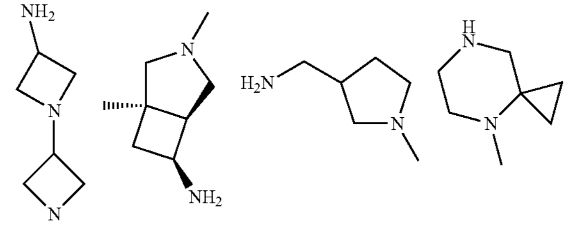
-continued
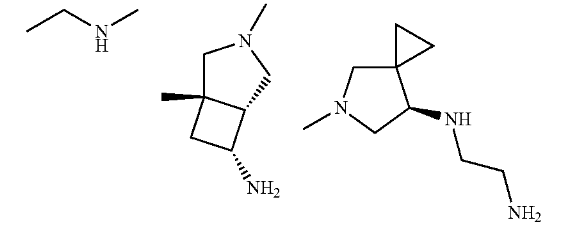
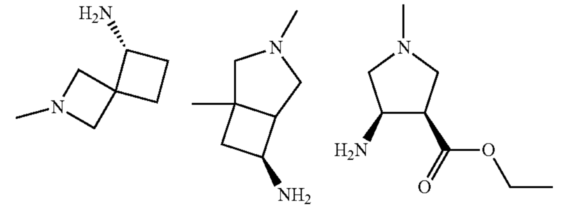
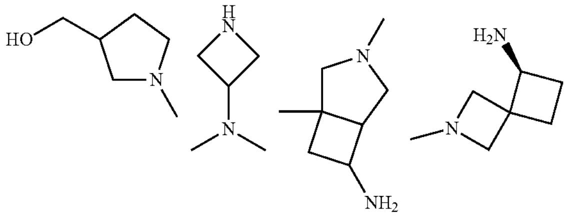
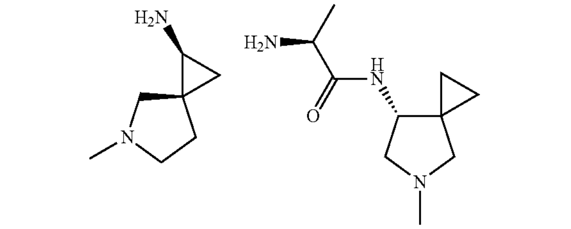
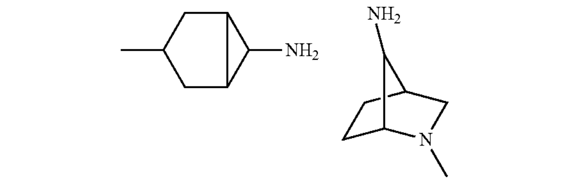
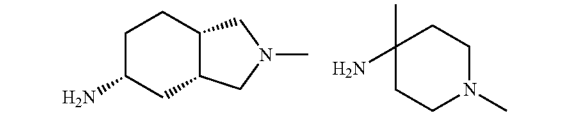
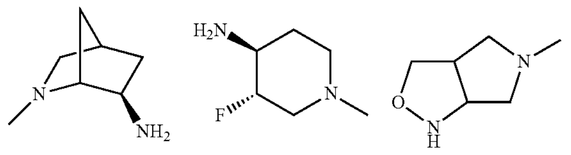
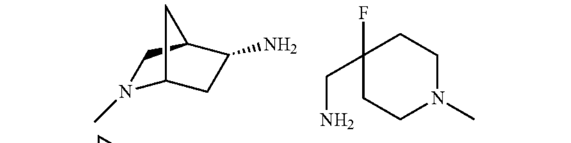
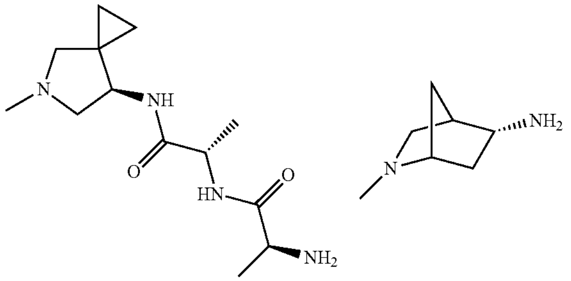

-continued

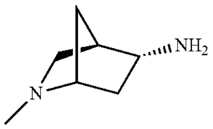
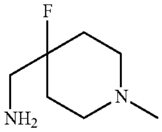
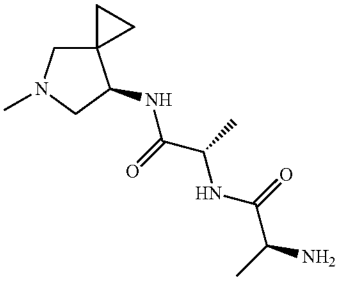
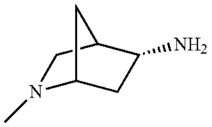
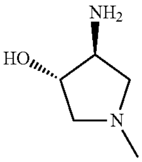
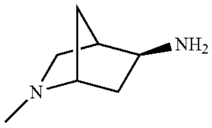
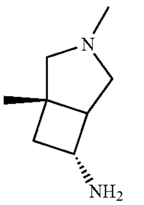
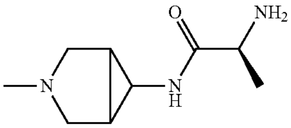
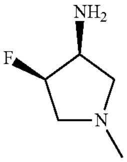
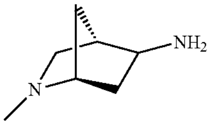
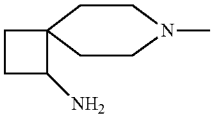
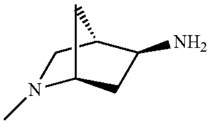
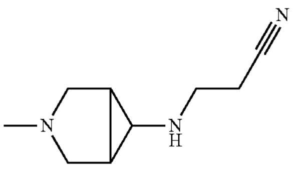

In some aspects, $R^4$ may be a noncyclic secondary or tertiary amine substituted with 1-2 noninterfering substituents.

In some aspects, $R^4$ may be selected from the group consisting of optionally substituted pyrazolyl, phenyl, piperazinyl, pyridinyl, and tetrahydropyridinyl.

In some aspects, $R^4$ may be an optionally substituted 5-10 membered unsaturated cyclic or heterocyclic residue containing 0-3N, O or S heteroatoms. The optional substituents may include 0-2 optional substituents selected from the group consisting of $CH_3$, $NH_2$, F, Cl, and $CH_2NH_2$. In some aspects, the optionally substituted 5-10 membered unsaturated cyclic or heterocyclic residue containing 0-3N, O or S heteroatoms of $R^4$ is one of the following substituents in Chart 5.

Chart 5

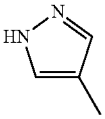
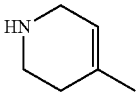
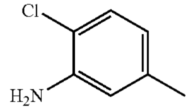

-continued

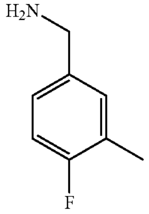
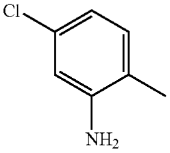
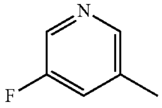
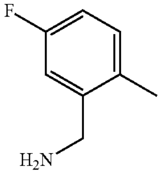
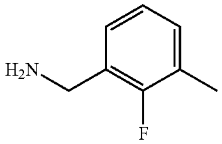
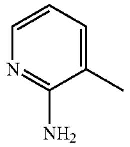
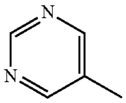
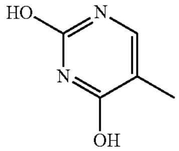

The optional substituent on $R^4$ may include 0-3 noninterfering substituents. A noninterfering substituent on $R^4$ may be a substituent selected from the group consisting of OH, NO, $CO_2H$, CN, $NH_2$, Br, Cl, F, $SO_3H$, and $NO_2$, or is a C1-15 hydrocarbyl residue containing 0-5 O, S, or N heteroatoms, optionally substituted with OH, CN, =O, $NH_2$, =NOH, =$NNH_2$, =$NOCH_3$, Br, F, Cl, $SO_3H$, or $NO_2$. Substitutions may be on a C or a heteroatom thus permitting groups such as S=O. In addition, an OH substituent may be in the form of an oxide, thus for example, permitting a pyridyl having an N-oxide wherein the N is a ring heteroatom. The C1-15 hydrocarbyl residue containing 0-5 O, S, or N heteroatoms may include a combination of hydrocarbyl groups such as a combination of aliphatic rings or chains and aromatic rings linked together.

In some aspects, $R^4$ may be selected from the substituents in the following Chart 6.

Chart 6

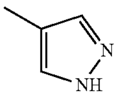
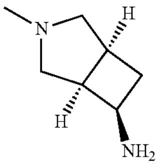
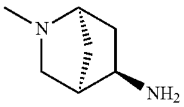
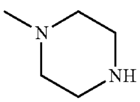
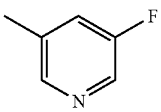
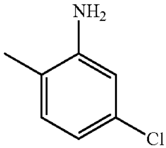
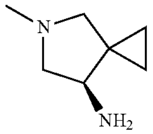
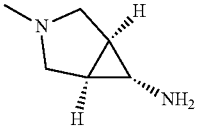
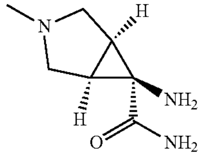
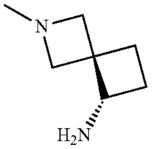
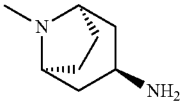
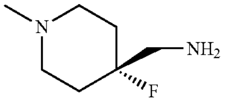

-continued
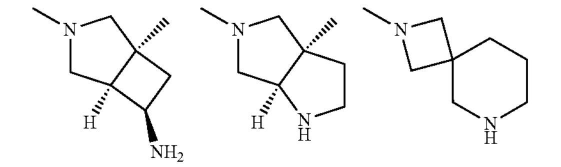
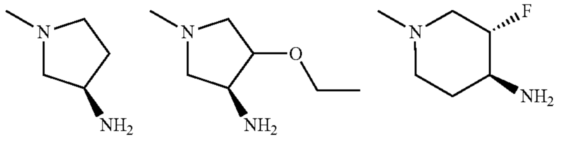
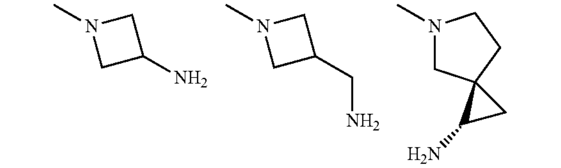
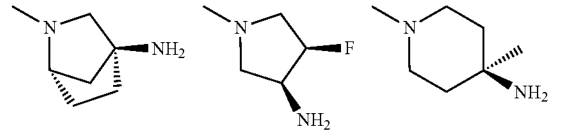
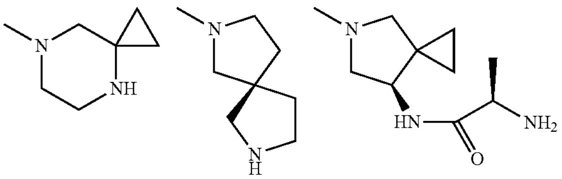
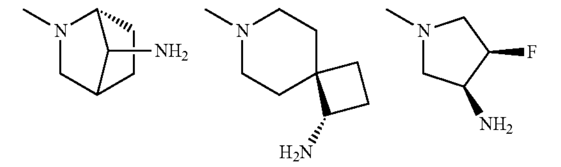
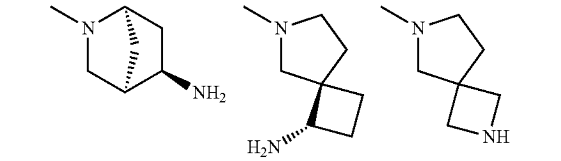
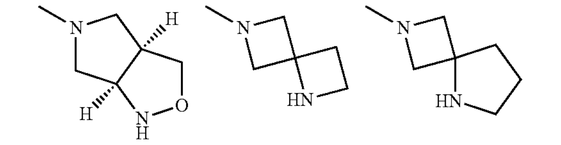
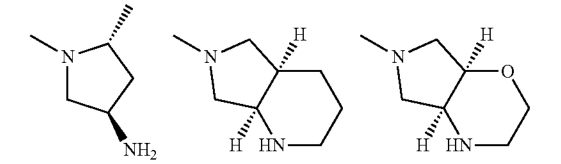
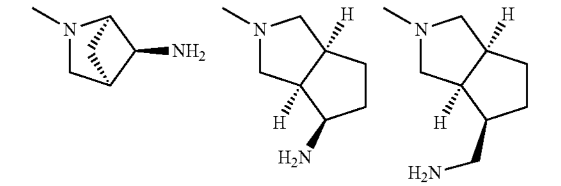
-continued
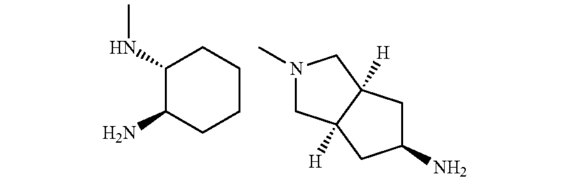
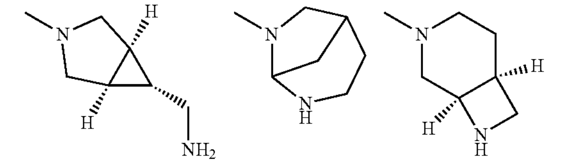
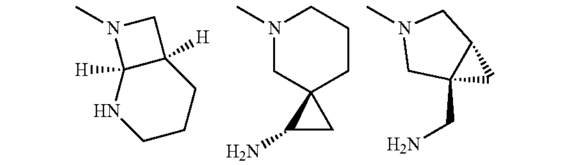
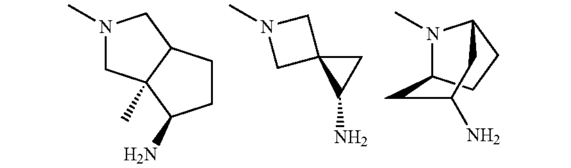
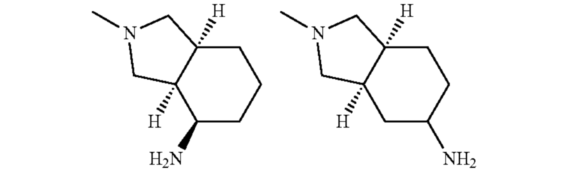
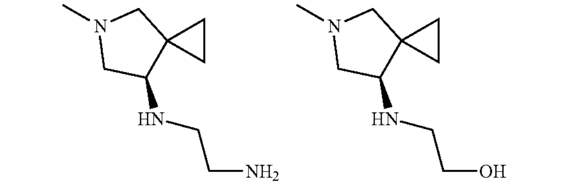
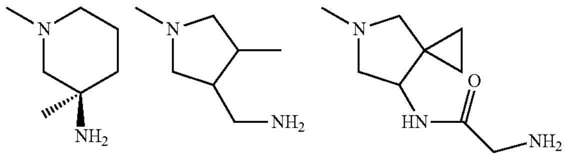
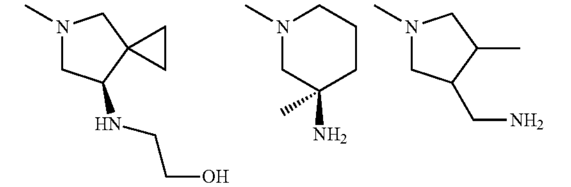
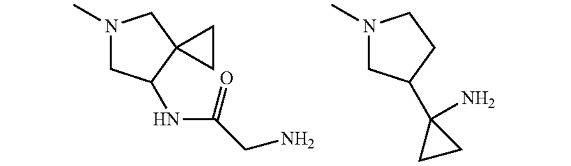
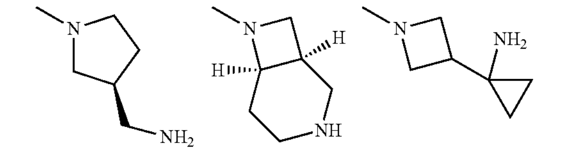

-continued
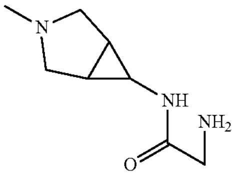
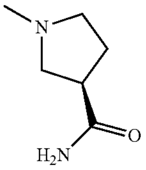
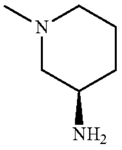
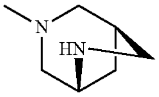
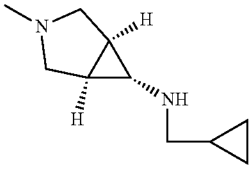
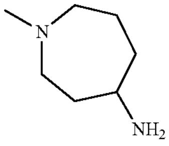
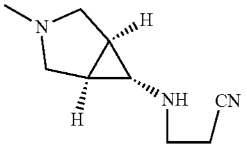
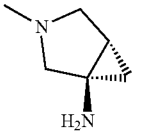
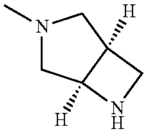
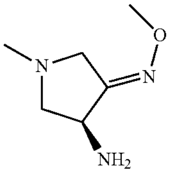
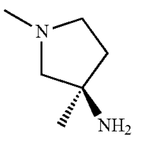
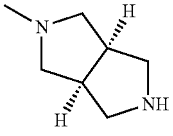
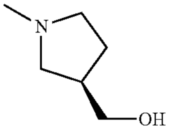
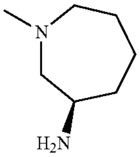
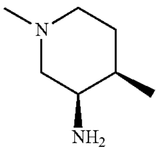
The compound may be one of the compounds exemplified in the Examples.
In some aspects, the compound may be a compound in Chart 7.
Chart 7
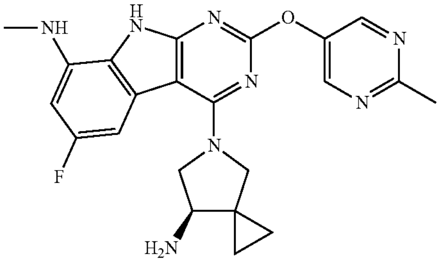
-continued
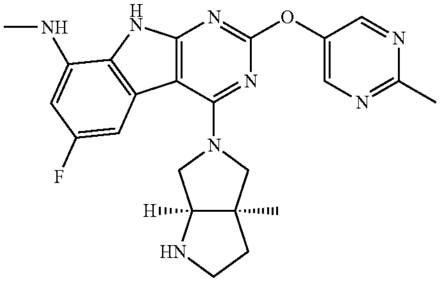
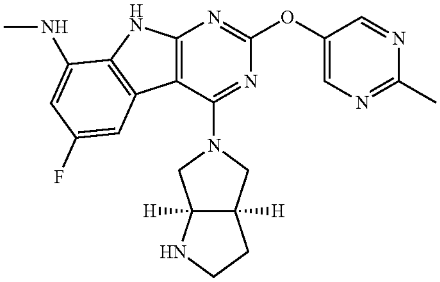
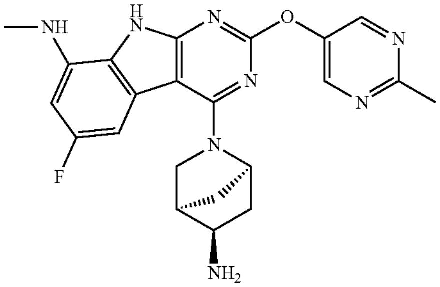
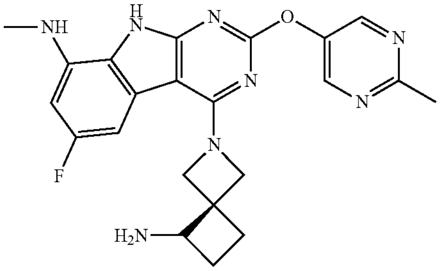
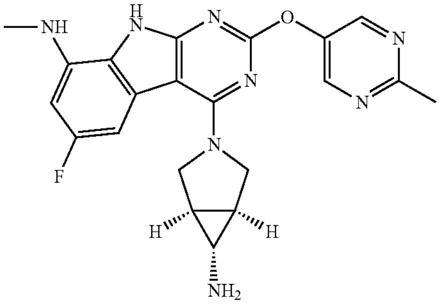
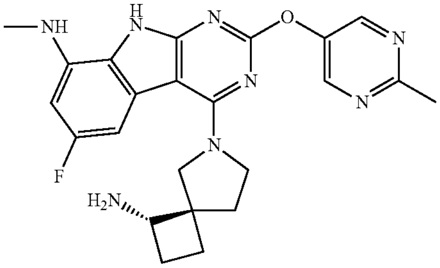

-continued
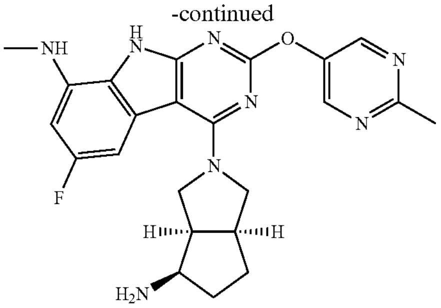
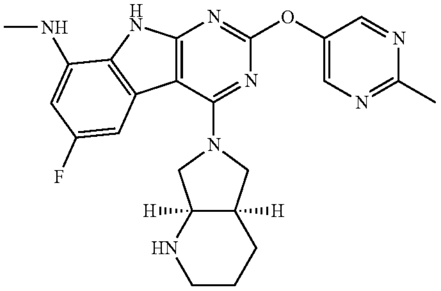
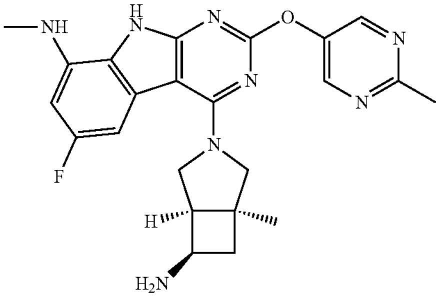
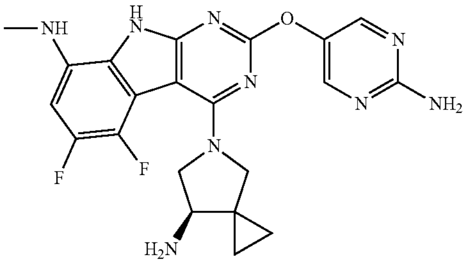
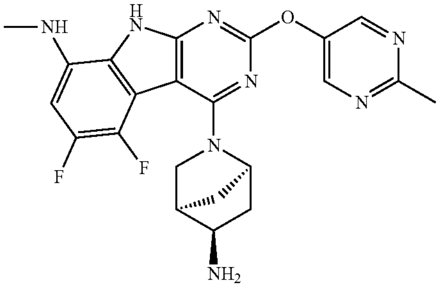
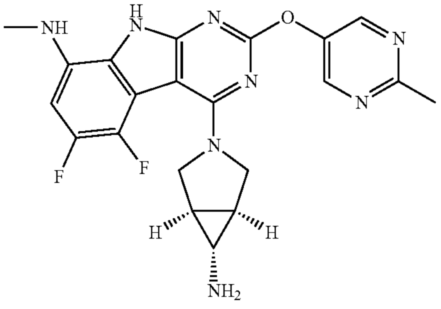
-continued
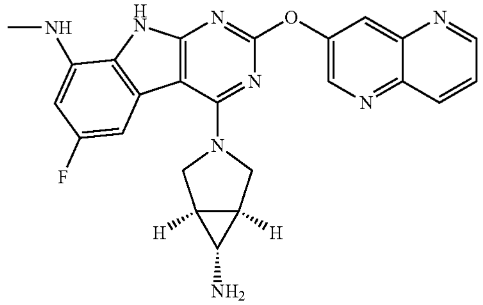
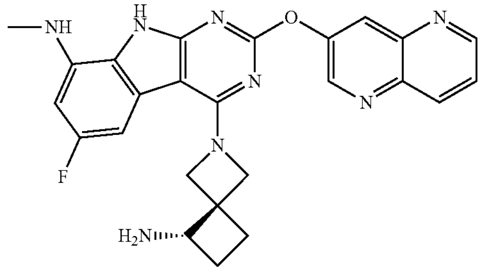
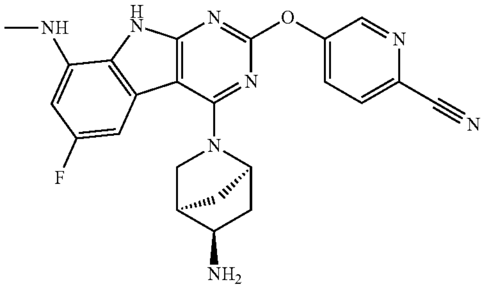
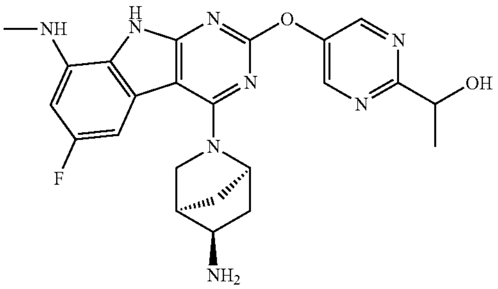
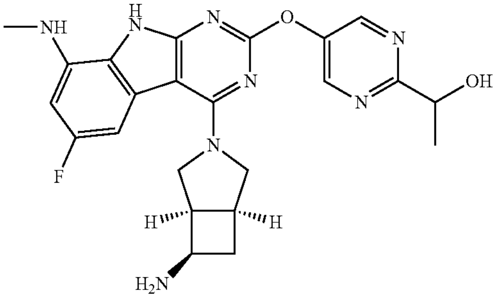 [SMILES: CNc1cc(F)cc2c1[nH]c1nc(Oc3cnc(C(C)O)nc3)nc(N3C[C@@H]4[C@H](N)C[C@]4(C)C3)c12]
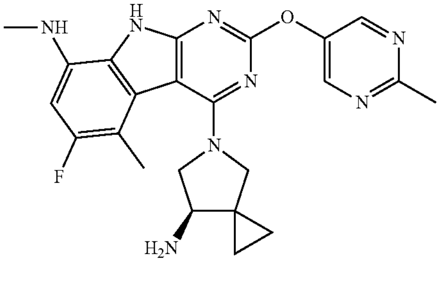

-continued

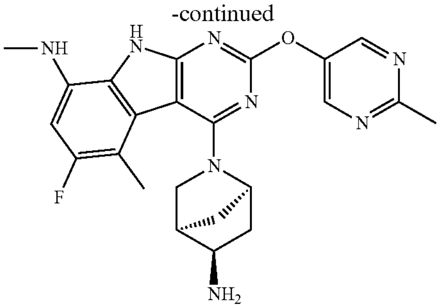

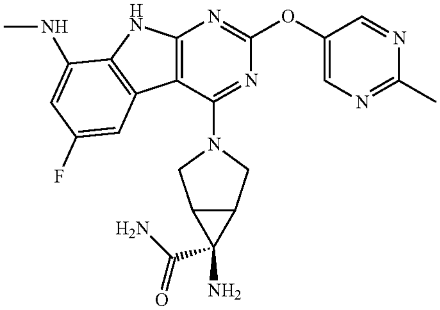

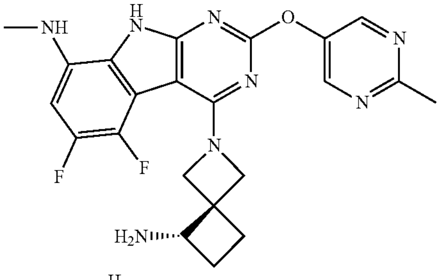

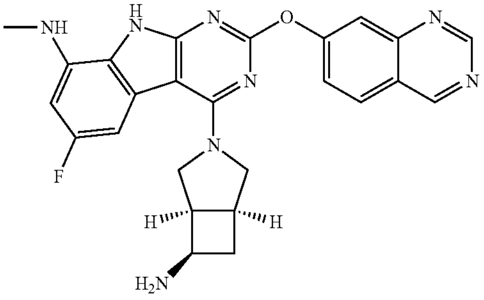

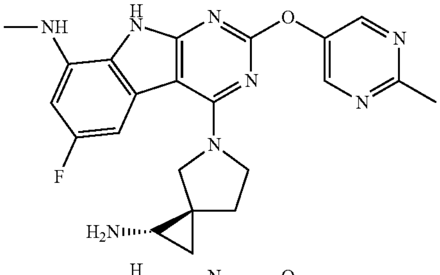

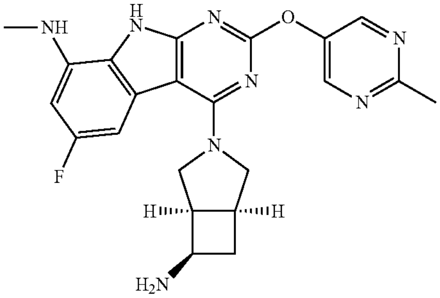

-continued

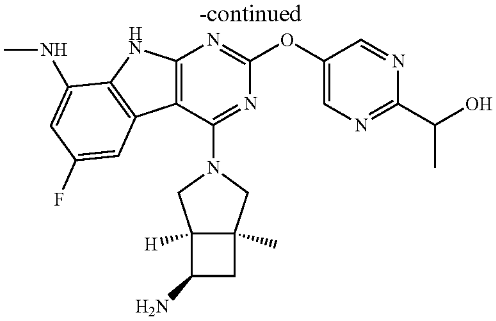

When the compounds of Formula I contain one or more chiral centers, optically pure forms as well as mixtures of stereoisomers or enantiomers are also contemplated.

Various processes of making the compounds are also contemplated. The substituents unless noted are the same substituents as in Formula I. In some aspects wherein $R^4$ is an optionally substituted secondary or tertiary amine attached to the C Ring through the secondary or tertiary amine N, the process comprises treating

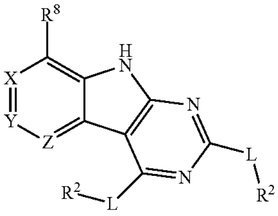

with $HR^4$ to make the compound of Formula I; and optionally further comprising, before the treating step, protecting $R^8$ with a protecting group, or protecting an amine in $R^4$ which is not the secondary or tertiary amine N, if present, with a protecting group; and optionally removing the protecting groups after the treating step.

Protecting groups are useful for chemoselectivity and are known in the art. Typical protecting groups included tert-butyloxycarbonyl (BOC) and carbobenzyloxy (Cbz). When the protecting group is BOC, an acid may be used for deprotection, protecting group is Cbz, catalytic hydrogenation may be used for deprotection.

Before the treating step immediately above, the process may further comprise reacting the compound of Formula II Formula II

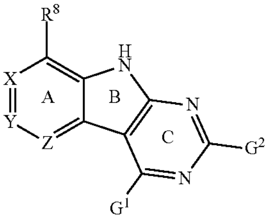

with $R^2LH$ under basic conditions, wherein $G^1$ and $G^2$ are leaving groups independently selected from the group consisting of Cl, Br, F, I, SR, SOR, $SO_2R$, $OSO_2R$, and O-benzotriazole (OBt); wherein R may be C1-8 alkyl, aryl, or heteroaryl containing 0-5 O, S, or N atoms optionally substituted with C1-4 alkyl, C1-4 alkyloxy, Cl, Br, F, I, or $NO_2$, such as methyl, benzyl and p-methoxybenzyl, to make the compound having the structure

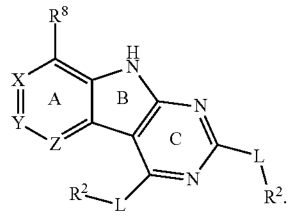

In some aspects, the compounds wherein $R^4$ is an optionally substituted secondary or tertiary amine attached to the C Ring through the secondary or tertiary amine N, may also be made using a process comprising treating

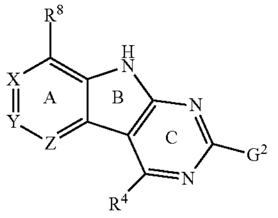

with $R^2LH$ under basic conditions such as with the anion of phenol, thiophenol, heteroarylhydroxy or heteroarylthiol, wherein $G^2$ is a leaving group selected from the group consisting of Cl, Br, F, and I; and optionally further comprising, before the treating step immediately above, protecting $R^8$ with a protecting group, or protecting an amine in $R^4$ which is not the secondary or tertiary amine N, if present, with a protecting group; and deprotecting $R^8$ and $R^4$ after the treating step.

Before the treating step immediately above, the process may further comprise reacting the compound of Formula II Formula II

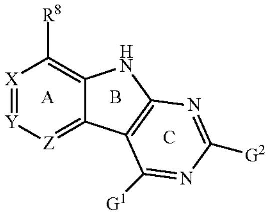

with $HR^4$ to make

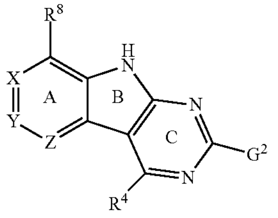

wherein $G^1$ is a leaving group selected from the group consisting of Cl, Br, F, and I.

In some aspects, when L is S, a process of making the compound wherein $R^4$ is an optionally substituted secondary or tertiary amine attached to the C Ring through the secondary or tertiary amine N, may comprise treating

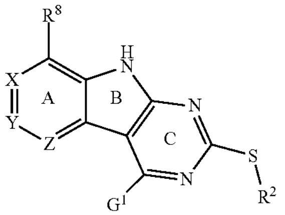

wherein $G^1$ is a leaving group derived from $SO_2$halide, bis(2-oxo-3-oxazolidinyl)phosphine (BOP), or benzotriazol-1-yl-oxytripyrrolidinophosphonium hexafluorophosphate (pyBOP), with $HR^4$ to make the compounds herein. This process may also optionally further comprise, before the treating step immediately above, protecting $R^8$ with a protecting group, or protecting an amine in $R^4$ which is not the secondary or tertiary amine N, if present, with a protecting group; and deprotecting $R^8$ and $R^4$ after the treating step.

Before the treating step immediately above, the process may further comprise reacting

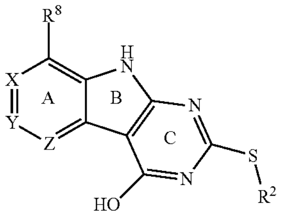

with $G^1X^1$ to provide

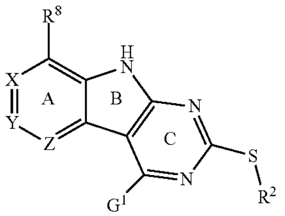

wherein $G^1X^1$ is $SO_2$halide, bis(2-oxo-3-oxazolidinyl)phosphine (BOP), or benzotriazol-1-yl-oxytripyrrolidinophosphonium hexafluorophosphate (pyBOP).

Before the treating step immediately above, the process may further comprise coupling

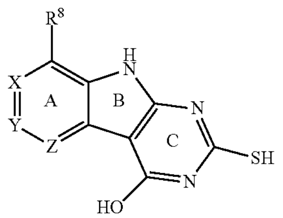

with $R^2X^2$ wherein $X^2$ is Br or I to form

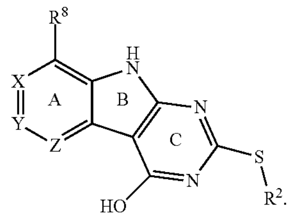

In another aspect, an intermediate compound has the structure of Formula II:

Formula II

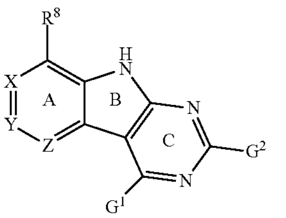

or an amine-protected intermediate thereof; wherein: $G^1$ and $G^2$ are leaving groups independently selected from the group consisting of SH, OH, Cl, Br, F, I, SR, SOR, $SO_2R$, $OSO_2R$, OAr, and OBt; R is C1-8 alkyl, aryl, or heteroaryl; Ar is aryl or heteroaryl containing 0-5 O, S, or N atoms optionally substituted with C1-4 alkyl, C1-4 alkoxy, halo or $NO_2$; Bt is benzotriazole; $R^8$ is an interacting substituent having a length of about 1 Å to about 5 Å from the carbon attachment point on the A Ring to the terminal atom in $R^8$ and a width of about 3.3 Å or less; and X, Y and Z are independently selected from the group consisting of N, $CR^X$, $CR^Y$, and $CR^Z$ respectively, provided that no more than two of X, Y and Z are N, wherein $R^X$ is H or an interacting substituent having a length of about 1 Å to about 2 Å from the carbon in $CR^X$ to the terminal atom in $R^X$; wherein $R^Y$ is H or an interacting substituent having a length of about 1 Å to about 3 Å from the carbon in $CR^Y$ to the terminal atom in $R^Y$; wherein $R^Z$ is H or an interacting substituent having a length of about 1 Å to about 2 Å from the carbon in $CR^Z$ to the terminal atom in $R^Z$; with a proviso wherein $R^8$ is not $CH_3$, and with a proviso when $R^8$ is $OCH_3$, then $R^X$ and $R^Y$ are not OH.

When the intermediate compound is an amine-protected intermediate, one or more nitrogens in the compound may be protected with carbobenzyloxy (Cbz) or BOC. $G^1$ and $G^2$ may be leaving groups independently selected from the group consisting tosylate, mesylate, trifilate, O-pyrimidine, O-phenyl and O-pyridine.

The following schemes outline aspects of reaction steps to make the starting materials, intermediates and compounds herein, which are detailed in the Examples. The starting materials for the $R^2$ and $R^4$ substituents are available commercially or can be made by a skilled artisan using methods reported in the literature.

1. General Procedures for the Preparation of the Tricyclic pymirido[4,5-b]indole Core A wide variety of amines and substituted amines can be introduced into the A Ring of the pyrimidoindole system as shown in Scheme 1. Ortho-fluoro-nitrobenzenes S1 can be readily displaced by amines to yield the orthoamino analogs S2. A protecting group can be introduced by incorporation in the starting material (as in S 3b) or introduced after the fluoroaryl displacement reaction (as in S 3c). With an alkyl or alkoxy $R^8$ group, nitration may be used to introduce the nitro group ortho to the $R^8$ group S3d. When the nitration reaction provides mixtures of regioisomers, chromatography may be used to isolate the desired isomer.

Scheme 1: general procedure for preparing substituted phenyl starting materials

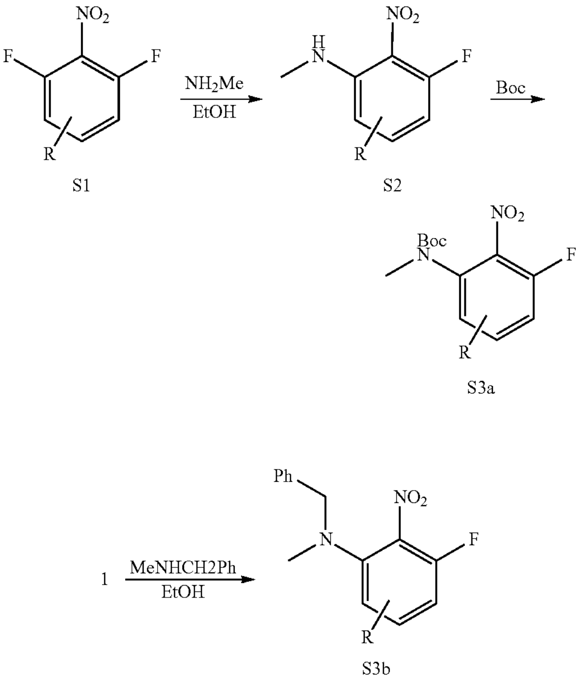

R = H, F, Cl, Me, $CF_3$

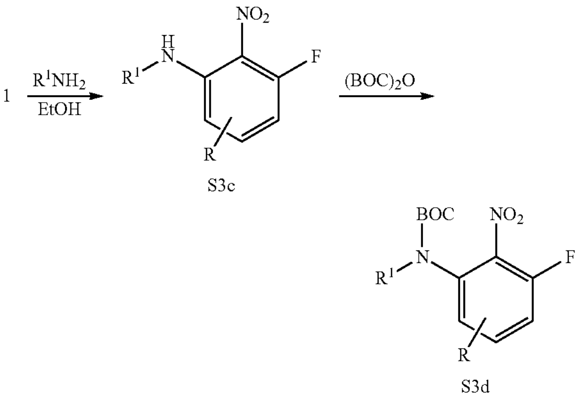

R = H, F, Cl, Me, $CF_3$
$R^1$ = H, Me, Et, Cyclopropyl

Scheme 2 outlines the general methods for preparing a wide variety of pyridine and pyrimidine starting materials. Nitration of 4,6-dihydroxypyrimidine followed by conversion of the hydroxyl groups to a chloro group with $POCl_3$ affords intermediate S4c. The chloro is readily displaced by amines and alcohols to provide the desired intermediate S3e. In a similar fashion, commercially available pyridine S4d is readily substituted with amines and alcohols to form intermediate S3f.

Scheme 2: general procedure for preparing substituted pyrimidine and pyridine starting materials

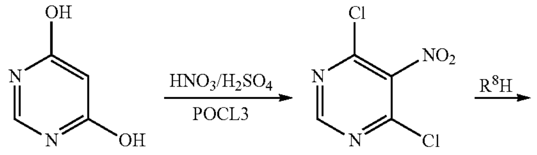

S4b

S4c

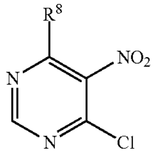

S3e

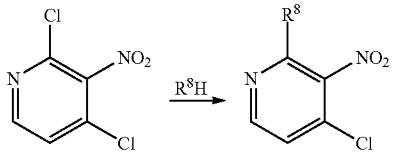

S4d

S3f $R^8$ = $NH_2$, NHR, OR

The orthofluoro-nitroaromatics S3 are converted (Scheme 2) to indoles, and nitrogen substituted indoles S6a and S6b (pyrrolopyrimidines and pyrrolopyridines) by treatment with cyano ethyl acetate or cyanomalonate followed by reduction with zinc in acetic acid alternatively the nitro group can be reduced with many alternative reduction agents such as sodium bisulfite.

Scheme 3: Formation of indole intermediates

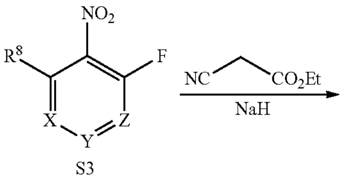

S3

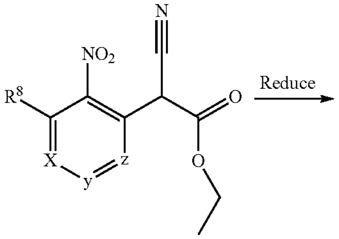

S5a

-continued

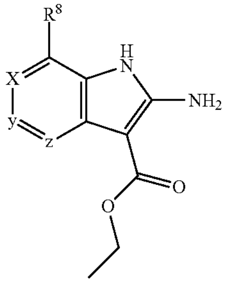

S6a

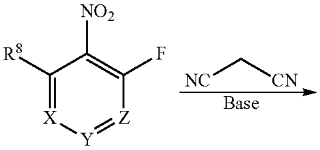

S3

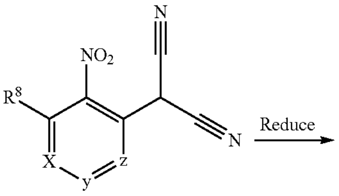

S5b

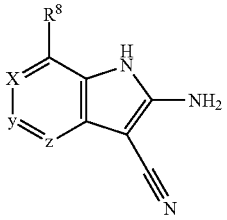

S6b

The indole intermediates are converted to tricyclic intermediates as shown in Scheme 4. Reaction of an amino ester indole S6a with an acylisothiocynate followed by treatment with base provides the tricycle S8a with an SH at the 2 position and an OH in the 4 position. Alternatively, treatment with an acylisocynate followed by base provides S8b with an OH substituent at both the 2 and 4 positions of the tricycle. These are versatile intermediates as S8a can be converted to a bis-sulfone by first alkylation at the 2-position sulfur, followed by activation of the 4-position with a reagent such as BOP or mesyl chloride followed by displacement with a sulfide then oxidation to the bis-sulfone S8f with a reagent such as sulfone.

Scheme 4. Preparation of Key Tricyclic Intermediates

Alternatively, the dihydroxy core S8b can be converted to the dichloro-tricycle S8g. Amino nitrile indole intermediates S6b may be converted to the bissulfone by treatment with carbon disulfide and an alkoide to provide the anion of the 2,4 dithiol tricylcle. This intermediate can be alkylated in situ and then oxidized to provide the bissulfone S8f.

Scheme 4. Preparation of key tricyclic intermediates (cont.)
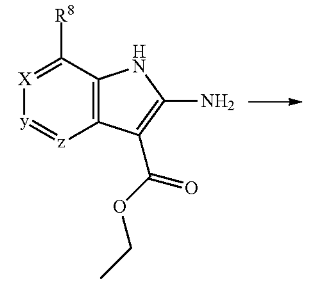
S6a
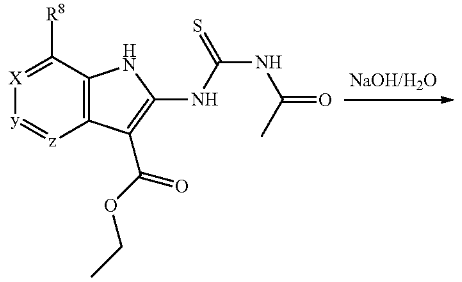
S7a
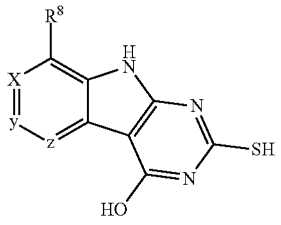
S8a
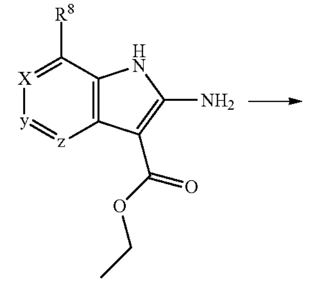
S6a
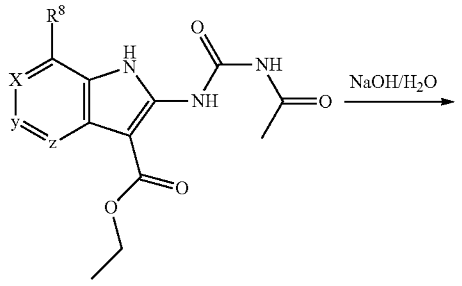
S7b
-continued
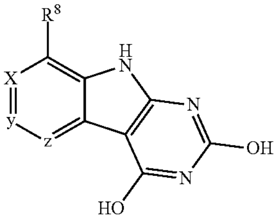
S8b
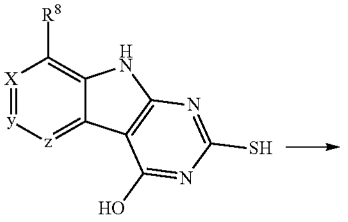
S8a
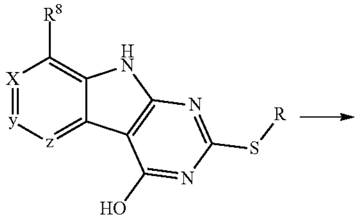
S8c
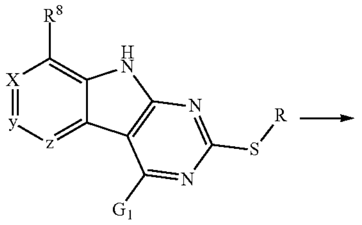
S8d
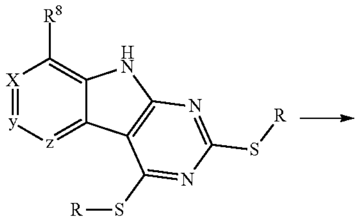
S8e
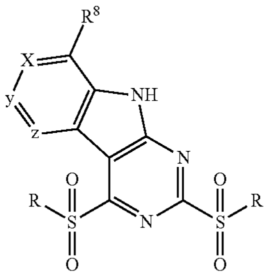
S8f
2. General Procedures for Conversion of Tricyclic Cores to Formula I Compounds
There are multiple methods for converting key tricyclic intermediates to Formula I compounds.

In Scheme 5, either intermediate S8f or S8g may be converted to the bis-aryloxy compound 9. The Aryloxy group in the 4 position can be displaced by amines or alcohols to provide the desired Formula I compound when $R^4$ is either an amine of an alkoxide. In some cases it is desirable to use protection groups on the S8 intermediates and/or the $R^4$ group. In those cases, an additional step may be required to remove the protecting group.

Scheme 5:

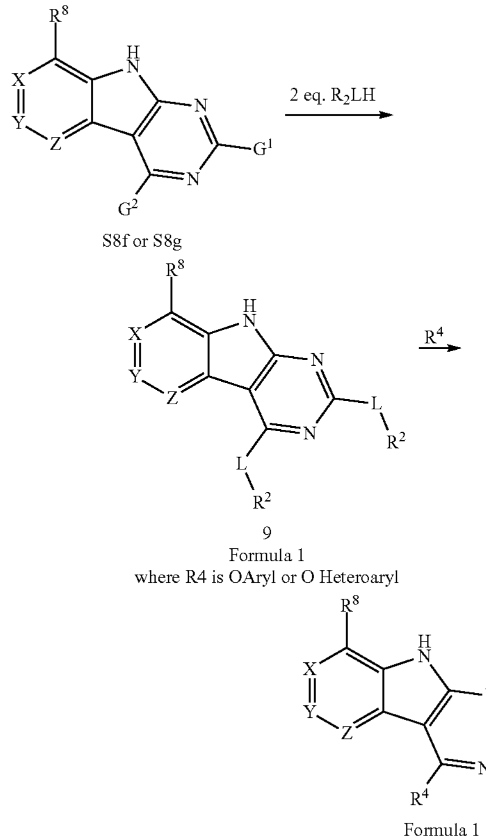

S8f or S8g

9

Formula 1 where R4 is OAryl or O Heteroaryl

Formula 1 where R4 is an amine

As an alternative method, the dichloro tricyclic intermediate S8g may be treated with the $R^4$ group first, then followed by displacement of at the 2 position with an alkoxide of $R^2OH$ (Scheme 6). Typically this method requires protecting groups especially when a diamine is used as the $R^4$ group. In these cases, removal of the protecting groups provides Formula I compound. This method is particularly useful when a costly $R^2OH$ group is used or the $R^2$ group is electron rich.

Scheme 6:

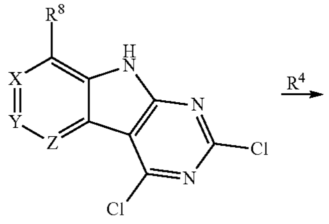

S8g

-continued

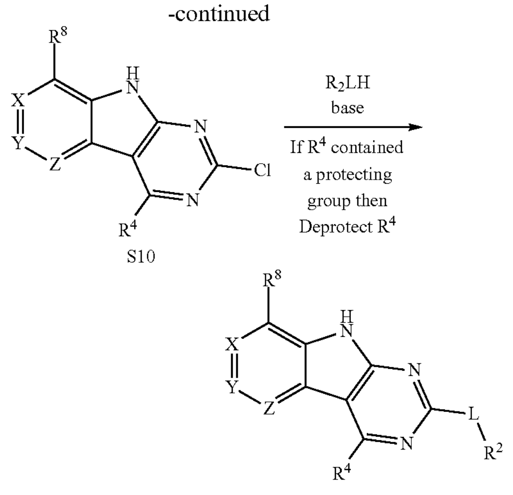

S10

Formula 1

In cases where L is S, the Formula I compounds can be prepared directly from S8a by the method in Scheme 7. In this method the sulfide is coupled to an aryl halide (preferably an iodo or bromo aromatic). Activation of the 4 position hydroxyl group by reagents such as a sulfonylhalide or a coupling reagent such as BOP followed by displacement with an amine provides the desired Formula I compound.

Scheme 7

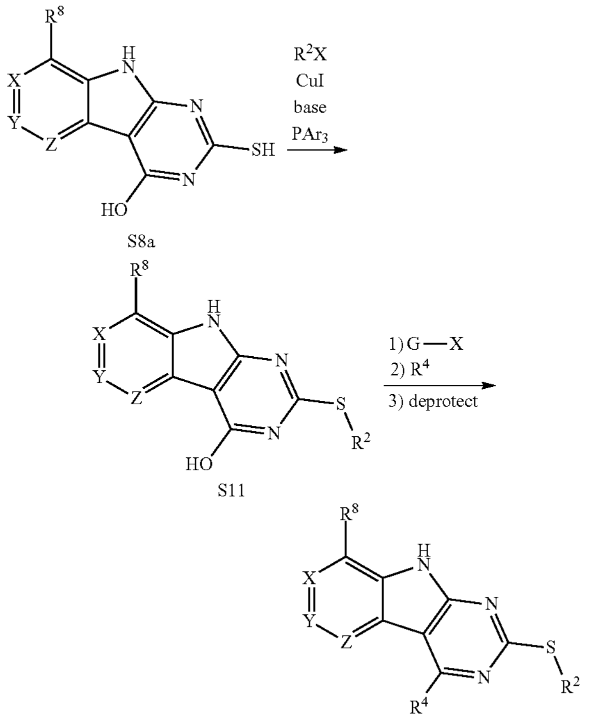

S8a

S11

Formula 1 where $R^4$ is an amine

Formula I compounds where $R^4$ is an aryl or heteroaryl may be made as shown in Scheme 8. In this case, the dichloro intermediate S8g is coupled to a boronic acid using Suzuki coupling conditions. The resulting product is then treated with an alkoxide to provide the Formula I compound.

Scheme 8:

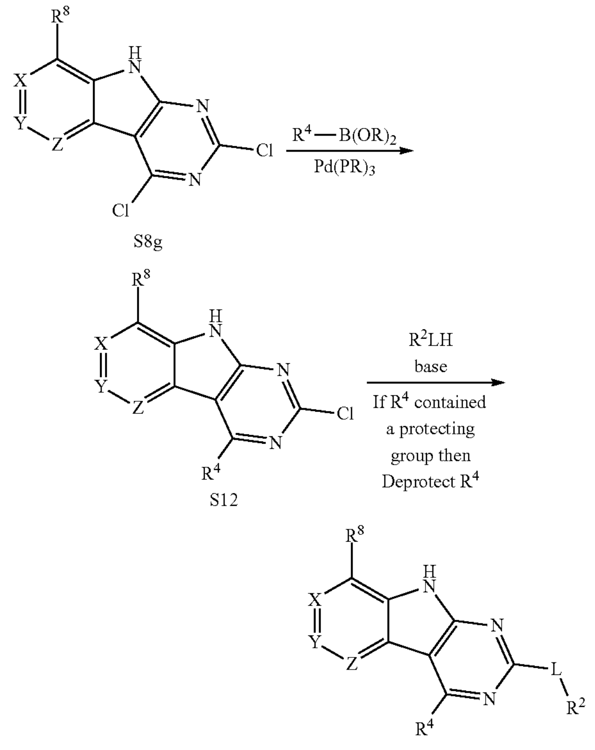

S8g

S12

Formula 1
where R4 is aryl or
heteroaryl

Prodrugs may also be prepared from the compounds of Formula I or II. The term "prodrug," as used herein, represents compounds which can be transformed in vivo to the active parent compounds defined herein.

Examples of prodrugs for example on $R^4$ include NHN-$HCH_3$,

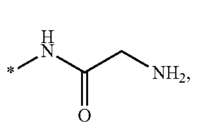, 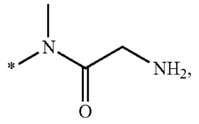,

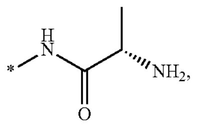, 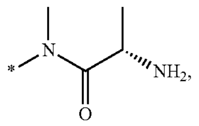,

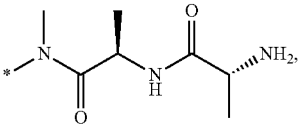,

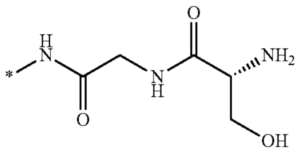 or

-continued

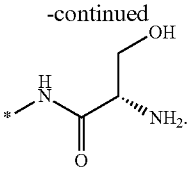.

A pharmaceutically-acceptable salt, ester, or prodrug of the compounds herein is also contemplated. Those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}C$ for carbon, $^{15}N$ for nitrogen, or $^{32}P$ for phosphorus) known as "isotopomers" can also be readily produced. All such derivatives are contemplated within the scope of this disclosure.

Many of the compounds here are disclosed as hydrochloride or other salts, but those skilled in medicinal chemistry will appreciate that the choice of salt is not critical, and other pharmaceutically-acceptable salts can be prepared by well-known methods. Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499 discuss such salts in detail.

Compounds herein include those structures that are set out throughout the examples, and pharmaceutically acceptable salts, esters and prodrugs thereof. In some embodiments, the compound is in a pharmaceutical composition or a dosage form, wherein the pharmaceutical composition or dosage form provides an effective antibiotic amount of the compound for treating or preventing infection.

In another aspect, the present disclosure relates to a pharmaceutical composition comprising one or more physiologically acceptable surface active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds described herein can be administered to a human patient per se, or in pharmaceutical compositions where they are mixed with other active ingredient(s), as in combination therapy, or suitable carriers or excipient(s). In some embodiments, a dosage form includes those forms in which the compound is admistered per se. In addition, a dosage form may include a pharmaceutical composition. In any case, the dosage form may comprise a sufficient amount of the dimer compound to treat a bacterial infection as part of a particular administration protocol, as would be understood by those of skill in the art. Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest with pharmaceutically acceptable carriers well known in the art. Such carriers, which may be used in addition to the cationic polymeric carrier, enable the compositions to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner. Administration to the buccal mucosa and sublingually are contemplated.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Methods for treating bacterial infections may include administering a therapeutically effective amount of the therapeutic compounds as described herein. Treating a bacterial infection may also include prophylactically administering the therapeutic compounds to prevent infection or the spread of an infection in a subject at imminent risk of infection, such as a subject receiving or about to undergo surgery, an immunocompromised subject, or subject otherwise at risk of an infection if the compound was not administered. The compounds show inhibitory activity against a broad spectrum of bacteria including *H. influenzae, E. coli, S. aureus, E. faecalis, E. facium, K pneumonia, A. baumannii, S. pneumoniae*, and *P. aeruginosa*. The compounds show activity against most resistant strains for example methicillin resistant *Staphylococcus aureus* (MRSA). In addition, the compounds show broad-spectrum activity against all Category A, B, and C bacterial biodefense pathogens including *B. anthracis, B. pseudomallei, B. mallei, F. tularensis* and *Y. psetis*. See the Examples. The compounds have excellent relative antibiotic activity with a relatively low concentration. Further, the compounds may exert potent antibacterial activity versus various human and animal pathogens, including Gram-positive and Gram-negative bacteria. In an embodiment, the bacterial infection that may be treated or ameliorated is MRSA.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a bacterial infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

In some embodiments, in the pharmaceutical industry, it standard practice to provide substantially pure material when formulating pharmaceutical compositions. Therefore, in some embodiments, "substantially pure" refers to the amount of purity required for formulating pharmaceuticals, which may include, for example, a small amount of other material that will not affects the suitability for pharmaceutical use. In some embodiments, the substantially pure compound contains at least about 96% of the compound by weight, such as at least about 97%, 98%, 99%, or 100% of the compound.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

EXPERIMENTAL SECTION

Section A:

Synthesis of Unique $R^2$ Pieces

All of the non-commercially available 2-substituted pyrimidinols were prepared in accordance with the procedures described in U.S. Pat. No. 5,162,529 or the published paper Tetrahedron, 65(4), 757-764; 2009.

Examples

General Scheme :

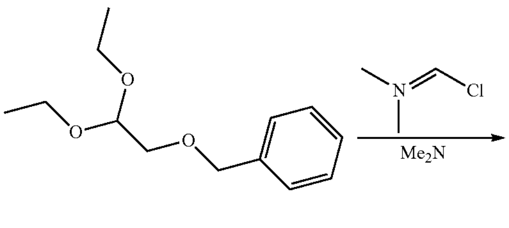

-continued

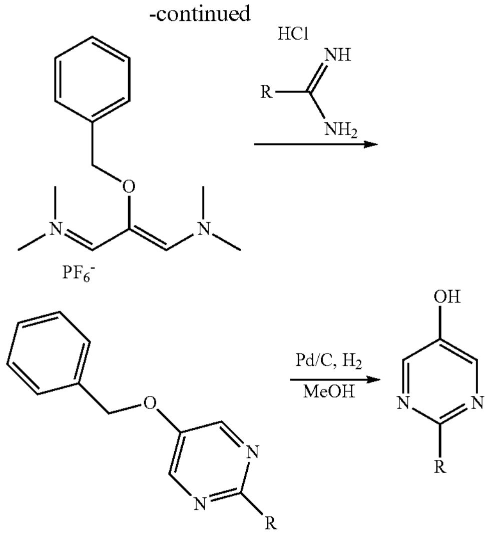

R = Cyclopropyl, Isobutyl, $CH_2OH$, $CHOHCH_3$, $C(CH_3)_2OH$, $CH_2F$, $CHF_2$, $CHF_3$

Experimental

Scheme 1:

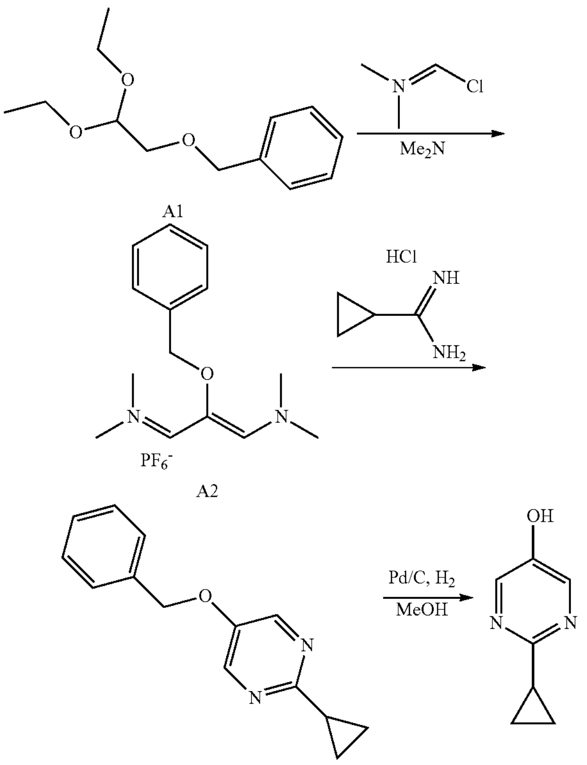

A1, A2, A3, A4

Preparation of Compound A2:

Phosphorus oxychloride (96 g, 0.62 mol) was added to anhydrous DMF (46 g, 0.62 mol) at 0° C. and the mixture was stirred at room temperature for 1 h. Then $CHCl_3$ (500 mL) was added and benzyloxyacetaldehyde diethyl acetate (40 g, 0.18 mol) was added dropwise. Once completed, the reaction mixture was heated at reflux for 2.5 h then allowed to cool to room temperature. The orange solution was slowly poured into cold water (500 mL) at 0° C., and the biphasic mixture was stirred for 15 min. The organic phase was washed with water (500 mL). The combined aqueous layers were added dropwise to a solution of dimethylamine hydrochloride (59 g, 0.72 mol) in water (200 mL). The pH was adjusted to 8.5 by addition of a 5N sodium hydroxide aqueous solution while keeping the temperature around 15° C. The solution was stirred for 1 h and sodium hexafluorophosphate (40 g, 0.23 mol) in water (100 mL) was added. The resulting precipitate was collected by filtration, washed with water, and dried under high vacuum to give compound 2 (22 g, yield: 30%) as a pale beige solid, which was used in the next step without any further purification.

$^1$H NMR (400 MHz, DMSO-$d_6$): δ: 7.42-7.39 (m, 5H), 4.74 (s, 2H), 3.32 (s, 3H), 3.21 (s, 3H).

Preparation of Compound A3:

To a stirred suspension of compound A2 (14 g, 39 mmol) and cyclopropanecarboximidamide hydrochloride (5.65 g, 47 mmol) in $CH_3CN$ (100 mL) was added potassium carbonate (16.2 g, 117 mmol). The reaction mixture was heated at 90° C. for 12 h, then cooled to room temperature, poured into ice water, extracted with ethyl acetate (2×50 mL). The organic layer was dried over $Na_2SO_4$, filtered and concentrated to afford the compound A3 (2.5 g, yield: 26%) as yellow solid.

$^1$H NMR (400 MHz, $CDCl_3$): δ: 8.44 (s, 2H), 7.46-7.28 (m, 5H), 5.24 (s, 2H), 2.18-2.12 (m, 1H), 0.99-0.90 (m, 2H), 0.89-0.86 (m, 2H).

Preparation of Compound A4:

A solution of compound A3 (3.50 g, 15.8 mmol) in MeOH (30 mL) was added palladium on charcoal 10% (350 mg) and the mixture was stirred under hydrogen atmosphere for 4 h. The solid was filtered off and the filtrate was concentrated to get compound A4 (2.0 g, yield: 98%).

$^1$H NMR (300 MHz, DMSO-$d_6$): δ: 10.05 (s, 1H), 8.17 (s, 2H), 2.12-2.05 (m, 1H), 0.93-0.91 (m, 2H), 0.86-0.83 (m, 2H). LCMS [mobile phase: 2-60% Acetonitrile-0.05% TFA in 6 min, finally under these conditions for 0.5 min.] purity is >95%, Rt=2.564 min; MS Calcd.: 136.1; MS Found: 137.1 ([M+1]$^+$)

Scheme 2:

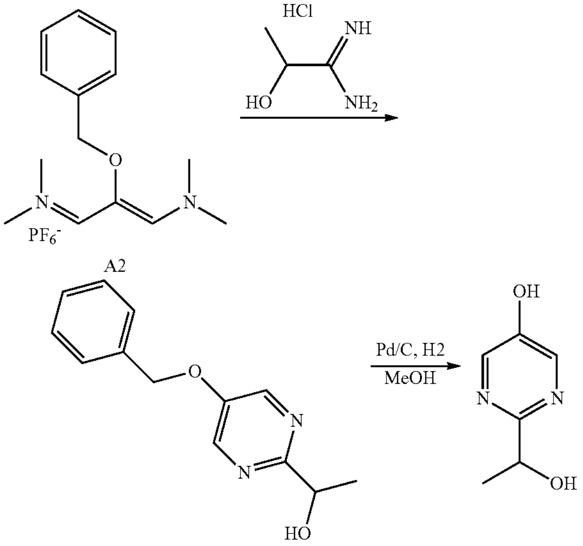

A2

A5

A6

Preparation of Compound A5:

To a stirred suspension of compound A2 (14 g, 39 mmol) and 2-hydroxypropanimidamide hydrochloride (5.65 g, 47 mmol) in $CH_3CN$ (100 mL) was added potassium carbonate (16.2 g, 117 mmol). The reaction mixture was heated at 90° C. for 12 h, then cooled to room temperature, poured into ice water, extracted with ethyl acetate (2×50 mL). The organic layer was dried over $Na_2SO_4$, filtered and concentrated to afford the compound A5 (2.5 g, yield: 26%) as yellow solid.

$^1$H NMR (300 MHz, $CDCl_3$): δ: 8.84 (s, 2H), 7.48 (m, 3H), 7.37 (m, 2H), 5.20 (s, 2H), 4.68 (m, 1H), 3.25 (m, 1H), 1.48 (d, 3H).

Preparation of Compound A6:

A solution of compound A5 (3.50 g, 15.8 mmol) in. MeOH (30 mL) was added palladium on charcoal 10% (350 mg) and the mixture was stirred under hydrogen atmosphere for 4 h. The solid was filtered off and the filtrate was concentrated to get compound A6 (2.0 g, yield: 98%).

$^1$H NMR (400 MHz, $CDCl_3$): δ: 8.84 (s, 2H), 5.40 (brd, 1H), 4.66 (m, 1H), 3.25 (m, 1H), 1.46 (d, 3H). LCMS Found: 141.1 ([M+1]$^+$)

Scheme 3:

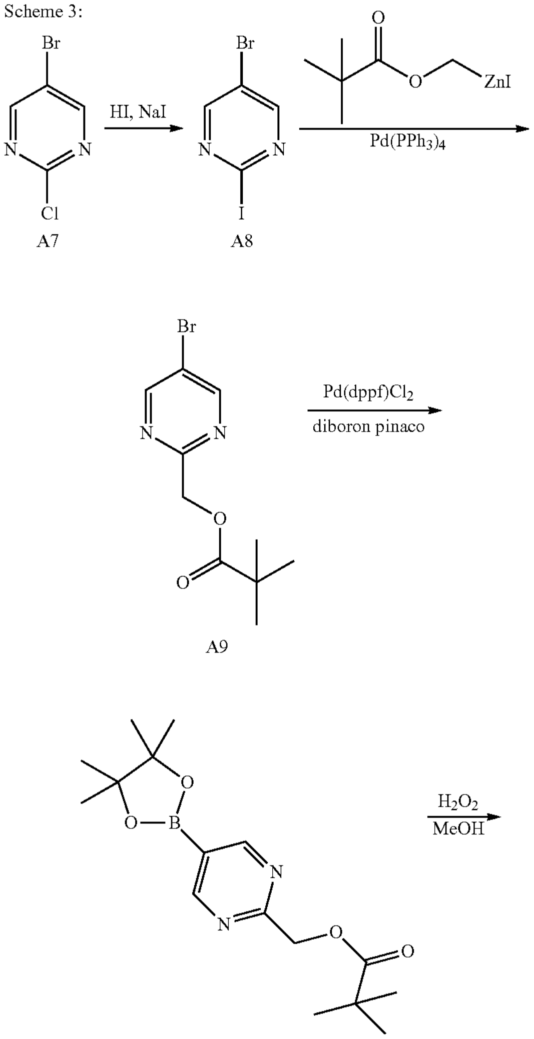

A7

A8

A9

A10

-continued

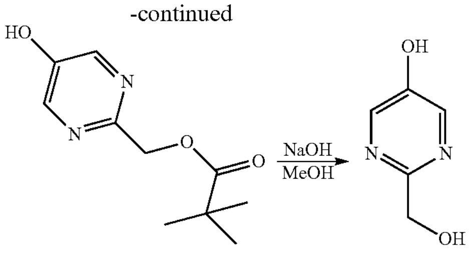

A11 A12

Preparation of Compound A8:

To a solution of compound A7 (50 g, 0.26 mol) in DCM (300 mL) was added NaI (80 g, 0.52 mol) at room temperature, then HI (75 g, 0.52 mol) was added. After stirred at 50° C. for 5 h, the mixture was poured into ice water and carefully neutralized by addition of solid sodium bicarbonate until mixture became colorless. Then the mixture was extracted with DCM (2×200 mL). The organic layer was dried over $Na_2SO_4$, filtered and concentrated to afford compound A8 (60 g, yield: 81%) as white solid.

$^1H$ NMR (400 MHz, $CDCl_3$): δ: 8.54 (s, 2H).

Preparation of Compound A9:

To the solution of compound A8 (50 g, 0.18 mol) in THF (300 mL) was added $Pd(PPh_3)_4$ (11.5 g, 0.01 mol), followed by addition of a solution of zinc reagent 3 (freshly prepared from iodomethyl 2,2-dimethylpropanoate) in THF (500 ml, 0.36 mol) and stirred at room temperature for 12 h. Then ice water was added and the mixture was extracted with ethyl acetate (2×200 mL). The organic layer was dried over $Na_2SO_4$, filtered and concentrated to afford crude product. The residue was purified by chromatography on silica gel (petroleum ether/ethyl acetate=10:1) to afford the compound A9 (41 g, yield: 85%) as yellow solid.

$^1H$ NMR (400 MHz, $CDCl_3$): δ: 8.75 (s, 2H), 5.26 (s, 2H), 5.06 (s, 1H), 1.28 (s, 9H).

Preparation of Compound A10:

To a stirred solution of compound A9 (15.0 g, 54.9 mmol) in dioxane (100 mL) was added bis(pinacolato)diboron (17.0 g, 65.4 mmol) under nitrogen, followed by Pd(dppf) $Cl_2$ (2.20 g, 2.72 mmol) and KOAc (16 g, 163 mmol). The reaction mixture was heated at 85° C. for 3 h. The black suspension was cooled to room temperature, filtered, concentrated to afford crude product. The residue was purified by chromatography on silica gel (petroleum ether/ethyl acetate=15:1) to afford compound A10 (15.4 g) as white solid, contaminated with pinacol derivatives.

$^1H$ NMR (400 MHz, $CDCl_3$): δ: 8.97 (s, 2H), 5.30 (s, 2H), 1.35 (s, 9H), 1.28 (s, 9H).

Preparation of Compound A11:

To a solution of compound A10 (15.6 g, 48.7 mmol) in MeOH (100 mL) was added $H_2O_2$ (16.0 g, 140 mmol). The mixture was stirred at room temperature for 12 h. 2N sodium thiosulphate (200 mL) was added and the mixture was extracted with ethyl acetate (200 mL). The aqueous phase was adjusted pH to 4-5 with 2N HCl; then the mixture was extracted with ethyl acetate (2×200 mL). The organic layer was dried over $Na_2SO_4$, filtered and concentrated to get compound A11 (9.4 g, yield: 82% in two steps).

$^1H$ NMR (400 MHz, DMSO-$d_6$): δ: 10.48 (s, 1H), 8.31 (s, 2H), 5.11 (s, 2H), 1.21 (s, 9H).

Preparation of Compound A12:

To a solution of compound A11 (10 g, 30 mmol) in MeOH (200 mL) was added MeONa (50 ml, 1M in MeOH). After stirred at room temperature for 12 h, the mixture was poured into water and extracted with ethyl acetate (2×200 mL). The organic layer was dried over $Na_2SO_4$, filtered and concentrated to afford the compound A12 (7.3 g, yield: 98%) as white solid.

$^1H$ NMR (300 MHz, $CDCl_3$): δ: 8.43 (s, 2H), 7.35 (d, J=8.8 Hz, 2H), 6.93 (d, J=8.8 Hz, 2H), 5.09 (s, 2H), 4.78 (s, 2H).

Scheme 4:

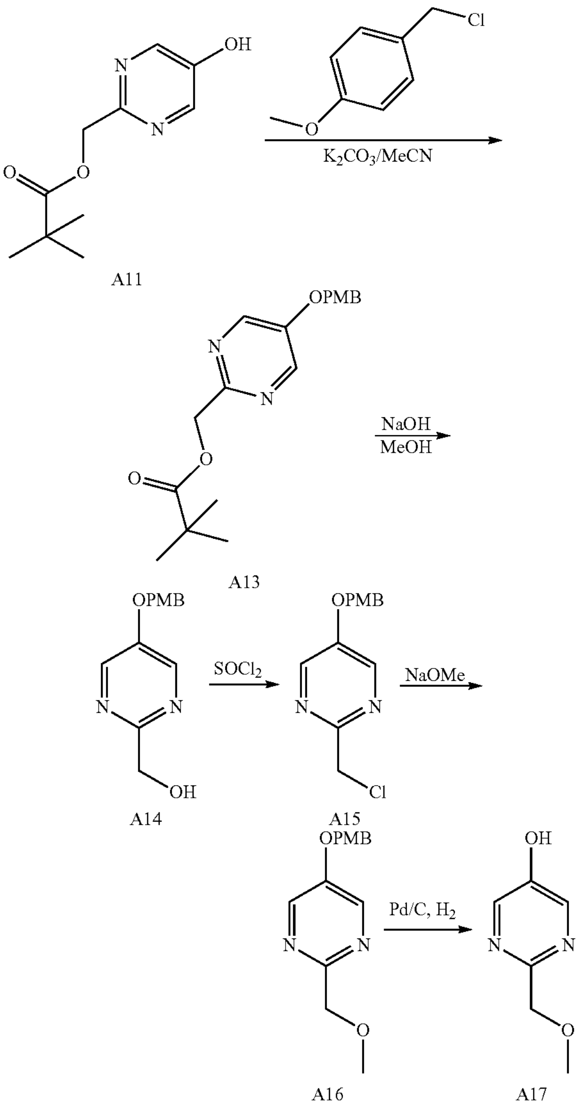

A11 A13 A14 A15 A16 A17

Preparation of Compound A13:

To a solution of compound A11 (12.3 g, 58.5 mmol) in $CH_3CN$ (100 mL) was added $K_2CO_3$ (10.5 g, 76 mmol) and PMBCl (12 g, 76 mmol) and the mixture was stirred at room temperature for 12 h and heated to 50° C. for 3 h. Then the mixture was poured into water and extracted with ethyl acetate (2×200 mL). The organic layer was dried over $Na_2SO_4$, filtered and concentrated, the residue was purified by chromatography on silica gel (petroleum ether/ethyl acetate=10:1) to afford the compound A13 (10.0 g, yield: 52%) as white solid.

$^1H$ NMR (300 MHz, $CDCl_3$): δ: 8.41 (s, 2H), 7.34 (d, J=8.8 Hz, 2H), 6.93 (d, J=8.8 Hz, 2H), 5.24 (s, 2H), 5.07 (s, 2H), 3.82 (s, 3H), 1.26 (s, 9H).

Preparation of Compound A14:

To a solution of compound A13 (10 g, 30 mmol) in MeOH (200 mL) was added MeONa (50 ml, 1M in MeOH). After stirred at room temperature for 12 h, the mixture was poured into water and extracted with ethyl acetate (2×200 mL). The organic layer was dried over $Na_2SO_4$, filtered and concentrated to afford the compound A14 (7.3 g, yield: 98%) as white solid.

$^1$H NMR (300 MHz, $CDCl_3$): δ: 8.43 (s, 2H), 7.35 (d, J=8.8 Hz, 2H), 6.93 (d, J=8.8 Hz, 2H), 4.78 (s, 2H).

Preparation of Compound A16:

To a solution of compound A14 (15 g, 61 mmol) in DCM (200 mL) was added thionyl chloride (10.8 g, 91 mmol). After stirred at room temperature for 2 h, then the mixture was poured into water and extracted with ethyl acetate (2×200 mL). The organic layer was dried over $Na_2SO_4$, filtered and concentrated to afford the compound A15 (16 g) as white solid. To a solution of compound A15 (15 g) in MeOH (200 mL) was added MeONa solution (50 mL, 50% in MeOH). The mixture was stirred at 50° C. for 5 h, then cooled to room temperature, concentrated to afford crude product. The residue was purified by chromatography on silica gel (petroleum ether/ethyl acetate=5:1) to afford the compound A16 (12.5 g, yield: 80%) as yellow solid.

$^1$H NMR (400 MHz, $CDCl_3$): δ: 8.45 (s, 2H), 7.34 (d, J=8.8 Hz, 2H), 6.92 (d, J=8.8 Hz, 2H), 5.08 (s, 2H), 4.64 (s, 2H), 3.82 (s, 3H), 3.52 (s, 3H).

Preparation of Compound A17:

A solution of compound A16 (3.0 g) in MeOH (30 mL) was added 10% palladium on charcoal (350 mg) and the mixture was stirred under hydrogen atmosphere for 4 h. The solid was filtered off and the filtrate was concentrated; the residue was purified by chromatography on silica gel (petroleum ether/ethyl acetate=1:1) to afford compound A17 (1.2 g, yield: 74%) as white solid.

$^1$H NMR (400 MHz, DMSO-$d_6$): δ: 10.45 (s, 1H), 8.33 (s, 2H), 4.44 (s, 2H), 3.31 (s, 3H). LCMS [mobile phase: 95-5% Acetonitrile-0.02% $NH_4$Ac in 6 min, finally under these conditions for 0.5 min.] purity is >95%, Rt=3.3 min; MS Calcd. 140.1.1; MS Found: 141.1 ([M+1]$^+$).

Scheme 5:

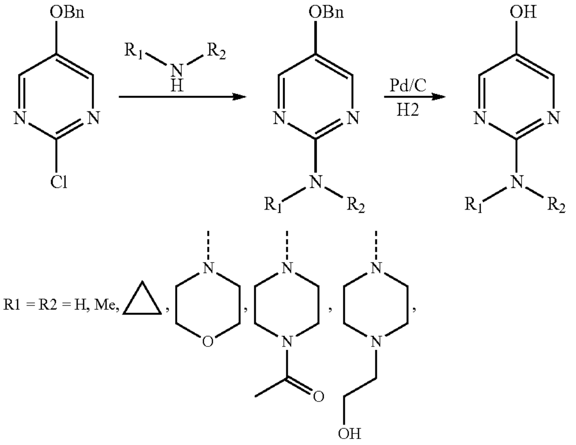

Examples

Scheme 6:

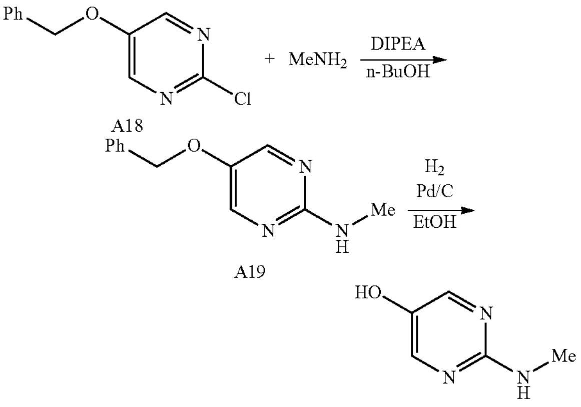

A18

A19

A20

Synthesis of 2-(Methylamino)pyrimidin-5-ol

The mixture of 5-(benzyloxy)-2-chloropyrimidine A18 (0.500 g, 2.27 mmol), methylamine (1.25 mL, 2.50 mmol, 2.0 M solution in MeOH) and DIPEA (0.594 mL, 3.41 mmol) in n-BuOH (5.0 mL) was stirred for 48 hr at 100° C. After being stirred for 48 hr, the reaction was checked by LC/MS. The resulting mixture was cooled to 23° C. and concentrated under reduced pressure. The crude material was purified by column chromatography ($SiO_2$, EtOAc:n-Hex 1:1 (v/v)) to provide 5-(benzyloxy)-N-methylpyrimidin-2-amine A19 (0.355 g, 1.65 mmol, 73%) as colorless crystal. LC/MS (M+H$^+$)=216. The mixture of palladium on carbon (0.176 g, 0.165 mmol, 10.0 mol %) and 5-(benzyloxy)-N-methylpyrimidin-2-amine A19 (0.355 g, 1.65 mmol) in ethanol (7.0 mL) was stirred for 20 h under hydrogen atmosphere at 23° C. The resulting mixture was filter through Celite and the pad was washed with methanol (25 mL). The filtrate was concentrated under reduced pressure to provide the title compound 2-(methylamino)pyrimidin-5-ol A20 (0.196 g, 1.57 mmol, 95%) as a light yellow solid. LC/MS (M+H$^+$)=126.

Scheme 7:

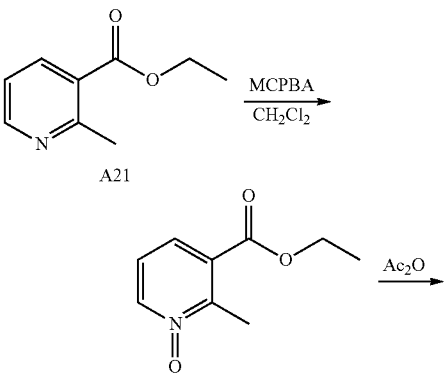

A21

A22

-continued

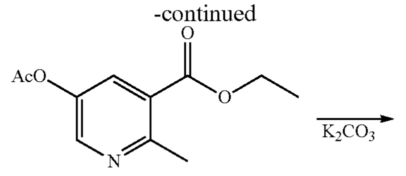

A23

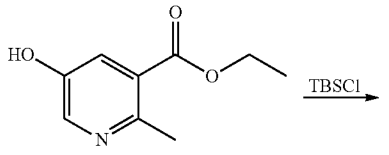

A24

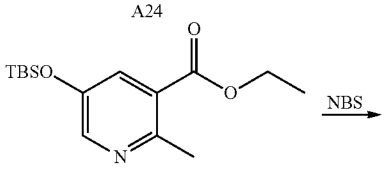

A25

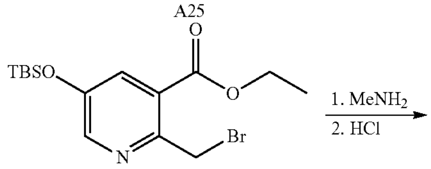

A26

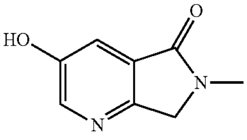

A27

Preparation of Compound A22:

To a solution of A21 (50.0 g, 0.303 mol) in DCM (200 mL) was added m-CPBA (80.0 g, 0.465 mol) at 0° C. After stirred at 0° C. for 1 hour at room temperature for overnight, the mixture was poured into ice water. 2N NaOH was added to adjust the pH to 8-9 and the resultant mixture was extracted with DCM (3×200 mL). The organic layer was dried over $Na_2SO_4$, filtered and concentrated to afford compound A22 (50.0 g, yield: 91%) as a yellow solid.

Preparation of Compound A23:

The solution of A22 (50.0 g, 0.276 mmol) in acetic anhydride (300 mL) was heated to 90° C. for 1.5 hour. Then the mixture was concentrated and the residue was poured into ice water; 2N NaOH was added to adjust the pH to 8-9 and the resultant mixture was extracted by ethyl acetate (3×100 mL). The organic layer was dried over $Na_2SO_4$ and concentrated to give the cured which was purified by chromatography on silica gel (petroleum ether/ethyl acetate=5:1) to afford the compound A23 (10.0 g, yield: 16%) as a yellow oil.

$^1$H NMR (400 MHz, $CDCl_3$): δ: 8.43 (d, J=2.4 Hz, 1H), 7.99 (d, J=1.6 Hz, 1H), 4.41-4.35 (q, J=3.2 Hz, 3H), 2.83 (s, 3H), 2.34 (s, 3H), 1.42-4.39 (t, J=3.2 Hz, 3H).

Preparation of Compound A24:

To a solution of A23 (10.0 g, 44.8 mmol) in MeOH (300 mL) was added potassium carbonate (12.4 g, 89.8 mmol). After stirred at room temperature for 12 hour, the mixture was poured into ice water. 2N HCl was added to adjust the pH to 8-9 and the mixture was extracted with ethyl acetate (2×100 mL). The organic layer was dried over $Na_2SO_4$, filtered and concentrated to afford compound A24 (8.00 g, yield 99%) as yellow solid.

$^1$H NMR (400 MHz, DMSO-$d_6$): δ: 10.0 (s, 1H), 8.18 (d, J=2.4 Hz, 1H), 7.54 (d, J=2.8 Hz, 1H), 4.32-4.26 (q, J=3.2 Hz, 3H), 2.57 (s, 3H), 1.33-1.29 (t, J=3.2 Hz, 3H).

Preparation of Compound A25:

To a solution of compound A24 (2.50 g, 13.8 mmol) in DCM (50 mL) was added imidazole (3.00 g, 44.1 mmol) and tert-Butyldimethylsilyl chloride (2.50 g, 16.7 mmol) and the mixture was stirred at room temperature for 3 hours. Then evaporated the solvent, the residue was purified by chromatography (petroleum ether/ethyl acetate=5:1) to give compound A25 (2.80 g, yield 69%) as a yellow oil.

$^1$H NMR (400 MHz, $CDCl_3$): δ: 8.12 (d, J=2.8 Hz, 1H), 7.54 (d, J=2.8 Hz, 1H), 4.30-4.26 (q, J=3.2 Hz, 3H), 2.64 (s, 3H), 1.32-1.28 (t, J=3.2 Hz, 3H), 0.92 (s, 9H), 0.12 (s, 6H).

Preparation of Compound A26:

To a solution of compound A25 (2.80 g, 9.48 mmol) in $CCl_4$ (100 mL) was added azodiisobutyronitrile (280 mg) and NBS (1.80 g, 10.1 mmol), the mixture was stirred at 70° C. for 15 hours, then the solvent was evaporated, the residue was purified by chromatography (petroleum ether/ethyl acetate=5:1) to give compound A26 (1.60 g, yield 45%) as a yellow oil.

$^1$H NMR (400 MHz, $CDCl_3$): δ: 8.28 (d, J=3.2 Hz, 1H), 7.68 (d, J=3.2 Hz, 1H), 4.98 (s, 3H), 4.45-4.40 (q, J=3.2 Hz, 3H), 1.45-1.42 (t, J=2.8 Hz, 3H), 1.00 (s, 9H), 0.26 (s, 6H).

Preparation of Compound A27:

To a solution of compound A26 (1.60 g, 4.27 mmol) in EtOH (100 mL) was added the solution of methylamine in EtOH (1.24 g, 12.0 mmol, 30% w/w) and the mixture was stirred at room temperature for 3 hour. Then the solvent was evaporated and the residue was purified by chromatography (petroleum ether/ethyl acetate=5:1) to give compound A27a (300 mg, yield: 25%) as a yellow solid.

$^1$H NMR (400 MHz, DMSO-$d_6$): δ: 8.34 (d, J=2.8 Hz, 1H), 7.43 (d, J=2.8 Hz, 1H), 4.42 (s, 2H), 3.06 (s, 3H), 0.95 (s, 9H), 0.20 (s, 6H).

To a solution of compound A27a (300 mg, 1.14 mmol) in THF (5 mL) was added 6N HCl (0.5 mL). After stirred at room temperature for 1 hour, the mixture was concentrated to get compound A27 (150 mg, yield 80%) as a yellow solid.

$^1$H NMR (400 MHz, DMSO-$d_6$): δ: 10.27 (s, 1H), 8.27 (d, J=2.4 Hz, 1H), 7.32 (d, J=2.8 Hz, 1H), 4.37 (s, 2H), 3.0 (s, 3H). LCMS mobile phase: from 40% water (0.05% TFA) and 60% $CH_3CN$ to 10% water (0.05% TFA) and 90% $CH_3CN$ in 6 min, finally under these conditions for 0.5 min.] Purity is >95%, Rt=3.7 min; MS Calcd.: 164.1; MS Found: 165.1 ([M+1]+).

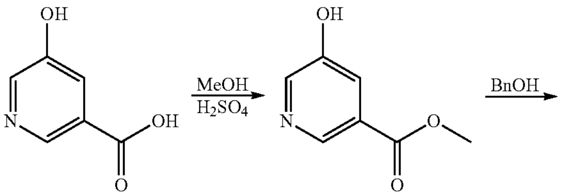

A28 A29

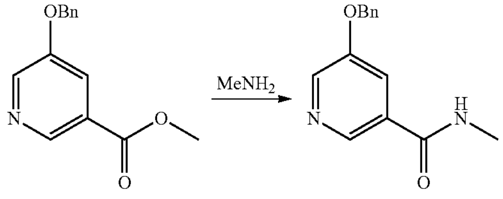

A30 A31

Preparation of Compound A29:

A mixture of compound A28 (25.0 g, 180 mmol) and concentrated $H_2SO_4$ (10 mL) in $CH_3OH$ (100 mL) was heated to reflux for overnight. The mixture was concentrated, the residue was washed with aqueous $NaHCO_3$ (50 mL) and extracted with ethyl acetate (2×100 mL). The organic layer was dried over $Na_2SO_4$, filtered and concentrated to afford compound A29 (18.7 g, yield: 68%).

$^1H$ NMR (300 MHz, DMSO-$d_6$): δ: 10.42 (s, 1H), 8.60 (d, J=1.6 Hz, 1H), 8.36 (d, J=2.8 Hz, 1H), 7.60-7.61 (m, 1H), 3.87 (s, 3H).

Preparation of Compound A30:

BnOH (3.90 g, 36.1 mmol, 1.1 eq) and $PPh_3$ (17.1 g, 65.4 mmol, 2.0 eq) was added to a solution of compound A29 (5.00 g, 32.7 mmol) in THF (100 mL), then DEAD (6.80 g, 39.2 mmol, 1.2 eq) was added at 0° C. The mixture was stirred at room temperature for overnight. The solvent was evaporated, the residue was purified by chromatography on silica gel (petroleum ether/ethyl acetate=10:1) to afford the compound A30 (5.70 g, yield: 71%) as white solid.

$^1H$ NMR (300 MHz, $CDCl_3$): δ: 8.83 (d, J=1.6 Hz, 1H), 8.54 (d, J=2.8 Hz, 1H), 7.85-7.86 (m, 1H), 7.27-7.46 (m, 5H), 5.15 (s, 2H), 3.95 (s, 3H).

Preparation of compound A31:

A solution of compound A30 (12.8 g, 52.9 mmol) in methylamine alcohol solution in sealed tube was stirred at 70° C. for overnight. Then the mixture was cooled to room temperature and the solvent was evaporated to afford the compound A31 (12.0 g, yield: 100%).

$^1H$ NMR (300 MHz, $CDCl_3$): δ: 8.50 (d, J=1.6 Hz, 1H), 8.48 (d, J=2.8 Hz, 1H), 7.73-7.74 (m, 1H), 7.73-7.74 (m, 5H), 6.16 (s, 1H), 3.15 (s, 2H), 3.04 (d, J=4.4 Hz, 3H).

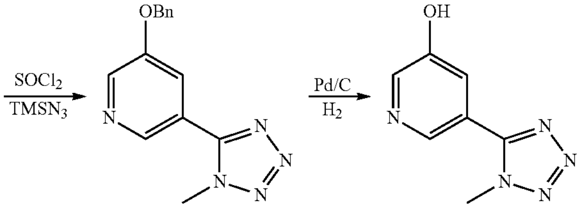

A32 A33

Preparation of Compound A32:

The solution of compound A31 (11.0 g, 45.5 mmol) in $SOCl_2$ (100 mL) was heated to reflux for 4 h. Then, $SOCl_2$ was removed under vacuum and the residue was dissolved in MeCN (200 mL). $TMSN_3$ (12.5 g, 90.0 mmol, 2.0 eq) was added slowly and the mixture was stirred at 90° C. for 3 h. Then the solvent was evaporated and the residue was purified by chromatography on silica gel (petroleum ether/ethyl acetate=2:3) to afford the compound A32 (9.50 g, yield: 78%).

$^1H$ NMR (300 MHz, $CDCl_3$): δ: 8.59 (d, J=2.8 Hz, 1H), 8.56 (d, J=1.6 Hz, 1H), 7.68-7.69 (m, 1H), 7.3-7.46 (m, 5H), 5.21 (s, 2H), 4.17 (s, 3H).

Preparation of Compound A33:

To a solution of compound A32 (5.00 g, 18.7 mmol) in $CH_3OH$ (100 mL) was added $Pd(OH)_2$ (0.50 g), The mixture was stirred at room temperature under $H_2$ atmosphere for 3 h. The solid was filtered off and the filtrate was concentrated to get compound A33 (1.60 g, yield: 48%).

$^1H$ NMR (300 MHz, DMSO-$d_6$): δ: 10.56 (s, 1H), 8.49 (d, J=1.6 Hz, 1H), 8.36 (d, J=2.8 Hz, 1H), 7.61-7.62 (m, 1H), 4.19 (s, 3H).

A31

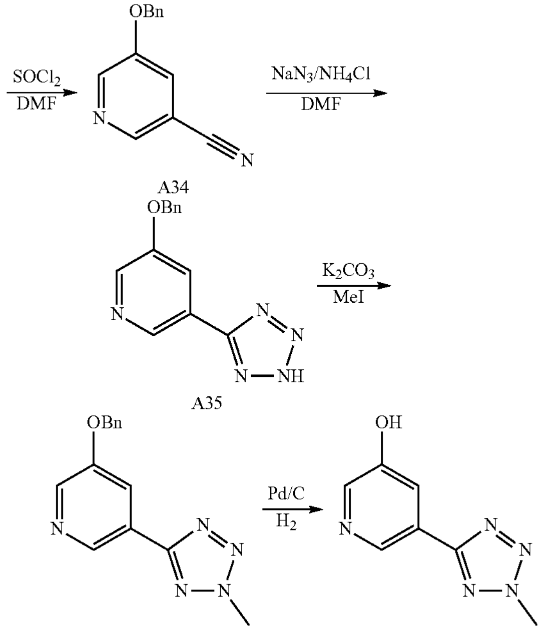

A34 A35 A36 A37

Preparation of Compound A34:

Thionyl chloride (15.0 g, 107 mmol) was added to DMF (200 mL) at 0° C., and the mixture was stirred at 0° C. for 30 min, then A31 (12.2 g, 53.5 mmol) was added to the mixture, and stirred at 0° C. for 1 h. Then the reaction mixture was poured into ice water and extracted with ethyl acetate (2×100 mL). The organic layer was dried over $Na_2SO_4$, filtered and concentrated to afford compound A34 (11.5 g, yield: 100%).

$^1H$ NMR (300 MHz, $CDCl_3$): δ: 8.57 (d, J=2.8 Hz, 1H), 8.48 (d, J=1.6 Hz, 1H), 7.45-7.39 (m, 6H), 5.15 (s, 2H).

Preparation of Compound A35:

To a solution of A34 (12.0 g, 57.1 mmol) in DMF (200 mL) was added $NH_4Cl$ (5.20 g, 97.1 mmol) and $NaN_3$ (6.31 g, 97.1 mmol). The resulting mixture was heated to 100° C. for 14 h, cooled to room temperature, poured into ice water, 2N HCl was added to adjust the PH to 3-4, and extracted with ethyl acetate (2×100 mL). The organic layer was dried over $Na_2SO_4$, filtered and concentrated to afford compound A35 (13.0 g, yield: 90%).

$^1H$ NMR (300 MHz, DMSO-$d_6$): δ: 8.82 (d, J=1.6 Hz, 1H), 8.57 (d, J=2.8 Hz, 1H), 8.04-8.02 (m, 1H), 7.52-7.35 (m, 5H), 5.30 (s, 2H).

Preparation of Compound A36:

Compound A35 (7.00 g, 27.7 mmol) was dissolved in acetone (150 mL), potassium carbonate (5.70 g, 41.2 mmol) was added to the mixture, and stirred at room temperature for 20 min, then iodomethane (5.89 g, 41.2 mmol) was added to mixture, and heated to 45° C. for 1 h, cooled to room temperature, poured into ice water, extracted with ethyl acetate (2×100 mL). The organic layer was dried over $Na_2SO_4$, filtered and concentrated to afford crude product, the residue was purified by chromatography on silica gel (petroleum ether/ethyl acetate=3:1) to afford the compound A36 (4.5 g, yield: 61%) as white solid.

$^1H$ NMR (300 MHz, $CDCl_3$): δ: 8.97 (d, J=1.6 Hz, 1H), 8.48 (d, J=2.4 Hz, 1H), 8.00-7.99 (m, 1H), 7.47-7.26 (m, 5H), 5.19 (s, 2H), 4.43 (s, 3H).

Preparation of Compound A37:

To a solution of compound A36 (7.5 g, 28.0 mmol) in $CH_3OH$ (100 mL) was added $Pd(OH)_2$ (500 mg), The mixture was stirred at room temperature under $H_2$ atmosphere for 3 h. The solid was filtered off and the filtrate was concentrated to get compound A37 (4.3 g, yield: 87%). LC-MS: M+1:178.16.

$^1$H NMR (300 MHz, DMSO-$d_6$): δ: 10.42 (s, 1H), 8.68 (d, J=1.6, 1H), 8.28 (d, J=2.8, 1H), 7.74-7.73 (m, 1H), 4.45 (s, 3H).

Section B:

Synthesis of Unique R4 Pieces

Asymmetric Synthesis of (1R,4R,5R)tert-butyl5-amino-2-azabicyclo[2.2.1]heptane-2-carboxylate General Scheme:

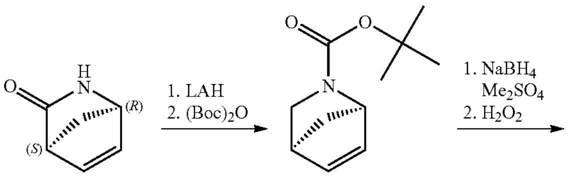

B1 B2

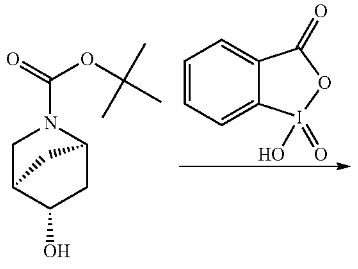

B3

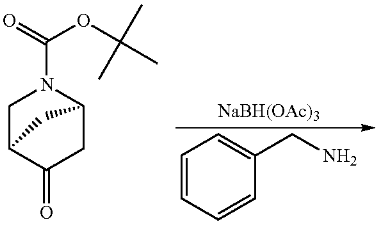

B4

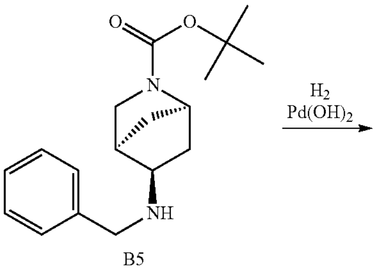

B5

-continued

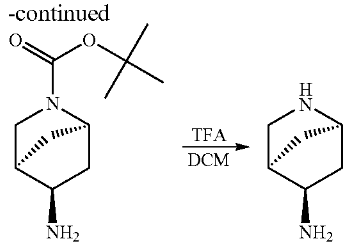

B6 B7

Experimental

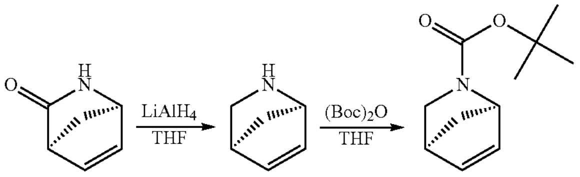

THF Sol.

(1R,4S)-tert-Butyl 2-azabicyclo[2.2.1]hept-5-ene-2-carboxylate (B2)

(1R)-(−)-2-Azabicyclo[2.2.1]hept-5-en-3-one (5.00 g, 45.8 mmol, ee=99%) dissolved in anhydrous THF (15.0 mL) was slowly added to a solution of lithium aluminum hydride (57.3 mL, 57.3 mmol, 1M solution in THF) in anhydrous THF (35.0 mL) under nitrogen atmosphere at 0° C. After the addition was successfully completed, the mixture was stirred for 3 h at 23° C. and then heated at 60° C. for 12 h. The resulting heterogeneous mixture was cooled to 0° C. and $H_2O$ (5.00 mL) was carefully added to the mixture via syringe. The white colored suspension was filtered through a Celite filter aid and the pad was washed with anhydrous diethyl ether (50.0 mL). The filtrate was then treated with $(Boc)_2O$ (15.0 g, 68.7 mmol) and stirred for 24 h at 23° C. The mixture was concentrated in vacuo and the crude material was purified by column chromatography ($SiO_2$, EtOAc:n-Hex 1:7 (v/v)) to provide the title compound B2 as a colorless crystal. (After the solvent was evaporated by rotavap, the resulting colorless oil quickly crystallized at 23° C.)

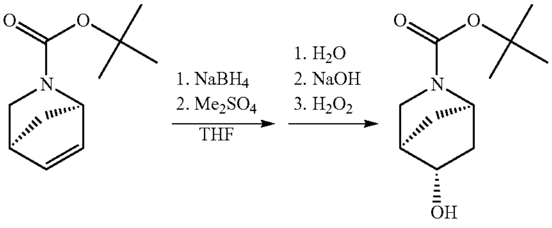

(1R,4R,5S)-tert-Butyl 5-hydroxy-2-azabicyclo[2.2.1]heptanes-2-carboxylate (B3)

The mixture of (1R,4S)-tert-butyl 2-azabicyclo[2.2.1]hept-5-ene-2-carboxylate (1.50 g, 7.68 mmol) and sodium borohydride (0.24 g, 6.30 mmol) in THF (9.5 mL) was stirred for 0.5 h under nitrogen atmosphere at 23° C. After being stirred for 0.5 h, the mixture was warmed to 35° C. and then dimethylsulfate (0.57 mL, 6.30 mmol) dissolved in THF (2.0 mL) was added dropwise via syringe. The resulting mixture was stirred for 4 h at 35° C., then cooled to 0° C. and quenched by dropwise addition of $H_2O$ (5.0 mL). A solution of sodium hydroxide (15.0 mL, 15.0 mmol, 1 M solution of NaOH) was added at 0° C. followed by addition of hydrogen peroxide (0.96 mL, 30 wt. % in $H_2O$). The mixture was warmed to 23° C. and stirred for additional 1 h. The resulting colorless solution was diluted with diethyl ether (75.0 mL) and the organic layer was separated, washed with brine (50.0 mL) and dried over magnesium sulfate. The mixture was concentrated by rotavap and the resulting colorless oil as crude product was purified by column chromatography ($SiO_2$, EtOAc:n-Hex 1:1 (v/v)) to provide the title compound B3 (1.00 g, 4.69 mmol, 61%) as a colorless oil.

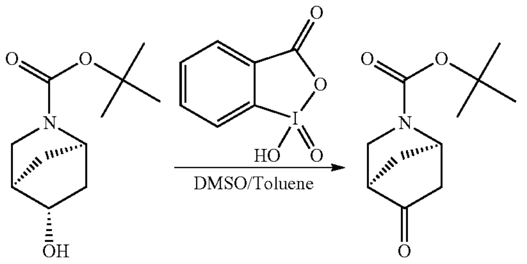

(1R,4R)-tert-Butyl 5-oxo-2-azabicyclo[2.2.1]heptanes-2-carboxylate (B4)

2-Iodoxybenzoic acid (3.43 g, 5.52 mmol, 45 wt. % (SIBX)) was added to a solution of (1R,4R,5S)-tert-butyl 5-hydroxy-2-azabicyclo[2.2.1]heptanes-2-carboxylate (0.87 g, 4.09 mmol) dissolved in dimethylsulfoxide (5.0 mL) and toluene (10.0 mL) under nitrogen atmosphere at 23° C. The mixture was stirred for 3 h at 60° C. and cooled to 23° C. The resulting mixture was treated with saturated sodium carbonate (aq.) (50.0 mL) and filtered under reduced pressure to remove a white solid. The filtrate was extracted with ethyl acetate (75.0 mL×3) and the organic extracts were washed with brine, dried over magnesium sulfate and concentrated in vacuo. The crude material as colorless oil was purified by column chromatography ($SiO_2$, EtOAc:n-Hex 1:2 (v/v)) to provide the title compound B4 (0.62 g, 2.91 mmol, 71%) as a white solid.

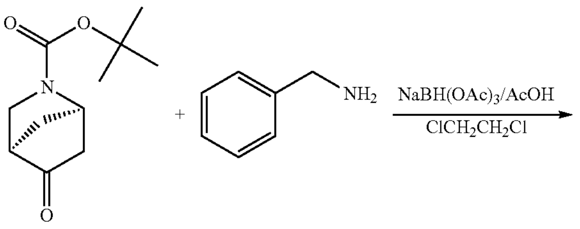

-continued

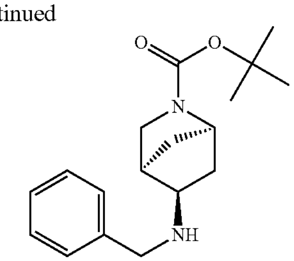

(1R,4R,5R)-tert-Butyl 5-(benzylamino)-2-azabicyclo[2.2.1]heptanes-2-carboxylate (B5)

Sodium triacetoxyborohydride (23.4 g, 105 mmol) and glacial acetic acid (4.66 g, 77.6 mmol) were added to a solution of (1R,4R)-tert-butyl 5-oxo-2-azabicyclo[2.2.1]heptane-2-carboxylate (16.4 g, 77.6 mmol) and benzylamine (8.32 g, 77.6 mmol) in 1,2-dichloroethane (250 mL) under nitrogen atmosphere at 23° C. The resulting mixture was stirred for 5 h at 23° C. and then quenched with saturated sodium bicarbonate (aq.) (300 mL). The mixture was extracted with ethyl acetate (350 mL×3) and the organic extracts were washed with brine, dried over magnesium sulfate and concentrated in vacuo. The crude material was purified by column chromatography ($SiO_2$, EtOAc:n-Hex. 9:1 (v/v)) to provide the title compound B5 (20.0 g, 66.1 mmol, 85%) as colorless oil.

$^1H$ NMR (300 MHz, $CDCl_3$): δ 7.35-7.27 (m, 5H), 4.21 (s, 0.5H), 4.08 (s, 0.5H), 3.80-3.68 (m, 2H), 3.58 (d, J=10.0 Hz, 1H), 3.28-3.22 (m, 1H), 3.20-3.11 (m, 1H), 2.62 (m, 1H), 2.05-1.97 (m, 1H), 1.76-1.69 (m, 1H), 1.55-1.51 (m, 1H), 1.48 (s, 9H), 1.30-1.14 (m, 1H).

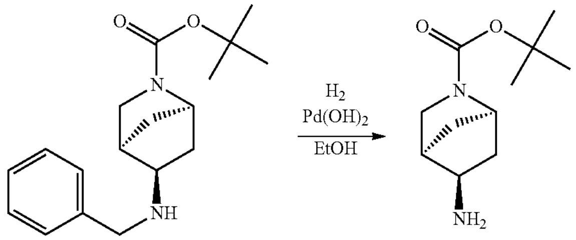 [SMILES: "EtOH" ; CC(C)(C)OC(=O)N1C[C@H]2C[C@@H]1C[C@H]2NCc1ccccc1 ; CC(C)(C)OC(=O)N1C[C@H]2C[C@@H]1C[C@H]2N]

(1R,4R,5R)-tert-Butyl 5-amino-2-azabicyclo[2.2.1]heptanes-2-carboxylate (B6)

The mixture of palladium hydroxide (4.30 g, 6.12 mmol, 10.0 mol %, 20 wt. % on carbon, 50% wet) and (1R,4R,5R)-tert-butyl 5-(benzylamino)-2-azabicyclo[2.2.1]heptane-2-carboxylate (18.5 g, 61.2 mmol) in ethanol (100 mL) was stirred for 36 h under hydrogen atmosphere at 23° C. The resulting mixture was filter through Celite and the pad was washed with ethyl acetate (500 mL). The filtrate was concentrated under reduced pressure to provide the title compound B6 (12.8 g, 60.3 mmol, 99%) as a colorless crystal.

$^1H$ NMR (300 MHz, MeOD): δ 4.11 (s, 1H), 3.56-3.51 (m, 1H), 3.43-3.39 (m, 1H), 3.18-3.15 (m, 1H), 2.49 (bs, 1H), 2.14-2.05 (m, 1H), 1.74-1.68 (m, 1H), 1.61 (d, J=10.0 Hz, 1H), 1.48 (s, 9H), 1.18-1.10 (m, 1H).

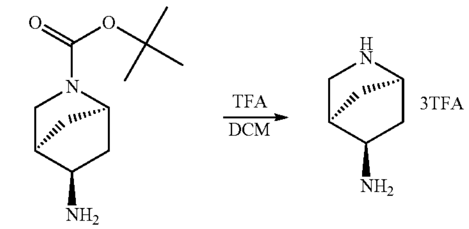

Preparation of (1R,4R,5R)-2-azabicyclo[2.2.1]heptan-5-amine (B7): The Boc protected amine (200 mg, 0.94 mmol) in $CH_2Cl_2$ (10 mL) was added dropwise of TFA (5 mL) and the mixture was stirred at RT for 10 minutes. The solvent was removed at vacuum and the amine (100 mg, 99%) was used for the reactions without further purification.

Synthesis of octahydrocyclopenta[c]pyrrol-4-amine

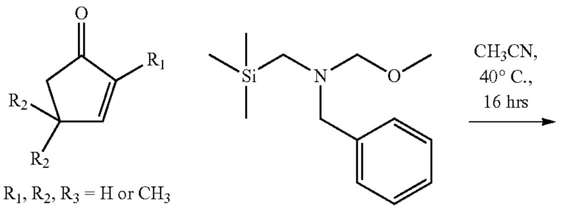

$R_1$, $R_2$, $R_3$ = H or $CH_3$

B8

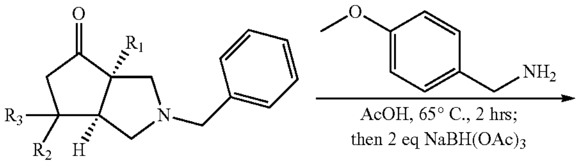

$B_9$

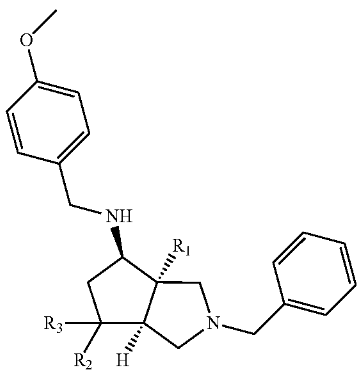

+

B10(a)

3:1

-continued

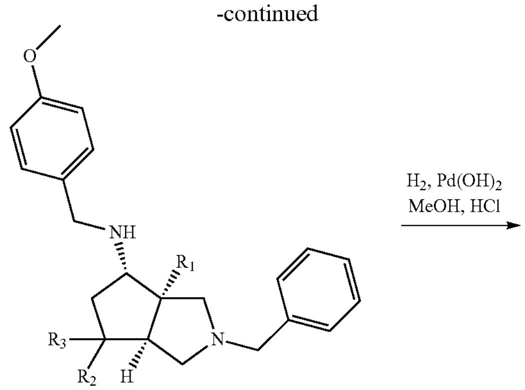

B10(b)

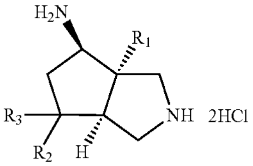

B11

(3aR,6aS)-2-benzylhexahydrocyclopenta[c]pyrro-4-(5H)-one (B9)

To a solution of N-methoxymethyl)-N-(trimethylsilylmethyl)benzyl amine (50 g, 0.21 mol) in acetonitrile (134 ml) was added 2-cyclopenten-1-one. The mixture was stirred under argon at 45° C. overnight. After the solvent was removed by rotary evaporation, the residue was purified through C18 column chromatography to afford the title compound as clear oil (30 g, 66.4%). The chirality was resolved by chiral HPLC to obtain the desired enantiomer (B9) with an ee of >99%.

(3aR,4R,6aS)-2-benzyl-N-(4-methoxybenzyl)octahydrocyclopenta[c]pyrrol-4-amine B10(a) and B10(b)

To the solution of compound (B9) (2.9 g, 13.43 mmol) in acetic acid (25 ml) was added 4 Å molecular sieve (5.7 g) and 4-methoxy benzylamine (2.76 g, 20.15 mmol). After the mixture was stirred at 75° C. for one hour, it was added with sodium triacetoxyborohydride by portion of total 1.2 equivalences (285 mg, 1.35 mmol in every 20 minutes interval). The reaction was continued at 75° C. to room temperature overnight. The molecular sieve was filtered off and washed with MeOH. The solution was concentrated by rotary evaporation, and the resulting residue was purified through C18 column chromatography. The PH of the combined collected eluents was adjusted to slightly basic by sodium carbonate and extracted with DCM (150 ml×3). The combined organic layers were dried over sodium sulfate and concentrated by rotary evaporation to afford the title product B10(a) as yellow oil (2.56 g, 56.7%).

(3aR,4R,6aS)-octahydrocyclopenta[c]pyrrol-4-amine HCl salt (B11)

To the solution of compound B10(a) (2.56 g, 7.61 mmol) in MeOH (100 ml) was added $Pd(OH)_2$ on 20% carbon-50% water (2 g) followed by the slow addition of concentrated HCl 37% (3 g). Hydrogen from a double-layer balloon was bubbled through the reaction mixture for 16 hours. Palladium on carbon was filtered out and washed with MeOH (10 ml). The filtrate was concentrated by rotary evaporation and excess HCl was removed through MeOH-toluene azeotrope to yield the tile compound (B11) as light yellow HCl salt (1.51 g, 100% yield).

Asymmetric Synthesis of tert-butyl (1R,4R,5R)-2-azabicyclo[2.2.1]heptan-5-ylcarbamate

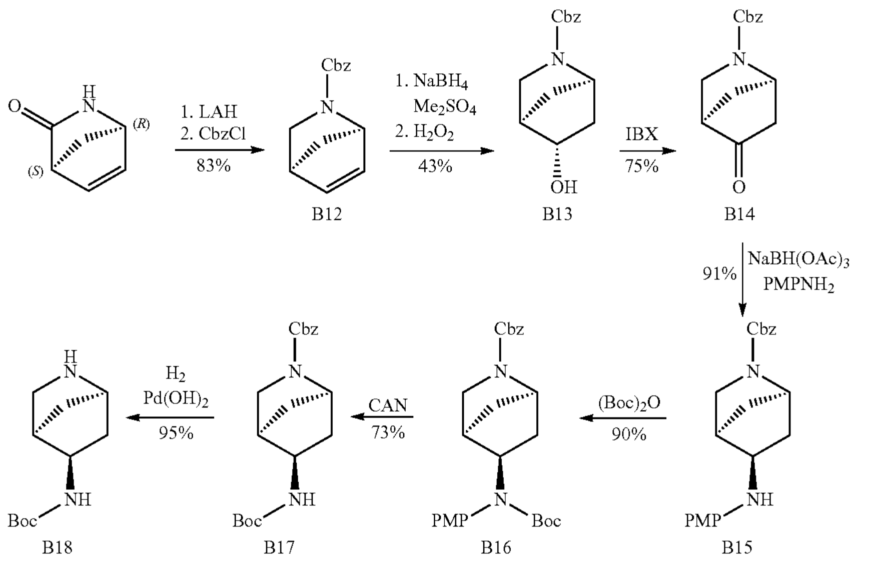

Asymmetric Synthesis of tert-butyl (1R,4R,5R)-2-azabicyclo[2.2.1]heptan-5-ylcarbamate

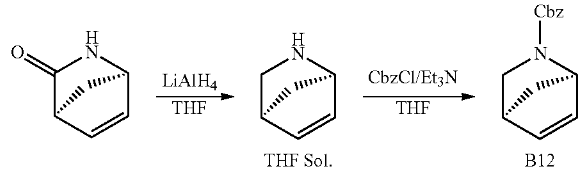

(1R,4S)-Benzyl 2-azabicyclo[2.2.1]hept-5-ene-2-carboxylate (B12)

(1R)-(−)-2-Azabicyclo[2.2.1]hept-5-en-3-one (5.00 g, 45.8 mmol, ee=99%) dissolved in anhydrous THF (45.0 mL) was slowly added to a solution of lithium aluminum hydride (28.7 mL, 57.3 mmol, 2M solution in THF) in anhydrous THF (50.0 mL) under nitrogen atmosphere at 0° C. After the addition was successfully completed, the mixture was stirred for 3 h at 23° C. and then heated for 24 h at 60° C. The resulting heterogeneous mixture was cooled to 0° C. and $H_2O$ (5.00 mL) was carefully added to the mixture via syringe. The white suspension was filtered through a Celite filter aid and the pad was washed with anhydrous THF (250.0 mL). The filtrate as a clear solution was cooled to 0° C. and then treated with triethylamine (12.8 mL, 91.6 mmol) and CbzCl (10.3 mL, 68.7 mmol) in that order. The resulting heterogeneous mixture including a white precipitate was slowly warmed to 23° C. and allowed to stir for 48 h. The white precipitates were filtered by reduced pressure and the resulting clear solution was concentrated in vacuo. The crude material as light yellow oil was purified by column chromatography ($SiO_2$, EtOAc:n-Hex 1:4 (v/v)) to provide the title compound B12 (8.68 g, 37.9 mmol, 83%) as a colorless oil.

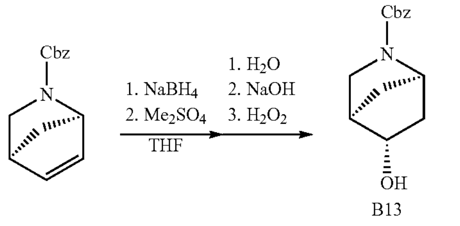 [SMILES: O=C(OCc1ccccc1)N1C[C@@H]2C=C[C@H]1C2 ; "B13" ; O=C(OCc1ccccc1)N1C[C@H]2C[C@@H]1C[C@@H]2O ; "THF"]

(1R,4R,5S)-Benzyl 5-hydroxy-2-azabicyclo[2.2.1]heptane-2-carboxylate (B13)

The mixture of (1R,4S)-benzyl 2-azabicyclo[2.2.1]hept-5-ene-2-carboxylate (8.679 g, 37.86 mmol) and sodium borohydride (1.17 g, 31.0 mmol) in THF (60.0 mL) was stirred for 0.5 h under nitrogen atmosphere at 23° C. After being stirred for 0.5 h, the mixture was warmed to 35° C. and then dimethylsulfate (2.93 mL, 31.0 mmol) dissolved in THF (2.0 mL) was added dropwise via syringe. (Note: dimethylsulfate was slowly added due to gas evolution) The resulting heterogeneous mixture was stirred for 4 h at 35° C., then cooled to 0° C. and quenched by dropwise addition of $H_2O$ (5.0 mL). A solution of sodium hydroxide (80.0 mL, 80.0 mmol, 1 M solution of NaOH) was added at 0° C. followed by addition of hydrogen peroxide (5.0 mL, 30 wt. % in $H_2O$). The mixture was warmed to 23° C. and stirred for additional 1 h. The resulting colorless solution was diluted with ethylacetate (250 mL) and the organic layer was separated, washed with brine (150 mL) and dried over magnesium sulfate. The mixture was concentrated by rotavap and the resulting colorless oil as crude product was purified by column chromatography ($SiO_2$, EtOAc:n-Hex 1:1 (v/v)) to provide the title compound B13 (4.02 g, 16.3 mmol, 43%) as a colorless oil.

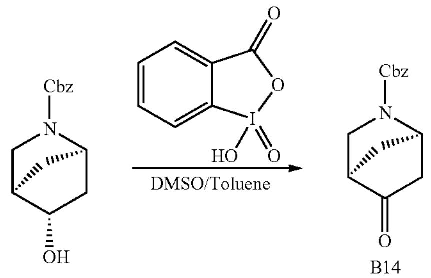

B14

(1R,4R)-Benzyl 5-oxo-2-azabicyclo[2.2.1]heptanes-2-carboxylate (B14)

2-Iodoxybenzoic acid (13.7 g, 22.0 mmol, 45 wt. % (SIBX)) was added to a solution of (1R,4R,5S)-benzyl 5-hydroxy-2-azabicyclo[2.2.1]heptanes-2-carboxylate (4.02 g, 16.3 mmol) dissolved in dimethylsulfoxide (20.0 mL) and toluene (40.0 mL) under nitrogen atmosphere at 23° C. The mixture was stirred for 3 h 30 min at 60° C. and then cooled to 23° C. The resulting heterogeneous mixture was treated with saturated sodium carbonate (aq.) (250 mL) and filtered under reduced pressure to remove a white solid. The filtrate was extracted with ethyl acetate (250 mL×3) and the organic extracts were washed with brine, dried over magnesium sulfate and concentrated in vacuo. The crude material as colorless oil was purified by column chromatography ($SiO_2$, EtOAc:n-Hex 1:2 (v/v)) to provide the title compound B14 (2.99 g, 12.2 mmol, 75%) as a colorless oil.

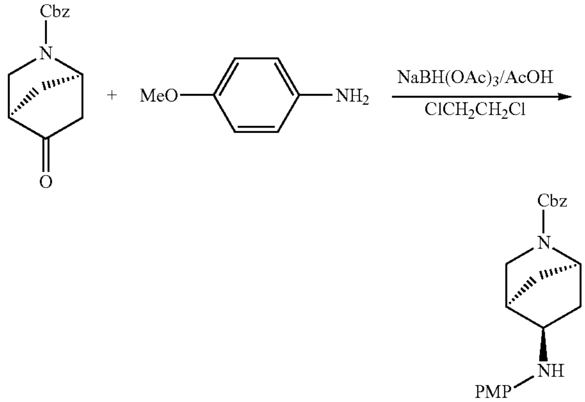

B15

(1R,4R,5R)-Benzyl 5-(4-methoxyphenylamino)-2-azabicyclo[2.2.1]heptanes-2-carboxylate (B15)

Sodium triacetoxyborohydride (0.904 g, 4.05 mmol) and glacial acetic acid (0.180 g, 3.00 mmol) were added to a solution of (1R,4R)-benzyl 5-oxo-2-azabicyclo[2.2.1]heptanes-2-carboxylate (0.736 g, 3.00 mmol) and p-anisidine (0.370 g, 3.00 mmol) in 1,2-dichloroethane (10.0 mL) under nitrogen atmosphere at 23° C. The resulting mixture was stirred for 3 h at 23° C. The heterogeneous mixture was cooled to 0° C. and quenched with saturated sodium bicarbonate (aq.) (150 mL). The mixture was extracted with ethyl acetate (200 mL×3) and the organic extracts were washed with brine, dried over magnesium sulfate and concentrated in vacuo. The crude material as clear yellow oil was purified by column chromatography ($SiO_2$, EtOAc:n-Hex. 1:2 (v/v)) to provide the title compound B15 (0.964 g, 2.73 mmol, 91%) as a white solid.

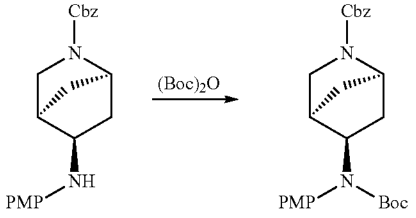

B16

(1R,4R,5R)-Benzyl 5-(tert-butoxycarbonyl(4-methoxyphenyl)amino)-2-azabicyclo[2.2.1]heptane-2-carboxylate (B16)

The mixture of (1R,4R,5R)-benzyl 5-(4-methoxyphenylamino)-2-azabicyclo[2.2.1]heptanes-2-carboxylate (0.352 g, 1.00 mmol) and KHMDS (1.30 mL, 1.30 mmol, 1.0 M solution of THF) in anhydrous THF (15.0 mL) was stirred for 15 min under nitrogen atmosphere at 23° C. The resulting greenish mixture was treated with $(Boc)_2O$ (0.470 g, 2.15 mmol) and then was stirred for 16 h at 23° C. The mixture was concentrated under reduced pressure to provide yellow oil. The crude material was purified by column chromatography ($SiO_2$, EtOAc:n-Hex. 1:2 (v/v)) to give the title compound B16 (0.408 g, 0.901 mmol, 90%) as a colorless oil.

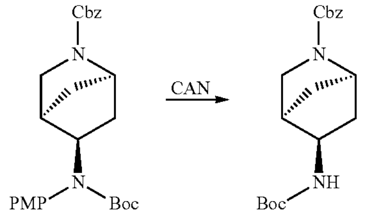

B17

(1R,4R,5R)-Benzyl 5-(tert-butoxycarbonylamino)-2-azabicyclo[2.2.1]heptane-2-carboxylate (B17)

Ceric ammonium nitrate (1.73 g, 3.15 mmol) dissolved in $H_2O$ (5.0 mL) was added to a solution of (1R,4R,5R)-benzyl 5-(tert-butoxycarbonyl(4-methoxyphenyl)amino)-2-azabicyclo[2.2.1]heptane-2-carboxylate (0.408 g, 0.901 mmol) in acetonitrile (25 mL) under nitrogen atmosphere at 0° C. The resulting mixture was stirred for 1 hr at 0° C. and then diluted with $H_2O$ (100 mL), extracted with ethyl acetate (150 mL×3). The combined organic phase was washed with 1N $Ns_2SO_3$ (75 mL), dried over $MgSO_4$ and concentrated in vacuo. The crude material was purified by column chromatography ($SiO_2$, EtOAc:n-Hex. 1:2 (v/v)) to give the title compound B17 (0.229 g, 0.661 mmol, 73%) as a colorless oil.

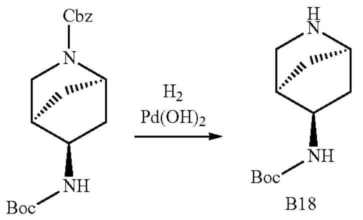 [SMILES: CC(C)(C)OC(=O)N[C@@H]1C[C@H]2C[C@@H]1CN2C(=O)OCc1ccccc1 ; "B18" ; CC(C)(C)OC(=O)N[C@@H]1C[C@H]2C[C@@H]1CN2]

B18 tert-Butyl (1R,4R,5R)-2-azabicyclo[2.2.1]heptane-5-carboxylate (B18)

The mixture of palladium hydroxide (0.015 g, 0.022 mmol, 10.0 mol %, 20 wt. % on carbon, 50% wet) and (1R,4R,5R)-benzyl 5-(tert-butoxycarbonylamino)-2-azabicyclo[2.2.1]heptane-2-carboxylate (0.077 g, 0.222 mmol) in ethanol (5.0 mL) was stirred for 3 h 30 min under hydrogen atmosphere at 23° C. The resulting mixture was filter through Celite and the pad was washed with ethyl acetate (100 mL). The filtrate was concentrated under reduced pressure to provide the title compound B18 (0.045 g, 0.212 mmol, 95%) as colorless oil.

$^1$H NMR (300 MHz, MeOD): δ 3.89 (d, J=11.2 Hz, 1H), 3.42 (s, 1H), 3.01 (d, J=10.4 Hz, 1H), 2.74-2.69 (m, 1H), 2.58 (bs, 1H), 2.12-2.02 (m, 1H), 1.64 (s, 2H), 1.46 (s, 9H), 1.19-1.13 (m, 1H).

Section C:

Section for Compounds where L=S

General Scheme 1:

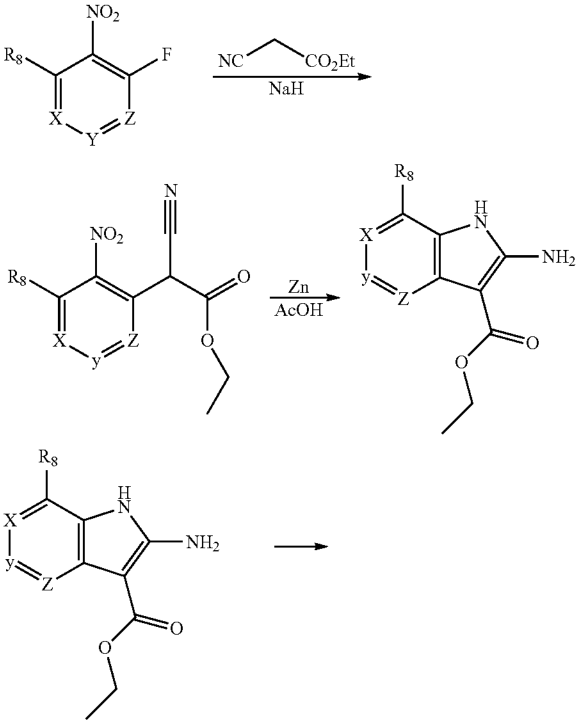

-continued

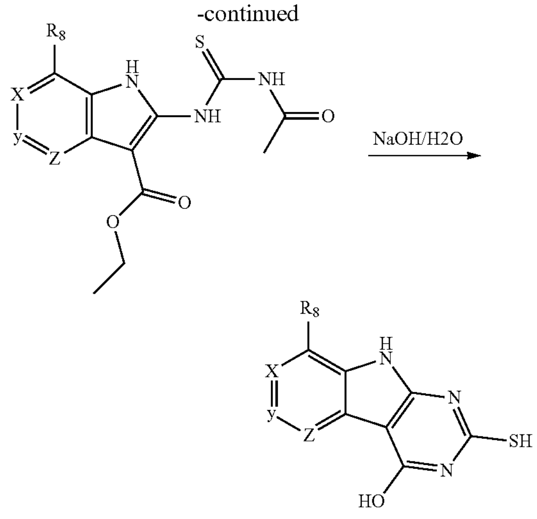

Experimental

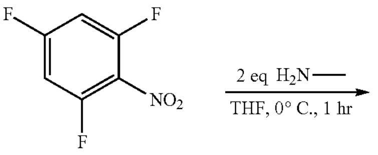

C1

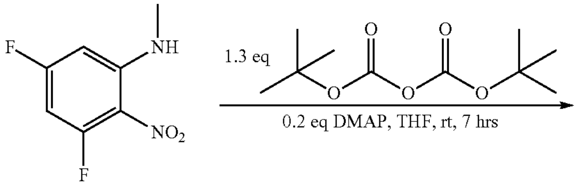

C2

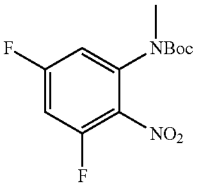

C3

3,5-difluoro-N-methyl-2-nitroaniline (C2)

1,3,5-Trifluoro-2-nitrobenzene (35.16 g, 0.2 mol) was dissolved in 100 ml of THF and cooled in an ice-water bath. To this solution was added drop-wise the 40% aqueous solution of methylamine (23.25 g, 0.3 mol) over ~20 minutes through an additional funnel. The reaction mixture was stirred for 1 hour. It was then diluted with hexane (50 ml), and the solvents were partitioned into two layers. The aqueous solution was removed, and the organic layer was washed with water (20 ml). The solution was concentrated by gentle rotary evaporation at room temperature and further dried under high vacuum to afford the crude product (C2) as orange solid (36 g, 96%).

$^1$H NMR ($CDCl_3$, 300 MHz): δ=6.97-6.88 (m, 2H), 3.27 (s, 3H).

Tert-butyl 3,5-difluoro-2-nitrophenyl(methyl)carbamate (C3)

To the solution of crude 3,5-difluoro-N-methyl-2-nitroaniline (C2) (36 g, 0.191 mol) in 100 ml of THF was added di-tert-butyl-dicarbonate (54.3 g, 0.249 mol) followed by 4-dimethylaminopyridine (4.68 g, 0.038 mol). The reaction mixture was stirred at room temperature for 7 hours. Water (50 ml) was then added and the resulting solution was stirred for 1.5 hours. After diluted with hexane (100 ml), the solution was partitioned into two layers, and the aqueous phase was removed through an extraction funnel and back extracted with ethyl acetate (50 ml). The combined organic layer was then washed first with 5% $NH_4Cl$ solution (100 ml) and then with 5% $K_2CO_3$ solution (100 ml). After the combined organic solvent was concentrated by rotary evaporation at room temperature, the resulting residue was re-dissolved in MeOH (~50 ml) and then added drop-wise into 600 ml of ~0.01% $K_2CO_3$ solution. The orange solid product (C3) was filtered, washed with water, and dried under high vacuum (46.78 g, 85%).

$^1$H NMR ($CDCl_3$, 300 MHz): δ=6.93-6.85 (m, 2H), 3.20 (s, 3H), 1.32 (s, 9H).

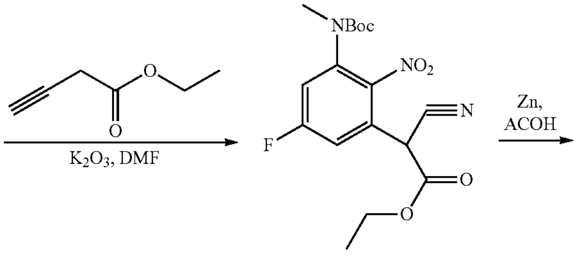

C4

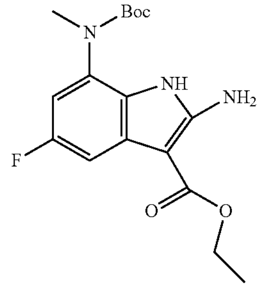

C5

Synthesis of compound C4: To a solution of C3 (40 g, 0.14 mol) in DMF (200 mL) was added potassium carbonate (19 g, 0.14 mol), followed by a portion of ethyl cyano acetate (15 g, 0.14 mol). The mixture was stirred at room temperature for 2 h. Then an additional portion of potassium carbonate (19 g, 0.14 mol) and a portion of ethyl cyano acetate (15 g, 0.14 mol) were added. After the mixture was stirred at room temperature for 4 h, potassium carbonate (19 g, 0.14 mol) was added and the mixture was stirred at room temperature for another 12 h. Then the mixture was poured into ice water and extracted with ethyl acetate (2×200 mL). The organic layer was dried over $Na_2SO_4$, filtered, concentrated and purified by chromatography on silica gel (petroleum ether/ethyl acetate=5:1) to afford the compound C4 (33 g, yield: 63%) as yellow solid.

$^1$H NMR ($CDCl_3$, 300 MHz): δ=6.93-6.85 (m, 2H), 4.88 (m, 1H), 4.33 (m, 2H), 3.20 (s, 3H), 1.32 (s, 9H), 1.28 (t, 3H).

Synthesis of compound C5: To a solution of C4 (20 g, 52 mmol) in toluene (100 mL) and acetic acid (100 mL) was added zinc powder (30 g, 0.46 mol) and the mixture was stirred at 75° C. for 2 h. Then another Zn powder (10 g, 0.15 mol) was added. After stirred at 75° C. for more 0.5 h, the mixture was cooled to room temperature, filtered and poured into ice water. 2N NaOH was added to adjust the pH to 8-9 and the resultant mixture was extracted with ethyl acetate (2×200 mL). The organic layer was dried over $Na_2SO_4$, filtered, concentrated and purified by chromatography on silica gel (petroleum ether/ethyl acetate=5:1) to afford compound C5 as a brown solid (8.3 g, yield: 45%).

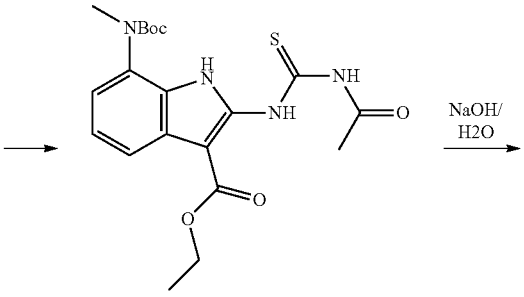

C6

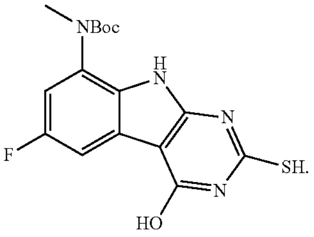

C7

Synthesis of compound C7: To a stirred suspension of compound C5 (7.4 g, 20 mmol) in acetone (140 mL) was added dropwise a solution of acetyl thioisocynate (12 mL, 140 mmol) in acetone (50 mL) at room temperature. The reaction mixture was heated to reflux for 16 h. LCMS showed the reaction was completed. The reaction mixture was concentrated for next step without purification. LC-MS: M+1:453.21.

Above residue was disolved into 50 ml methanol and 50 ml H2O, then was added 10 ml 10% KOH solution, the mixture solution was heated to reflux for 30 minutes. When LCMS showed the reaction was completed the reaction was cooled to room temperature, acidified to pH 5 with 1 M aq. HCl, and the precipitate collected by filtration to give compound C7 as a solid (5 g, 65.4% in two steps). LC-MS: M+1: 365.13.

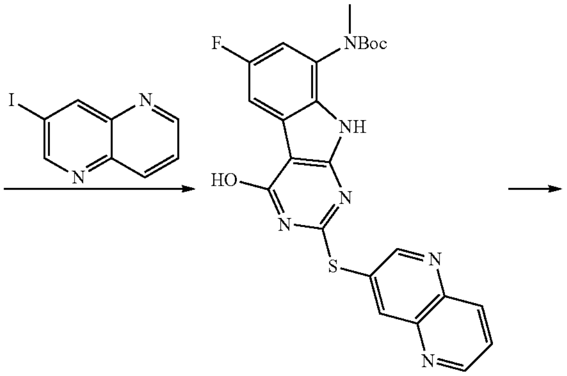

C8

-continued

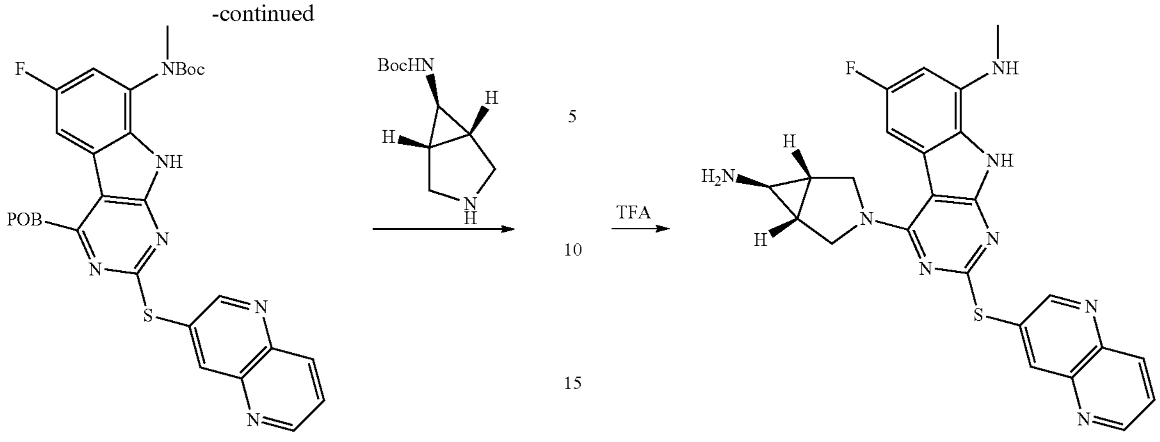

C9 C11 (1.12)

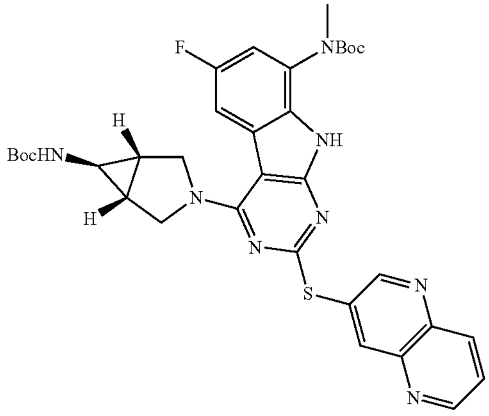

C10

Synthesis of compound C10: The solution of CuI (67 mg, 0.35 mmol), N,N'-dimethyl cyclohexane-1,2-diamine (100 mg, 0.70 mmol) in 9 mL of NMP was added to a stirring suspension of tert-butyl (4-hydroxy-2-mercapto-9H-pyrimido[4,5-b]indol-8-yl)(methyl) carbamate (5, 350 mg, 1.0 mmol), a proper I—Ar (1.17 mmol), $K_2CO_3$ (324 mg, 2.35 mmol) and $PPh_3$ (400 mg, 1.53 mmol) in NMP (9 mL). The mixture was heated to 130° C. for 2 to 12 hrs monitored by LC-MS for the completion of the reaction. When the reaction completed, the mixture was cooled to 0° C., BOP (621 mg, 1.40 mmol) and $Et_3N$ (0.41 mL, 2.93 mmol) was added, stirred for 30 minutes at 0° C., then warmed up to room temperature, a suitable Boc-protected diamine (2.34 mmol) was added. The reaction mixture was heated to 50° C. for 30 minutes. LC-MS indicated the completed reaction. After completed the reaction, the mixture was partitioned with ethyl acetate and water, the aqueous layer was extracted by ethyl acetate twice, the combined organic layer was dried and purified by flash chromatography to give products compound C10 as a solid (420 mg, 63% in two steps). LC-MS: M+1: 673.25.

Synthesis of compound C11: The above compound (420 mg, 0.63 mmol) was dissolved in 10 mL of TFA and stirred for 30 minute at room temperature. After removal of the solvents, the residue was re-dissolved into 10 ml methanol and 10 ml H2O, then 1N NaOH was added to neutralize the solution to PH 14, the basic solution then was diluted by another 100 ml H2O, and the solution was stirred vigorously for another 1 hour, collected the precipate, and dried to give final compounds as a white solid (200 mg, 70%). LC-MS: M+1: 473.13.

$^1$H NMR (300 MHz, DMSO) δ (ppm): 11.75 (s, 1H), 8.09 (d, 1H), 8.95 (s, 1H), 8.52 (m, 1H), 8.35 (s, 1H), 7.75 (m, 1H), 7.01 (d, 1H), 5.96 (d, 1H), 4.10 (s, 1H), 2.98 (s, 3H), 2.85 (m, 2H), 2.67 (m, 2H), 1.38 (m, 1H), 0.75 (br m, 2H).

Experimental

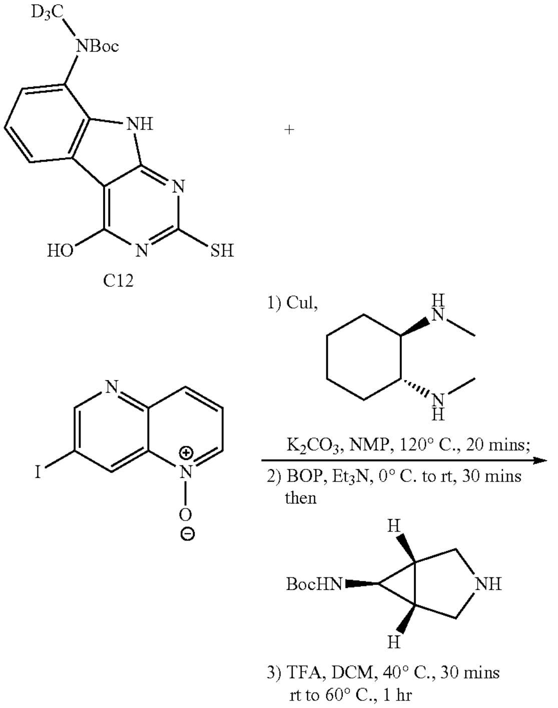

-continued

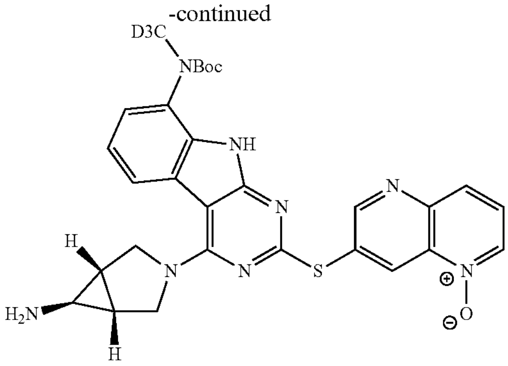

C13

7-(4-(6-amino-3-azabicyclo[3.1.0]hexan-3-yl)-8-(deuteratedmethylamino)-9H-pyrimido[4,5-b]indol-2-ylthio)-1,5-naphthyridine 1-oxide C13 (CD3 analog of 1.13): To the mixture of CuI (76 mg, 0.4 mmol) and $K_2CO_3$ (112 mg, 0.8 mmol) in NMP (1 ml) was added trans-N,N'-dimethylcyclohexane-1,2-diamine (113.6 mg (0.8 mmol). The mixture was stirred at 120° C. for 10 minutes. It was then added with compound (1) (70 mg, 0.2 mmol) and 7-iodo-1,5-naphthyridine 1-oxide (59.8 mg, 0.22 mmol). The reaction was continued at 120° C. for 20 minutes. It was cooled down to ~4° C. and then added with $Et_3N$ (0.3 ml) followed by [benzotriazole-1-yl-oxy-tris-(dimethylamino)phosphonium hexafluorophosphate] (BOP reagent) (97.3 mg, 0.22 mmol). After stirred at ~4° C. to room temperature for 30 minutes, the reaction mixture was added with the amine (3) (79.3 mg, 0.4 mmol) and then heated at 60° C. for one hour. It was then purified through HPLC. Water in the collected Boc-adduct eluents was removed by extraction with DCM (20 ml×2). The combined organic layers were concentrated by rotary evaporation. The residue was re-dissolved in DCM (2 ml) and trifluoroacetic acid (~0.2 ml). It was stirred at 40° C. for 30 minutes to remove the BOC-protection. The reaction mixture was flash purified through HPLC to afford the title compound (C13) as white solid (52.1 mg, 55%).

$^1H$ NMR (300 MHz, DMSO) δ (ppm): 11.75 (s, 1H), 8.09 (d, 1H), 8.95 (s, 1H), 8.52 (m, 1H), 8.35 (s, 1H), 7.75 (m, 1H), 7.01 (d, J=11.2, 1H), 5.96 (d, 1H), 4.10 (s, 1H), 2.85 (m, 2H), 2.67 (m, 2H), 1.38 (m, 1H), 0.75 (br m, 2H).

Table of Formula I compounds where L = S

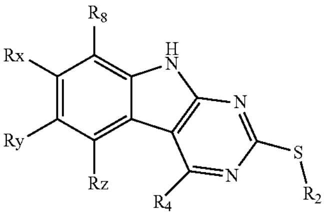

| Cmpd ID | R8 | Rx | Ry | Rz | R4 | R2 |
|---|---|---|---|---|---|---|
| 1.1 | 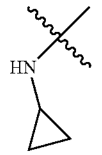 | H | F | H | 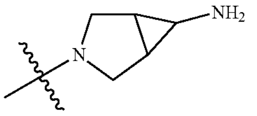 [SMILES: *N1CC2C(N)C2C1] | 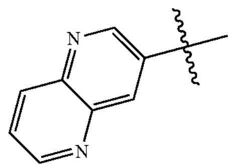 [SMILES: *c1cnc2cccnc2c1] |
| 1.2 | 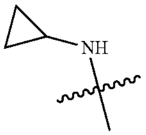 [SMILES: *NC1CC1] | H | F | H | 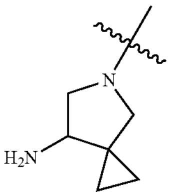 [SMILES: *N1CC(N)C2(CC2)C1] | 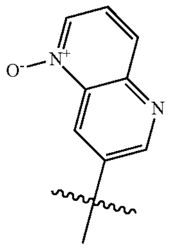 [SMILES: *c1cnc2ccc[n+]([O-])c2c1] |
| 1.3 | Cl | H | H | H | 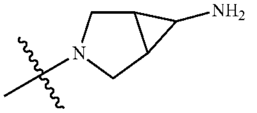 [SMILES: *N1CC2C(N)C2C1] | 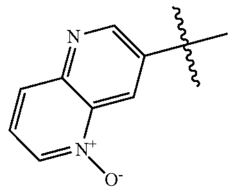 [SMILES: *c1cnc2ccc[n+]([O-])c2c1] |

-continued
Table of Formula I compounds where L = S
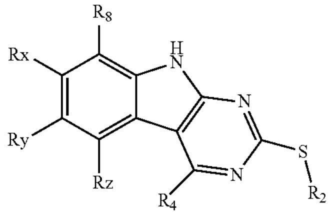
| Cmpd ID | R8 | Rx | Ry | Rz | R4 | R2 |
|---|---|---|---|---|---|---|
| 1.4 | Cl | H | H | H | 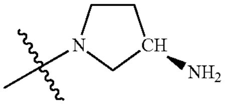 [SMILES: *N1CC[C@@H](N)C1] | 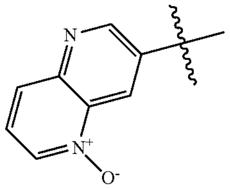 [SMILES: *c1cnc2ccc[n+]([O-])c2c1] |
| 1.5 | H | H | H | H | 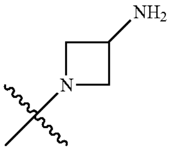 [SMILES: *N1CC(N)C1] | 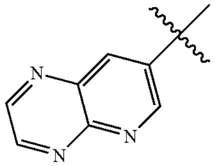 [SMILES: *c1cnc2nccnc2c1] |
| 1.6 | H | H | H | H | 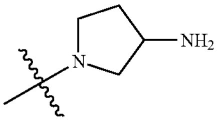 [SMILES: *N1CCC(N)C1] | 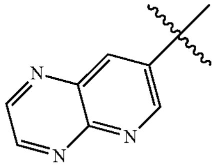 [SMILES: *c1cnc2nccnc2c1] |
| 1.7 | Me | H | H | H | 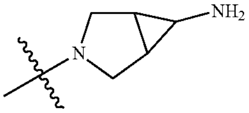 [SMILES: *N1CC2C(N)C2C1] | 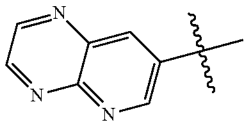 [SMILES: *c1cnc2nccnc2c1] |
| 1.8 | NH2 | H | H | H | 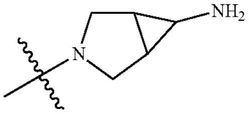 [SMILES: *N1CC2C(N)C2C1] | 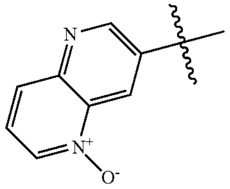 [SMILES: *c1cnc2ccc[n+]([O-])c2c1] |
| 1.9 | NH2 | H | H | H | 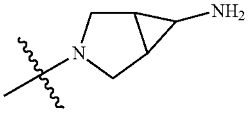 [SMILES: *N1CC2C(N)C2C1] | 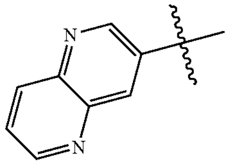 [SMILES: *c1cnc2cccnc2c1] |
| 1.10 | NHEt | H | H | H | 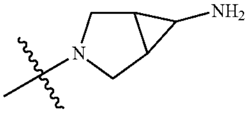 [SMILES: *N1CC2C(N)C2C1] | 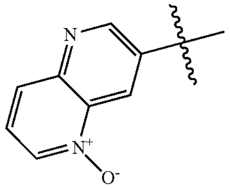 [SMILES: *c1cnc2ccc[n+]([O-])c2c1] |

-continued
Table of Formula I compounds where L = S
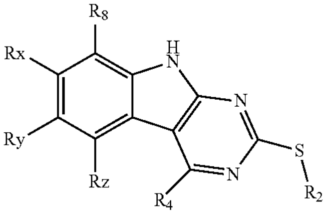
| Cmpd ID | R8 | Rx | Ry | Rz | R4 | R2 |
|---|---|---|---|---|---|---|
| 1.11 | NHEt | H | H | H | 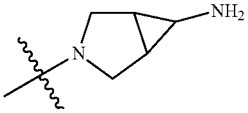 [SMILES: *N1CC2C(N)C2C1] | 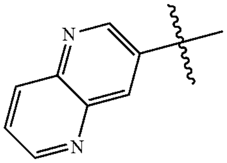 [SMILES: *c1cnc2cccnc2c1] |
| 1.12 | NHMe | H | H | H | 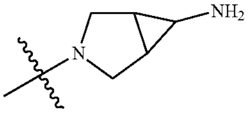 [SMILES: *N1CC2C(N)C2C1] | 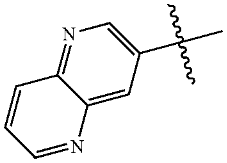 [SMILES: *c1cnc2cccnc2c1] |
| 1.13 | NHMe | H | H | H | 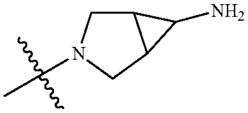 [SMILES: *N1CC2C(N)C2C1] | 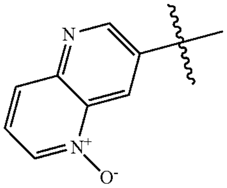 [SMILES: *c1cnc2ccc[n+]([O-])c2c1] |
| 1.14 | NHMe | H | H | H | 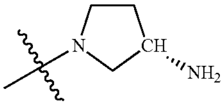 [SMILES: *N1CC[C@H](N)C1] | 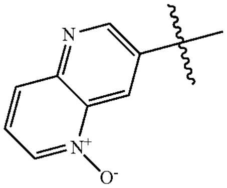 [SMILES: *c1cnc2ccc[n+]([O-])c2c1] |
| 1.15 | NHMe | H | H | H | 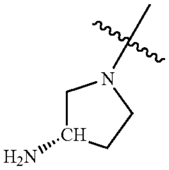 [SMILES: *N1CC[C@H](N)C1] | 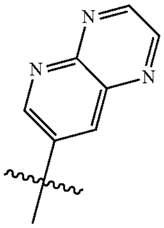 [SMILES: *c1cnc2nccnc2c1] |
| 1.16 | NHMe | H | H | H | 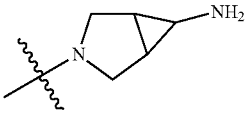 [SMILES: *N1CC2C(N)C2C1] | 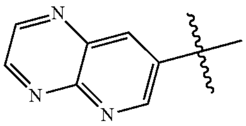 [SMILES: *c1cnc2nccnc2c1] |
| 1.17 | NHMe | H | H | H | 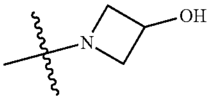 [SMILES: *N1CC(O)C1] | 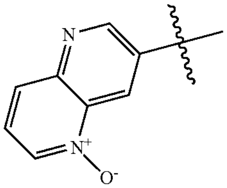 [SMILES: *c1cnc2ccc[n+]([O-])c2c1] |

-continued
Table of Formula I compounds where L = S
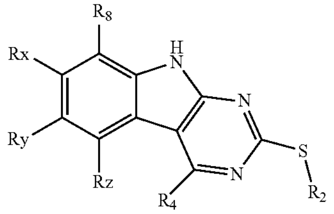
| Cmpd ID | R8 | Rx | Ry | Rz | R4 | R2 |
|---|---|---|---|---|---|---|
| 1.18 | NHMe | H | H | H | 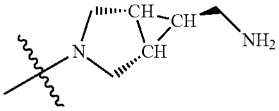 [SMILES: *N1C[C@@H]2[C@@H](CN)[C@@H]2C1] | 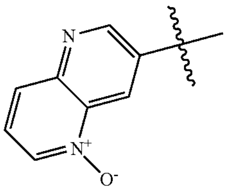 [SMILES: *c1cnc2ccc[n+]([O-])c2c1] |
| 1.19 | NHMe | H | H | H | 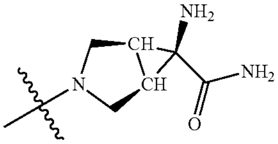 [SMILES: *N1C[C@@H]2[C@H](C1)[C@@]2(N)C(N)=O] | 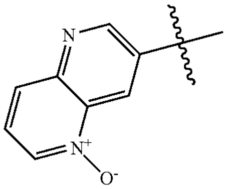 [SMILES: *c1cnc2ccc[n+]([O-])c2c1] |
| 1.20 | NHMe | H | H | H | 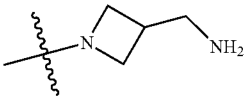 [SMILES: *N1CC(CN)C1] | 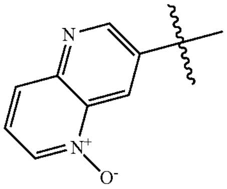 [SMILES: *c1cnc2ccc[n+]([O-])c2c1] |
| 1.21 | NHMe | H | H | H | 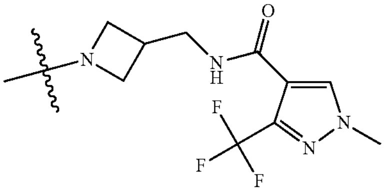 [SMILES: *N1CC(CNC(=O)c2cn(C)nc2C(F)(F)F)C1] | 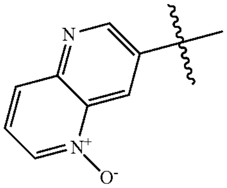 [SMILES: *c1cnc2ccc[n+]([O-])c2c1] |
| 1.22 | NHMe | H | H | H | 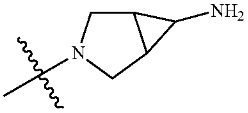 [SMILES: *N1CC2C(N)C2C1] | 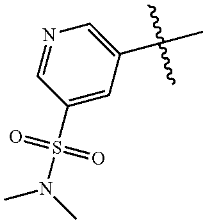 [SMILES: *c1cncc(S(=O)(=O)N(C)C)c1] |
| 1.23 | NHMe | H | H | H | 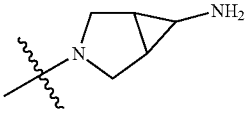 [SMILES: *N1CC2C(N)C2C1] | 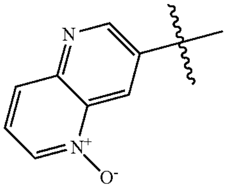 [SMILES: *c1cnc2ccc[n+]([O-])c2c1] |

-continued
Table of Formula I compounds where L = S
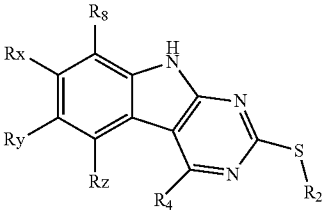
| Cmpd ID | R8 | Rx | Ry | Rz | R4 | R2 |
|---|---|---|---|---|---|---|
| 1.24 | NHMe | H | H | H | 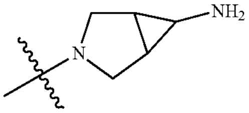 [SMILES: *N1CC2C(N)C2C1] | 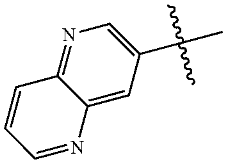 [SMILES: *c1cnc2cccnc2c1] |
| 1.25 | NHMe | H | H | H | 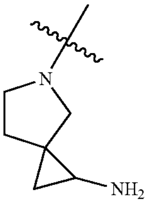 [SMILES: *N1CCC2(CC2N)C1] | 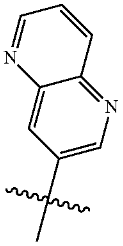 [SMILES: *c1cnc2cccnc2c1] |
| 1.26 | NHMe | H | H | H | 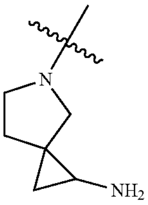 [SMILES: *N1CCC2(CC2N)C1] | 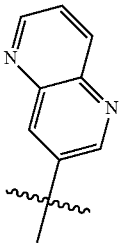 |
| 1.27 | NHMe | H | H | H | 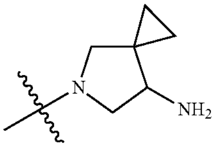 [SMILES: *N1CC(N)C2(CC2)C1] | 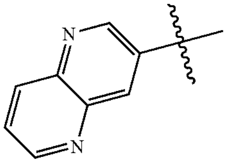 [SMILES: *c1cnc2cccnc2c1] |
| 1.28 | NHMe | H | H | H | 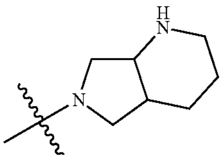 [SMILES: *N1CC2CCCNC2C1] | 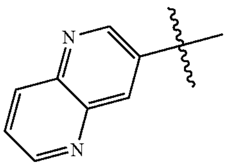 [SMILES: *c1cnc2cccnc2c1] |
| 1.29 | NHMe | H | H | H | 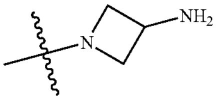 [SMILES: *N1CC(N)C1] | 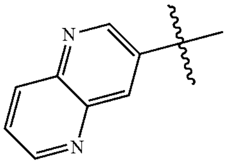 [SMILES: *c1cnc2cccnc2c1] |

-continued
Table of Formula I compounds where L = S
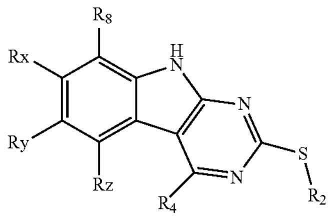
| Cmpd ID | R8 | Rx | Ry | Rz | R4 | R2 |
|---|---|---|---|---|---|---|
| 1.30 | NHMe | H | H | H | 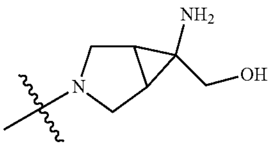 [SMILES: *N1CC2C(C1)C2(N)CO] | 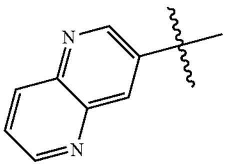 [SMILES: *c1cnc2cccnc2c1] |
| 1.31 | NHMe | H | H | H | 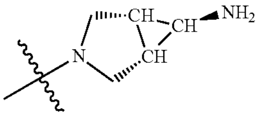 [SMILES: *N1C[C@@H]2[C@@H](N)[C@@H]2C1] | 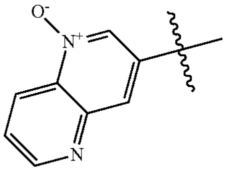 [SMILES: *c1cc2ncccc2[n+]([O-])c1] |
| 1.32 | NHMe | H | H | H | 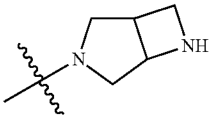 [SMILES: *N1CC2CNC2C1] | 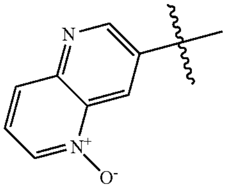 [SMILES: *c1cnc2ccc[n+]([O-])c2c1] |
| 1.33 | NHMe | H | H | H | 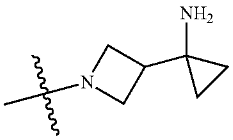 [SMILES: *N1CC(C2(N)CC2)C1] | 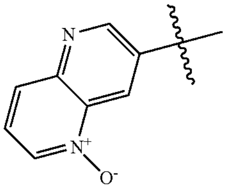 [SMILES: *c1cnc2ccc[n+]([O-])c2c1] |
| 1.34 | NHMe | H | H | H | 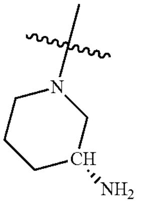 [SMILES: *N1CCC[C@@H](N)C1] | 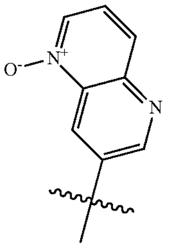 [SMILES: *c1cnc2ccc[n+]([O-])c2c1] |
| 1.35 | NHMe | H | H | H | 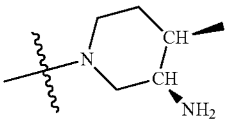 [SMILES: *N1CC[C@@H](C)[C@@H](N)C1] | 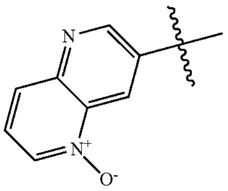 [SMILES: *c1cnc2ccc[n+]([O-])c2c1] |

-continued
Table of Formula I compounds where L = S
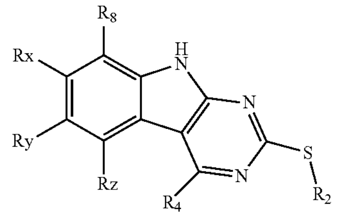
| Cmpd ID | R8 | Rx | Ry | Rz | R4 | R2 |
|---|---|---|---|---|---|---|
| 1.36 | NHMe | H | H | H | 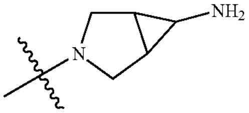 [SMILES: *N1CC2C(N)C2C1] | 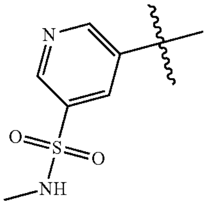 [SMILES: *c1cncc(S(=O)(=O)NC)c1] |
| 1.37 | NHMe | H | H | H | 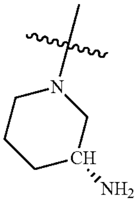 [SMILES: *N1CCC[C@@H](N)C1] | 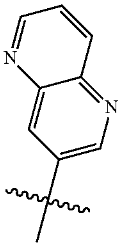 |
| 1.38 | NHMe | H | H | H | 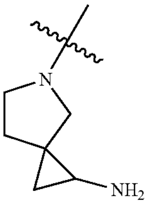 [SMILES: *N1CCC2(CC2N)C1] | 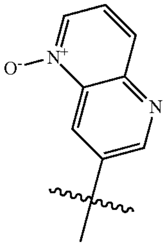 [SMILES: *c1cnc2ccc[n+]([O-])c2c1] |
| 1.39 | NHMe | H | H | H | 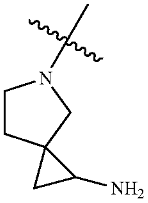 [SMILES: *N1CCC2(CC2N)C1] | 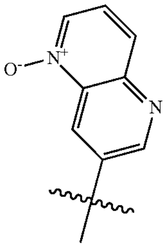 [SMILES: *c1cnc2ccc[n+]([O-])c2c1] |
| 1.40 | NHMe | H | H | H | 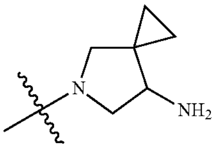 [SMILES: *N1CC(N)C2(CC2)C1] | 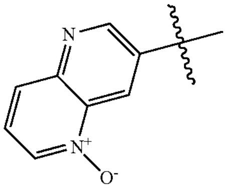 [SMILES: *c1cnc2ccc[n+]([O-])c2c1] |

-continued
Table of Formula I compounds where L = S
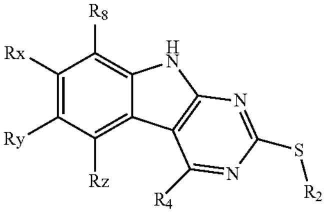
| Cmpd ID | R8 | Rx | Ry | Rz | R4 | R2 |
|---|---|---|---|---|---|---|
| 1.41 | NHMe | H | H | H | 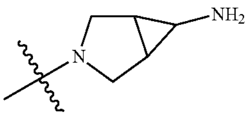 [SMILES: *N1CC2C(N)C2C1] | 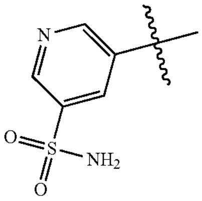 [SMILES: *c1cncc(S(N)(=O)=O)c1] |
| 1.42 | NHMe | H | H | H | 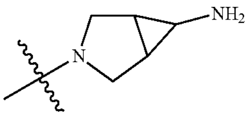 [SMILES: *N1CC2C(N)C2C1] | 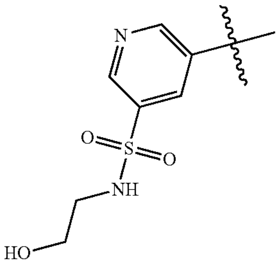 [SMILES: *c1cncc(S(=O)(=O)NCCO)c1] |
| 1.43 | NHMe | H | H | H | 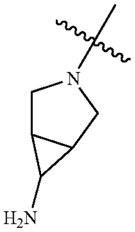 [SMILES: *N1CC2C(N)C2C1] | 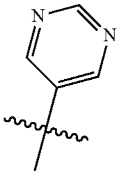 [SMILES: *c1cncnc1] |
| 1.44 | NHMe | H | H | H | 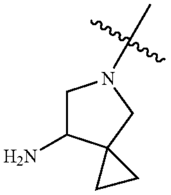 [SMILES: *N1CC(N)C2(CC2)C1] | 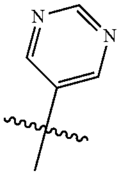 [SMILES: *c1cncnc1] |
| 1.45 | NHMe | H | H | H | 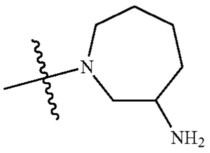 | 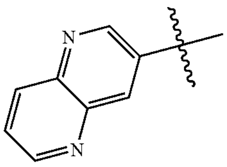 [SMILES: *c1cnc2cccnc2c1] |

-continued
Table of Formula I compounds where L = S
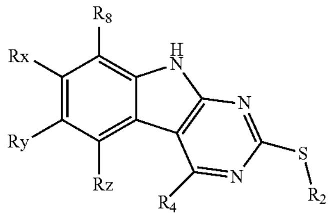
| Cmpd ID | R8 | Rx | Ry | Rz | R4 | R2 |
|---|---|---|---|---|---|---|
| 1.46 | NHMe | H | H | H | 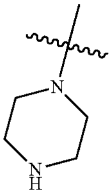 [SMILES: *N1CCNCC1] | 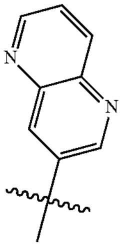 |
| 1.47 | NHMe | H | H | H | 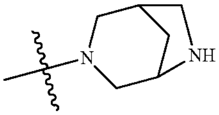 [SMILES: *N1CC2CNC(C2)C1] | 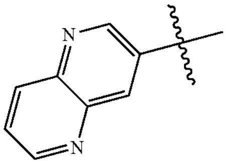 [SMILES: *c1cnc2cccnc2c1] |
| 1.48 | NHMe | H | H | H | 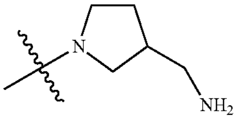 [SMILES: *N1CCC(CN)C1] | 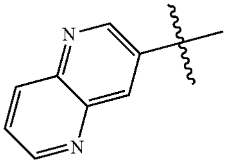 [SMILES: *c1cnc2cccnc2c1] |
| 1.49 | NHMe | H | H | H | 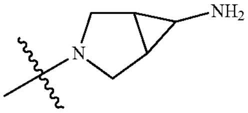 [SMILES: *N1CC2C(N)C2C1] | 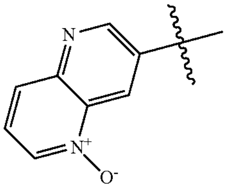 [SMILES: *c1cnc2ccc[n+]([O-])c2c1] |
| 1.50 | NHMe | H | F | H | 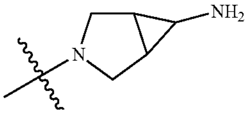 | 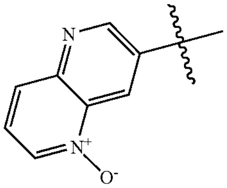 [SMILES: *c1cnc2ccc[n+]([O-])c2c1] |
| 1.51 | NHMe | H | F | H | 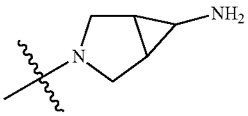 | 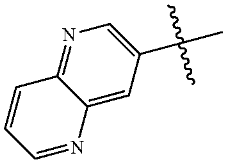 [SMILES: *c1cnc2cccnc2c1] |

-continued
Table of Formula I compounds where L = S
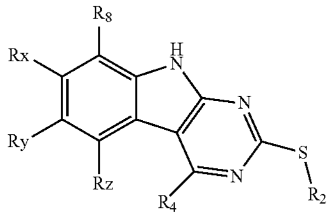
| Cmpd ID | R8 | Rx | Ry | Rz | R4 | R2 |
|---|---|---|---|---|---|---|
| 1.52 | NHMe | H | H | H | 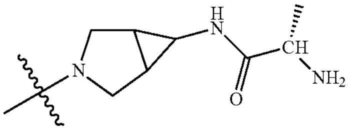 [SMILES: *N1CC2C(C1)C2NC(=O)[C@H](C)N] | 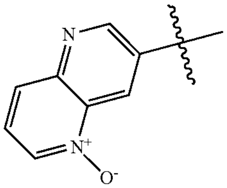 [SMILES: *c1cnc2ccc[n+]([O-])c2c1] |
| 1.53 | NHMe | H | H | H | 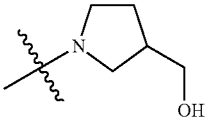 [SMILES: *N1CCC(CO)C1] | 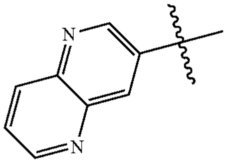 [SMILES: *c1cnc2cccnc2c1] |
| 1.54 | NHMe | H | H | H | 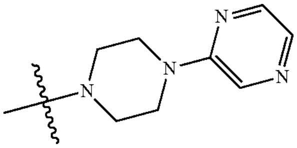 [SMILES: *N1CCN(c2cnccn2)CC1] | 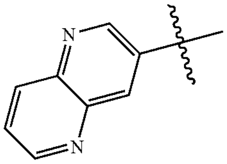 [SMILES: *c1cnc2cccnc2c1] |
| 1.55 | NHMe | H | H | H | 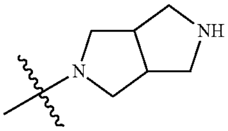 [SMILES: *N1CC2CNCC2C1] | 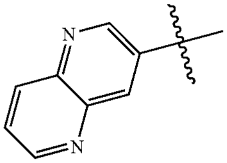 [SMILES: *c1cnc2cccnc2c1] |
| 1.56 | NHMe | H | H | H | 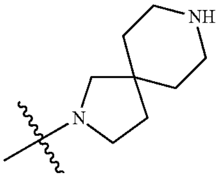 [SMILES: *N1CCC2(CCNCC2)C1] | 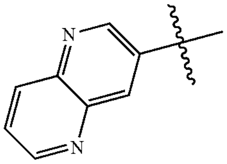 [SMILES: *c1cnc2cccnc2c1] |
| 1.57 | NHMe | H | H | H | 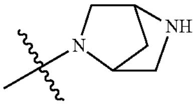 [SMILES: *N1CC2CC1CN2] | 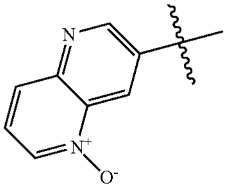 [SMILES: *c1cnc2ccc[n+]([O-])c2c1] |
| 1.58 | NHMe | H | H | Me | 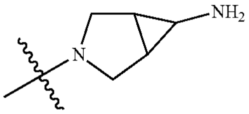 [SMILES: *N1CC2C(N)C2C1] | 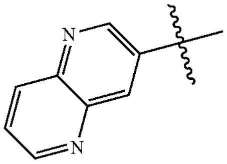 [SMILES: *c1cnc2cccnc2c1] |

-continued
Table of Formula I compounds where L = S
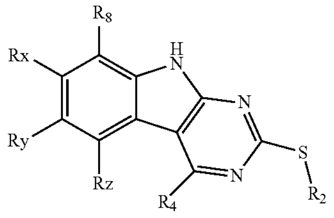
| Cmpd ID | R8 | Rx | Ry | Rz | R4 | R2 |
| --- | --- | --- | --- | --- | --- | --- |
| 1.59 | NHMe | H | H | H | 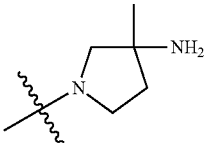 [SMILES: *N1CCC(C)(N)C1] | 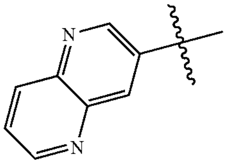 [SMILES: *c1cnc2cccnc2c1] |
| 1.60 | NHMe | H | H | H | 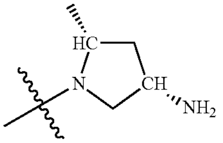 | 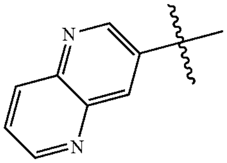 [SMILES: *c1cnc2cccnc2c1] |
| 1.61 | NHMe | H | H | H | 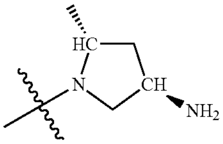 [SMILES: *N1C[C@H](N)C[C@H]1C] | 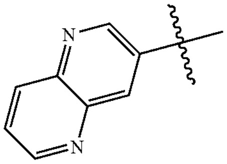 [SMILES: *c1cnc2cccnc2c1] |
| 1.62 | NHMe | H | F | H | 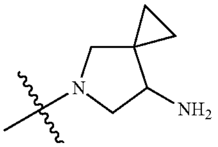 [SMILES: *N1CC(N)C2(CC2)C1] | 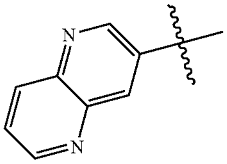 [SMILES: *c1cnc2cccnc2c1] |
| 1.63 | NHMe | H | F | H | 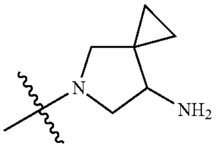 [SMILES: *N1CC(N)C2(CC2)C1] | 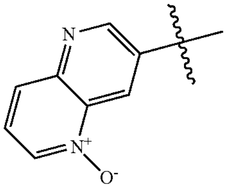 [SMILES: *c1cnc2ccc[n+]([O-])c2c1] |
| 1.64 | NHMe | H | F | H | 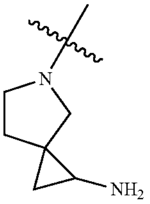 [SMILES: *N1CCC2(CC2N)C1] | 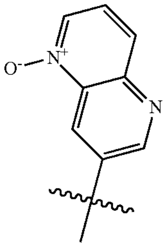 [SMILES: *c1cnc2ccc[n+]([O-])c2c1] |

-continued
Table of Formula I compounds where L = S
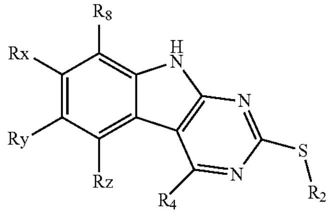
| Cmpd ID | R8 | Rx | Ry | Rz | R4 | R2 |
| --- | --- | --- | --- | --- | --- | --- |
| 1.65 | NHMe | H | F | H | 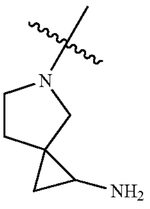 | 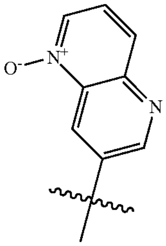 [SMILES: *c1cnc2ccc[n+]([O-])c2c1] |
| 1.66 | NHMe | H | H | H | 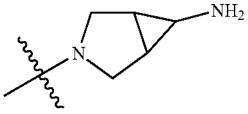 [SMILES: *N1CC2C(N)C2C1] | 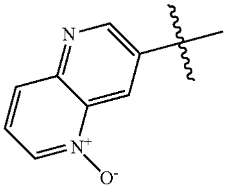 [SMILES: *c1cnc2ccc[n+]([O-])c2c1] |
| 1.67 | NHMe | H | H | H | 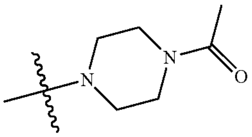 [SMILES: *N1CCN(C(C)=O)CC1] | 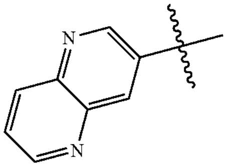 [SMILES: *c1cnc2cccnc2c1] |
| 1.68 | NHMe | H | H | H | 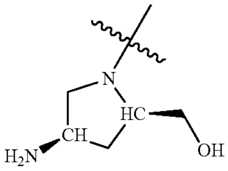 [SMILES: *N1C[C@H](N)C[C@@H]1CO] | 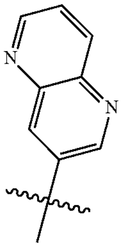 [SMILES: *c1cnc2cccnc2c1] |
| 1.69 | NHMe | H | H | H | 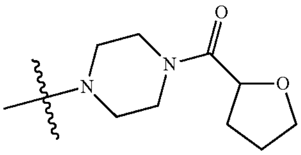 [SMILES: *N1CCN(C(=O)C2CCCO2)CC1] | 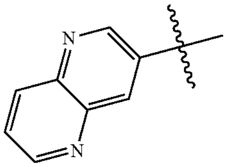 [SMILES: *c1cnc2cccnc2c1] |
| 1.70 | NHMe | H | H | H | 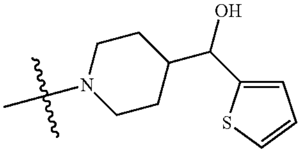 [SMILES: *N1CCC(C(O)c2cccs2)CC1] | 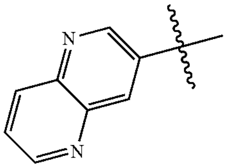 [SMILES: *c1cnc2cccnc2c1] |

-continued
Table of Formula I compounds where L = S
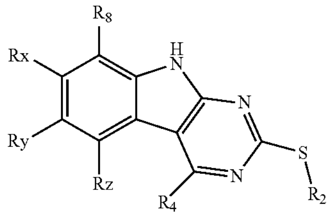
| Cmpd ID | R8 | Rx | Ry | Rz | R4 | R2 |
| --- | --- | --- | --- | --- | --- | --- |
| 1.71 | NHMe | H | H | H | 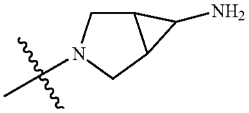 [SMILES: *N1CC2C(N)C2C1] | 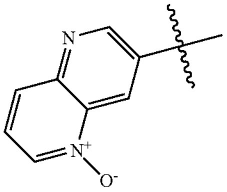 [SMILES: *c1cnc2ccc[n+]([O-])c2c1] |
| 1.72 | NHMe | H | H | Me | 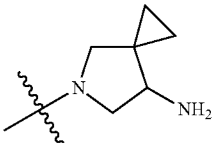 [SMILES: *N1CC(N)C2(CC2)C1] | 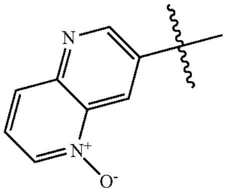 [SMILES: *c1cnc2ccc[n+]([O-])c2c1] |
| 1.73 | NHMe | H | H | Me | 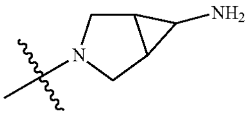 [SMILES: *N1CC2C(N)C2C1] | 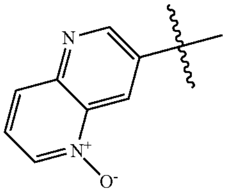 [SMILES: *c1cnc2ccc[n+]([O-])c2c1] |
| 1.74 | NHMe | H | H | H | 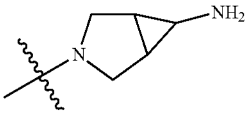 [SMILES: *N1CC2C(N)C2C1] | 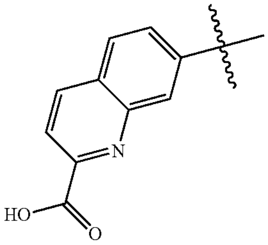 [SMILES: *c1ccc2ccc(C(=O)O)nc2c1] |
| 1.75 | OMe | H | H | H | 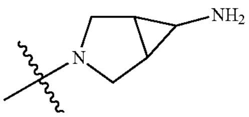 [SMILES: *N1CC2C(N)C2C1] | 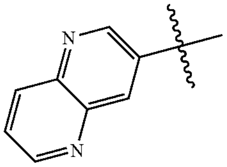 [SMILES: *c1cnc2cccnc2c1] |
| 1.76 | OMe | H | H | H | 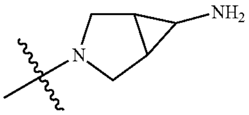 [SMILES: *N1CC2C(N)C2C1] | 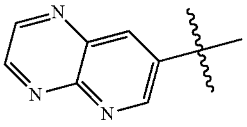 [SMILES: *c1cnc2nccnc2c1] |

-continued

Table of Formula I compounds where L = S

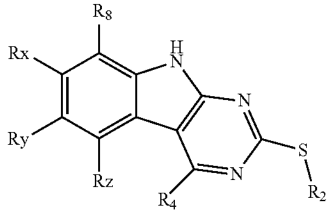

| Cmpd ID | R8 | Rx | Ry | Rz | R4 | R2 |
|---|---|---|---|---|---|---|
| 1.77 | OMe | H | H | H | 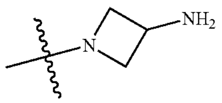 [SMILES: *N1CC(N)C1] | 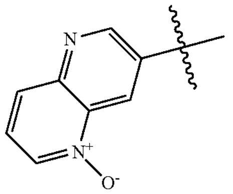 [SMILES: *c1cnc2ccc[n+]([O-])c2c1] |
| 1.78 | OMe | H | H | H | 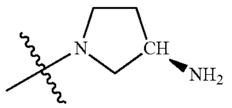 [SMILES: *N1CC[C@@H](N)C1] | 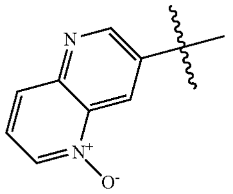 [SMILES: *c1cnc2ccc[n+]([O-])c2c1] |

Section D: Synthesis of Formula 1 Compounds where L=O

Synthesis of Tricyclic Cores L=O where R8 is not NHalkyl

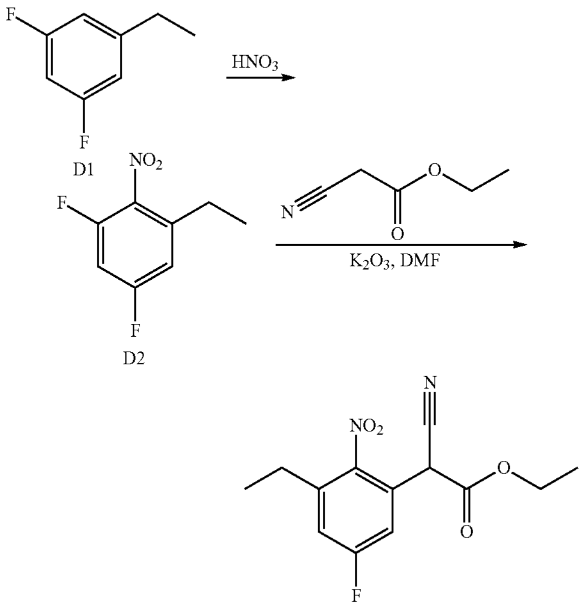

D1

D2

D3

Synthesis of compound D2: To a solution of D1 (40 g, 0.28 mol) in $H_2SO_4$ (200 mL) was added HNO3 (26 g, 0.42 mol) at 0° C. After stirred at 0° C. for 1 h, the mixture was poured into ice water and extracted with ethyl acetate (2×200 mL). The organic layer was dried over $Na_2SO_4$, filtered, concentrated and purified by chromatography on silica gel (petroleum ether/ethyl acetate=15:1) to afford the compound D2 (37 g, yield: 70%) as yellow oil.

$^1$H NMR (400 MHz, $CDCl_3$): δ: 6.93 (s, 1H), 6.91 (s, 1H), 4.33-4.27 (m, 2H), 2.73-2.68 (m, 2H), 1.29-1.25 (t, J=7.6 Hz, 2H).

Synthesis of compound D3: To a solution of 2 (37 g, 0.20 mol) in DMF (200 mL) was added potassium carbonate (54.8 g, 0.40 mol), followed by a portion of ethyl cyano acetate (22.3 g, 0.20 mol). The mixture was stirred at room temperature for 2 h. Then an additional portion of potassium carbonate (54.8 g, 0.40 mol) and a portion of ethyl cyano acetate (22.3 g, 0.20 mol) were added. After the mixture was stirred at room temperature for 4 h, potassium carbonate (27.4 g, 0.2 mol) was added and the mixture was stirred at room temperature for another 12 h. Then the mixture was poured into ice water and extracted with ethyl acetate (2×200 mL). The organic layer was dried over $Na_2SO_4$, filtered, concentrated and purified by chromatography on silica gel (petroleum ether/ethyl acetate=5:1) to afford the compound D3 (25 g, yield: 67%) as yellow solid.

$^1$H NMR (400 MHz, $CDCl_3$): δ: 7.33-7.04 (dd, J=4.4, 2.4 Hz, 1H), 7.16-7.13 (dd, J=4.4, 2.4 Hz, 1H), 5.06 (s, 1H), 4.32-4.27 (m, 2H), 2.74-2.68 (m, 2H), 1.35-1.26 (m, 6H).

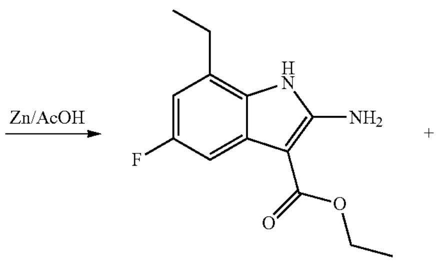

D4

-continued

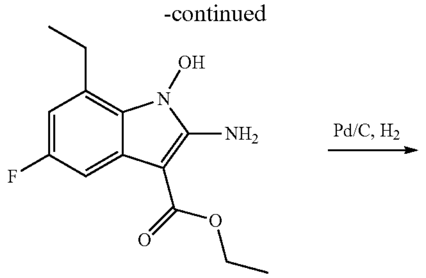

D4'

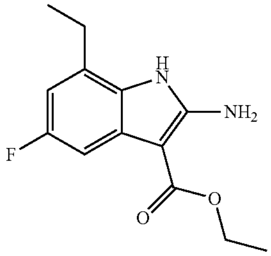

D5

Synthesis of compound D4 and D4': To a solution of D3 (22 g, 79 mmol) in toluene (100 mL) and acetic acid (100 mL) was added zinc powder (30 g, 0.46 mol) and the mixture was stirred at 75° C. for 2 h. Then another Zn powder (10 g, 0.15 mol) was added. After stirred at 75° C. for more 0.5 h, the mixture was cooled to room temperature, filtered and poured into ice water. 2N NaOH was added to adjust the pH to 8-9 and the resultant mixture was extracted with ethyl acetate (2×200 mL). The organic layer was dried over $Na_2SO_4$, filtered, concentrated and purified by chromatography on silica gel (petroleum ether/ethyl acetate=5:1) to afford a brown solid, which was recrystallized in petroleum ether/EtOAc (10:1) to give a mixture of compound D4 and D4' (7.2 g, yield: 35%) as brown solid.

Synthesis of compound D5: A solution of mixture of compound D4 and D4' (5.8 g) in EtOH (100 mL)/HOAc (5 mL) was hydrogenated with catalyst of 10% Pd/C (580 mg) for overnight under 50 Psi pressure. The catalyst was filtered off and the filtrate was concentrated to get compound D5 (5.3 g, yield: 93%).

$^1$H NMR (400 MHz, DMSO-$d_6$): δ: 10.75 (s, 1H), 7.08 (dd, J=9.6, 2.4 Hz, 1H), 6.55 (dd, J=10.8, 2.4 Hz, 1H), 6.44 (s, 2H), 4.21 (q, J=7.2 Hz, 2H), 2.71 (q, J=7.6 Hz, 2H), 1.31 (t, J=6.8 Hz, 3H), 1.20 (t, J=7.6 Hz, 3H). LCMS [mobile phase: 30%-95% Acetonitrile-0.02% NH4Ac in 6 min, finally under these conditions for 0.5 min.] purity is >95%, Rt=2.953 min; MS Calcd.: 250; MS Found: 251 ($[M+1]^+$).

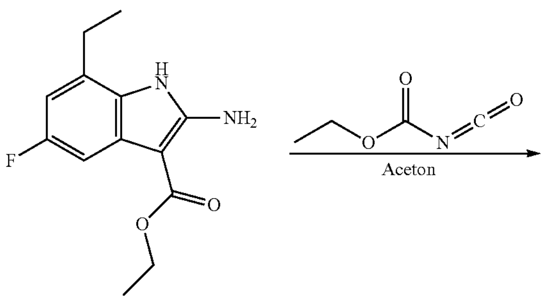

D5

-continued

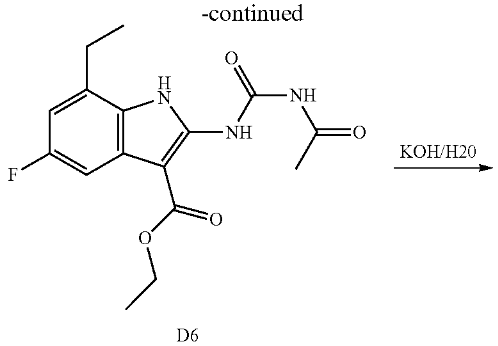

D6

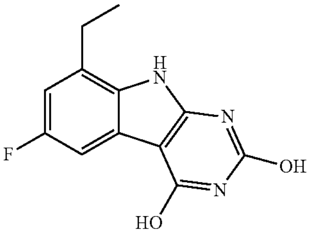

D7

To a stirred suspension of compound D5 (7.4 g, 20 mmol) in acetone (140 mL) was added dropwise a solution of acetyl thioisocynate (12 mL, 140 mmol) in acetone (50 mL) at room temperature. The reaction mixture was heated to reflux for 16 h. LCMS showed the reaction was completed. The reaction mixture was concentrated for next step without purification. LC-MS: M+1: 453.21.

To a stirred suspension of D6 (9.13 g, 20.0 mmol.) in water/EtOH (75 mL/25 mL) was added a KOH solution in 20 mL of water at r.t. After addition, the resulting mixture was reflux for 4 h. TLC showed the reaction was completed, then the reaction was cooled to r.t., acidified with 1M HCl aq. until pH=5, the precipitate was collected by filter, washed with water (200 mL X1) then ethyl acetate (200 mL×1) to give the product D7 as a pale yellow solid. (5.90 g, 87.1% yield). TLC: $R_{f=0.05}$ (silica gel, methanol:DCM=1:10, v/v). LC-MS: M−1: 248.10

$^1$H NMR (400 MHz, DMSO-$d_6$): δ: 11.44 (s, 1H), 10.75 (s, 1H), 7.22 (s, 1H), 7.08 (dd, J=9.6, 2.4 Hz, 1H), 6.55 (dd, J=10.8, 2.4 Hz, 1H), 2.70 (q, J=7.6 Hz, 2H), 1.22 (t, J=7.6 Hz, 3H).

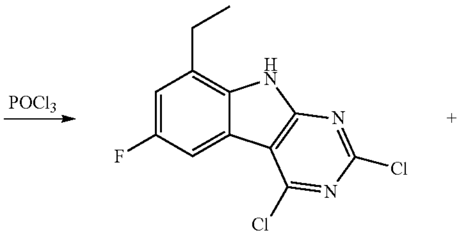

D8

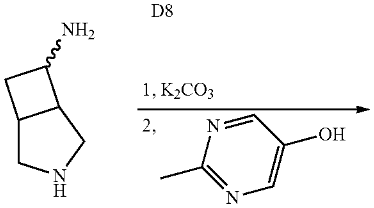

-continued

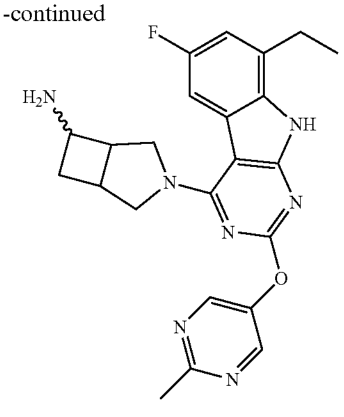

D9 (2.04)

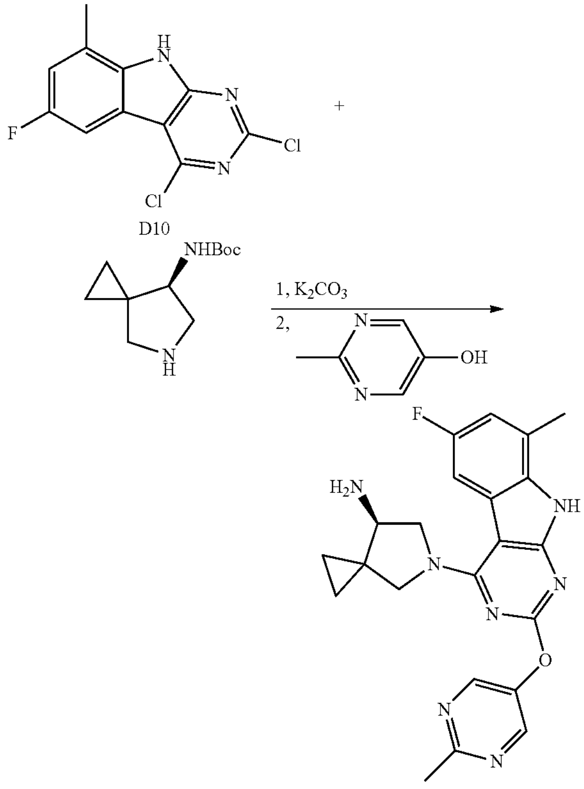

D11 (2.06)

Compound D7 (2 g, 8.06 mmol) was placed with a solution of $POCl_3$ (50 ml) in a pressure tube and few drops of N-ethyldiisopropyl amine. The reaction mixture was heated to at 185° C. under sealed condition over 10 h. The mixture was cooled and poured into ice water and the yellow solid was collected by filtration, dried under reduced press to give D8 (2.1 g, 95% yield) as a yellow solid. LC-MS: M+1: 285.01

To a stirred solution of compound D8 (250 mg, 0.88 mmol) in 2 mL of NMP at 110° C. was added (R)-tert-butyl 5-azaspiro[2.4]heptan-7-ylcarbamate (98 mg, 0.88 mmol) and $K_2CO_3$ (7 mg, 0.05 mmol). After the completion of the reaction in 10 minutes, the reaction mixture was added 2-methylpymiridin-5-ol (28 mg, 0.25 mmol) in a microwave tube. The reaction mixture was sealed and placed in Microwave at 180° C. for 10 minutes. The desired product was obtained by HPLC purification to give D9 (115 mg, 30%) as a white solid. LC-MS: M+1': 434.25.

$^1$H NMR (300 MHz, DMSO-$d_6$): δ: 11.44 (s, 1H), 10.75 (s, 1H), 7.22 (s, 1H), 7.08 (dd, J=9.6, 2.4 Hz, 1H), 6.55 (dd, J=10.8, 2.4 Hz, 1H), 2.70 (q, J=7.6 Hz, 2H), 2.64 (m, 2H), 2.62 (m, 2H), 2.01-2.41 (m, 4H), 1.22 (t, J=7.6 Hz, 3H).

Synthesis of compound D11 (2.06): The subtitle compound was synthesised using the same method described for compound 1629 starting with 2,4-dichloro-6-fluoro-8-methyl-9H-pyrimido[4,5-b]indole and (R)-tert-butyl 5-azaspiro[2.4]heptan-7-ylcarbamate. LC-MS: M+1: 434.25.

$^1$H NMR (300 MHz, DMSO) δ (ppm): 11.75 (s, 1H), 8.72 (s, 2H), 8.09 (br s, 3H), 7.01 (d, J=11.2, 1H), 6.31 (d, J=9.7, 1H), 4.40 (d, J=9.9, 1H), 4.32 (dd, J=7.6, 4.5, 1H), 4.03 (d, J=12.3, 1H), 3.50 (d, J=9.8, 2H), 2.67 (s, 3H), 2.05 (s, 3H), 1.09 (m, 1H), 0.81 (br m, 3H).

Table of Formula I Compounds Where L is O and R8 is not $NHCH_3$

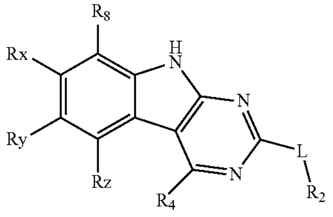

| Cmpd ID | L—R2 | R4 | Rz | Ry | Rx | R8 |
|---|---|---|---|---|---|---|
| 2.1 | 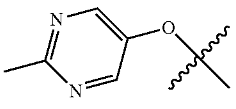 [SMILES: *Oc1cnc(C)nc1] | 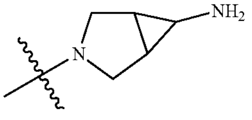 [SMILES: *N1CC2C(N)C2C1] | H | F | H | 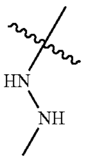 |

-continued
| | | | | | | |
|---|---|---|---|---|---|---|
| 2.2 | 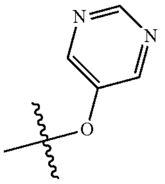 [SMILES: *Oc1cncnc1] | 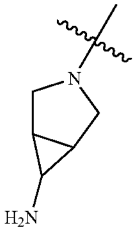 [SMILES: *N1CC2C(N)C2C1] | H | F | H | Et |
| 2.3 | 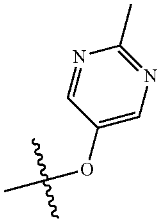 [SMILES: *Oc1cnc(C)nc1] | 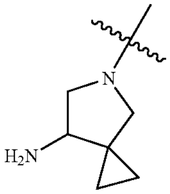 [SMILES: *N1CC(N)C2(CC2)C1] | H | F | H | Et |
| 2.4 | 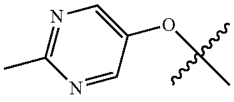 [SMILES: *Oc1cnc(C)nc1] | 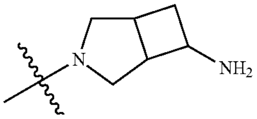 | H | F | H | Et |
| 2.5 | 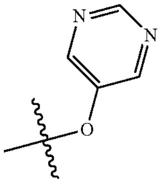 [SMILES: *Oc1cncnc1] | 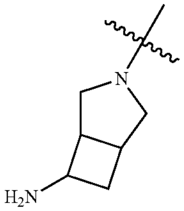 [SMILES: *N1CC2CC(N)C2C1] | H | F | H | Et |
| 2.6 | 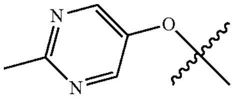 [SMILES: *Oc1cnc(C)nc1] | 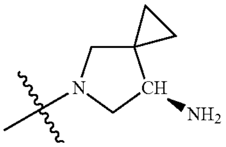 [SMILES: *N1C[C@H](N)C2(CC2)C1] | H | F | H | Me |
| 2.7 | 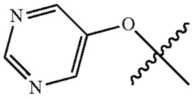 [SMILES: *Oc1cncnc1] | 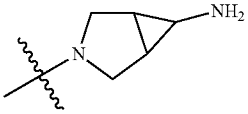 [SMILES: *N1CC2C(N)C2C1] | H | F | H | Me |
| 2.8 | 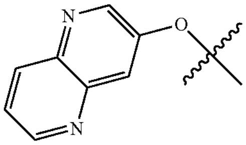 [SMILES: *Oc1cnc2cccnc2c1] | 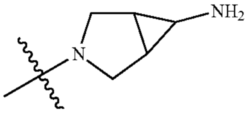 [SMILES: *N1CC2C(N)C2C1] | H | H | H | NH2 |
| 2.9 | 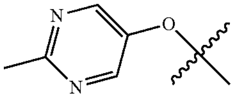 [SMILES: *Oc1cnc(C)nc1] | 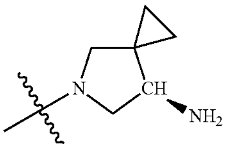 [SMILES: *N1C[C@H](N)C2(CC2)C1] | H | F | H | NH2 |

-continued
| | | | | | | |
|---|---|---|---|---|---|---|
| 2.10 | 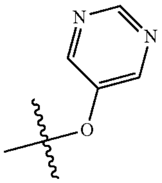 [SMILES: *Oc1cncnc1] | 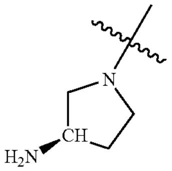 [SMILES: *N1CC[C@@H](N)C1] | H | H | H | OMe |
| 2.11 | 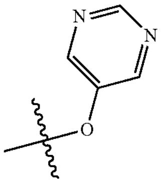 [SMILES: *Oc1cncnc1] | 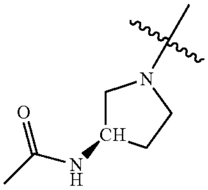 [SMILES: *N1CC[C@@H](NC(C)=O)C1] | H | H | H | OMe |
| 2.12 | 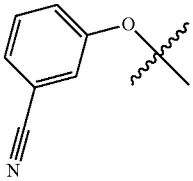 [SMILES: *Oc1cccc(C#N)c1] | 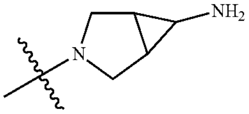 | H | H | H | OMe |
| 2.13 | 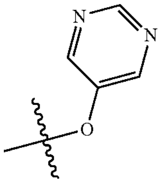 [SMILES: *Oc1cncnc1] | 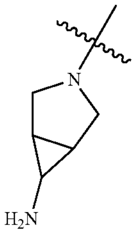 | H | H | H | OMe |
| 2.14 | 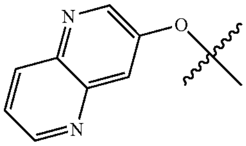 [SMILES: *Oc1cnc2cccnc2c1] | 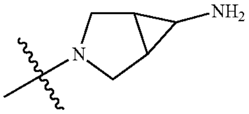 [SMILES: *N1CC2C(N)C2C1] | H | H | H | OMe |
| 2.15 | 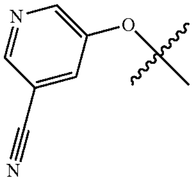 [SMILES: *Oc1cncc(C#N)c1] | 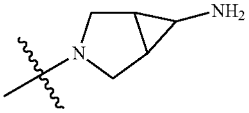 [SMILES: *N1CC2C(N)C2C1] | H | H | H | OMe |
| Cmpd ID | |
|---|---|
| 2.160 | 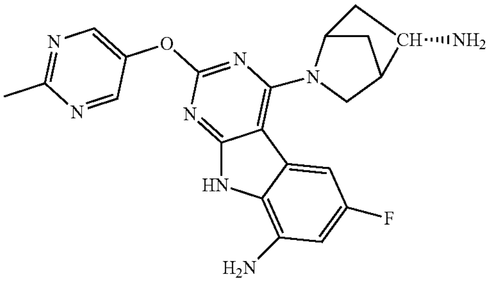 [SMILES: Cc1ncc(Oc2nc(N3CC4CC3C[C@@H]4N)c3c(n2)[nH]c2c(N)cc(F)cc23)cn1] |

Synthesis of Formula I Compounds where L=O and R8 is NHalkyl
General Scheme for the bis-sulfone Route:
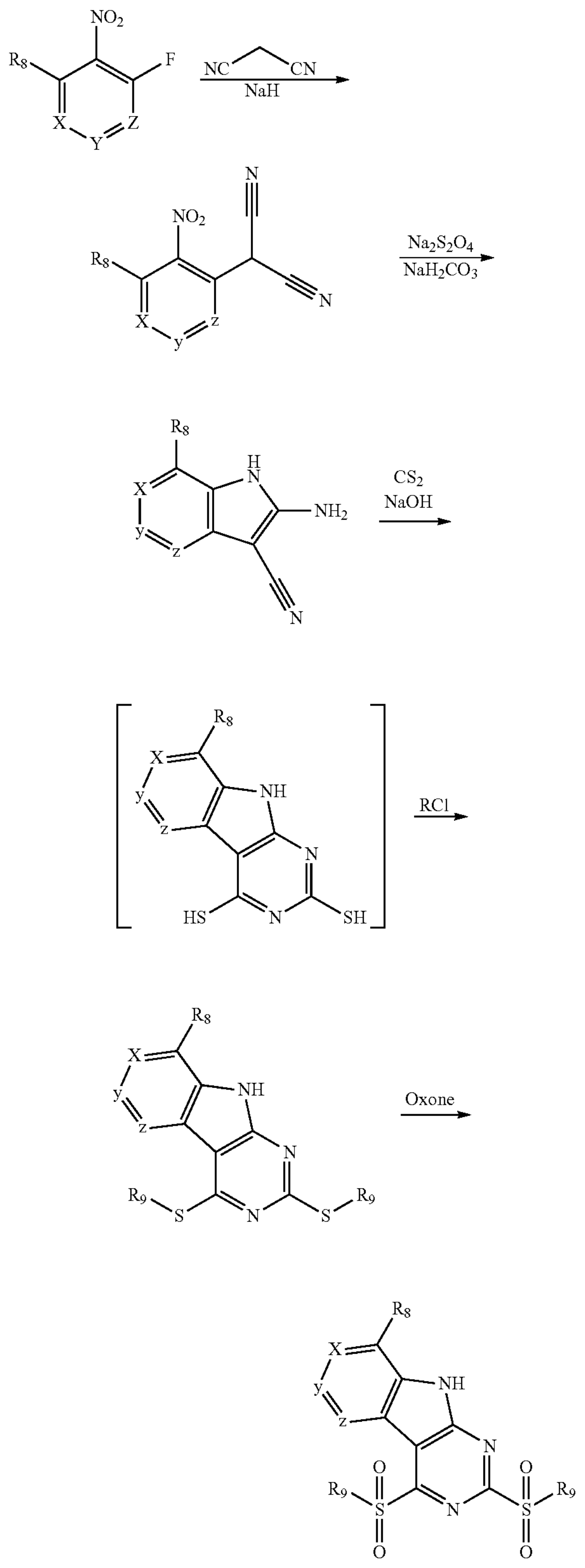
Experimental
Scheme
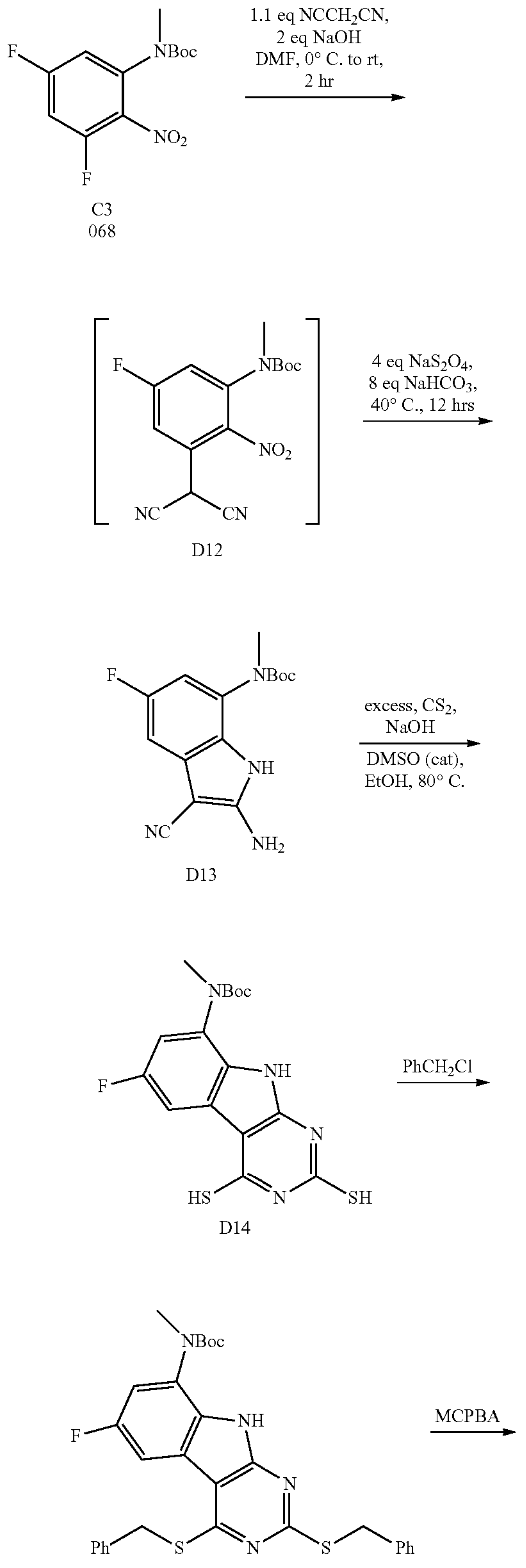
C3
068
D12
D13
D14
D15

-continued

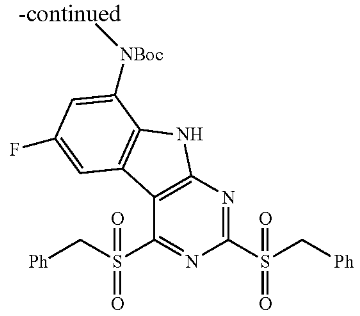

D16

Tert-butyl 2-amino-3-cyano-5-fluoro-1H-indol-7-yl (methyl)carbamate (D13)

Crude tert-butyl 3,5-difluoro-2-nitrophenyl(methyl)carbamate (C3) (46.12 g, 0.162 mol) was dissolved in DMF (80 ml) and cooled in an ice-water bath. To it was added malononitrile (11.8 g, 179 mmol) followed by the addition of the NaOH solution (12.98 g, 325 mmol) in water (20 ml). After the exothermic reaction mixture was stirred for one hour, the ice-water bath was removed and the reaction was stirred for another one hour. It was then diluted with DMF (80 ml) and water (80 ml), and the atmosphere was displaced with argon. Sodium bicarbonate (109 g, 1.3 mol) followed by sodium hydrosulfite (123 g, 649 mmol) was added. The mixture was well stirred under argon at 40° C. for 12 hours (Additional sodium hydrosulfite could be added if the reaction took longer time to complete). After the reaction was cooled down to room temperature, it was diluted with EtOAc (100 ml) and then filtered through a flitted glass funnel. The solids were washed with EtOAc/hexane (1:1, 400 ml). The aqueous layer was separated, and the organic layer was extracted with 10% buffer 7 solution (3×100 ml). The combined aqueous layers were back extracted with EtOAc/hexane (1:1, 200 ml). The combined organic phases was washed with 5% $K_2CO_3$ solution (300 ml). The extractions were then dried over sodium sulfate and concentrated by rotary evaporation to afford the crude compound (D13) as brown color solid (32.6 g, 66%). LC-MS: M+1: 305.16.

$^1$H NMR (DMSO, 300 MHz): δ=10.77 (s, 1H), 6.84-6.80 (m, 1H), 6.69 (s, 2H), 6.69-6.66 (m, 1H), 3.14 (s, 3H), 1.33 (s, 9H).

Tert-butyl 2,4-bis(benzylthio)-6-fluoro-9H-pyrimido [4,5-b]indol-8-yl(methyl)carbamate (D15)

Crude tert-butyl 2-amino-3-cyano-5-fluoro-1H-indol-7-yl (methyl)carbamate (D13) (4 g, 13.14 mmol), sodium hydroxide (756 mg, 18.9 mmol), and EtOH (40 ml) were added in a 350 ml seal tube. The mixture was stirred at 50° C. for 15 mins to dissolve all NaOH and then cooled down to room temperature. After the atmosphere was displaced with argon, the solution was added with carbon disulfide (10 ml) and dimethyl sulfoxide (1 ml). The reaction was stirred at room temperature for 1 hour then refluxed at 80° C. for 42 hours. It was then cooled down to room temperature and placed in an ice-water bath. Water (20 ml) was added followed by the addition of benzyl chloride (3.33 g, 26.27 mmol). The ice-water bath was removed, and the reaction was stirred at ambient temperature for 5 hours. An additional of benzyl chloride (1.66 g, 13.13 mmol) was added, and the resulting solution was stirred at room temperature overnight. It was diluted with EtOAc (60 ml) and water (100 ml). The resulting solution was partitioned into two layers, and the aqueous phase was removed through an extraction funnel and back extracted with 50 ml of ethyl acetate. The combined organic layers were concentrated by rotary evaporation, and the residue was purified through silica gel column chromatography (15% EtOAc in hexane) to afford the tile compound (D15) as yellow foam (2.65 g, 36%). LC-MS: M+1: 561.05.

$^1$H NMR ($CDCl_3$, 300 MHz): δ=8.72 (s, 1H), 7.66-7.62 (dd, J=8.37, 2.28 Hz, 1H), 7.48-7.27 (m, 10H), 7.05-7.01 (dd, J=10.14, 2.28 Hz, 1H), 4.69 (s, 2H), 4.55 (s, 2H), 3.37 (s, 3H), 1.48 (s, 9H).

Tert-butyl 2,4-bis(benzylsulfonyl)-6-fluoro-9H-pyrimido[4,5-b]indol-8-ylmethyl)carbamate (D16)

The solution of tert-butyl 2,4-bis(benzylthio)-6-fluoro-9H-pyrimido[4,5-b]indol-8-yl(methyl)carbamate (D15) (2.28 g, 4.07 mmol) in DCM (50 ml) was cooled in an ice-water bath and added with 3-chloroperoxybenzoic acid 77% (2.01 g, 8.95 mmol). After the reaction was stirred for 1 hour, the ice-water bath was removed and an additional mCPBA (2.01 g) was added. The resulting solution was stirred at ambient temperature for 7 hours. It was then extract with 5% $K_2CO_3$ solution (100 ml), and the aqueous layer was back extracted with DCM (100 ml). The combined organic layers were washed first with 5% $K_2CO_3$ (100 ml) then with 5% NaCl solution (50 ml). It was dried over sodium sulfate and concentrated by rotary evaporation to afford the crude title compound (D16) as bright yellow solid (2.54 g, quantitative yield). LC-MS: M+1: 625.05.

$^1$H NMR ($CDCl_3$, 300 MHz): δ=10.07 (s, 1H), 8.49-8.46 (dd, J=8.64, 2.22 Hz, 1H), 7.54-7.51 (m, 1H), 7.38-7.27 (m, 10H), 4.95 (s, 2H), 4.84 (s, 2H), 3.40 (s, 3H), 1.52 (s, 9H).

Scheme:

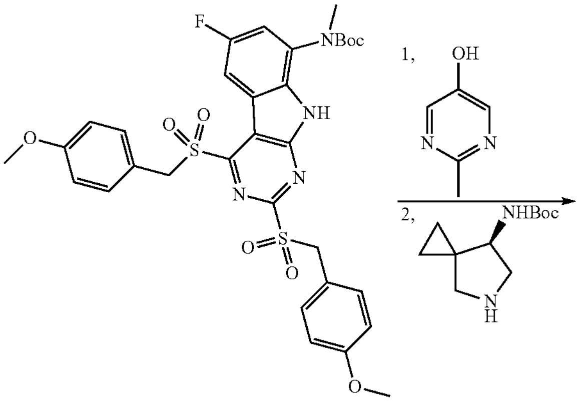

D16

-continued

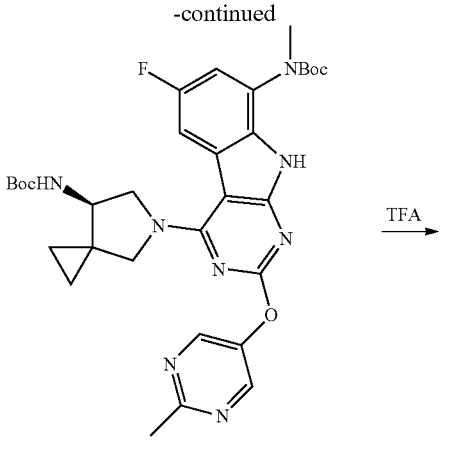

D17

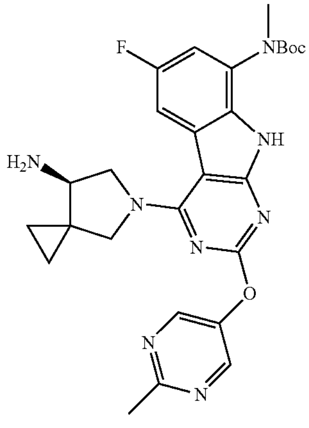

D18 (4.069)

Preparation of D17: The bis-sulfone 2 (11.80 g, 17.23 mmol) was dissolved in NMP (60 mL), followed by adding 2-methylpyrimidin-5-ol 1 (7.59 g, 68.93 mmol). The homogeneous solution was obtained. $K_2CO_3$ (9.53 g, 68.93 mmol) was added and the resulting suspension was heated to 100 C for 1 hr, then Boc protected amine (7.32 g, 34.46 mmol) was added and the resulting mixture was heated to 100 C for one more hour, cooled to the room temperature and water (450 mL) was poured into the mixture with stirring. The mixture was cooled to 0 C, filtered and washed the precipitates with water (2×25 mL), dried to give about 12 g of the white solid crude product. The crude solid was dissolved in dichloromethane and silica gel was added. Solvents were removed. Flash chromatography of the residue over silica gel (EtOAc/hexane: 20% to 50% to 90%) to give the pure D17 as a white solid (7.76 g, 75%). LC-MS: M+1: 635.30.

Preparation of D18 (4.069):

The compound D17 was dissolved in 50 mL of TFA and stirred for 1 minute at room temperature. After removal of the solvent, water (50 mL) and EtOH (25 mL) was added. The homogeneous solution was neutralized with 1N NaOH (about 150 mL, PH>10). The gummy solid was formed and separated. The gummy solid was suspended in water (50 mL) and broke the gummy solid into small pieces with spatula. The precipitates were filtered, washed with water twice and dried in the air to give 4.40 gram pure D18 (4.069) as a light white solid (85%, overall 63% from D16). LC-MS: M+1: 435.24.

$^1$H NMR (300 MHz, DMSO) δ (ppm): 11.75 (s, 1H), 8.72 (s, 2H), 8.09 (br s, 3H), 7.01 (d, J=11.2, 1H), 6.31 (d, J=9.7, 1H), 4.40 (d, J=9.9, 1H), 4.32 (dd, J=7.6, 4.5, 1H), 4.03 (d, J=12.3, 1H), 3.50 (d, J=9.8, 2H), 2.85 (s, 3H), 2.67 (s, 3H), 1.09 (m, 1H), 0.81 (br m, 3H).

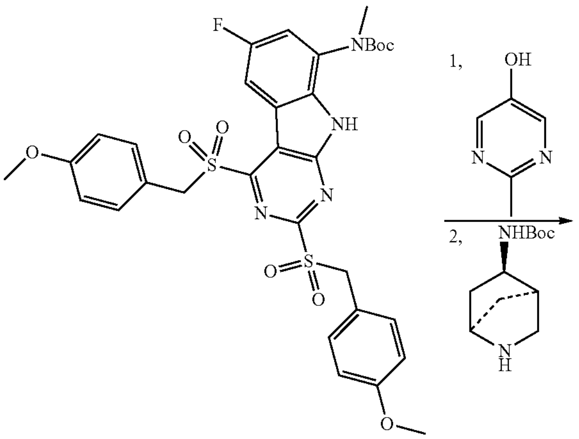

D16

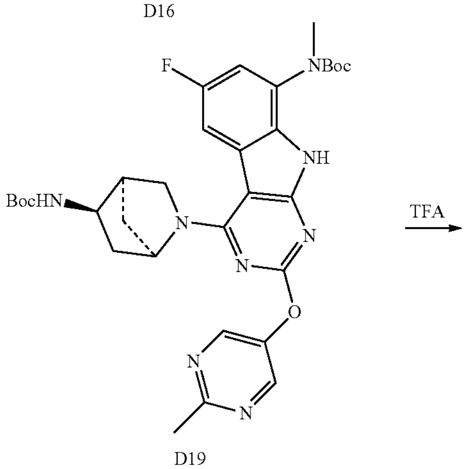

D19

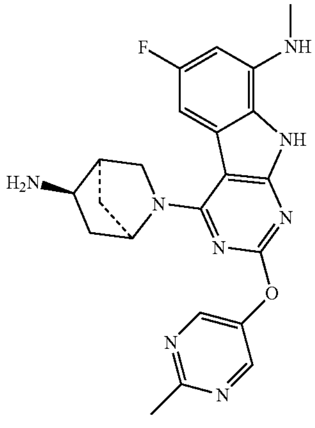

D20 (4.131)

Preparation of $D_2O$ (4.131): The subtitle compound was synthesised using the method described above starting with tert-butyl (1R,4R,5R)-2-azabicyclo[2.2.1]heptan-5-ylcarbamate.

LC-MS: M+1: 435.24.

$^1$H NMR (500 MHz, DMSO) δ (ppm): 11.75 (brm, 1H), 8.92 (brm, 1H), 8.66 (brs, 1H), 7.44 (d, J=9.7, 1H), 7.04 (d, J=5.2), 6.31 (d, J=12.2, 1H), 5.56 (s, 1H), 4.38 (m, 1H), 4.04

(s, 1H), 3.37 (m, 1H), 3.01 (m, 1H), 2.87 (m, 1H), 2.85 (m, 3H), 2.66 (s, 3H), 2.16 (m, 1H), 1.86 (m, 1H), 1.79 (m, 1H), 1.75 (m, 1H).

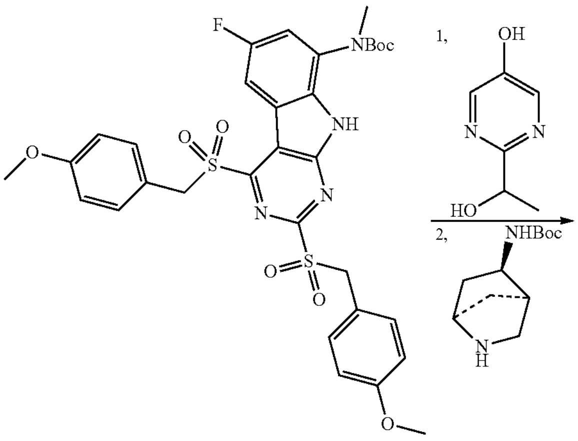

D16

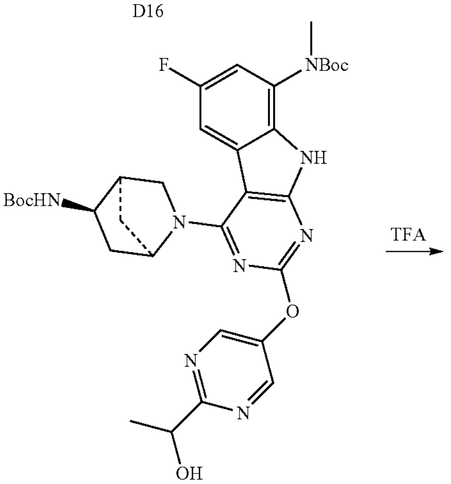

D21

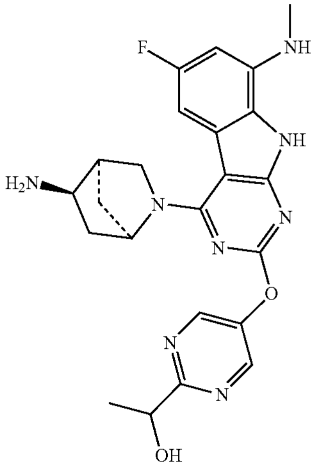

D22 (4.408)

Preparation of D22 (4.408): The subtitle compound was synthesised using the method described above starting with 2-(1-hydroxyethyl)pyrimidin-5-ol.

LC-MS: M+1: 465.22.

$^1$H NMR (300 MHz, DMSO) δ (ppm): 11.75 (s, 1H), 8.72 (s, 2H), 7.01 (d, J=11.2, 1H), 6.31 (d, J=9.7, 1H), 4.82 (brm, 1H), 4.02 (m, 1H), 3.81 (m, 1H), 3.49 (m, 1H), 2.85 (s, 3H), 2.63 (brs, 1H), 2.14 (m, 1H), 1.65-182 (m, 2H), 1.47 (d, 3H), 1.38 (m, 1H).

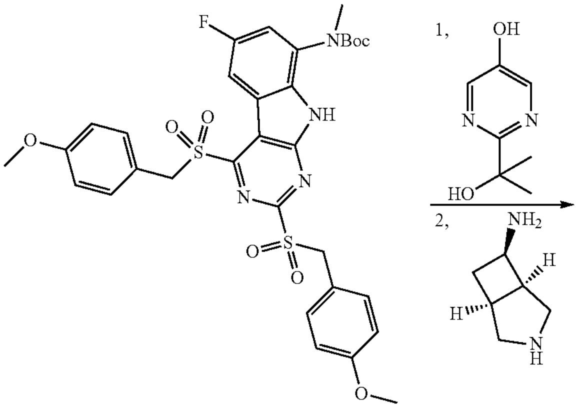

D16

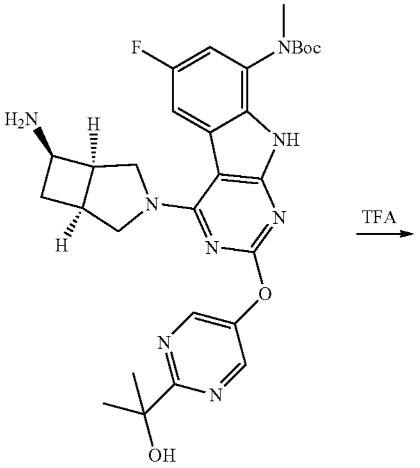

D23

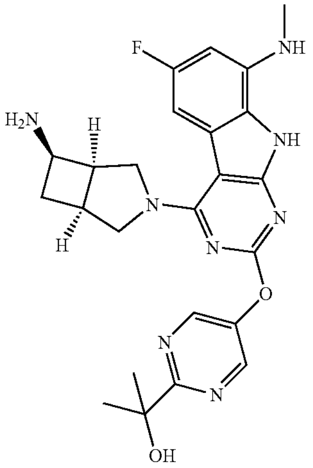

D24 (4.412)

Preparation of D24 (4.412): The subtitle compound was synthesised using the method described above starting with 2-(2-hydroxypropan-2-yl)pyrimidin-5-ol and (6R)-3-azabicyclo[3.2.0]heptan-6-amine.

LC-MS: M+1: 479.25.

$^1$H NMR (500 MHz, DMSO) δ (ppm): 11.35 (brm, 1H), 8.82 (s, 2H), 7.07 (d, J=9.7, 1H), 6.31 (d, J=12.2, 1H), 5.63

(m, 2H), 5.11 (brs, 1H), 4.67 (m, 1H), 3.96 (m, 1H), 3.33-3.53 (m, 6H), 3.01 (m, 1H), 2.85 (s, 3H), 2.70 (m, 1H), 2.51 (m, 1H), 1.55 (s, 6H).

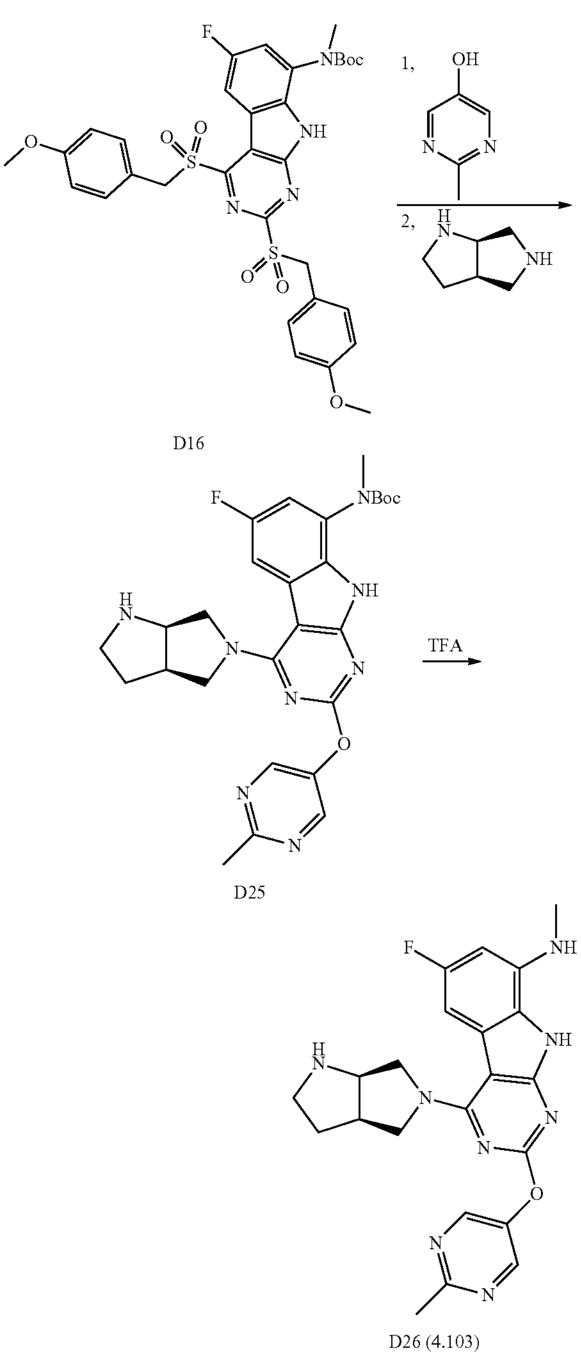

D16

D25

D26 (4.103)

Preparation of D26 (4.103): The subtitle compound was synthesised using the method described above starting with (3aR,6aR)-octahydropyrrolo[3,4-b]pyrrole.

LC-MS: M+1: 435.21.

$^1$H NMR (300 MHz, DMSO) δ (ppm): 8.71 (s, 2H), 6.96 (d, J=11.2, 1H), 6.28 (d, J=11.9, 1H), 5.56 (m, 1H), 3.85 (m, 1H), 3.73 (m, 1H), 3.68 (d, J=11.2, 1H), 3.60 (d, J=11.3, 1H), 2.92 (m, 1H), 2.83 (m, 4H), 2.77 (m, 1H), 2.67 (s, 3H), 1.85 (m, 1H), 1.62 (m, 1H).

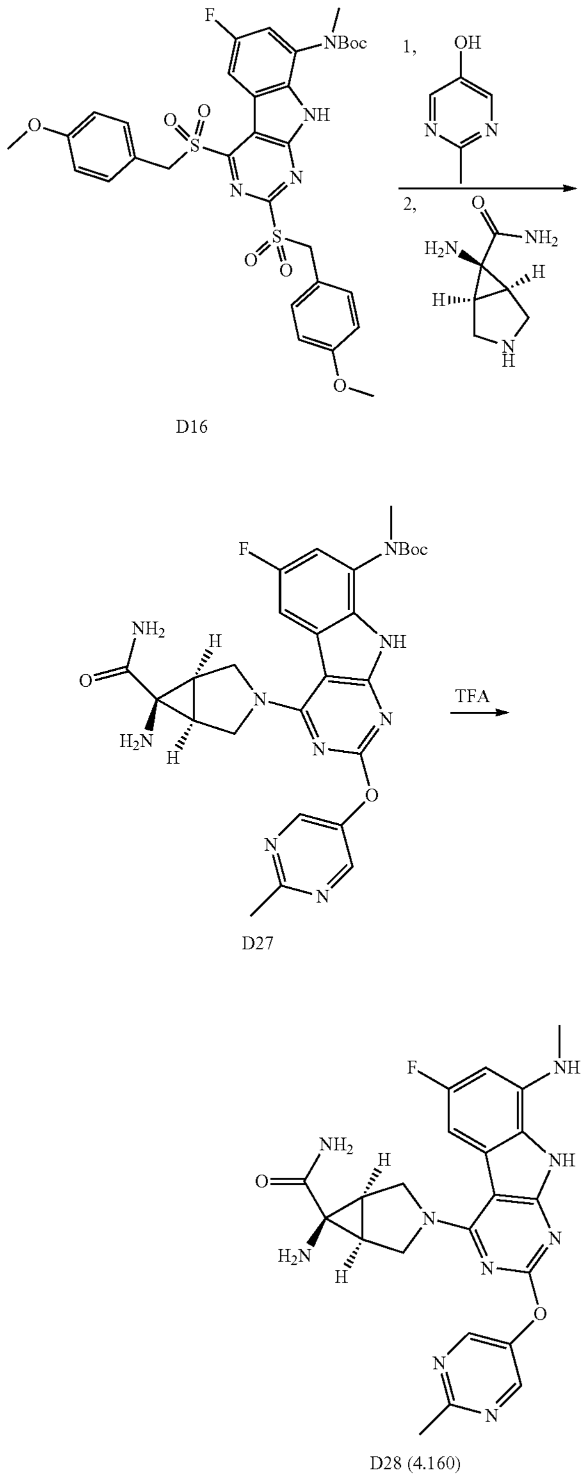

D16

D27

D28 (4.160)

Preparation of D28 (4.160): The subtitle compound was synthesised using the method described above starting with (1R,5S,6r)-6-amino-3-azabicyclo[3.1.0]hexane-6-carboxamide. LC-MS: M+1: 435.24.

$^1$H NMR (300 MHz, DMSO) δ (ppm): 11.05 (s, 1H), 8.72 (s, 2H), 7.21 (s, 2H), 7.01 (d, J=11.2, 1H), 6.11 (d, J=9.7, 1H), 5.01 (s, 2H), 4.03 (d, J=12.3, 1H), 2.95 (s, 3H), 2.81 (m, 2H), 2.75 (m, 2H), 2.67 (s, 3H), 0.85 (br m, 2H).

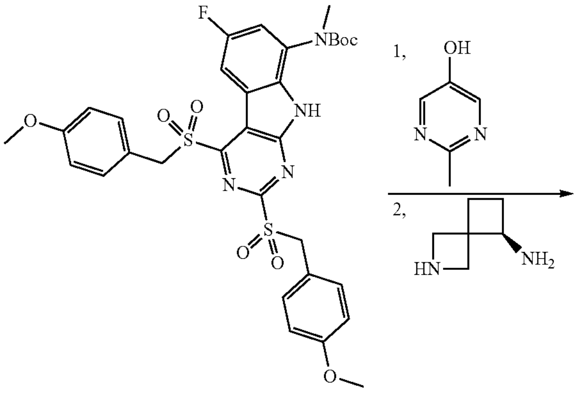

D16

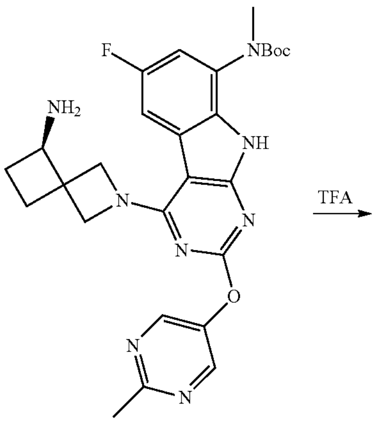

D29

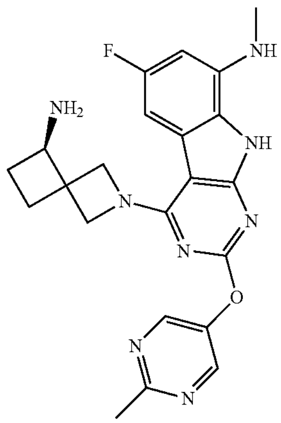

D30 (4.105)

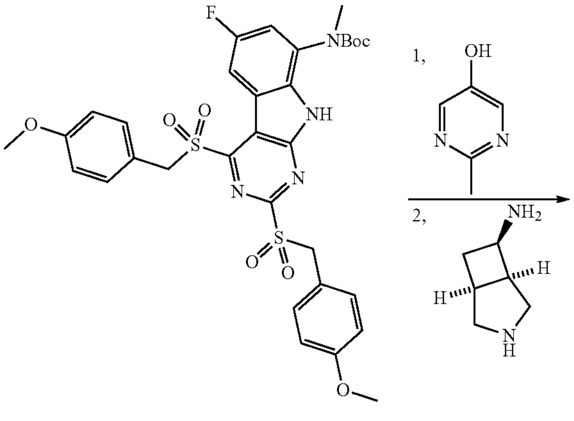

D16

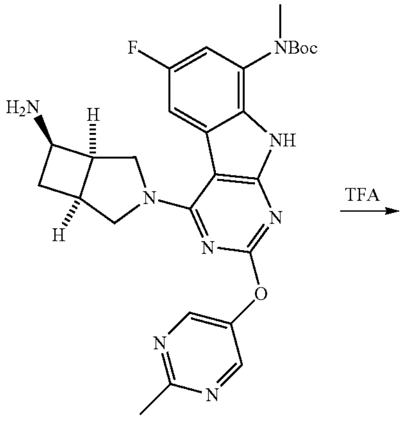

D31

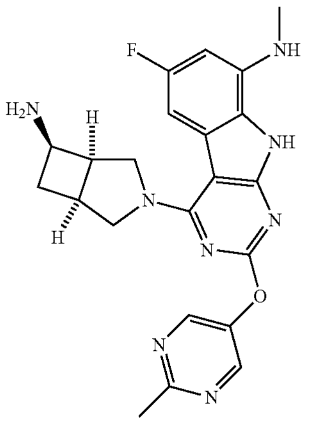

D32 (4.084)

The subtitle compound D30 was synthesised using the same method described for the above compound starting with bis-sulfone and (R)-2-azaspiro[3.3]heptan-5-amine (the diamine was prepared from chiro column seperation from commercially available racemics). LC-MS: M+1: 435.21.

The subtitle compound D32 was synthesised using the same method described for the above compound starting with bis-sulfone and (1S,5R,6R)-3-azabicyclo[3.2.0]heptan-6-amine (the diamine was prepared according patent procedure PCT Int. Appl. (1994), WO 9415933 A1 19940721 and the separation from chiro column). LC-MS: M+1: 435.21.

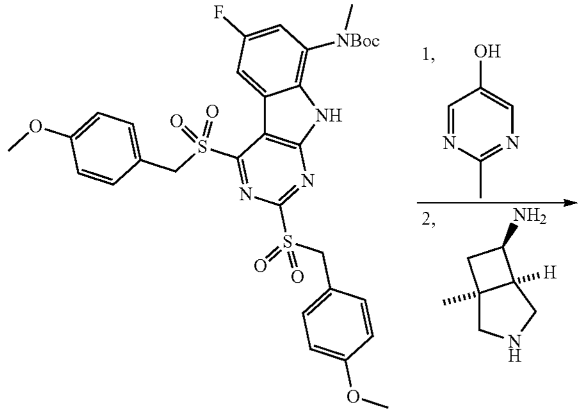

D16

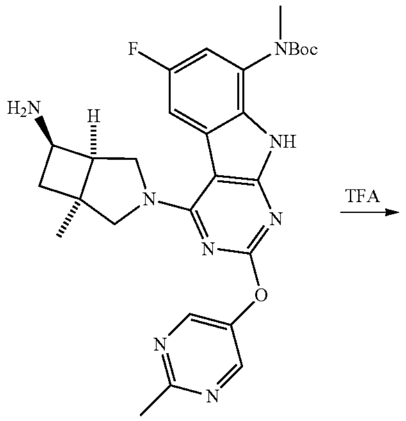

D33

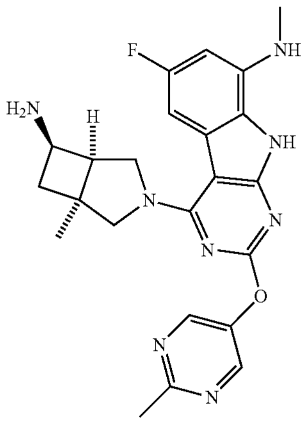

D34 (4.151)

The subtitle compound D34 was synthesized using the same method described for the above compound starting with bis-sulfone and (1S,5R,6R)-1-methyl-3-azabicyclo[3.2.0]heptan-6-amine (the diamine was prepared according patent procedure WO 2001053273 A1 and the separation from chiro column). LC-MS: M+1: 449.25.

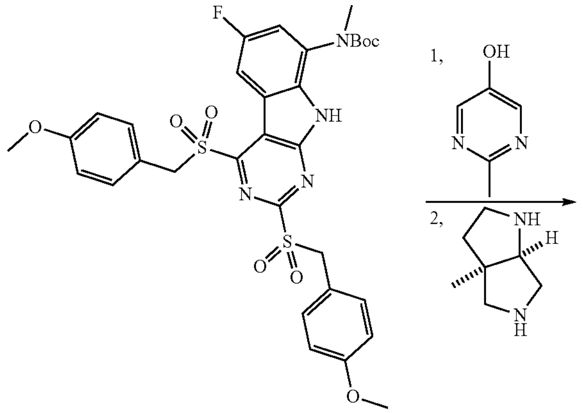

D16

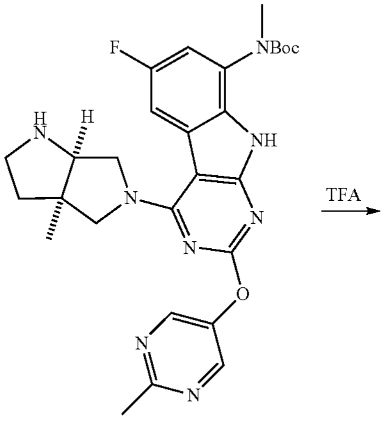

D35

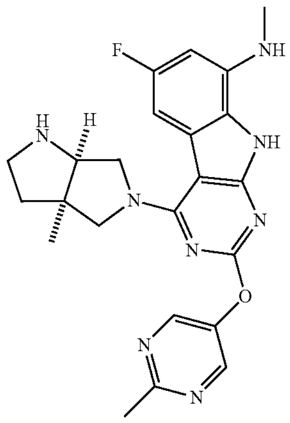

D36 (4.157)

The subtitle compound D36 was synthesized using the same method described for the above compound starting with bis-sulfone and (3aR,6aR)-3a-methyloctahydropyrrolo[3,4-b]pyrrole (the diamine was prepared according patent procedure from U.S. Pat. No. 5,202,337 (A) and the separation from chiro column). LC-MS: M+1: 449.23.

Dichloro Route

General Scheme:

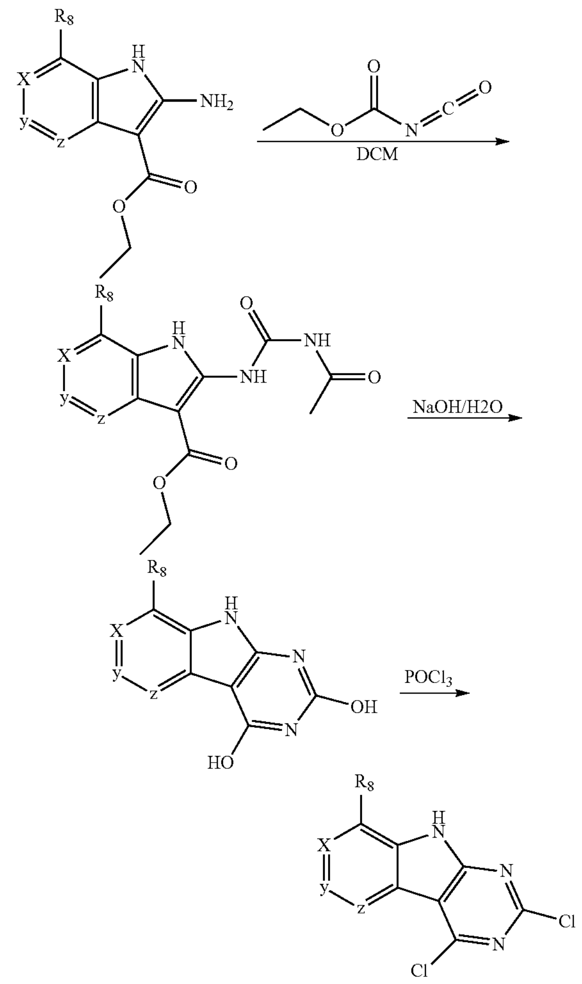

Experimental

Example of compounds made by the R4 addition first then R2

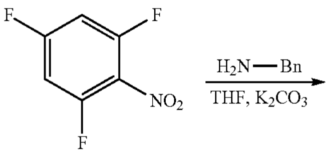

C1

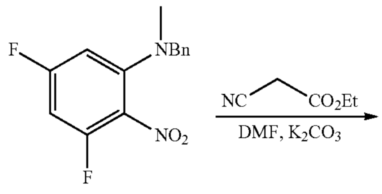

D37

-continued

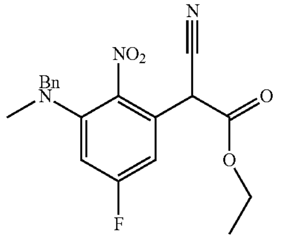

D38

To a stirred suspension of BnNHMe (34.2 g, 0.282 mol.) and $K_2CO_3$ (50.6 g, 0.367 mol.) in 400 mL of THF was added dropwise a solution of compound 1 (50.0 g, 0.282 mol.) in 100 mL THF below 10° C. After addition, the reaction was warmed to r.t. slowly and stirred overnight. TCL showed the reaction was completed; the reaction mixture was concentrated under vacuum. The residue was partitioned by ethyl acetate (300 mL) and water (500 mL), the organic layer was washed with brine (300 mL×3), dried over $Na_2SO_4$, filtered, and concentrated under vacuum. The crude product was purified by flash chromatography (pet. ether/EtOAc, 100/1 to 50/1, v/v) to give the product D37 as a pale yellow solid. (69.0 g, 87.9% yield). LC-MS: M+1: 279

$^1$H-NMR (400 MHz, $CDCl_3$) δ (ppm):=7.37 (5H, m), 6.43 (2H, m), 4.40 (2H, s), 2.84 (3H, s).

To a stirred suspension of $K_2CO_3$ (57.6 g, 0.417 mol.) and ethyl cyanoacetate (35.4 g, 0.313 mol.) in 200 mL DMF was added a solution of compound D37 (58.0 g, 0.208 mol.) in 100 mL DMF under $N_2$ protection. After addition, the reaction was stirred at r.t. for two days. TLC showed the SM was consumed, then the reaction mixture was diluted with ethyl acetate (400 mL) and water (1500 mL), the organic layer was separated, the aqueous layer extracted by ethyl acetate (200 mL). The combined organic layer was washed with brine (300 mL×3), dried over $Na_2SO_4$, filtered, and concentrated in vacuum. The crude product was purified by chromatography (pet. ether/EtOAc, 100/1 to 20/1, v/v) to give the product D38 as a pale yellow solid. (61.0 g, 79.2% yield). LC-MS: M+1: 371

$^1$H-NMR (400 MHz, $CDCl_3$) δ (ppm): 7.33 (5H, m), 6.92 (1H, d, J=8 Hz), 6.84 (1H, d, J=8 Hz), 5.13 (1H, s), 4.37 (2H, s). 4.30 (2H, dd, J=14.4 Hz), 2.78 (3H, s), 1.35 (3H, t, J=7.2 Hz).

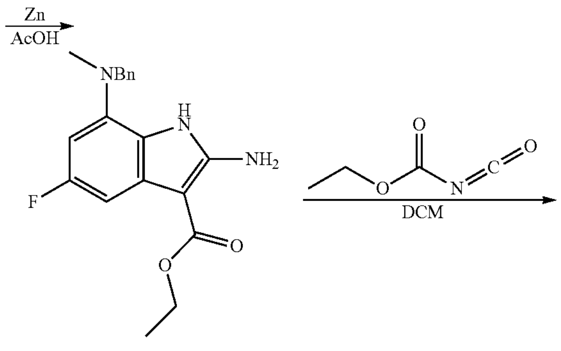

D39

-continued

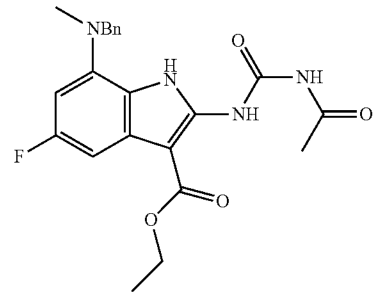

D40

To a stirred solution of compound D38 (61.0 g, 0.164 mol.) in 400 mL AcOH cooled on an ice bath was added zinc powder in portions. After addition, the reaction was heated to 60° C. and stirred at this temperature for 5 h. TLC showed the reaction was completed. The reaction mixture was cooled to r.t., filtered, the filtrate was concentrated under vacuum, the residue was dissolved in ethyl acetate (400 mL), basified by saturated $NaHCO_3$ aqueous solution (400 mL), then the organic layer was separated, washed with brine (200 mL×3), dried over $Na_2SO_4$, filtered and concentrated in vacuo to give a dark oil which was purified by chromatography (pet. ether/DCM, 5/1 to DCM, v/v) to give the product D39 as a pale yellow solid. (26.0 g, 46.4% yield). LC-MS: M+1: 342

$^1$H-NMR (400 MHz, $CDCl_3$) δ (ppm): 8.02 (1H, S), 7.33 (5H, m), 6.52 (1H, d, J=2.4 Hz), 6.49 (1H, d, J=2.4 Hz), 5.73 (2H, s), 4.35 (2H, dd, J=15.2 Hz). 4.19 (2H, s), 2.73 (3H, s), 1.44 (3H, t, J=7.2 Hz).

To a stirred suspension of D39 (16.0 g, 46.9 mmol.) in 200 mL of DCM was added dropwise ethyl isocyanatoformate (resolved in 50 mL of DCM) with an ice bath cooling. After addition, the resulting mixture was stirred at r.t. the SM was dissolved gradually then precipitate was generated from the reaction. 4 hours later, TLC showed the reaction was completed. The reaction mixture was filtered. The filtration was concentrated in vacuo. The residue was suspended in 50 mL of DCM, stirred then filtered. The two batch filter cakes were combined, dried in vacuo to give the product D40 as a pale yellow solid. (14.4 g, 67.3% yield). LC-MS: M+1: 457

$^1$H-NMR (400 MHz, DMSO-d6) δ (ppm): 12.01 (1H, S), 11.12 (1H, S), 11.06 (1H, S), 10.41 (1H, S), 7.33 (5H, m), 6.63 (1H, d, J=2.0 Hz), 6.60 (1H, d, J=2.4 Hz), 4.34 (2H, dd, J=7.2 Hz), 4.28 (2H, s), 4.24 (2H, dd, J=7.2 Hz), 4.14 (2H, dd, J=7.2 Hz), 2.75 (3H, s), 1.37 (3H, t, J=7.2 Hz) 1.27 (3H, t, J=7.2 Hz), 1.22 (3H, t, J=6.8 Hz).

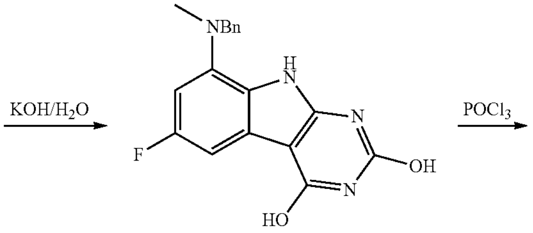

D41

-continued

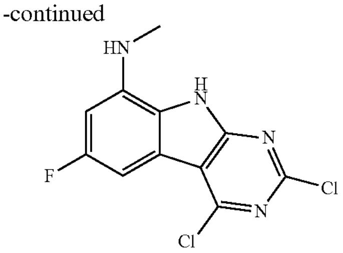

D42

To a stirred suspension of D40 (9.13 g, 20.0 mmol.) in water/EtOH (75 mL/25 mL) was added a KOH solution in 20 mL of water at r.t. After addition, the resulting mixture was reflux for 4 h. TLC showed the reaction was completed, then the reaction was cooled to r.t., acidified with 1M HCl aq. until pH=5, the precipitate was collected by filter, washed with water (200 mL X1) then ethyl acetate (200 mL×1) to give the product D41 as a pale yellow solid. (5.90 g, 87.1% yield). LC-MS: M−1: 337.

$^1$H-NMR (400 MHz, DMSO-d6) δ (ppm): 7.25 (5H, m), 7.01 (1H, dd, J=8.8 Hz), 6.35 (1H, d, J=12.0 Hz), 4.45 (2H, s), 2.76 (3H, s).

Compound D41 (2 g, 5.75 mmol) was placed with a solution of $POCl_3$ (100 ml) in a pressure tube and few drops of N-ethyldiisopropyl amine. The reaction mixture was heated to at 185° C. under sealed condition over 10 h. The mixture was cooled and poured into ice water and the yellow solid was collected by filtration, dried under reduced press to give D42 (1.6 g, 98% yield) as a yellow solid. LC-MS: M+1: 286.02

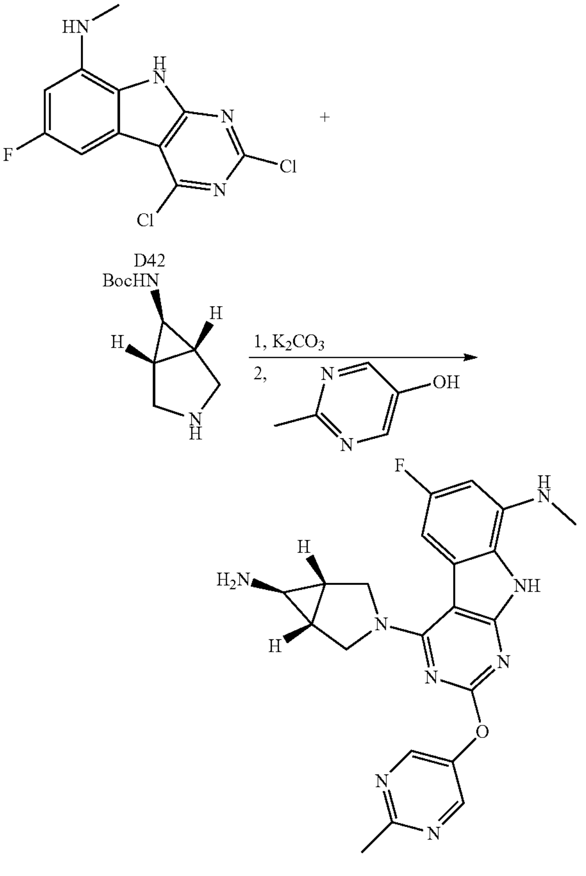

D43 (4.073)

To a stirred solution of compound D42 (250 mg, 0.87 mmol) in 5 mL of NMP at 110° C. was added (R)-tert-butyl 5-azaspiro[2.4]heptan-7-ylcarbamate (175 mg, 0.88 mmol) and $K_2CO_3$ (7 mg, 0.05 mmol). After the completion of the reaction in 10 minutes, the reaction mixture added to a solution of 2-methylpymiridin-5-ol (90 mg, 0.90 mmol) in a microwave tube. The reaction mixture was sealed and placed in Microwave at 220° C. for 10 minutes. The desired product was obtained by HPLC purification to give D43 (90 mg, 25%) as a white solid. LC-MS: M+1: 421.18.

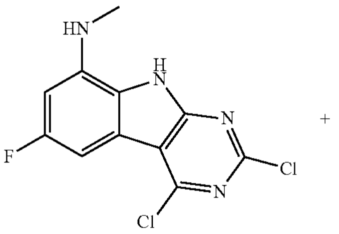

D42

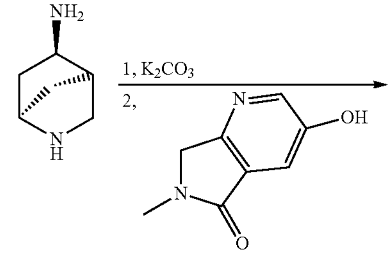

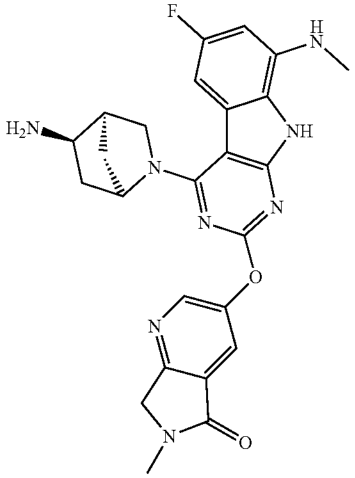

D44 (4.361)

The subtitle compound D44 was synthesized using the method described above starting with (1R,4R,5R)-2-azabicyclo[2.2.1]heptan-5-amine and 3-hydroxy-6-methyl-6,7-dihydro-5H-pyrrolo[3,4-b]pyridin-5-one. LC-MS: M+1: 489.22.

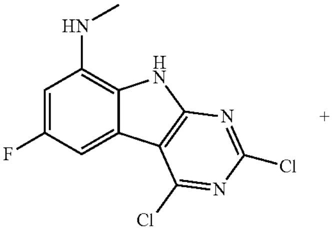

D42

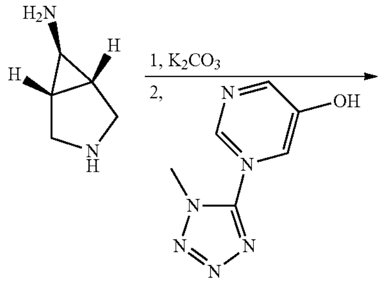

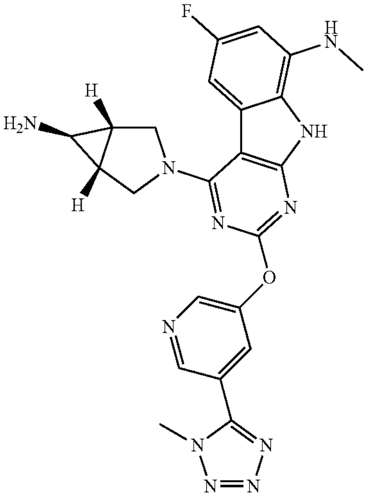

D45 (4.168)

The subtitle compound D45 was synthesized using the method described above starting with tert-butyl 3-azabicyclo[3.1.0]hexan-6-ylcarbamate and 5-(1-methyl-1H-tetrazol-5-yl)pyridin-3-ol. LC-MS: M+1: 488.20.

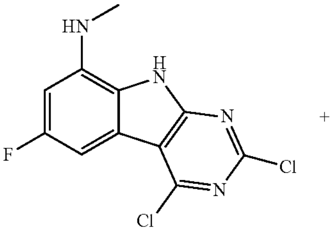

D42

-continued
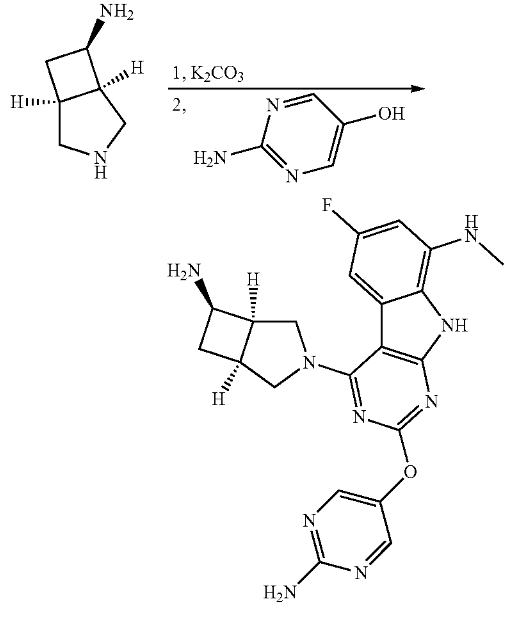
D46 (4.190)
The subtitle compound D46 was synthesized using the method described above starting with (6R)-3-azabicyclo[3.2.0]heptan-6-amine and 2-aminopyrimidin-5-ol. LC-MS: M+1: 436.20.
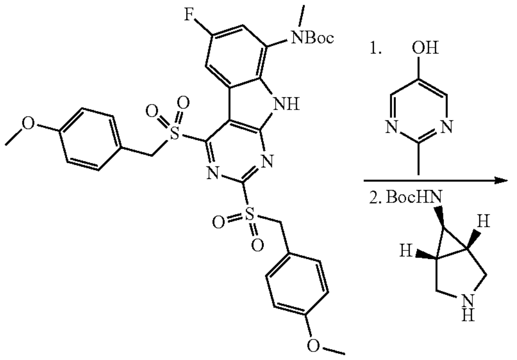
D16
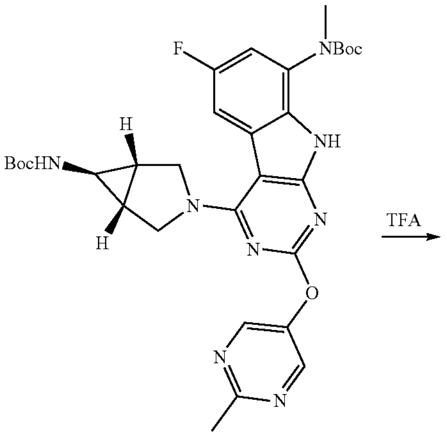
D47
-continued
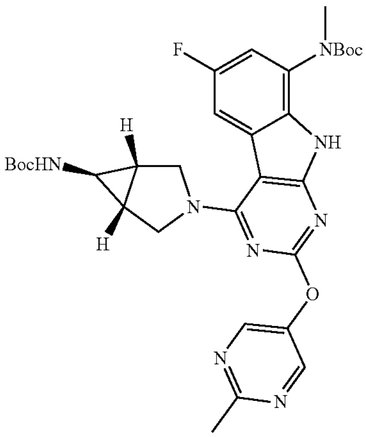
D43
(4.073)
The subtitle compound D43 was synthesized using the same method described for the above compound starting with bis-sulfone and tert-butyl 3-azabicyclo[3.1.0]hexan-6-ylcarbamate. LC-MS: M+1: 421.18.
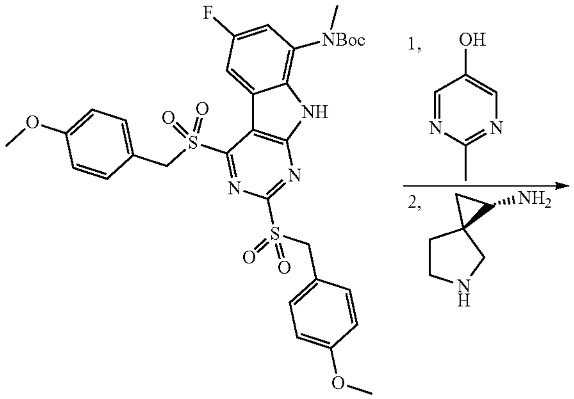
D16
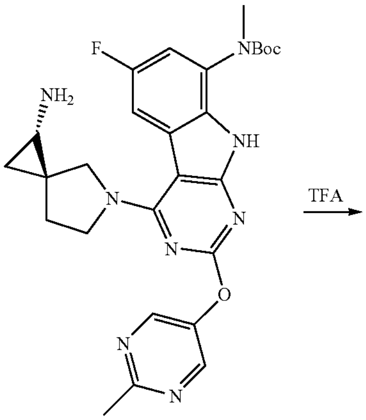
D48

-continued
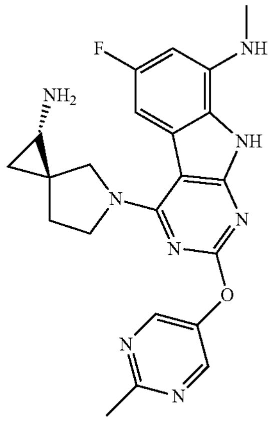
D49 (4.066)
The subtitle compound D49 was synthesised using the same method described for the above compound starting with bis-sulfone and (1R)-5-azaspiro[2.4]heptan-1-amine. LC-MS: M+1: 435.23.
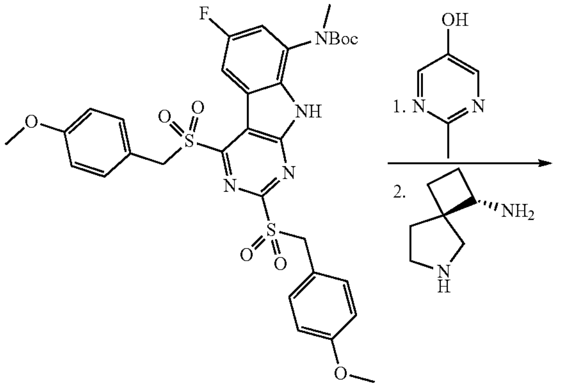
D16
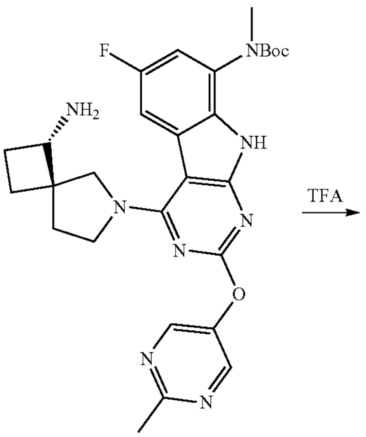
D50
-continued
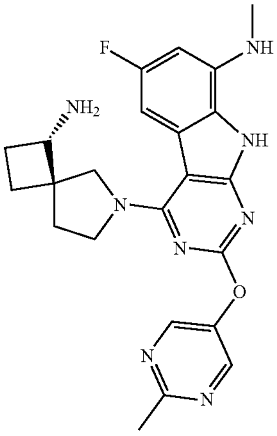
D51 (4.117)
The subtitle compound D51 was synthesized using the same method described for the above compound starting with bis-sulfone and (1S,4R)-6-azaspiro[3.4]octan-1-amine. LC-MS: M+1: 449.25.
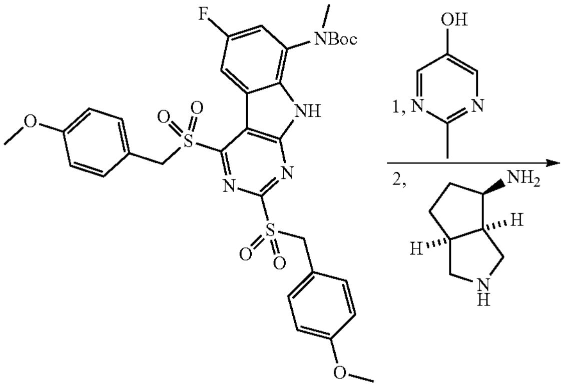
D16
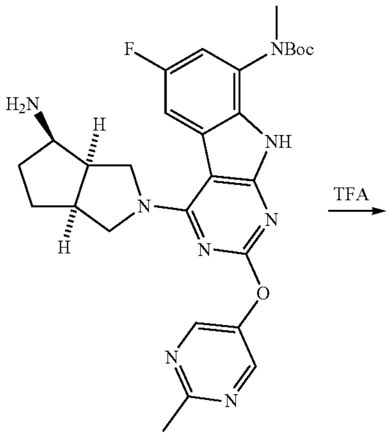
D52

-continued

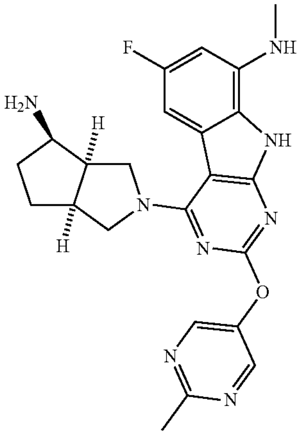

D53 (4.076)

The subtitle compound D53 was synthesized using the same method described for the above compound starting with bis-sulfone and (3aR,4R,6aS)-octahydrocyclopenta[c]pyrrol-4-amine. LC-MS: M+1: 449.21.

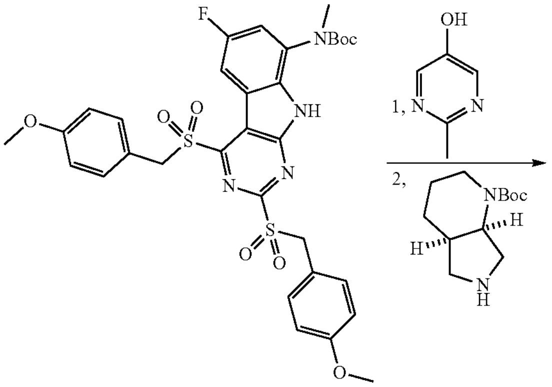

D16

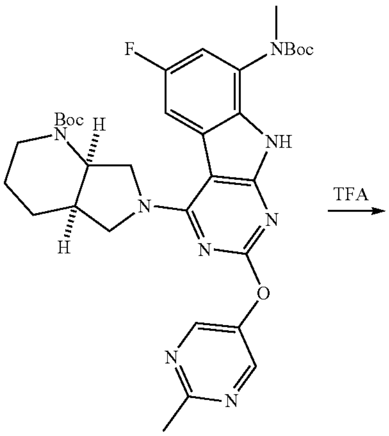

D54

-continued

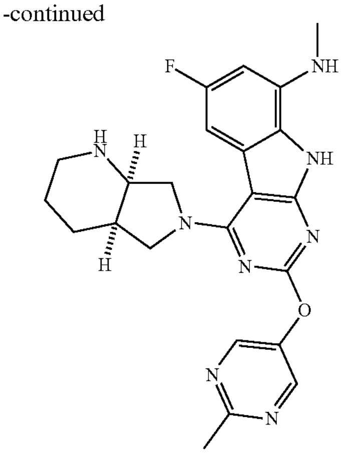

D55 (4.079)

The subtitle compound D55 was synthesized using the same method described for the above compound starting with bis-sulfone and (4aR,7aR)-tert-butyl octahydro-1H-pyrrolo[3,4-1)]pyridine-1-carboxylate. LC-MS: M+1: 449.23.

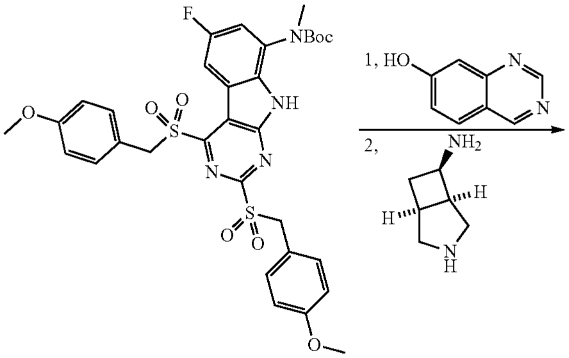

D16

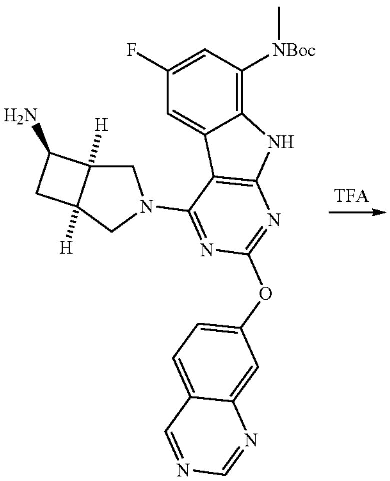

D56

-continued

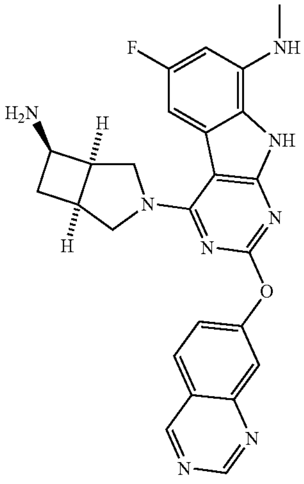

D57 (4.365)

The subtitle compound D57 was synthesized using the same method described for the above compound starting with bis-sulfone, quinazolin-7-ol and (1S,5R,6R)-3-azabicyclo[3.2.0]heptan-6-amine. LC-MS: M+1: 471.26.

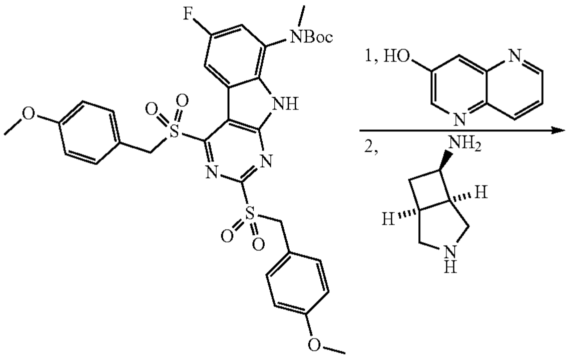

D16

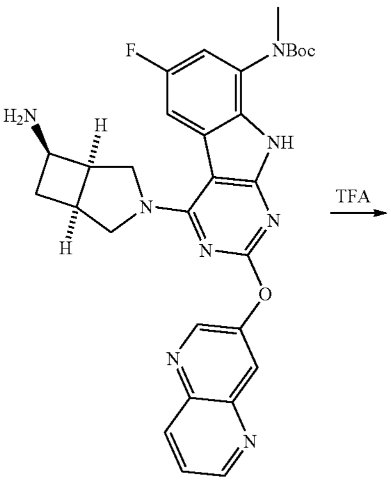

D58

-continued

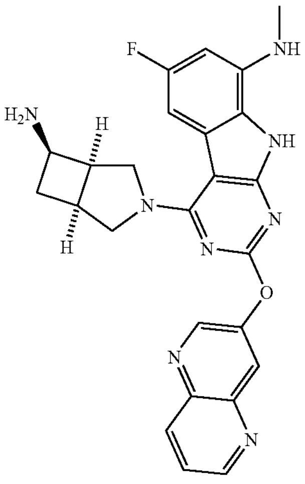

D59 (4.043)

The subtitle compound D59 was synthesized using the same method described for the above compound starting with bis-sulfone, 1,5-naphthyridin-3-ol and (1S,5R,6R)-3-azabicyclo[3.2.0]heptan-6-amine. LC-MS: M+1: 471.20.

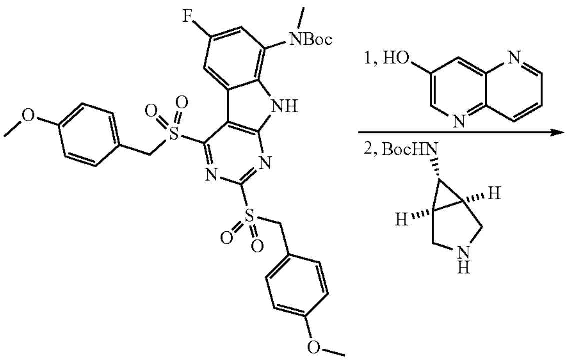

D16

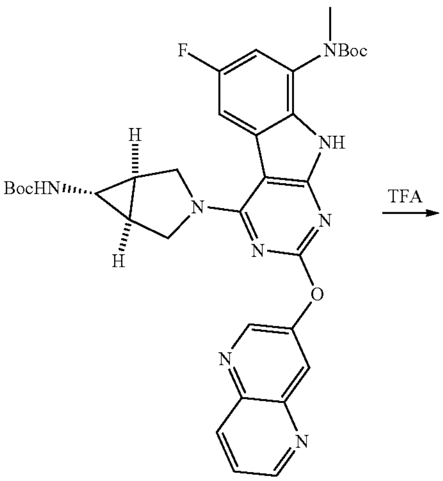

D60

-continued

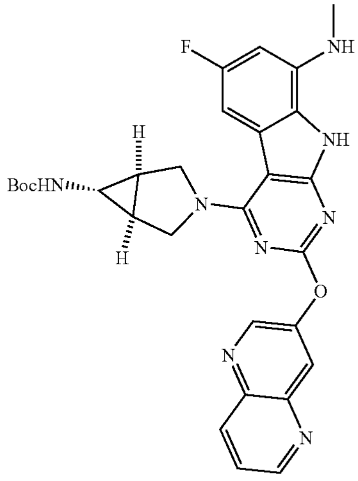

D61 (4.035)

The subtitle compound D61 was synthesized using the same method described for the above compound starting with bis-sulfone, 1,5-naphthyridin-3-ol and tert-butyl 3-azabicyclo[3.1.0]hexan-6-ylcarbamate. LC-MS: M+1: 457.20.

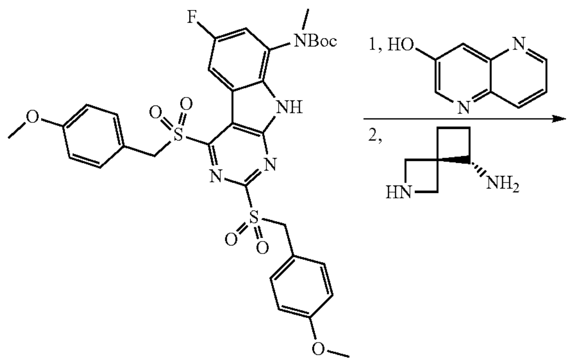

D16

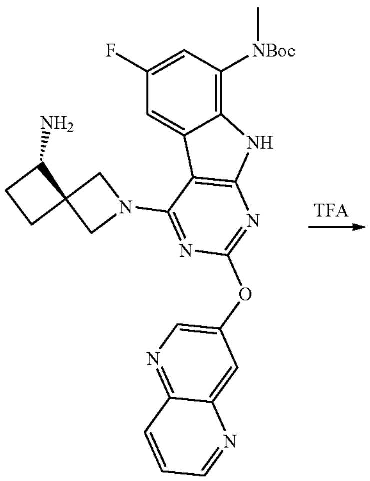

D62

-continued

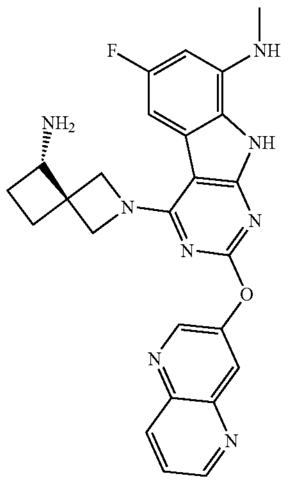

D63 (4.045)

The subtitle compound D63 was synthesized using the same method described for the above compound starting with bis-sulfone, 1,5-naphthyridin-3-ol and (S)-2-azaspiro [3.3]heptan-5-amine. LC-MS: M+1: 471.22.

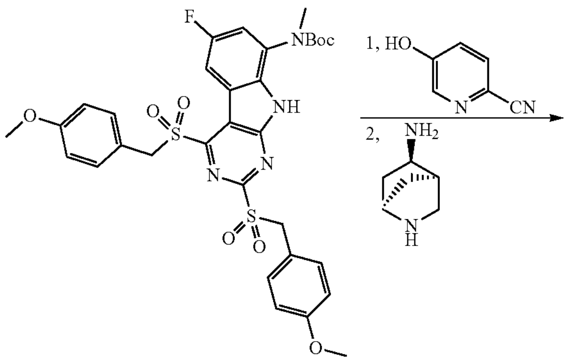

D16

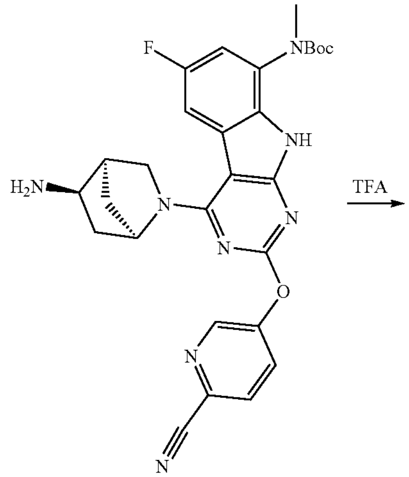

D64

-continued

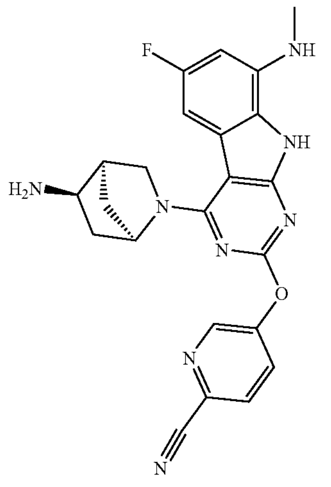

D65 (4.434)

The subtitle compound D65 was synthesized using the same method described for the above compound starting with bis-sulfone, 5-hydroxypicolinonitrile and (1R,4R,5R)-2-azabicyclo[2.2.1]heptan-5-amine. LC-MS: M+1: 445.18.

Synthesis of Analogs where R4 not Attached by a Nitrogen 2-chloro-6-fluoro-4-(1H-imidazol-4-yl)-N-methyl-9H-pyrimido[4,5-b]indol-8-amine The mixture of compound (1) (150 mg, 0.52 mmol), 4-(4,4,5,5-tetramethyl-1,3,2-dioxaborolan-2-yl)-1H-imidazole (2) (100 mg, O. 52 mmol), $K_2CO_3$ (100 mg, 0.5 mmol), and catalytic amount of $Pd[(PPh_3)]Cl_2$ was dissolved in DMF (3 ml) and water (0.3 ml). It was heated at 150° C. at microwave for 10 minutes. The mixture was then purified through HPLC to afford the title compound as yellow solid (91 mg; 55% yield). LC-MS: M+1: 317.08.

$^1$H NMR (300 MHz, DMSO) δ (ppm): 14.01 (S, 1H), 11.71 (s, 1H), 7.98 (s, 2H), 7.51 (d, J=11.2, 1H), 6.30 (d, J=9.7, 1H), 4.12 (s, 1H), 3.15 (s, 3H).

6-fluoro-4-(1H-imidazol-4-yl)-N-methyl-2-(2-methylpyrimidin-5-yloxy)-9H-pyrimido[4,5-b]indol-8-amine D66

To the solution of compound (3)(80 mg, 2.52 mmol) in NMP (5 ml) was added 2-methylpyrimidine-5-ol (33 mg, 3.0 mmol) and potassium carbonate (43.6 mg, 0.31 mmol). It was then heated at 160° C. under microwave condition for 15 minutes. The mixture was then purified through HPLC to afford the title compound as yellow solid (59 mg, 60%). LC-MS: M+1: 391.15.

$^1$H NMR (300 MHz, DMSO) δ (ppm): 14.01 (s, 1H), 11.71 (s, 1H), 7.98 (s, 2H), 7.69 (s, 2H), 7.51 (d, J=11.2, 1H), 5.98 (d, J=9.7, 1H), 4.02 (s, 1H), 3.10 (s, 3H), 2.65 (s, 3H).

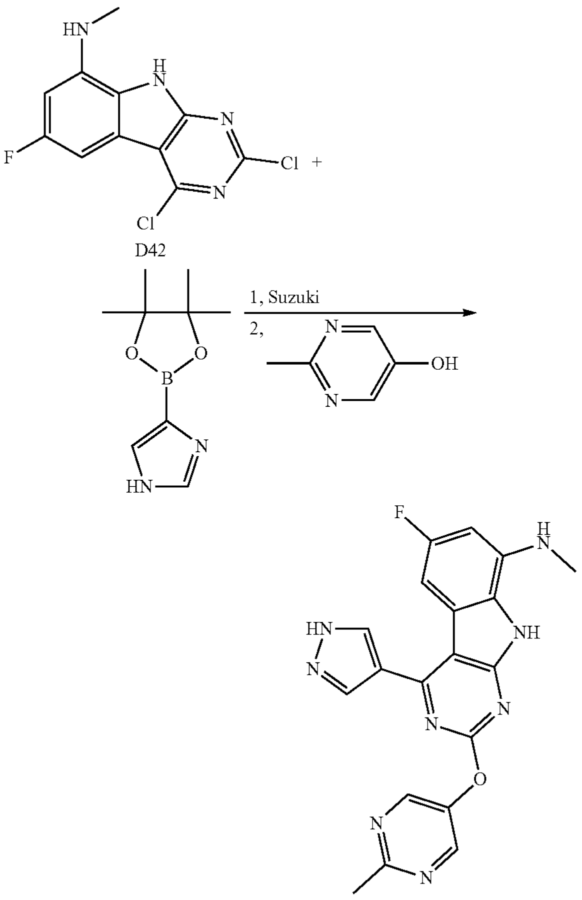

D66 (4.418)

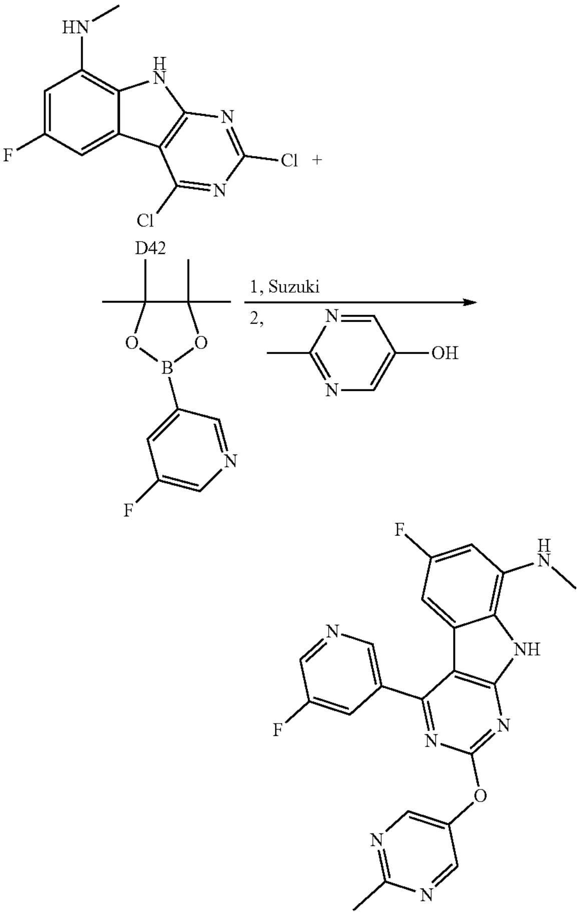

D67 (4.417)

The subtitle compound D67 was synthesized using the method described above starting with 3-fluoro-5-(4,4,5,5-tetramethyl-1,3,2-dioxaborolan-2-yl)pyridine. LC-MS: M+1: 420.16.

$^1$H NMR (300 MHz, DMSO) δ (ppm): 11.71 (s, 1H), 9.10 (s, 1H), 8.52 (d, 1H), 7.63-7.80 (m, 3H), 7.31 (brs, 1H), 5.98 (d, J=9.7, 1H), 4.10 (s, 1H), 2.98 (s, 3H), 2.66 (s, 3H).

6-Fluoro-8-(methylamino)-2-(2-methylpyrimidin-5-yloxy)-9H-pyrimido[4,5-b]indol-4-61 (D70)

To the solution of compound (3) (2.48 g, 4.3 mmol) in dioxane (12 ml) was added 3-chloroperoxy benzoic acid (1.484 g, 8.6 mmol) by portion over 10 minutes. After the reaction was stirred at room temperature for 30 minutes, lithium hydroxide (1.8 g, 75 mmol) and water (5 ml) were

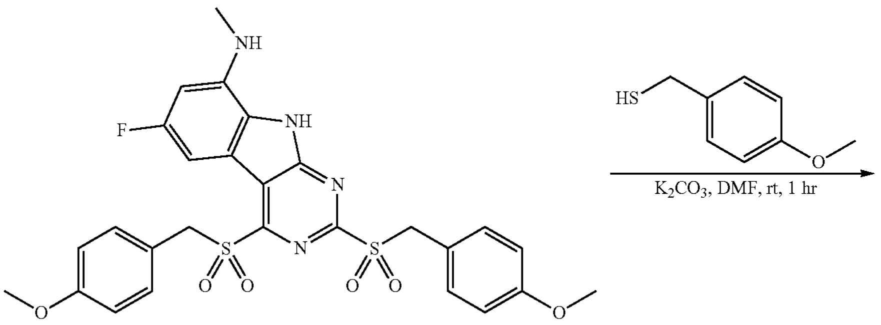

D16

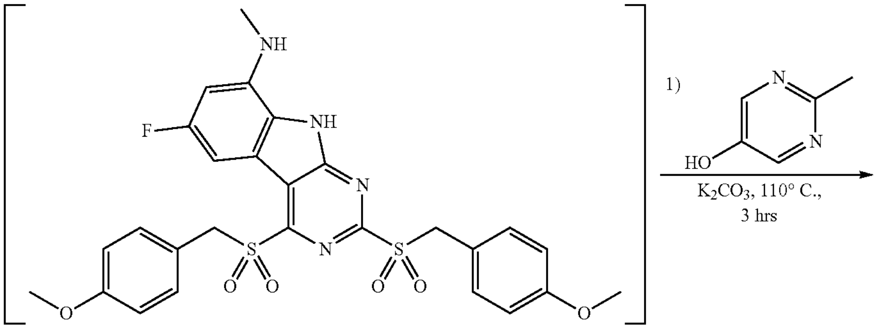

D68

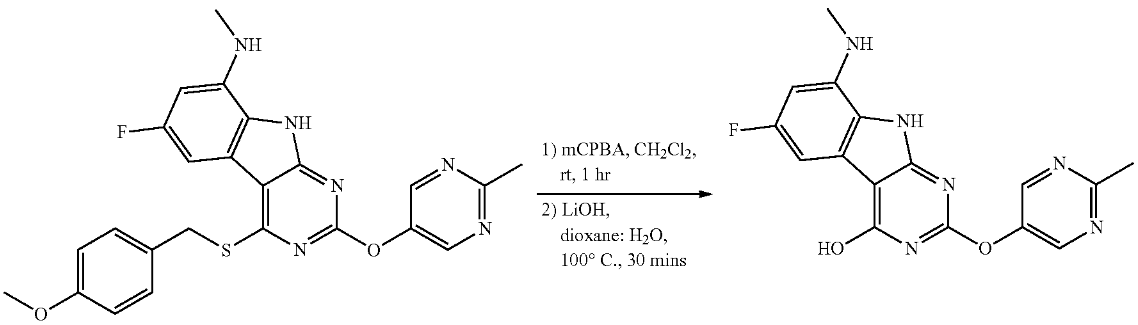

D69

D70

6-Fluoro-4-(4-methoxybenzylthio)-N-methyl-2-(2-methylpyrimidin-5-yloxy)-9H-pyrimido[4,5-b]indol-8-amine (D69)

To the solution of compound (1) (2.923 g, 5 mmol) in NMP (12 ml) was added potassium carbonate (2.073 g, 15 mmol) followed by 4-methoxyphenyl)methanethiol (0.771 g, 5 mmol). The reaction mixture was stirred at room temperature for one hour. 2-Methylpyrimidine-5-ol (1.101 g, 10 mmol) was then added. The resulting mixture was heated at 100° C. for 3 hours. It was purified through C18 column chromatography to afford the title compound as light yellow solid (2.4 g, 83%).

added. The resulting solution was stirred at room temperature to 100° C. for one hour. It was then purified through C18 column chromatography to afford the title compound as white solid (1.39 g, 95%).

4-Chloro-6-fluoro-N-methyl-2-(2-methylpyrimidin-5-yloxy)-9H-pyrimido[4,5-b]indol-8-amine (D71)

Compound (D70) (1.06 g, 2.407 mmol) was dissolved in $POCl_3$ (20 ml) and N-ethyl-isopropylpropan-2-amine (0.43 g, 3.33 mmol). The mixture was heated at 50° C. for 4 hours. After the reaction was cooled down to room temperature, it was poured into a 1 L-flask containing ice (~500 g) and NaOH (20 g) and the resulting was sat for one hour. It was then extracted with ethyl acetate (100 ml×3). The combined organic layers were dried over $Na_2SO_4$ and concentrated by rotary evaporation to afford the title compound as white solid (492 mg, 57%).

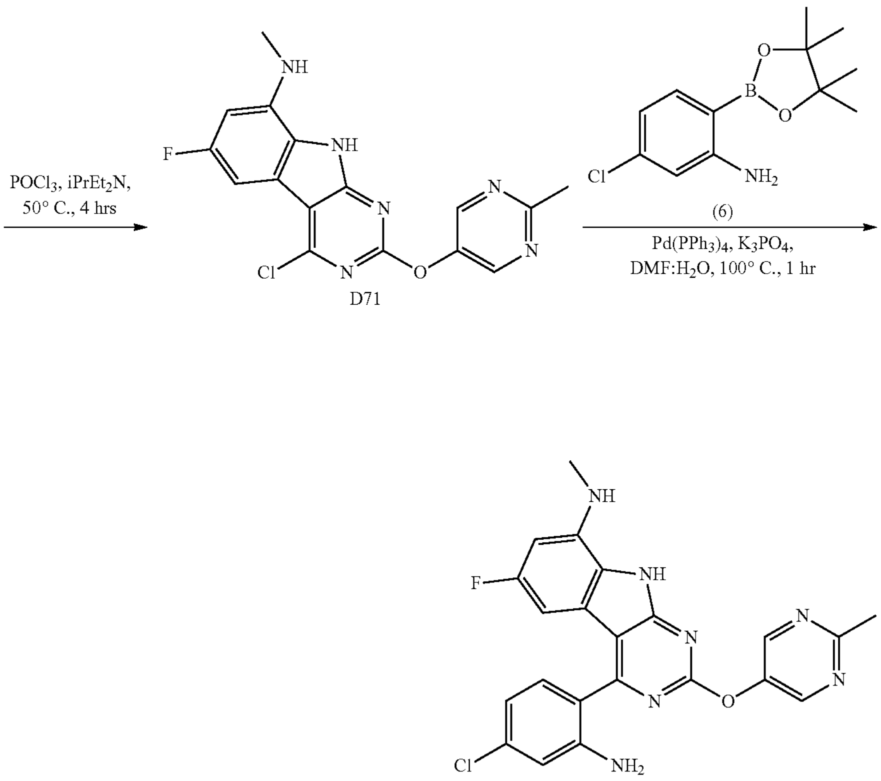

D72 (4.161)

4-(2-amino-4-chlorophenyl)-6-fluoro-N-methyl-2-(2-methylpyrimidin-5-yloxy)-9H-pyrimido[4,5-b]indol-8-amine (D72)

The mixture of compound (D71) (36 mg, 0.1 mmol), the boronic acid pinacol ester (6) (38 mg, 0.15 mmol), potassium phosphate (64 mg, 0.3 mmol), and catalytic amount of $Pd(PPh_3)_4$ was dissolved in DMF (1 ml) and water (0.3 ml). The reaction mixture was refluxed at 100° C. for one hour. It was then purified through HPLC to afford the title compound as yellow product (17 mg, 37.8%).

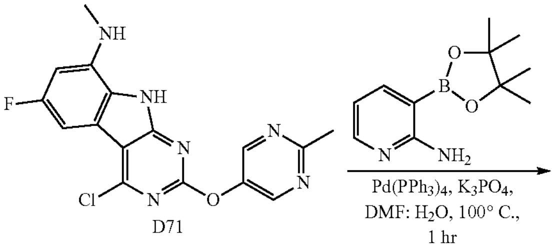

-continued

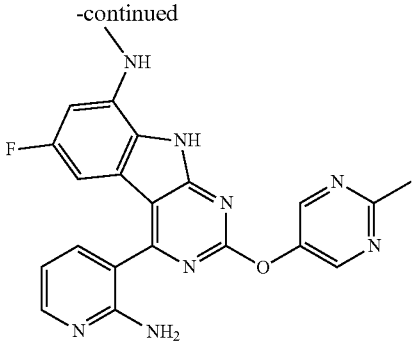

D73 (4.448)

The subtitle compound D73 was synthesized using the method described above starting with 3-(4,4,5,5-tetramethyl-1,3,2-dioxaborolan-2-yl)pyridin-2-amine.

Synthesis of Prodrugs at R4
(S)-2-Amino-N—((R)-5-(6-fluoro-8-(methylamino)-2-(2-methylpyrimidin-5-yloxy)-9H-pyrimido[4.5-b]indol-4-yl)-5-azaspiro[2.4]heptan-7-yl)propanamide D76 (4.424)
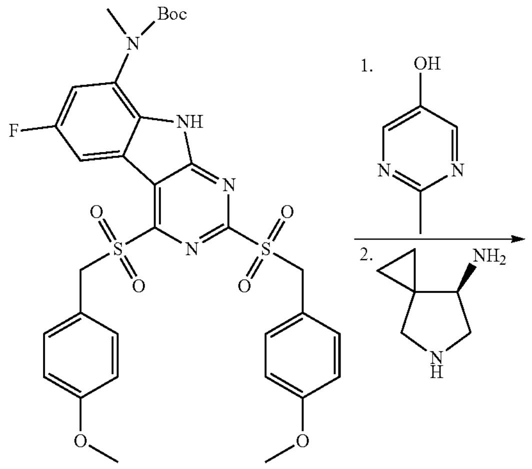
D16
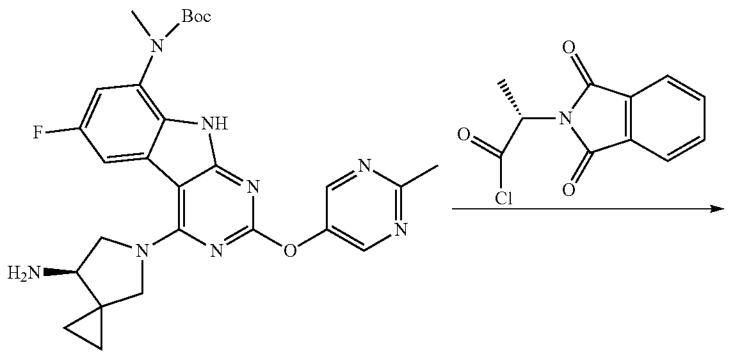
D74
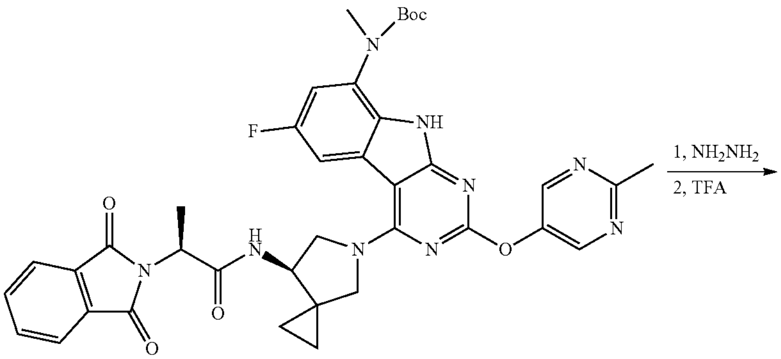
D75

-continued

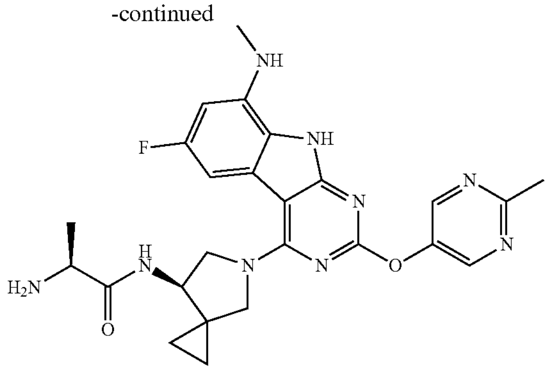

D76

The mixture of D16 (0.342 g, 0.500 mmol), 2-methylpyrimidin-5-ol (0.165 g, 1.50 mmol) and $K_2CO_3$ (0.276 g, 2.00 mmol) in NMP (5.0 mL) was stirred for 1 hr 30 min at 100° C. After being stirred for 1 hr 30 min, the reaction was checked by LC/MS. (R)-5-azaspiro[2.4]hepten-7-amine (0.168 g, 1.50 mmol) was added at once, the mixture was allowed to stir for 1 hr 30 min at 100° C. The resulting heterogeneous mixture was cooled to 23° C. and purified by HPLC to give D74 (0.100 g, 0.187 mmol) as light yellow solid. LC/MS (ESI, $M+H^+$)=535. To a solution of D74 (0.100 g, 0.187 mmol) and $K_2CO_3$ (0.052 g, 0.374 mmol) in $CH_2Cl_2$ (8.0 mL) was added (S)-2-(1,3-dioxoisoindolin-2-yl)propanoyl chloride (0.089 g, 0.374 mmol) dissolved in $CH_2Cl_2$ (2.0 mL) at 23° C. The mixture was allowed to stir for 1 hr 30 min at 60° C. and then cooled to 23° C. The reaction mixture was concentrated by Rotavap and the crude material was purified by HPLC to give D75 as yellow solid. LC/MS (ESI, $M+H^+$)=736. To a solution of D75 in ethanol (7.0 mL) was added hydrazine (1.5 mL, 30 wt. % solution in water) via syringe at 23° C. The mixture was stirred for 1 hr at 23° C. The reaction mixture was concentrated by Rotavap and the crude material was purified by HPLC to provide D76 as light yellow solid. LC/MS (ESI, $M+H^+$)=606. The mixture of D76 in trifluoroacetic acid (1.00 mL) was stirred for 1 hr at 23° C. The crude material was purified by HPLC to provide a title compound D76 (0.026 g, 0.051 mmol) as white solid. LC/MS (ESI, $M+H^+$)=506.

Synthesis of Prodrugs at R8

(S)-2-Amino-N-(4-((R)-7-amino-5-azaspiro[2.4]heptan-5-yl)-6-fluoro-2-(2-methylpyrimidin-5-yloxy)-9H-pyrimido[4.5-b]indol-8-yl)-N-methylpropanamide

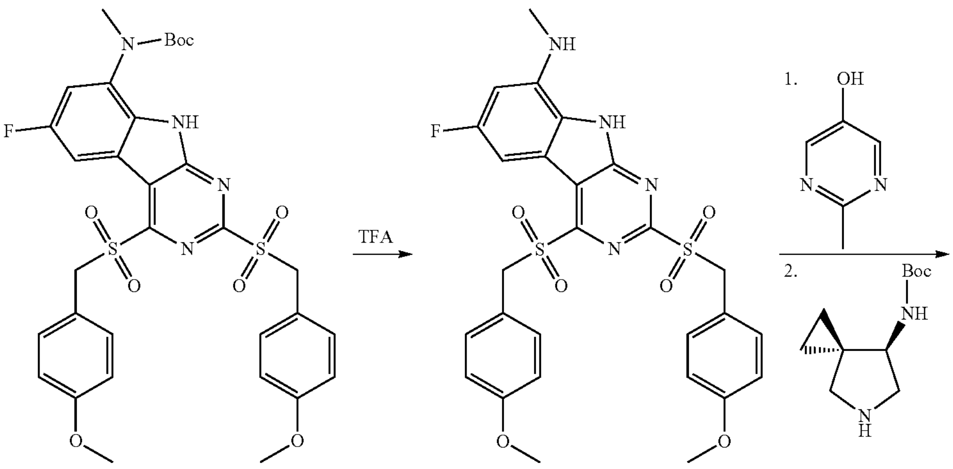

D16 D77

-continued

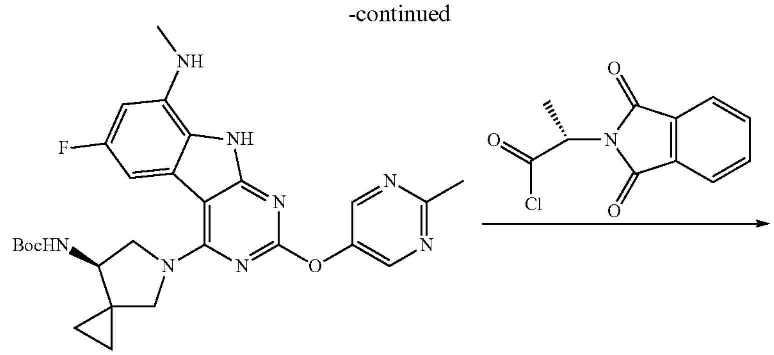

D78

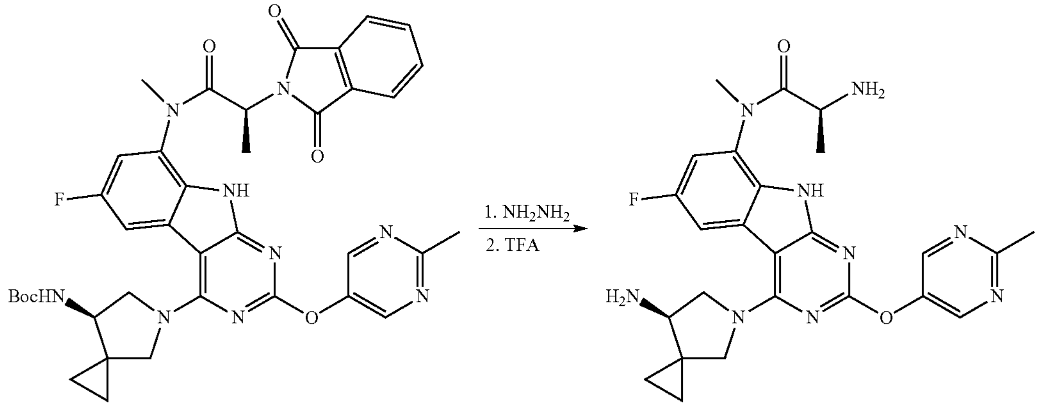

D79

D80
(4.423)

The mixture of D16 (1.00 g, 1.46 mmol) in trifluoroacetic acid (3.0 mL) was stirred for 30 min at 23° C. Trifluoroacetic acid was evaporated by reduced pressure to provide D77 (quantitative yield) as deep orange solid. This crude material was used for next reaction without further purification. LC/MS (ESI, $M+H^+$)=585. The mixture of D77 (0.292 g, 0.50 mmol), 2-methylpyrimidin-5-ol (0.165 g, 1.50 mmol) and $K_2CO_3$ (0.276 g, 2.00 mmol) in NMP (5.0 mL) was stirred for 2 hr at 100° C. After being stirred for 2 hr, the reaction was checked by LC/MS. (R)-tert-butyl 5-azaspiro [2.4]hepten-7-ylcarbamate (0.318 g, 1.50 mmol) was added at once, the mixture was allowed to stir for 1 hr 30 min at 100° C. The resulting heterogeneous mixture was cooled to 23° C. and purified by HPLC to provide D78 (0.182 g, 0.34 mmol) as yellow solid. LC/MS (ESI, $M+H^+$)=535. To a solution of D78 (0.182 g, 0.34 mmol) and $K_2CO_3$ (0.094 g, 0.68 mmol) in $CH_2Cl_2$ (10.0 mL) was added (S)-2-(1,3-dioxoisoindolin-2-yl)propanoyl chloride (0.161 g, 0.68 mmol) dissolved in $CH_2Cl_2$ (2.0 mL) at 23° C. The mixture was allowed to stir for 2 hr at 60° C. and then cooled to 23° C. The reaction mixture was concentrated by Rotavap and the crude material was purified by HPLC to give D79 as yellow solid. LC/MS (ESI, $M+H^+$)=736. To a solution of D79 in ethanol (7.0 mL) was added hydrazine (1.5 mL, 30 wt. % solution in water) via syringe at 23° C. The mixture was stirred for 1 hr at 23° C. The reaction mixture was concentrated by Rotavap and the crude material was purified by HPLC to provide 5 as light yellow solid. LC/MS (ESI, $M+H^+$)=606. The mixture of 5 in trifluoroacetic acid (1.50 mL) was stirred for 30 min at 23° C. The crude material was purified by HPLC to provide a title compound D80 (0.031 g, 0.061 mmol) as white solid. LC/MS (ESI, $M+H^+$)=506.

Prodrug at R4 and R8:

(R)-2-Amino-N-(4-(7-(2-aminoacetamido)-5-azaspiro[2.4]heptan-5-yl)-6-fluoro-2-(2-methylpyrimidin-5-yloxy)-9H-pyrimido[4.5-b]ondol-8-yl)-N-methylacetamide

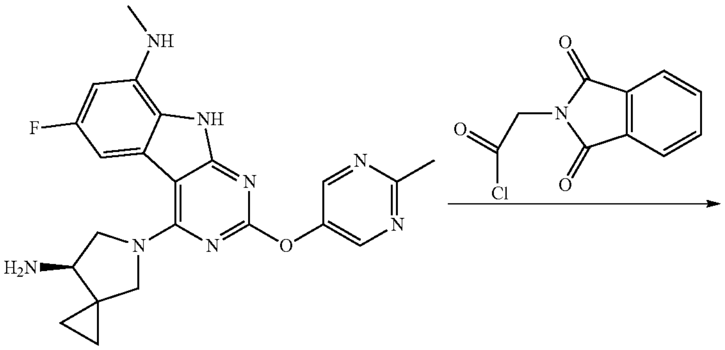

D18

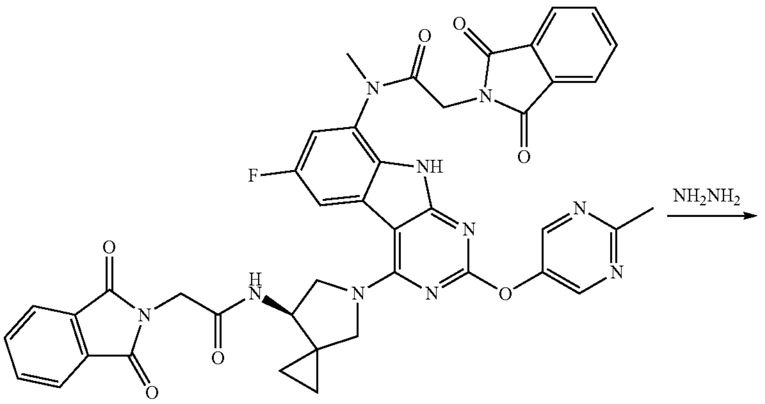

D81

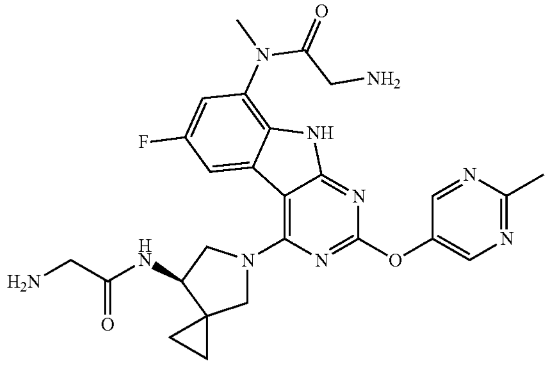

D82 (4.424)

To a solution of D16 (0.075 g, 0.173 mmol) and $K_2CO_3$ (0.084 g, 0.606 mmol) in $CH_2Cl_2$ (8.0 mL) was added 2-(1,3-dioxoisoindolin-2-yl)acetyl chloride (0.136 g, 0.606 mmol) dissolved in $CH_2Cl_2$ (2.0 mL) at 23° C. The mixture was allowed to stir for 3 hr 30 min at 60° C. and then cooled to 23° C. The reaction mixture was concentrated by Rotavap and the crude material was purified by HPLC to give D81 as light yellow solid. LC/MS (ESI, $M+H^+$)=809. To a solution of D81 in ethanol (5.0 mL) was added hydrazine (1.0 mL, 30 wt. % solution in water) via syringe at 23° C. The mixture was stirred for 1 hr at 23° C. The reaction mixture was concentrated by Rotavap and the crude material was purified by HPLC to provide a title compound D82 (0.084 g, 0.153 mmol) as white solid. LC/MS (ESI, $M+H^+$)=549.

Table of Formula I compounds where L = O, $R^x$, $R^y$, $R^z$ = H, $R^8$ = $NHCH_3$
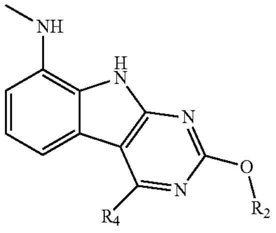
| Cmpd ID | R2 | R4 |
| --- | --- | --- |
| 3.1 | 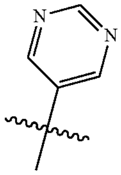 [SMILES: *c1cncnc1] | 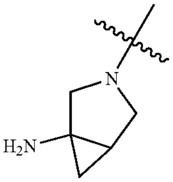 [SMILES: *N1CC2CC2(N)C1] |
| 3.2 | 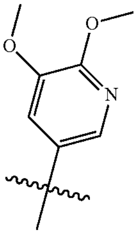 [SMILES: *c1cnc(OC)c(OC)c1] | 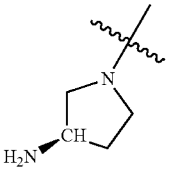 |
| 3.3 | 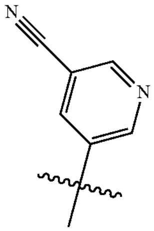 [SMILES: *c1cncc(C#N)c1] | 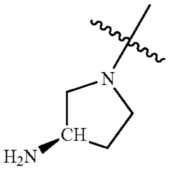 |
| 3.4 | 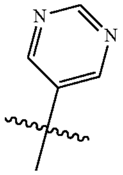 [SMILES: *c1cncnc1] | 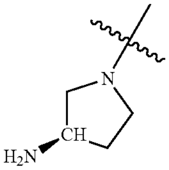 [SMILES: *N1CC[C@@H](N)C1] |
| 3.5 | 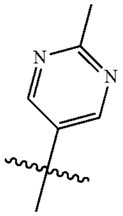 [SMILES: *c1cnc(C)nc1] | 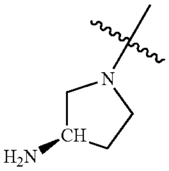 |
| 3.6 | 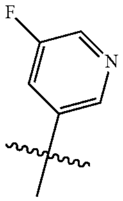 [SMILES: *c1cncc(F)c1] | 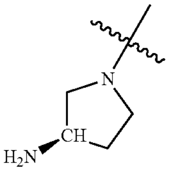 [SMILES: *N1CC[C@@H](N)C1] |

-continued
Table of Formula I compounds where L = O, $R^x$, $R^y$, $R^z$ = H, $R^8$ = $NHCH_3$
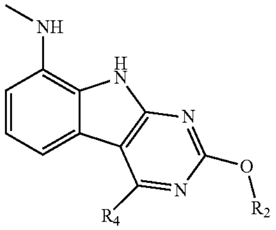
| Cmpd ID | R2 | R4 |
|---|---|---|
| 3.7 | 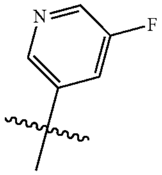 [SMILES: *c1cncc(F)c1] | 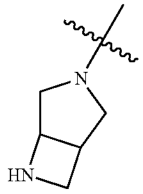 |
| 3.8 | 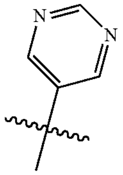 [SMILES: *c1cncnc1] | 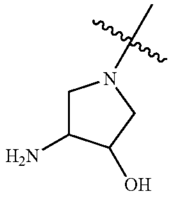 [SMILES: *N1CC(N)C(O)C1] |
| 3.9 | 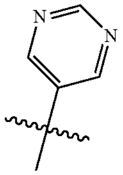 [SMILES: *c1cncnc1] | 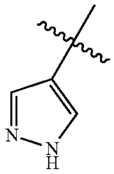 |
| 3.10 | 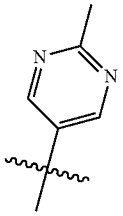 [SMILES: *c1cnc(C)nc1] | 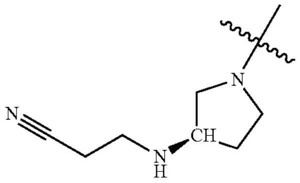 [SMILES: *N1CC[C@@H](NCCC#N)C1] |
| 3.11 | 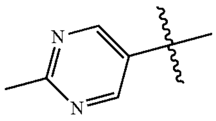 [SMILES: *c1cnc(C)nc1] | 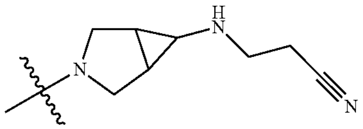 [SMILES: *N1CC2C(C1)C2NCCC#N] |
| 3.12 | 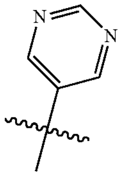 [SMILES: *c1cncnc1] | 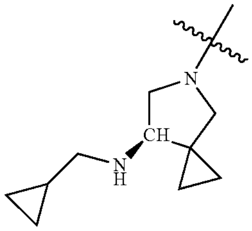 [SMILES: *N1C[C@H](NCC2CC2)C2(CC2)C1] |

-continued
Table of Formula I compounds where L = O, $R^x$, $R^y$, $R^z$ = H, $R^8$ = $NHCH_3$
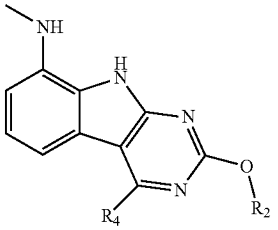
| Cmpd ID | R2 | R4 |
| --- | --- | --- |
| 3.13 | 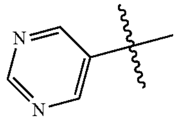 [SMILES: *c1cncnc1] | 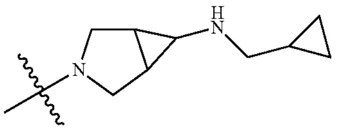 [SMILES: *N1CC2C(C1)C2NCC1CC1] |
| 3.14 | 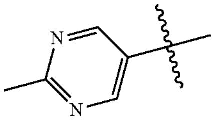 [SMILES: *c1cnc(C)nc1] | 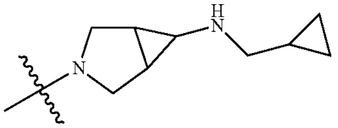 [SMILES: *N1CC2C(C1)C2NCC1CC1] |
| 3.15 | 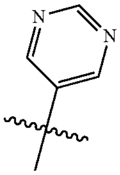 [SMILES: *c1cncnc1] | 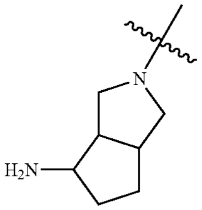 [SMILES: *N1CC2CCC(N)C2C1] |
| 3.16 | 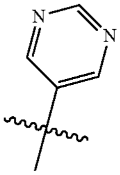 [SMILES: *c1cncnc1] | 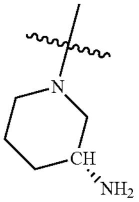 [SMILES: *N1CCC[C@@H](N)C1] |
| 3.17 | 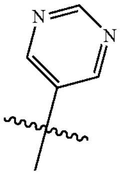 [SMILES: *c1cncnc1] | 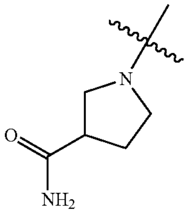 [SMILES: *N1CCC(C(N)=O)C1] |
| 3.18 | 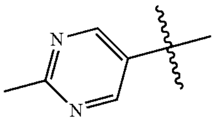 [SMILES: *c1cnc(C)nc1] | 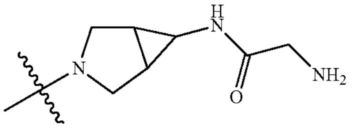 [SMILES: *N1CC2C(C1)C2NC(=O)CN] |
| 3.19 | 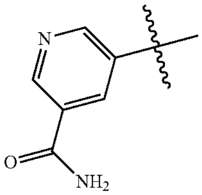 [SMILES: *c1cncc(C(N)=O)c1] | 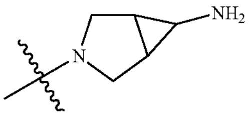 [SMILES: *N1CC2C(N)C2C1] |

-continued
Table of Formula I compounds where L = O, $R^x$, $R^y$, $R^z$ = H, $R^8$ = $NHCH_3$
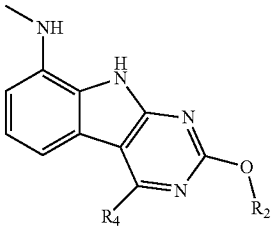
| Cmpd ID | R2 | R4 |
|---|---|---|
| 3.20 | 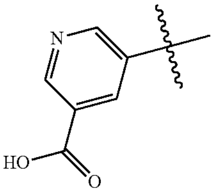 [SMILES: *c1cncc(C(=O)O)c1] | 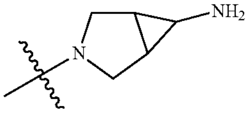 [SMILES: *N1CC2C(N)C2C1] |
| 3.21 | 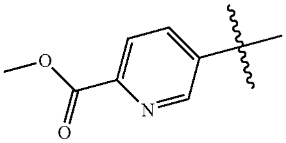 [SMILES: *c1ccc(C(=O)OC)nc1] | 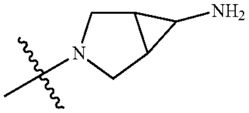 [SMILES: *N1CC2C(N)C2C1] |
| 3.22 | 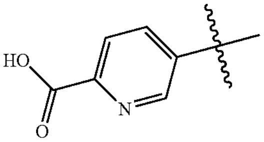 [SMILES: *c1ccc(C(=O)O)nc1] | 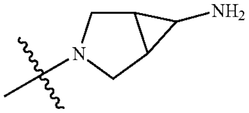 [SMILES: *N1CC2C(N)C2C1] |
| 3.23 | 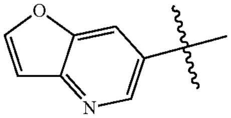 [SMILES: *c1cnc2ccoc2c1] | 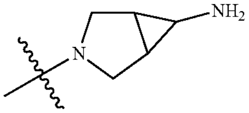 [SMILES: *N1CC2C(N)C2C1] |
| 3.24 | 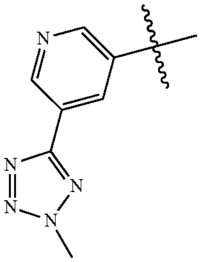 [SMILES: *c1cncc(-c2nnn(C)n2)c1] | 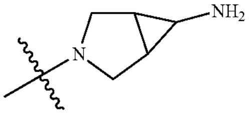 [SMILES: *N1CC2C(N)C2C1] |
| 3.25 | 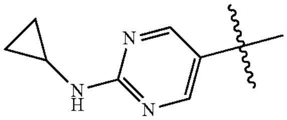 [SMILES: *c1cnc(NC2CC2)nc1] | 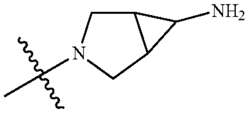 [SMILES: *N1CC2C(N)C2C1] |
| 3.26 | 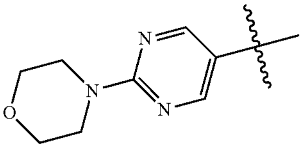 [SMILES: *c1cnc(N2CCOCC2)nc1] | 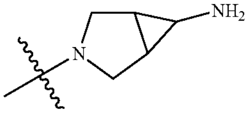 [SMILES: *N1CC2C(N)C2C1] |

-continued
Table of Formula I compounds where L = O, $R^x$, $R^y$, $R^z$ = H, $R^8$ = $NHCH_3$
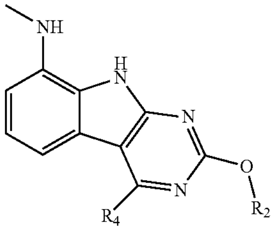
| Cmpd ID | R2 | R4 |
|---|---|---|
| 3.27 | 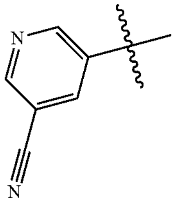 [SMILES: *c1cncc(C#N)c1] | 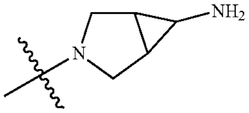 [SMILES: *N1CC2C(N)C2C1] |
| 3.28 | 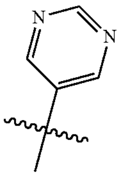 [SMILES: *c1cncnc1] | 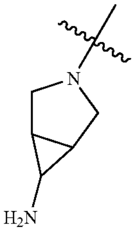 |
| 3.29 | 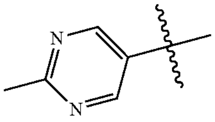 [SMILES: *c1cnc(C)nc1] | 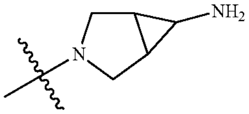 [SMILES: *N1CC2C(N)C2C1] |
| 3.30 | 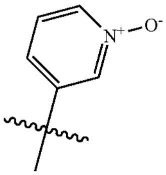 [SMILES: *c1ccc[n+]([O-])c1] | 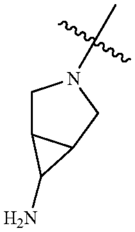 [SMILES: *N1CC2C(N)C2C1] |
| 3.31 | 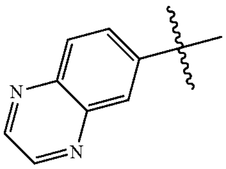 [SMILES: *c1ccc2nccnc2c1] | 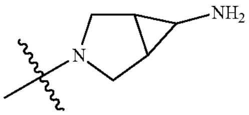 [SMILES: *N1CC2C(N)C2C1] |
| 3.32 | 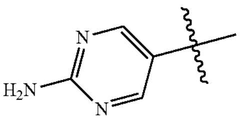 [SMILES: *c1cnc(N)nc1] | 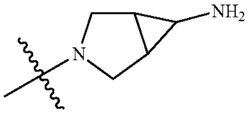 [SMILES: *N1CC2C(N)C2C1] |
| 3.33 | 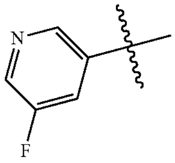 [SMILES: *c1cncc(F)c1] | 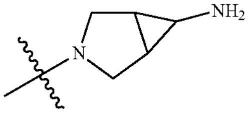 [SMILES: *N1CC2C(N)C2C1] |

-continued
Table of Formula I compounds where L = O, $R^x$, $R^y$, $R^z$ = H, $R^8$ = $NHCH_3$
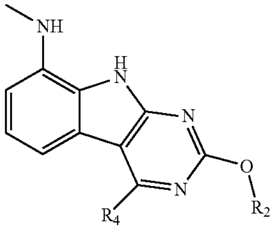
| Cmpd ID | R2 | R4 |
|---|---|---|
| 3.34 | 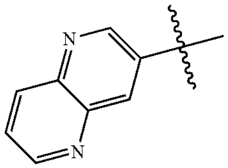 [SMILES: *c1cnc2cccnc2c1] | 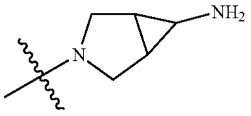 [SMILES: *N1CC2C(N)C2C1] |
| 3.35 | 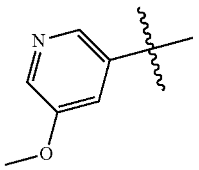 [SMILES: *c1cncc(OC)c1] | 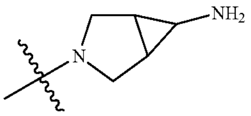 [SMILES: *N1CC2C(N)C2C1] |
| 3.36 | 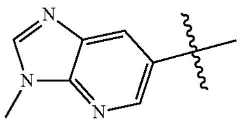 [SMILES: *c1cnc2c(c1)ncn2C] | 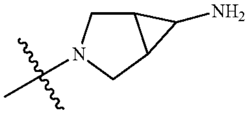 [SMILES: *N1CC2C(N)C2C1] |
| 3.37 | 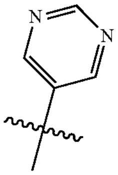 [SMILES: *c1cncnc1] | 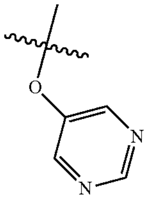 [SMILES: *Oc1cncnc1] |
| 3.38 | 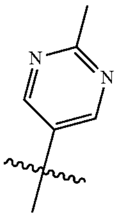 [SMILES: *c1cnc(C)nc1] | 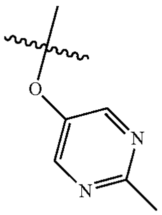 [SMILES: *Oc1cnc(C)nc1] |
| 3.39 | 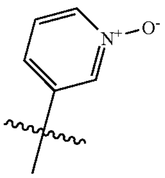 [SMILES: *c1ccc[n+]([O-])c1] | 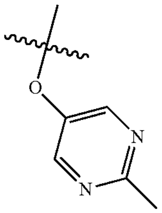 [SMILES: *Oc1cnc(C)nc1] |

-continued
Table of Formula I compounds where L = O, $R^x$, $R^y$, $R^z$ = H, $R^8$ = $NHCH_3$
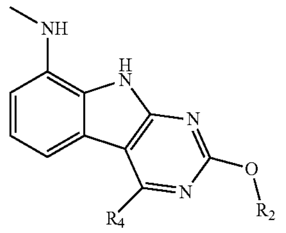
| Cmpd ID | R2 | R4 |
|---|---|---|
| 3.40 | 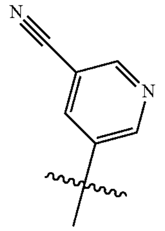 [SMILES: *c1cncc(C#N)c1] | 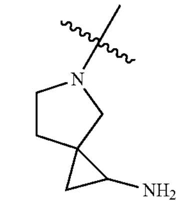 |
| 3.41 | 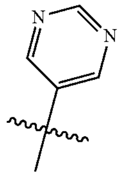 [SMILES: *c1cncnc1] | 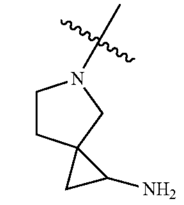 [SMILES: *N1CCC2(CC2N)C1] |
| 3.42 | 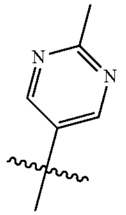 [SMILES: *c1cnc(C)nc1] | 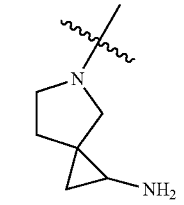 [SMILES: *N1CCC2(CC2N)C1] |
| 3.43 | 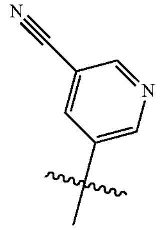 [SMILES: *c1cncc(C#N)c1] | 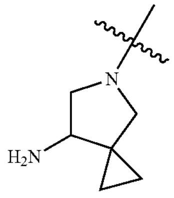 |
| 3.44 | 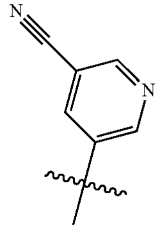 [SMILES: *c1cncc(C#N)c1] | 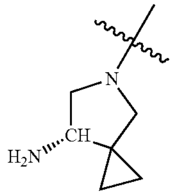 [SMILES: *N1C[C@@H](N)C2(CC2)C1] |

-continued
Table of Formula I compounds where L = O, $R^x$, $R^y$, $R^z$ = H, $R^8$ = $NHCH_3$
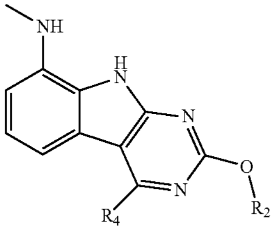
| Cmpd ID | R2 | R4 |
|---|---|---|
| 3.45 | 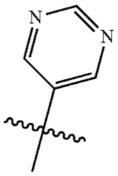 [SMILES: *c1cncnc1] | 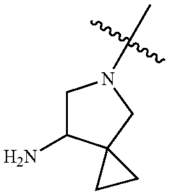 [SMILES: *N1CC(N)C2(CC2)C1] |
| 3.46 | 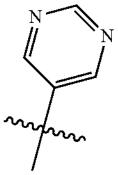 [SMILES: *c1cncnc1] | 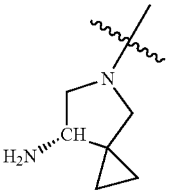 [SMILES: *N1C[C@@H](N)C2(CC2)C1] |
| 3.47 | 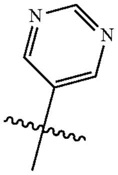 [SMILES: *c1cncnc1] | 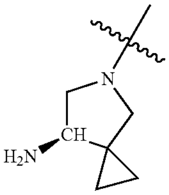 [SMILES: *N1C[C@H](N)C2(CC2)C1] |
| 3.48 | 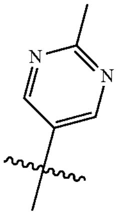 [SMILES: *c1cnc(C)nc1] | 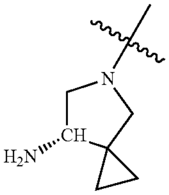 [SMILES: *N1C[C@@H](N)C2(CC2)C1] |
| 3.49 | 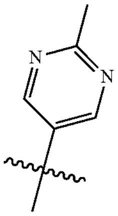 [SMILES: *c1cnc(C)nc1] | 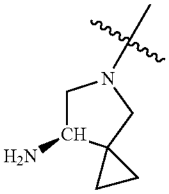 [SMILES: *N1C[C@H](N)C2(CC2)C1] |
| 3.50 | 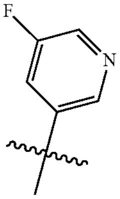 [SMILES: *c1cncc(F)c1] | 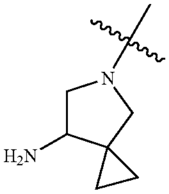 |

-continued
Table of Formula I compounds where L = O, $R^x$, $R^y$, $R^z$ = H, $R^8$ = $NHCH_3$
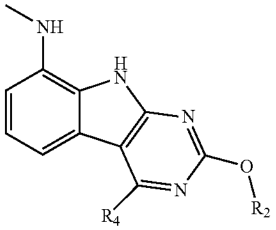
| Cmpd ID | R2 | R4 |
| --- | --- | --- |
| 3.51 | 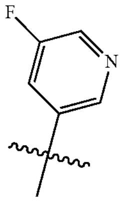 [SMILES: *c1cncc(F)c1] | 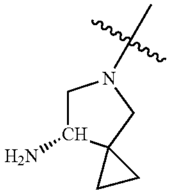 [SMILES: *N1C[C@@H](N)C2(CC2)C1] |
| 3.52 | 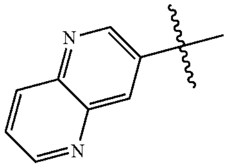 [SMILES: *c1cnc2cccnc2c1] | 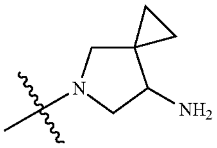 [SMILES: *N1CC(N)C2(CC2)C1] |
| 3.53 | 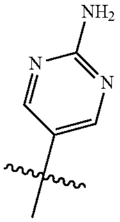 [SMILES: *c1cnc(N)nc1] | 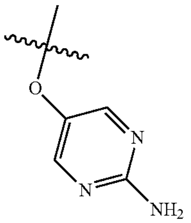 [SMILES: *Oc1cnc(N)nc1] |
| 3.54 | 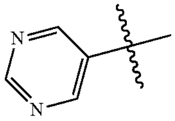 [SMILES: *c1cncnc1] | 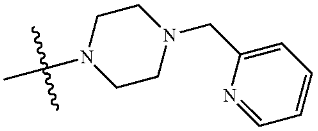 [SMILES: *N1CCN(Cc2ccccn2)CC1] |
| 3.55 | 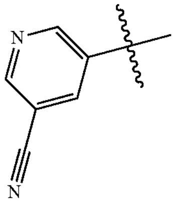 [SMILES: *c1cncc(C#N)c1] | 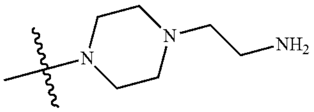 [SMILES: *N1CCN(CCN)CC1] |
| 3.56 | 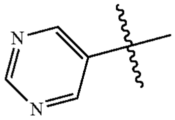 [SMILES: *c1cncnc1] | 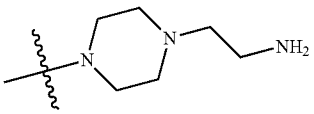 [SMILES: *N1CCN(CCN)CC1] |

-continued
Table of Formula I compounds where L = O, $R^x$, $R^y$, $R^z$ = H, $R^8$ = $NHCH_3$
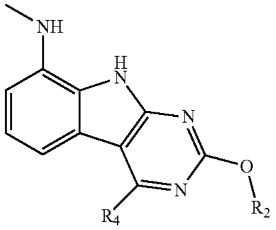
| Cmpd ID | R2 | R4 |
|---|---|---|
| 3.57 | 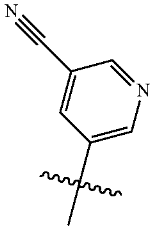 [SMILES: *c1cncc(C#N)c1] | 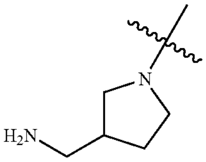 [SMILES: *N1CCC(CN)C1] |
| 3.58 | 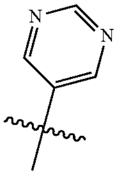 [SMILES: *c1cncnc1] | 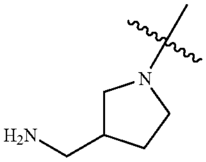 [SMILES: *N1CCC(CN)C1] |
| 3.59 | 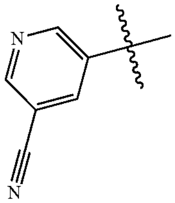 [SMILES: *c1cncc(C#N)c1] | 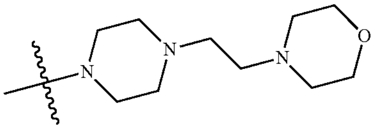 [SMILES: *N1CCN(CCN2CCOCC2)CC1] |
| 3.60 | 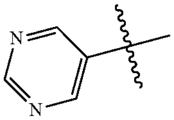 [SMILES: *c1cncnc1] | 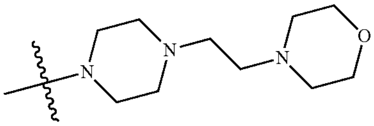 [SMILES: *N1CCN(CCN2CCOCC2)CC1] |
| 3.61 | 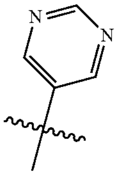 [SMILES: *c1cncnc1] | 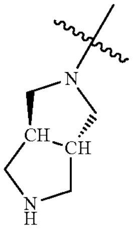 |
| 3.62 | 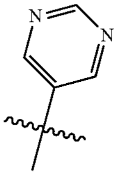 [SMILES: *c1cncnc1] | 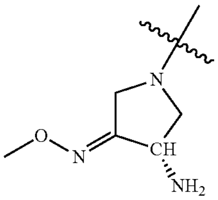 [SMILES: *N1C/C(=N\OC)[C@@H](N)C1] |

-continued
| Table of Formula I compounds where L = O, $R^x$, $R^y$, $R^z$ = H, $R^8$ = $NHCH_3$ | | |
|---|---|---|
| 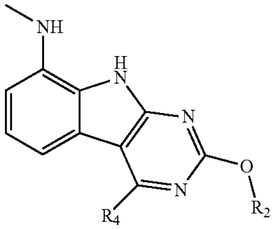 | | |
| Cmpd ID | R2 | R4 |
| 3.63 | 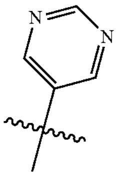 [SMILES: *c1cncnc1] | 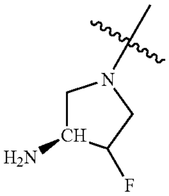 [SMILES: *N1CC(F)[C@@H](N)C1] |
| 3.64 | 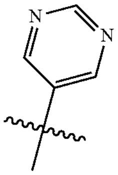 [SMILES: *c1cncnc1] | 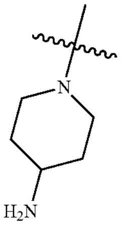 [SMILES: *N1CCC(N)CC1] |
| 3.65 | 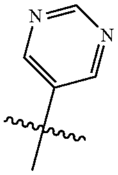 [SMILES: *c1cncnc1] | 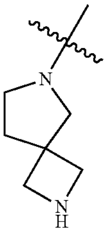 [SMILES: *N1CCC2(CNC2)C1] |
| 3.66 | 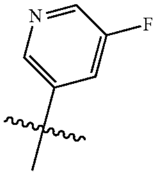 [SMILES: *c1cncc(F)c1] | 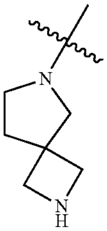 [SMILES: *N1CCC2(CNC2)C1] |
| 3.67 | 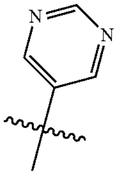 [SMILES: *c1cncnc1] | 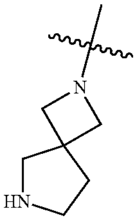 [SMILES: *N1CC2(CCNC2)C1] |

Table of Formula I Compounds Where L is O $R^x$, $R^z$ is CH, $R^y$ is F and $R^8$ is $NHCH_3$
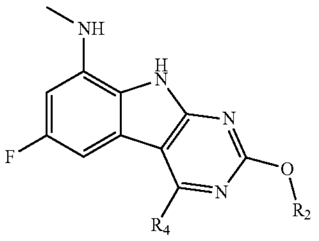
| Cmpd ID | R2 | R4 |
|---|---|---|
| 4.001 | 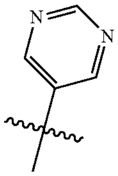 [SMILES: *c1cncnc1] | 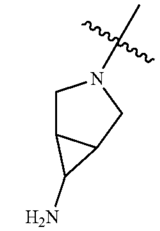 [SMILES: *N1CC2C(N)C2C1] |
| 4.002 | 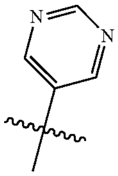 [SMILES: *c1cncnc1] | 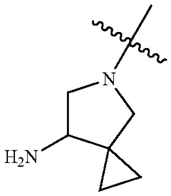 [SMILES: *N1CC(N)C2(CC2)C1] |
| 4.003 | 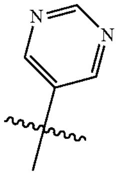 [SMILES: *c1cncnc1] | 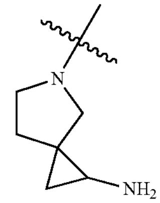 [SMILES: *N1CCC2(CC2N)C1] |
| 4.004 | 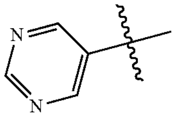 [SMILES: *c1cncnc1] | 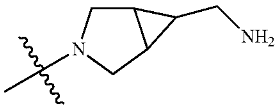 [SMILES: *N1CC2C(CN)C2C1] |
| 4.005 | 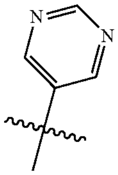 [SMILES: *c1cncnc1] | 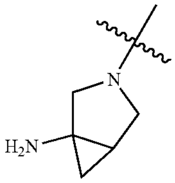 [SMILES: *N1CC2CC2(N)C1] |
| 4.006 | 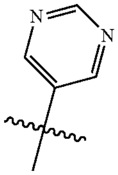 [SMILES: *c1cncnc1] | 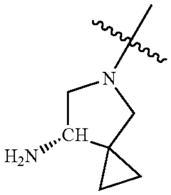 [SMILES: *N1C[C@@H](N)C2(CC2)C1] |

-continued
Table of Formula I Compounds Where L is O $R^x$, $R^z$ is CH, $R^y$ is F and $R^8$ is $NHCH_3$
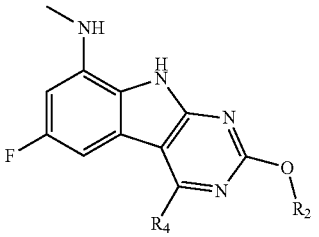
| | | |
|---|---|---|
| 4.007 | 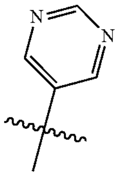 [SMILES: *c1cncnc1] | 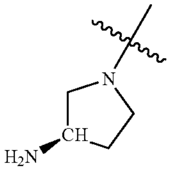 |
| 4.008 | 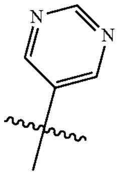 [SMILES: *c1cncnc1] | 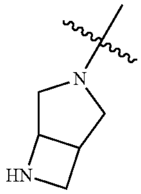 [SMILES: *N1CC2CNC2C1] |
| 4.009 | 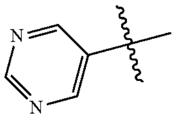 [SMILES: *c1cncnc1] | 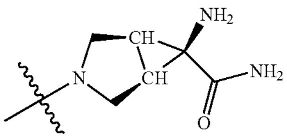 [SMILES: *N1C[C@@H]2[C@H](C1)[C@@]2(N)C(N)=O] |
| 4.010 | 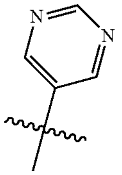 [SMILES: *c1cncnc1] | 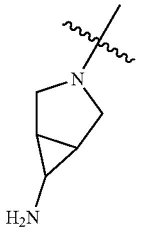 |
| 4.011 | 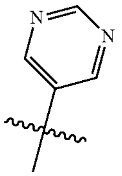 [SMILES: *c1cncnc1] | 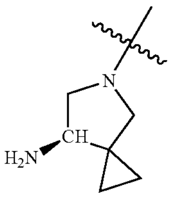 [SMILES: *N1C[C@H](N)C2(CC2)C1] |
| 4.012 | 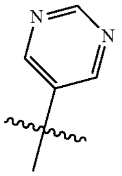 [SMILES: *c1cncnc1] | 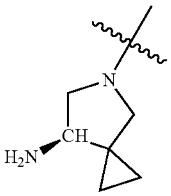 [SMILES: *N1C[C@H](N)C2(CC2)C1] |

-continued
| Table of Formula I Compounds Where L is O $R^x$, $R^z$ is CH, $R^y$ is F and $R^8$ is $NHCH_3$ | | |
|---|---|---|
| 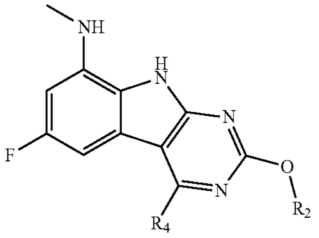 | | |
| 4.013 | 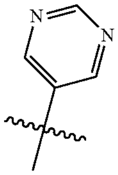 [SMILES: *c1cncnc1] | 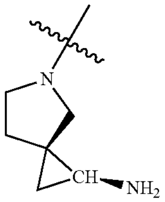 [SMILES: *N1CC[C@]2(C[C@@H]2N)C1] |
| 4.014 | 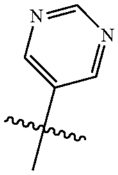 [SMILES: *c1cncnc1] | 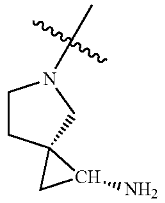 [SMILES: *N1CC[C@@]2(C[C@H]2N)C1] |
| 4.015 | 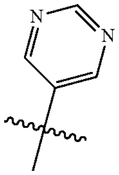 [SMILES: *c1cncnc1] | 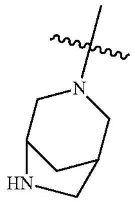 [SMILES: *N1CC2CNC(C2)C1] |
| 4.016 | 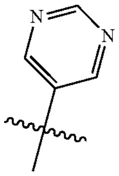 [SMILES: *c1cncnc1] | 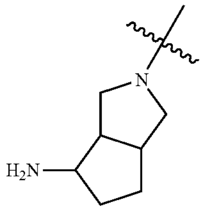 [SMILES: *N1CC2CCC(N)C2C1] |
| 4.017 | 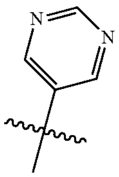 [SMILES: *c1cncnc1] | 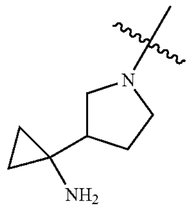 [SMILES: *N1CCC(C2(N)CC2)C1] |
| 4.018 | 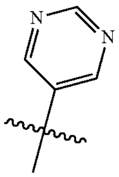 [SMILES: *c1cncnc1] | 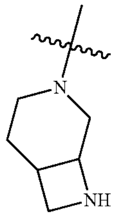 [SMILES: *N1CCC2CNC2C1] |

-continued
Table of Formula I Compounds Where L is O $R^x$, $R^z$ is CH, $R^y$ is F and $R^8$ is $NHCH_3$
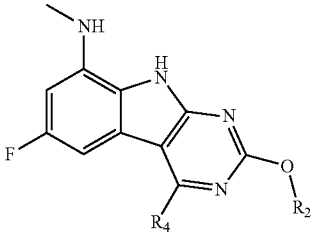
| | | |
|---|---|---|
| 4.019 | 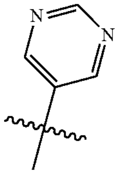 [SMILES: *c1cncnc1] | 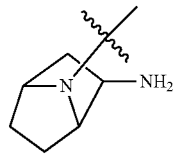 [SMILES: *N1C2CCC1C(N)C2] |
| 4.020 | 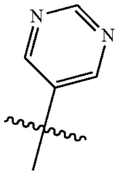 [SMILES: *c1cncnc1] | 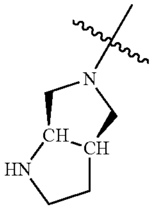 [SMILES: *N1C[C@H]2CCN[C@H]2C1] |
| 4.021 | 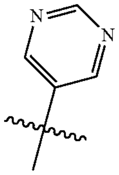 [SMILES: *c1cncnc1] | 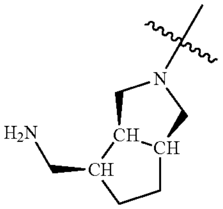 [SMILES: *N1C[C@H]2CC[C@@H](CN)[C@H]2C1] |
| 4.022 | 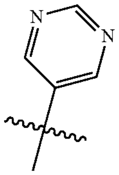 [SMILES: *c1cncnc1] | 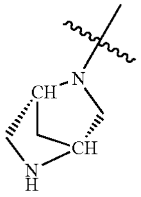 [SMILES: *N1C[C@H]2C[C@@H]1CN2] |
| 4.023 | 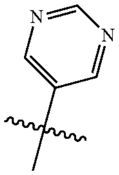 [SMILES: *c1cncnc1] | 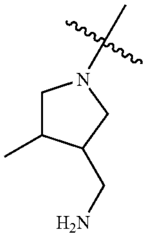 [SMILES: *N1CC(C)C(CN)C1] |
| 4.024 | 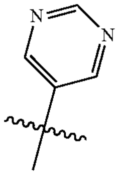 [SMILES: *c1cncnc1] | 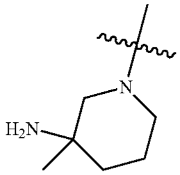 [SMILES: *N1CCCC(C)(N)C1] |

-continued
Table of Formula I Compounds Where L is O $R^x$, $R^z$ is CH, $R^y$ is F and $R^8$ is $NHCH_3$
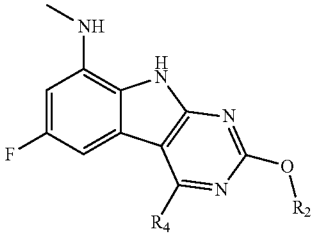
| | | |
|---|---|---|
| 4.025 | 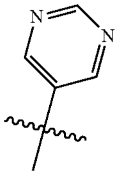 [SMILES: *c1cncnc1] | 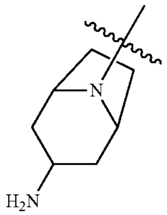 [SMILES: *N1C2CCC1CC(N)C2] |
| 4.026 | 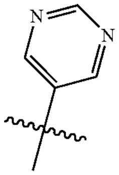 [SMILES: *c1cncnc1] | 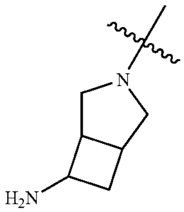 [SMILES: *N1CC2CC(N)C2C1] |
| 4.027 | 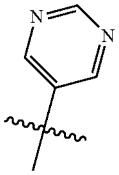 [SMILES: *c1cncnc1] | 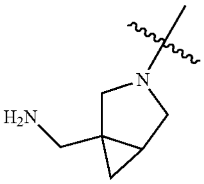 [SMILES: *N1CC2CC2(CN)C1] |
| 4.028 | 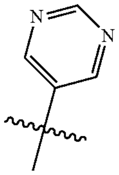 [SMILES: *c1cncnc1] | 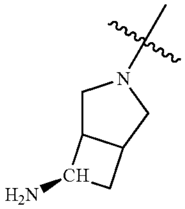 |
| 4.029 | 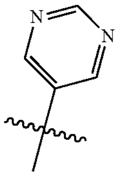 [SMILES: *c1cncnc1] | 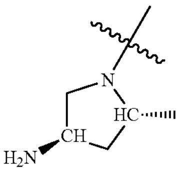 [SMILES: *N1C[C@H](N)C[C@H]1C] |
| 4.030 | 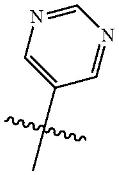 [SMILES: *c1cncnc1] | 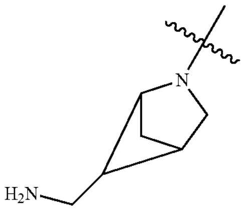 [SMILES: *N1CC2CC1C2CN] |

-continued
Table of Formula I Compounds Where L is O $R^x$, $R^z$ is CH, $R^y$ is F and $R^8$ is $NHCH_3$
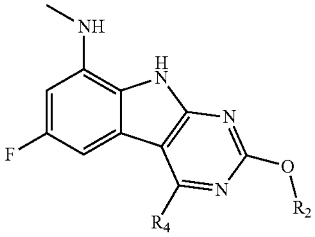
| | | |
|---|---|---|
| 4.031 | 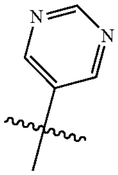 [SMILES: *c1cncnc1] | 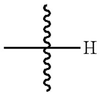 [SMILES: *[H]] |
| 4.032 | 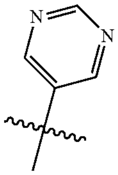 [SMILES: *c1cncnc1] | 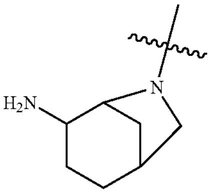 [SMILES: *N1CC2CCC(N)C1C2] |
| 4.033 | 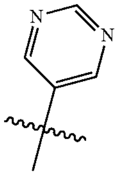 [SMILES: *c1cncnc1] | 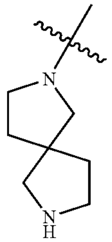 [SMILES: *N1CCC2(CCNC2)C1] |
| 4.034 | 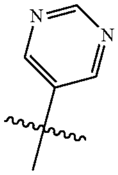 [SMILES: *c1cncnc1] | 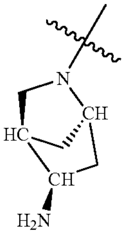 [SMILES: *N1C[C@H]2C[C@@H]1C[C@H]2N] |
| 4.035 | 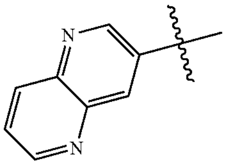 [SMILES: *c1cnc2cccnc2c1] | 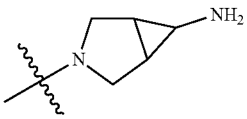 [SMILES: *N1CC2C(N)C2C1] |
| 4.036 | 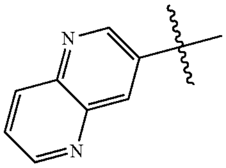 [SMILES: *c1cnc2cccnc2c1] | 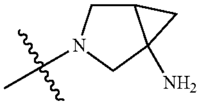 [SMILES: *N1CC2CC2(N)C1] |

-continued
Table of Formula I Compounds Where L is O $R^x$, $R^z$ is CH, $R^y$ is F and $R^8$ is $NHCH_3$
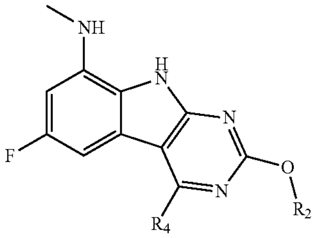
| | | |
|---|---|---|
| 4.037 | 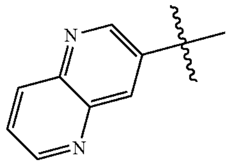 [SMILES: *c1cnc2cccnc2c1] | 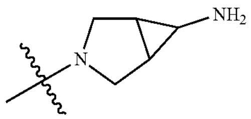 [SMILES: *N1CC2C(N)C2C1] |
| 4.038 | 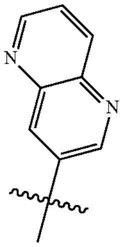 [SMILES: *c1cnc2cccnc2c1] | 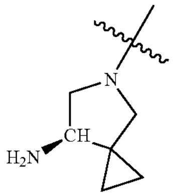 [SMILES: *N1C[C@H](N)C2(CC2)C1] |
| 4.039 | 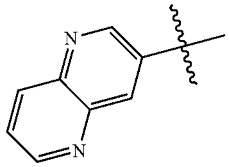 [SMILES: *c1cnc2cccnc2c1] | 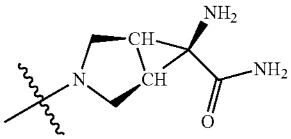 [SMILES: *N1C[C@@H]2[C@H](C1)[C@@]2(N)C(N)=O] |
| 4.040 | 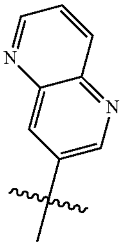 [SMILES: *c1cnc2cccnc2c1] | 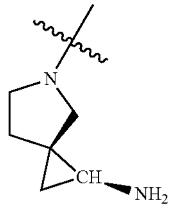 [SMILES: *N1CC[C@]2(C[C@@H]2N)C1] |
| 4.041 | 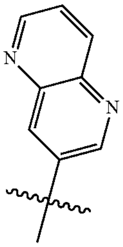 [SMILES: *c1cnc2cccnc2c1] | 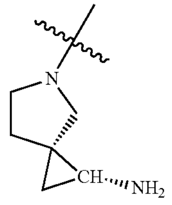 |
| 4.042 | 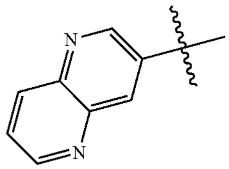 [SMILES: *c1cnc2cccnc2c1] | 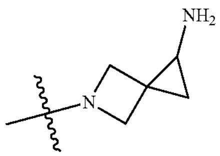 [SMILES: *N1CC2(CC2N)C1] |

-continued
Table of Formula I Compounds Where L is O $R^x$, $R^z$ is CH, $R^y$ is F and $R^8$ is $NHCH_3$
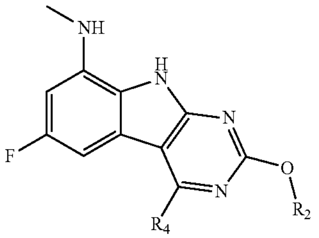
| | | |
|---|---|---|
| 4.043 | 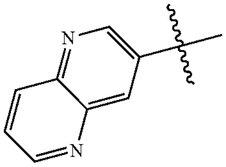 [SMILES: *c1cnc2cccnc2c1] | 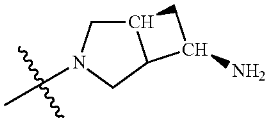 |
| 4.044 | 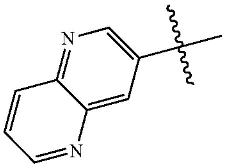 [SMILES: *c1cnc2cccnc2c1] | 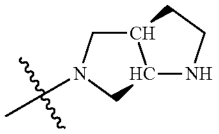 [SMILES: *N1C[C@H]2CCN[C@H]2C1] |
| 4.045 | 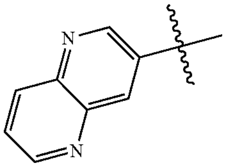 [SMILES: *c1cnc2cccnc2c1] | 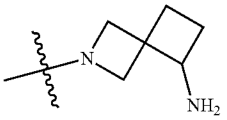 |
| 4.046 | 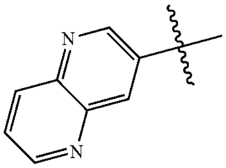 [SMILES: *c1cnc2cccnc2c1] | 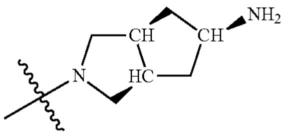 [SMILES: *N1C[C@H]2C[C@@H](N)C[C@H]2C1] |
| 4.047 | 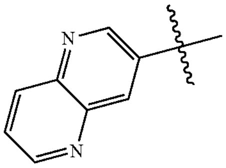 [SMILES: *c1cnc2cccnc2c1] | 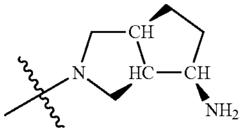 [SMILES: *N1C[C@H]2CC[C@@H](N)[C@H]2C1] |
| 4.048 | 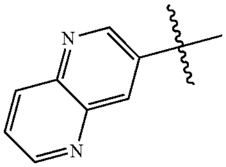 [SMILES: *c1cnc2cccnc2c1] | 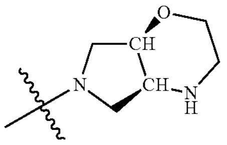 [SMILES: *N1C[C@@H]2NCCO[C@@H]2C1] |
| 4.049 | 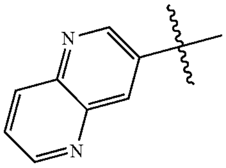 [SMILES: *c1cnc2cccnc2c1] | 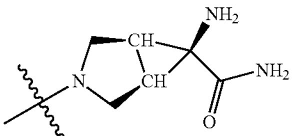 [SMILES: *N1C[C@@H]2[C@H](C1)[C@@]2(N)C(N)=O] |

-continued
Table of Formula I Compounds Where L is O $R^x$, $R^z$ is CH, $R^y$ is F and $R^8$ is $NHCH_3$
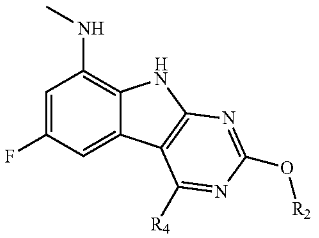
| | | |
|---|---|---|
| 4.050 | 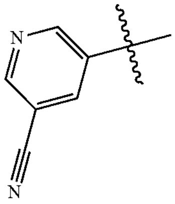 [SMILES: *c1cncc(C#N)c1] | 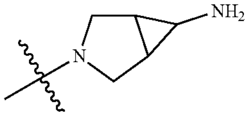 [SMILES: *N1CC2C(N)C2C1] |
| 4.051 | 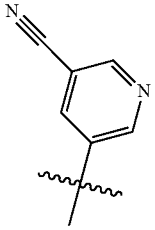 [SMILES: *c1cncc(C#N)c1] | 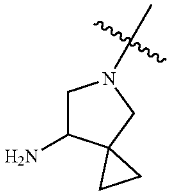 [SMILES: *N1CC(N)C2(CC2)C1] |
| 4.052 | 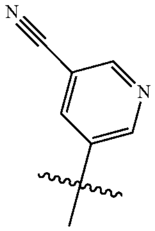 [SMILES: *c1cncc(C#N)c1] | 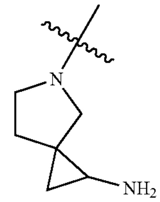 [SMILES: *N1CCC2(CC2N)C1] |
| 4.053 | 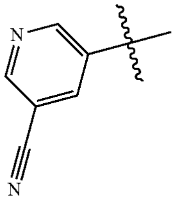 [SMILES: *c1cncc(C#N)c1] | 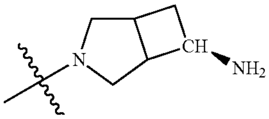 [SMILES: *N1CC2C[C@@H](N)C2C1] |
| 4.054 | 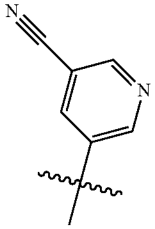 [SMILES: *c1cncc(C#N)c1] | 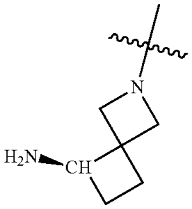 [SMILES: *N1CC2(CC[C@H]2N)C1] |
| 4.055 | 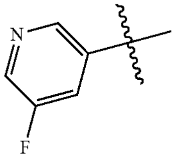 [SMILES: *c1cncc(F)c1] | 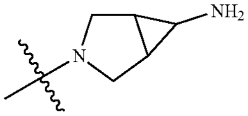 [SMILES: *N1CC2C(N)C2C1] |

-continued
Table of Formula I Compounds Where L is O $R^x$, $R^z$ is CH, $R^y$ is F and $R^8$ is $NHCH_3$
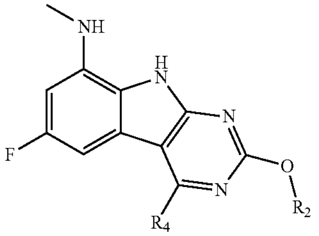
| | | |
|---|---|---|
| 4.056 | 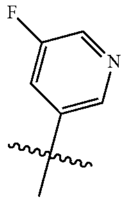 [SMILES: *c1cncc(F)c1] | 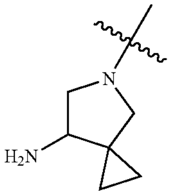 [SMILES: *N1CC(N)C2(CC2)C1] |
| 4.057 | 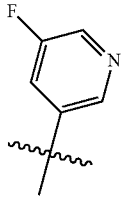 | 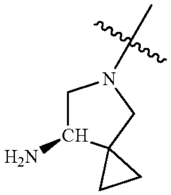 [SMILES: *N1C[C@H](N)C2(CC2)C1] |
| 4.058 | 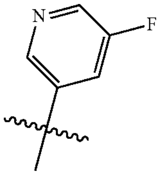 [SMILES: *c1cncc(F)c1] | 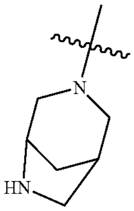 [SMILES: *N1CC2CNC(C2)C1] |
| 4.059 | 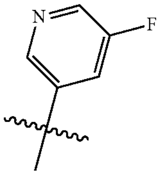 [SMILES: *c1cncc(F)c1] | 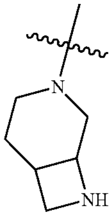 [SMILES: *N1CCC2CNC2C1] |
| 4.060 | 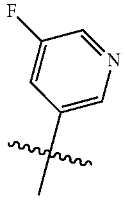 [SMILES: *c1cncc(F)c1] | 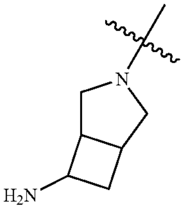 [SMILES: *N1CC2CC(N)C2C1] |
| 4.061 | 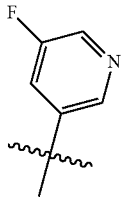 [SMILES: *c1cncc(F)c1] | 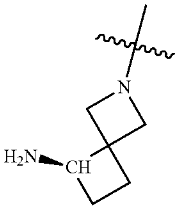 [SMILES: *N1CC2(CC[C@H]2N)C1] |

-continued
| Table of Formula I Compounds Where L is O $R^x$, $R^z$ is CH, $R^y$ is F and $R^8$ is $NHCH_3$ | | |
|---|---|---|
| | 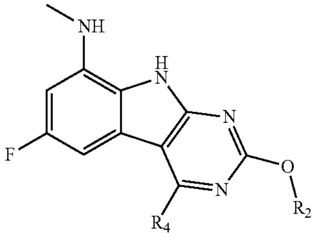 | |
| 4.062 | 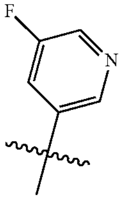 [SMILES: *c1cncc(F)c1] | 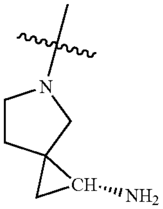 [SMILES: *N1CCC2(C[C@H]2N)C1] |
| 4.063 | 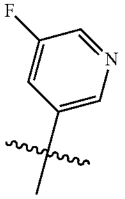 [SMILES: *c1cncc(F)c1] | 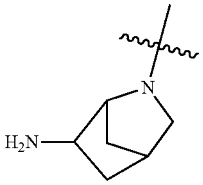 [SMILES: *N1CC2CC(N)C1C2] |
| 4.064 | 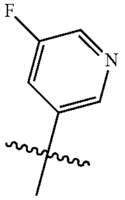 [SMILES: *c1cncc(F)c1] | 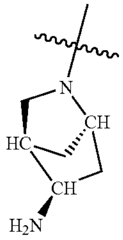 [SMILES: *N1C[C@H]2C[C@@H]1C[C@H]2N] |
| 4.065 | 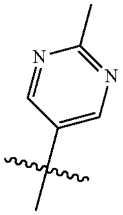 | 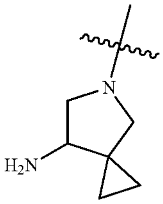 [SMILES: *N1CC(N)C2(CC2)C1] |
| 4.066 | 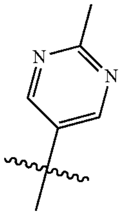 | 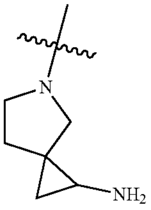 [SMILES: *N1CCC2(CC2N)C1] |
| 4.067 | 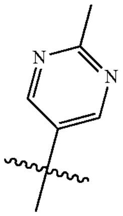 [SMILES: *c1cnc(C)nc1] | 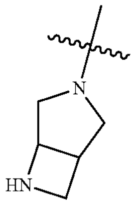 [SMILES: *N1CC2CNC2C1] |

-continued
Table of Formula I Compounds Where L is O $R^x$, $R^z$ is CH, $R^y$ is F and $R^8$ is $NHCH_3$
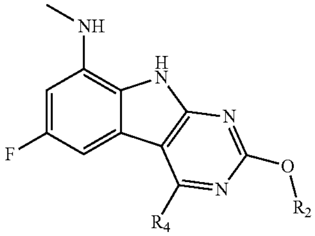
| | | |
|---|---|---|
| 4.068 | 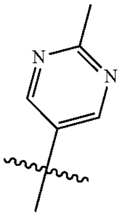 [SMILES: *c1cnc(C)nc1] | 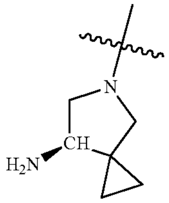 [SMILES: *N1C[C@H](N)C2(CC2)C1] |
| 4.069 | 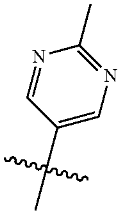 [SMILES: *c1cnc(C)nc1] | 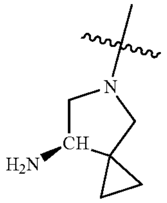 [SMILES: *N1C[C@H](N)C2(CC2)C1] |
| 4.070 | 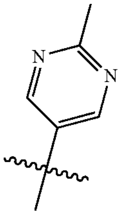 | 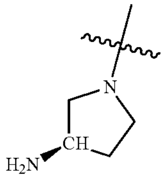 [SMILES: *N1CC[C@@H](N)C1] |
| 4.071 | 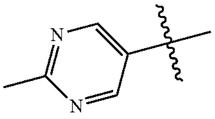 [SMILES: *c1cnc(C)nc1] | 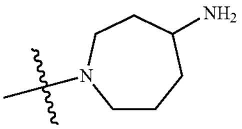 [SMILES: *N1CCCC(N)CC1] |
| 4.072 | 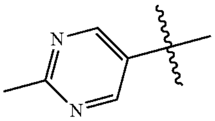 [SMILES: *c1cnc(C)nc1] | 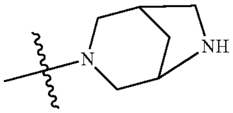 [SMILES: *N1CC2CNC(C2)C1] |
| 4.073 | 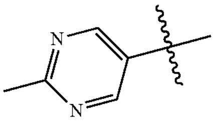 [SMILES: *c1cnc(C)nc1] | 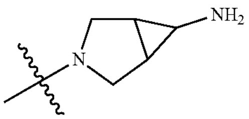 [SMILES: *N1CC2C(N)C2C1] |
| 4.074 | 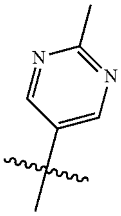 | 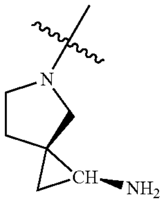 [SMILES: *N1CC[C@]2(C[C@@H]2N)C1] |

-continued
Table of Formula I Compounds Where L is O $R^x$, $R^z$ is CH, $R^y$ is F and $R^8$ is $NHCH_3$
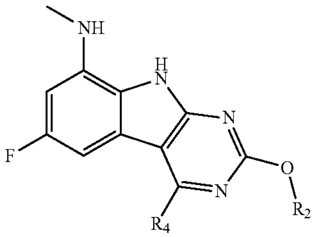
| | | |
|---|---|---|
| 4.075 | 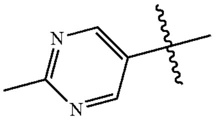 [SMILES: *c1cnc(C)nc1] | 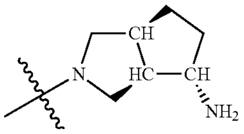 [SMILES: *N1C[C@H]2CC[C@H](N)[C@H]2C1] |
| 4.076 | 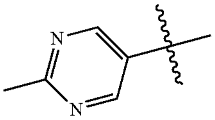 [SMILES: *c1cnc(C)nc1] | 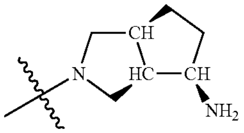 [SMILES: *N1C[C@H]2CC[C@@H](N)[C@H]2C1] |
| 4.077 | 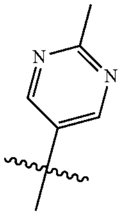 | 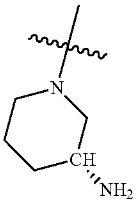 [SMILES: *N1CCC[C@@H](N)C1] |
| 4.078 | 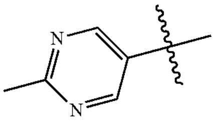 [SMILES: *c1cnc(C)nc1] | 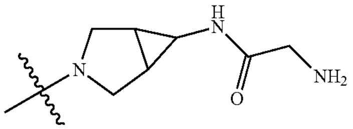 [SMILES: *N1CC2C(C1)C2NC(=O)CN] |
| 4.079 | 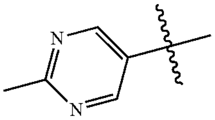 [SMILES: *c1cnc(C)nc1] | 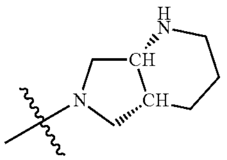 |
| 4.080 | 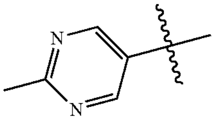 [SMILES: *c1cnc(C)nc1] | 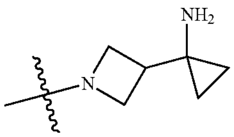 [SMILES: *N1CC(C2(N)CC2)C1] |
| 4.081 | 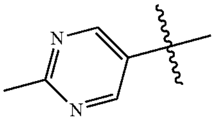 [SMILES: *c1cnc(C)nc1] | 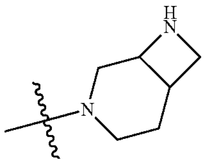 [SMILES: *N1CCC2CNC2C1] |

-continued
| Table of Formula I Compounds Where L is O $R^x$, $R^z$ is CH, $R^y$ is F and $R^8$ is $NHCH_3$ | | |
|---|---|---|
| 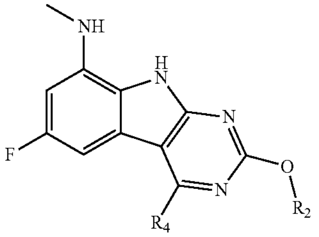 | | |
| 4.082 | 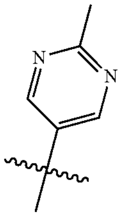 [SMILES: *c1cnc(C)nc1] | 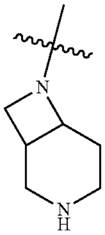 [SMILES: *N1CC2CNCCC21] |
| 4.083 | 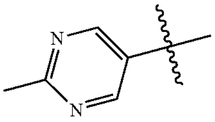 [SMILES: *c1cnc(C)nc1] | 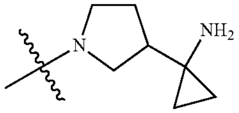 [SMILES: *N1CCC(C2(N)CC2)C1] |
| 4.084 | 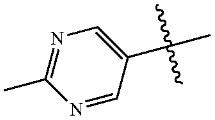 [SMILES: *c1cnc(C)nc1] | 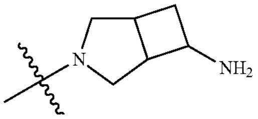 |
| 4.085 | 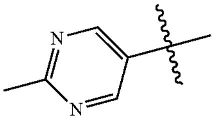 [SMILES: *c1cnc(C)nc1] | 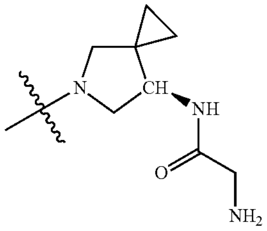 [SMILES: *N1C[C@H](NC(=O)CN)C2(CC2)C1] |
| 4.086 | 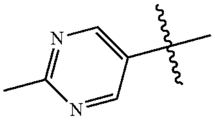 [SMILES: *c1cnc(C)nc1] | 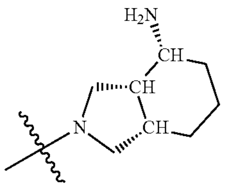 [SMILES: *N1C[C@H]2CCC[C@@H](N)[C@H]2C1] |
| 4.087 | 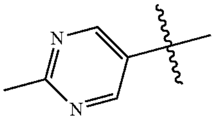 [SMILES: *c1cnc(C)nc1] | 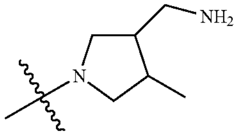 [SMILES: *N1CC(C)C(CN)C1] |
| 4.088 | 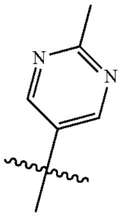 [SMILES: *c1cnc(C)nc1] | 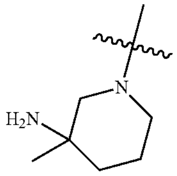 [SMILES: *N1CCCC(C)(N)C1] |

-continued
Table of Formula I Compounds Where L is O $R^x$, $R^z$ is CH, $R^y$ is F and $R^8$ is $NHCH_3$
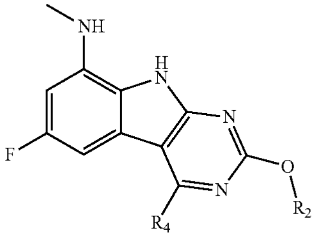
| | | |
|---|---|---|
| 4.089 | 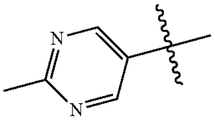 [SMILES: *c1cnc(C)nc1] | 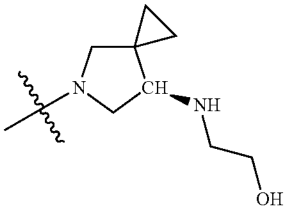 [SMILES: *N1C[C@H](NCCO)C2(CC2)C1] |
| 4.090 | 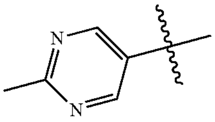 [SMILES: *c1cnc(C)nc1] | 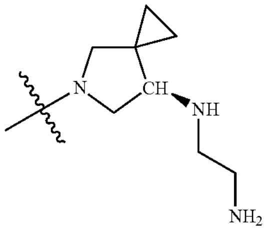 [SMILES: *N1C[C@H](NCCN)C2(CC2)C1] |
| 4.091 | 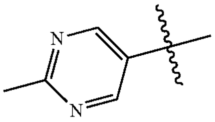 [SMILES: *c1cnc(C)nc1] | 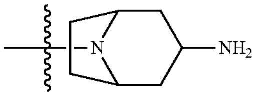 [SMILES: *N1C2CCC1CC(N)C2] |
| 4.092 | 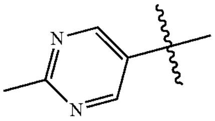 [SMILES: *c1cnc(C)nc1] | 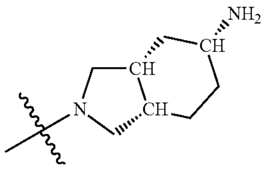 [SMILES: *N1C[C@H]2CC[C@@H](N)C[C@H]2C1] |
| 4.093 | 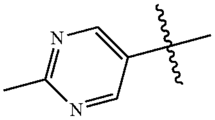 [SMILES: *c1cnc(C)nc1] | 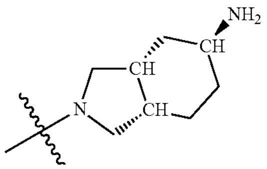 [SMILES: *N1C[C@H]2CC[C@H](N)C[C@H]2C1] |
| 4.094 | 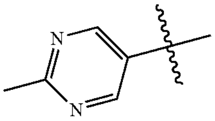 [SMILES: *c1cnc(C)nc1] | 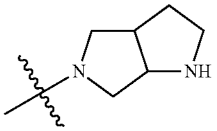 [SMILES: *N1CC2CCNC2C1] |
| 4.095 | 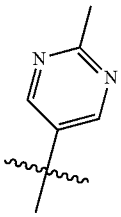 [SMILES: *c1cnc(C)nc1] | 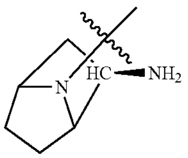 [SMILES: *N1C2CCC1[C@H](N)C2] |

-continued
Table of Formula I Compounds Where L is O $R^x$, $R^z$ is CH, $R^y$ is F and $R^8$ is $NHCH_3$
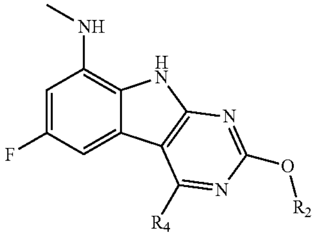
| | | |
|---|---|---|
| 4.096 | 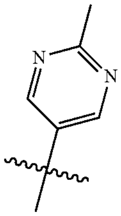 [SMILES: *c1cnc(C)nc1] | 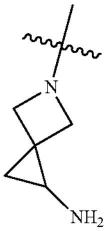 [SMILES: *N1CC2(CC2N)C1] |
| 4.097 | 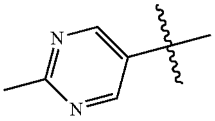 [SMILES: *c1cnc(C)nc1] | 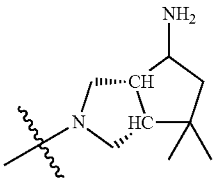 [SMILES: *N1C[C@@H]2C(N)CC(C)(C)[C@@H]2C1] |
| 4.098 | 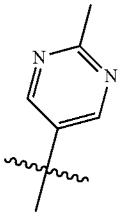 [SMILES: *c1cnc(C)nc1] | 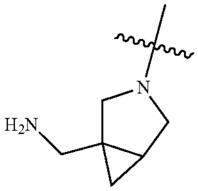 [SMILES: *N1CC2CC2(CN)C1] |
| 4.099 | 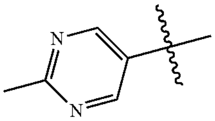 [SMILES: *c1cnc(C)nc1] | 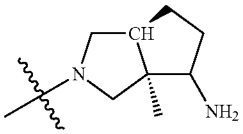 |
| 4.100 | 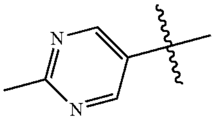 [SMILES: *c1cnc(C)nc1] | 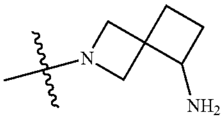 |
| 4.101 | 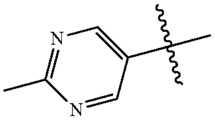 [SMILES: *c1cnc(C)nc1] | 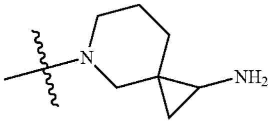 [SMILES: *N1CCCC2(CC2N)C1] |
| 4.102 | 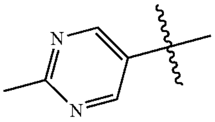 [SMILES: *c1cnc(C)nc1] | 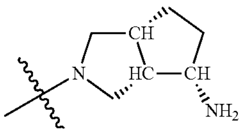 [SMILES: *N1C[C@@H]2CC[C@H](N)[C@@H]2C1] |

-continued
Table of Formula I Compounds Where L is O $R^x$, $R^z$ is CH, $R^y$ is F and $R^8$ is $NHCH_3$
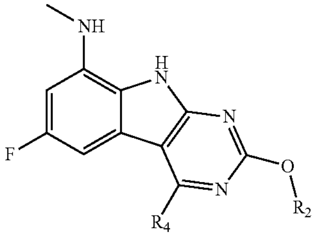
| | | |
|---|---|---|
| 4.103 | 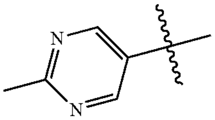 [SMILES: *c1cnc(C)nc1] | 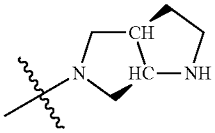 [SMILES: *N1C[C@H]2CCN[C@H]2C1] |
| 4.104 | 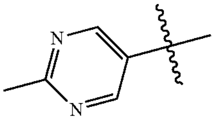 [SMILES: *c1cnc(C)nc1] | 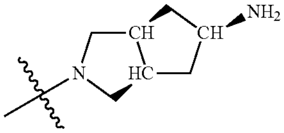 [SMILES: *N1C[C@H]2C[C@@H](N)C[C@H]2C1] |
| 4.105 | 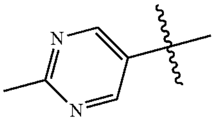 [SMILES: *c1cnc(C)nc1] | 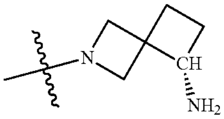 |
| 4.106 | 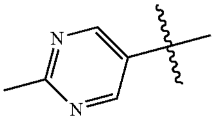 [SMILES: *c1cnc(C)nc1] | 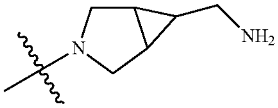 [SMILES: *N1CC2C(CN)C2C1] |
| 4.107 | 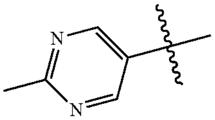 [SMILES: *c1cnc(C)nc1] | 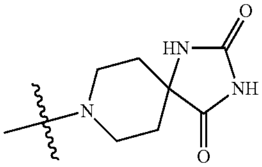 [SMILES: *N1CCC2(CC1)NC(=O)NC2=O] |
| 4.108 | 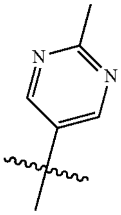 [SMILES: *c1cnc(C)nc1] | 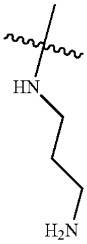 |
| 4.109 | 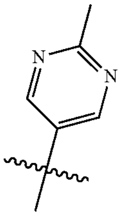 | 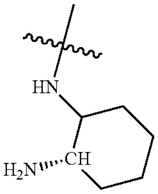 [SMILES: *NC1CCCC[C@@H]1N] |
| 4.110 | 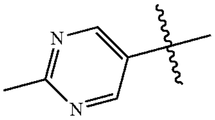 [SMILES: *c1cnc(C)nc1] | 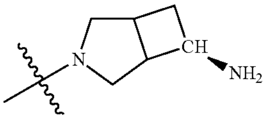 [SMILES: *N1CC2C[C@@H](N)C2C1] |

-continued
Table of Formula I Compounds Where L is O $R^x$, $R^z$ is CH, $R^y$ is F and $R^8$ is $NHCH_3$
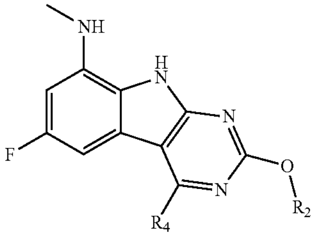
| | | |
|---|---|---|
| 4.111 | 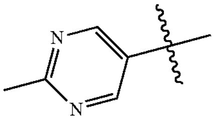 [SMILES: *c1cnc(C)nc1] | 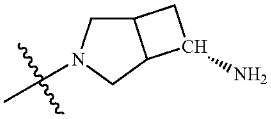 [SMILES: *N1CC2C[C@H](N)C2C1] |
| 4.112 | 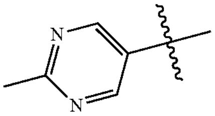 [SMILES: *c1cnc(C)nc1] | 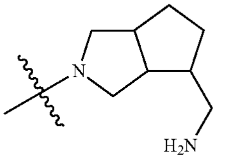 [SMILES: *N1CC2CCC(CN)C2C1] |
| 4.113 | 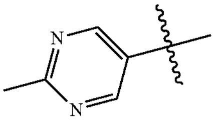 [SMILES: *c1cnc(C)nc1] | 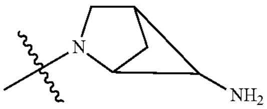 |
| 4.114 | 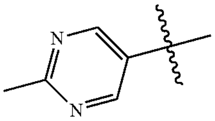 [SMILES: *c1cnc(C)nc1] | 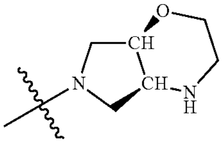 [SMILES: *N1C[C@@H]2NCCO[C@@H]2C1] |
| 4.115 | 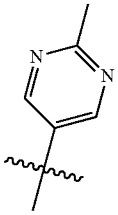 [SMILES: *c1cnc(C)nc1] | 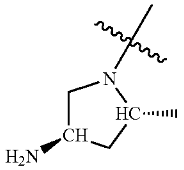 [SMILES: *N1C[C@H](N)C[C@H]1C] |
| 4.116 | 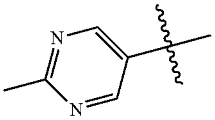 [SMILES: *c1cnc(C)nc1] | 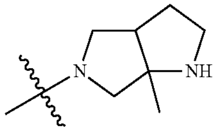 [SMILES: *N1CC2CCNC2(C)C1] |
| 4.117 | 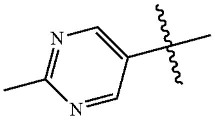 [SMILES: *c1cnc(C)nc1] | 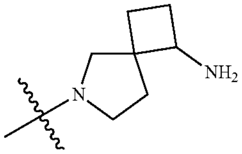 [SMILES: *N1CCC2(CCC2N)C1] |
| 4.118 | 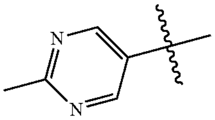 [SMILES: *c1cnc(C)nc1] | 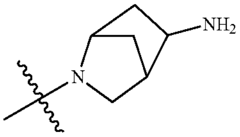 [SMILES: *N1CC2CC1CC2N] |

-continued
Table of Formula I Compounds Where L is O $R^x$, $R^z$ is CH, $R^y$ is F and $R^8$ is $NHCH_3$
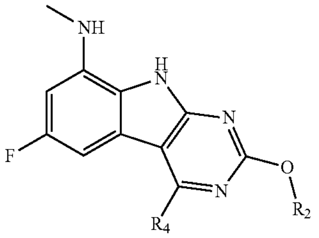
| | | |
|---|---|---|
| 4.119 | 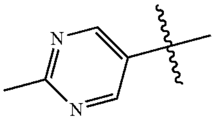 [SMILES: *c1cnc(C)nc1] | 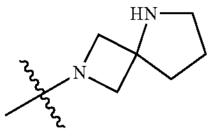 [SMILES: *N1CC2(CCCN2)C1] |
| 4.120 | 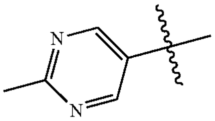 [SMILES: *c1cnc(C)nc1] | 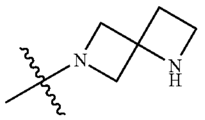 [SMILES: *N1CC2(CCN2)C1] |
| 4.121 | 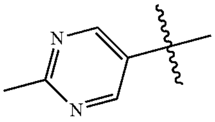 [SMILES: *c1cnc(C)nc1] | 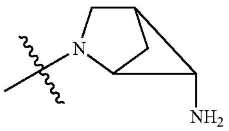 [SMILES: *N1CC2CC1C2N] |
| 4.122 | 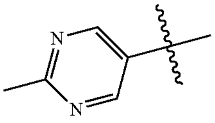 [SMILES: *c1cnc(C)nc1] | 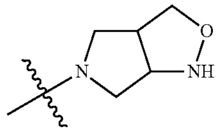 [SMILES: *N1CC2CONC2C1] |
| 4.123 | 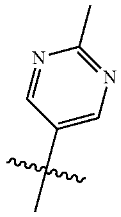 [SMILES: *c1cnc(C)nc1] | 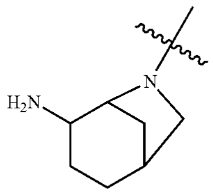 [SMILES: *N1CC2CCC(N)C1C2] |
| 4.124 | 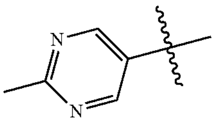 [SMILES: *c1cnc(C)nc1] | 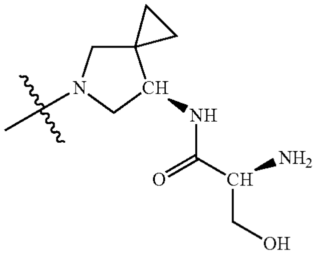 [SMILES: *N1C[C@H](NC(=O)[C@@H](N)CO)C2(CC2)C1] |
| 4.125 | 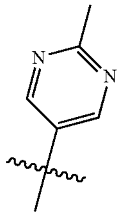 [SMILES: *c1cnc(C)nc1] | 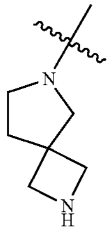 [SMILES: *N1CCC2(CNC2)C1] |

-continued
Table of Formula I Compounds Where L is O $R^x$, $R^z$ is CH, $R^y$ is F and $R^8$ is $NHCH_3$
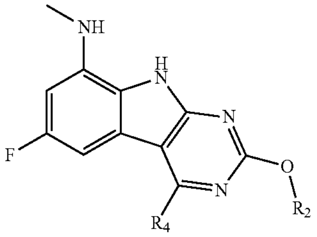
| | | |
|---|---|---|
| 4.126 | 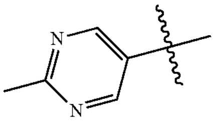 [SMILES: *c1cnc(C)nc1] | 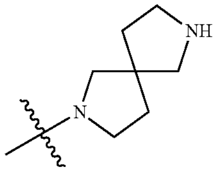 [SMILES: *N1CCC2(CCNC2)C1] |
| 4.127 | 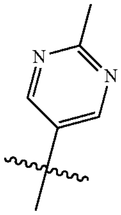 [SMILES: *c1cnc(C)nc1] | 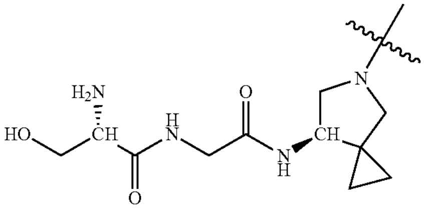 [SMILES: *N1C[C@H](NC(=O)CNC(=O)[C@@H](N)CO)C2(CC2)C1] |
| 4.128 | 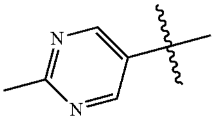 [SMILES: *c1cnc(C)nc1] | 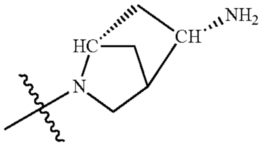 [SMILES: *N1CC2C[C@H]1C[C@@H]2N] |
| 4.129 | 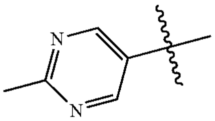 [SMILES: *c1cnc(C)nc1] | 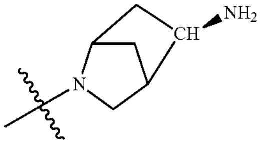 [SMILES: *N1CC2CC1C[C@H]2N] |
| 4.130 | 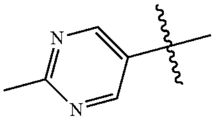 [SMILES: *c1cnc(C)nc1] | 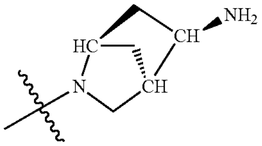 [SMILES: *N1C[C@H]2C[C@@H]1C[C@H]2N] |
| 4.131 | 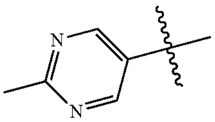 [SMILES: *c1cnc(C)nc1] | 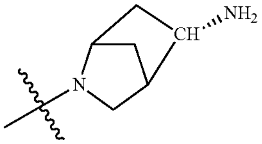 [SMILES: *N1CC2CC1C[C@@H]2N] |
| 4.132 | 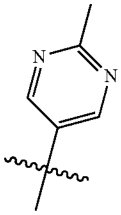 [SMILES: *c1cnc(C)nc1] | 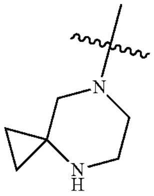 [SMILES: *N1CCNC2(CC2)C1] |

-continued
Table of Formula I Compounds Where L is O $R^x$, $R^z$ is CH, $R^y$ is F and $R^8$ is $NHCH_3$
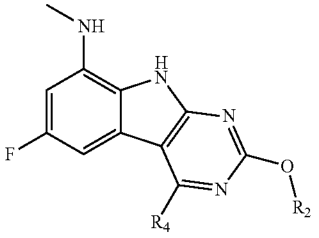
| | | |
|---|---|---|
| 4.133 | 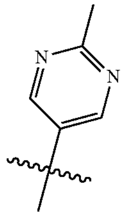 | 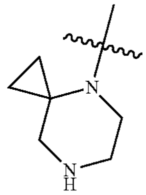 [SMILES: *N1CCNCC12CC2] |
| 4.134 | 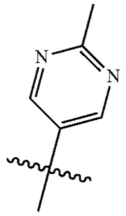 [SMILES: *c1cnc(C)nc1] | 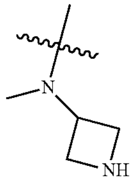 [SMILES: *N(C)C1CNC1] |
| 4.135 | 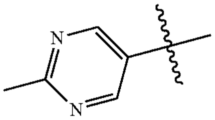 [SMILES: *c1cnc(C)nc1] | 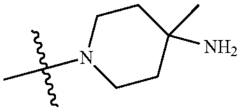 [SMILES: *N1CCC(C)(N)CC1] |
| 4.136 | 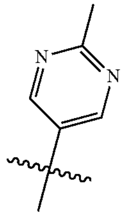 [SMILES: *c1cnc(C)nc1] | 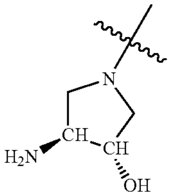 [SMILES: *N1C[C@H](N)[C@@H](O)C1] |
| 4.137 | 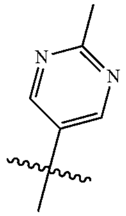 [SMILES: *c1cnc(C)nc1] | 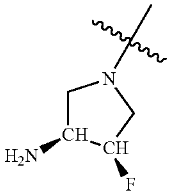 [SMILES: *N1C[C@@H](F)[C@@H](N)C1] |
| 4.138 | 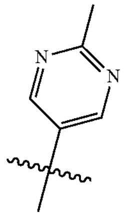 [SMILES: *c1cnc(C)nc1] | 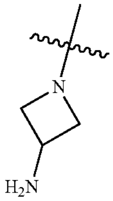 [SMILES: *N1CC(N)C1] |

-continued
Table of Formula I Compounds Where L is O $R^x$, $R^z$ is CH, $R^y$ is F and $R^8$ is $NHCH_3$
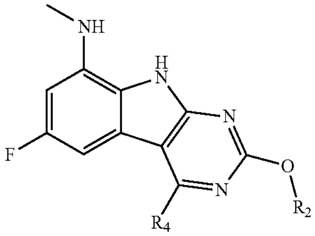
| | | |
|---|---|---|
| 4.139 | 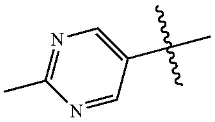 [SMILES: *c1cnc(C)nc1] | 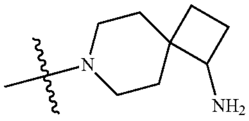 |
| 4.140 | 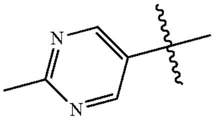 [SMILES: *c1cnc(C)nc1] | 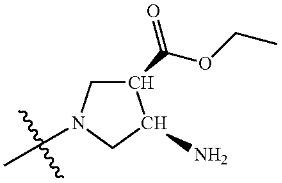 [SMILES: *N1C[C@H](N)[C@H](C(=O)OCC)C1] |
| 4.141 | 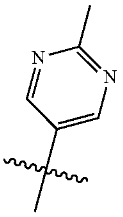 [SMILES: *c1cnc(C)nc1] | 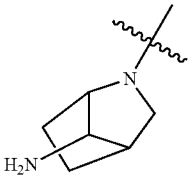 [SMILES: *N1CC2CCC1C2N] |
| 4.142 | 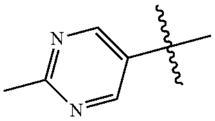 [SMILES: *c1cnc(C)nc1] | 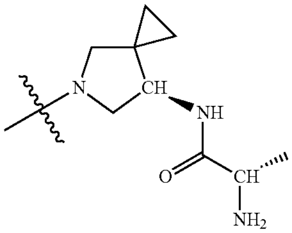 [SMILES: *N1C[C@H](NC(=O)[C@H](C)N)C2(CC2)C1] |
| 4.143 | 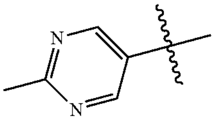 [SMILES: *c1cnc(C)nc1] | 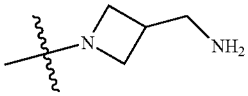 [SMILES: *N1CC(CN)C1] |
| 4.144 | 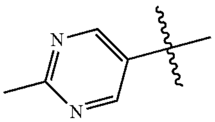 [SMILES: *c1cnc(C)nc1] | 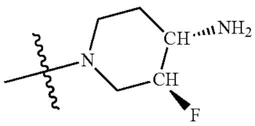 [SMILES: *N1CC[C@H](N)[C@@H](F)C1] |
| 4.145 | 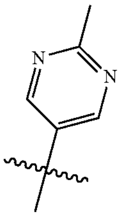 | 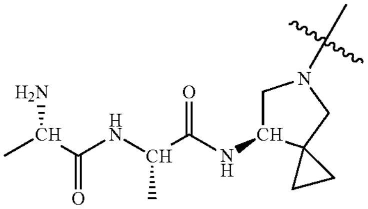 [SMILES: *N1C[C@H](NC(=O)[C@H](C)NC(=O)[C@H](C)N)C2(CC2)C1] |

-continued
Table of Formula I Compounds Where L is O $R^x$, $R^z$ is CH, $R^y$ is F and $R^8$ is $NHCH_3$
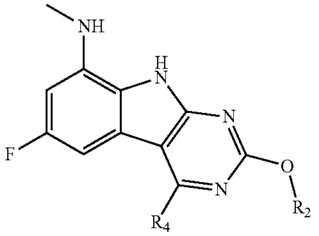
| | | |
|---|---|---|
| 4.146 | 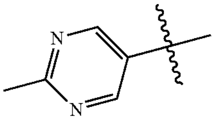 [SMILES: *c1cnc(C)nc1] | 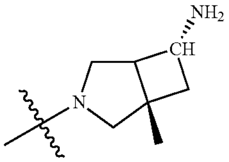 [SMILES: *N1CC2[C@H](N)C[C@]2(C)C1] |
| 4.147 | 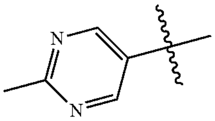 [SMILES: *c1cnc(C)nc1] | 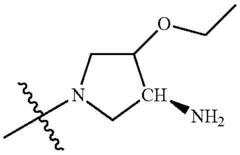 [SMILES: *N1CC(OCC)[C@@H](N)C1] |
| 4.148 | 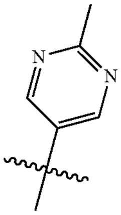 | 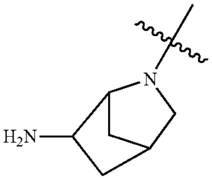 [SMILES: *N1CC2CC(N)C1C2] |
| 4.149 | 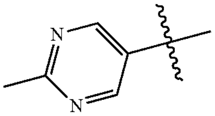 [SMILES: *c1cnc(C)nc1] | 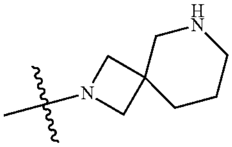 [SMILES: *N1CC2(CCCNC2)C1] |
| 4.150 | 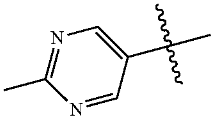 [SMILES: *c1cnc(C)nc1] | 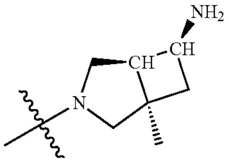 [SMILES: *N1C[C@H]2[C@@H](N)C[C@@]2(C)C1] |
| 4.151 | 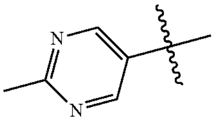 [SMILES: *c1cnc(C)nc1] | 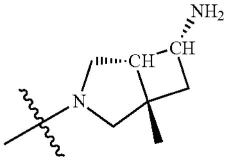 [SMILES: *N1C[C@@H]2[C@H](N)C[C@]2(C)C1] |
| 4.152 | 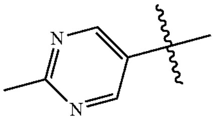 [SMILES: *c1cnc(C)nc1] | 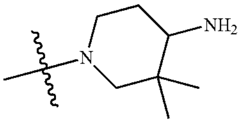 [SMILES: *N1CCC(N)C(C)(C)C1] |
| 4.153 | 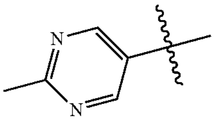 [SMILES: *c1cnc(C)nc1] | 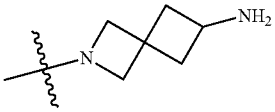 [SMILES: *N1CC2(CC(N)C2)C1] |

-continued
Table of Formula I Compounds Where L is O $R^x$, $R^z$ is CH, $R^y$ is F and $R^8$ is $NHCH_3$
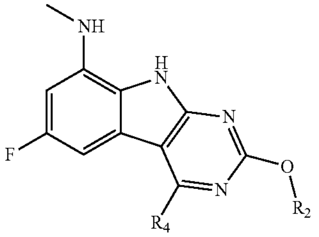
| | | |
|---|---|---|
| 4.154 | 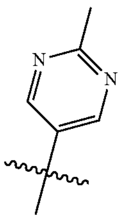 [SMILES: *c1cnc(C)nc1] | 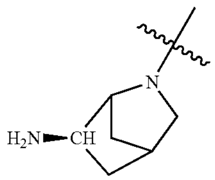 [SMILES: *N1CC2CC1[C@H](N)C2] |
| 4.155 | 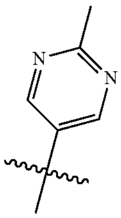 [SMILES: *c1cnc(C)nc1] | 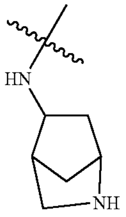 [SMILES: *NC1CC2CC1CN2] |
| 4.156 | 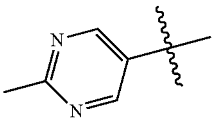 [SMILES: *c1cnc(C)nc1] | 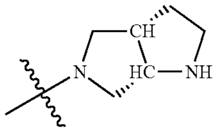 [SMILES: *N1C[C@@H]2CCN[C@@H]2C1] |
| 4.157 | 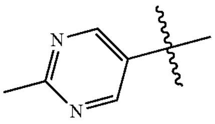 [SMILES: *c1cnc(C)nc1] | 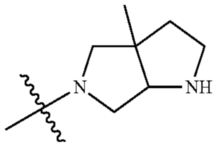 [SMILES: *N1CC2NCCC2(C)C1] |
| 4.158 | 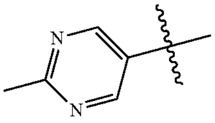 [SMILES: *c1cnc(C)nc1] | 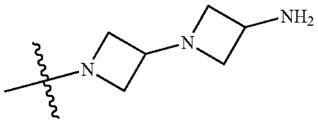 [SMILES: *N1CC(N2CC(N)C2)C1] |
| 4.159 | 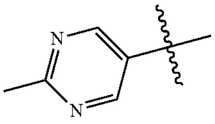 [SMILES: *c1cnc(C)nc1] | 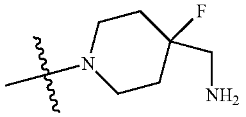 [SMILES: *N1CCC(F)(CN)CC1] |
| 4.160 | 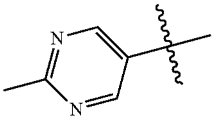 [SMILES: *c1cnc(C)nc1] | 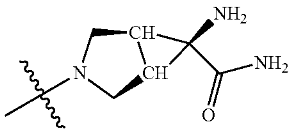 |
| 4.161 | 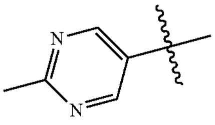 [SMILES: *c1cnc(C)nc1] | 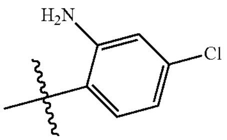 [SMILES: *c1ccc(Cl)cc1N] |

-continued
Table of Formula I Compounds Where L is O $R^x$, $R^z$ is CH, $R^y$ is F and $R^8$ is $NHCH_3$
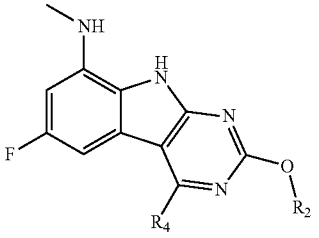
| | | |
|---|---|---|
| 4.162 | 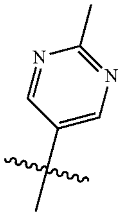 | 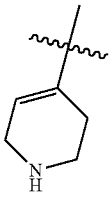 [SMILES: *C1=CCNCC1] |
| 4.163 | 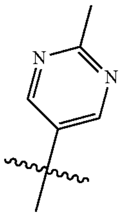 [SMILES: *c1cnc(C)nc1] | 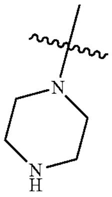 [SMILES: *N1CCNCC1] |
| 4.164 | 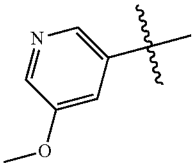 [SMILES: *c1cncc(OC)c1] | 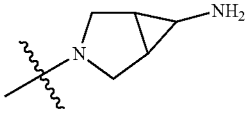 [SMILES: *N1CC2C(N)C2C1] |
| 4.165 | 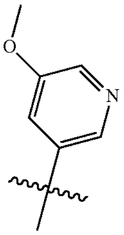 [SMILES: *c1cncc(OC)c1] | 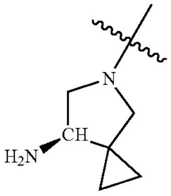 [SMILES: *N1C[C@H](N)C2(CC2)C1] |
| 4.166 | 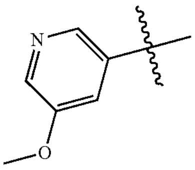 [SMILES: *c1cncc(OC)c1] | 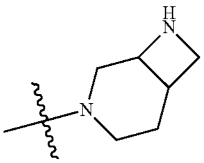 [SMILES: *N1CCC2CNC2C1] |
| 4.167 | 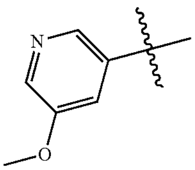 [SMILES: *c1cncc(OC)c1] | 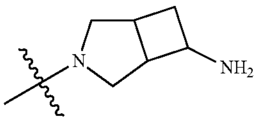 [SMILES: *N1CC2CC(N)C2C1] |

-continued
Table of Formula I Compounds Where L is O $R^x$, $R^z$ is CH, $R^y$ is F and $R^8$ is $NHCH_3$
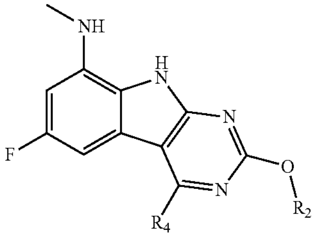
| | | |
|---|---|---|
| 4.168 | 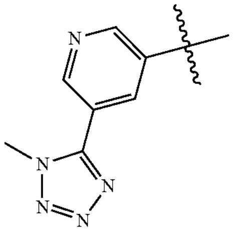 [SMILES: *c1cncc(-c2nnnn2C)c1] | 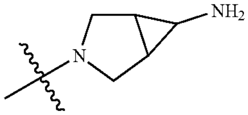 [SMILES: *N1CC2C(N)C2C1] |
| 4.169 | 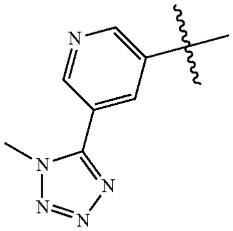 [SMILES: *c1cncc(-c2nnnn2C)c1] | 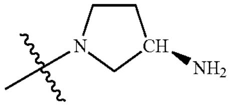 [SMILES: *N1CC[C@@H](N)C1] |
| 4.170 | 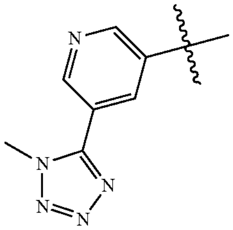 [SMILES: *c1cncc(-c2nnnn2C)c1] | 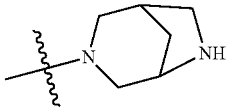 [SMILES: *N1CC2CNC(C2)C1] |
| 4.171 | 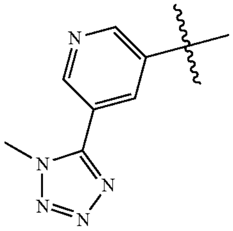 [SMILES: *c1cncc(-c2nnnn2C)c1] | 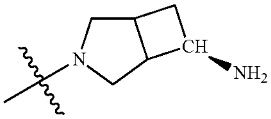 [SMILES: *N1CC2C[C@@H](N)C2C1] |
| 4.172 | 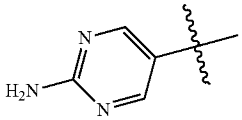 [SMILES: *c1cnc(N)nc1] | 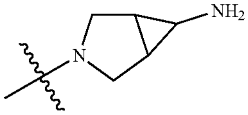 [SMILES: *N1CC2C(N)C2C1] |
| 4.173 | 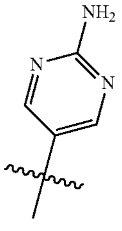 [SMILES: *c1cnc(N)nc1] | 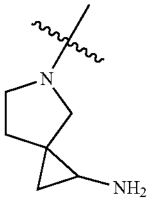 [SMILES: *N1CCC2(CC2N)C1] |

-continued
Table of Formula I Compounds Where L is O $R^x$, $R^z$ is CH, $R^y$ is F and $R^8$ is $NHCH_3$
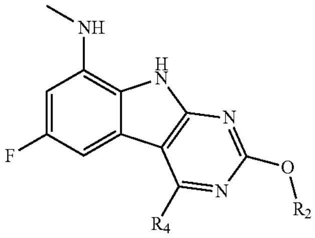
| | | |
|---|---|---|
| 4.174 | 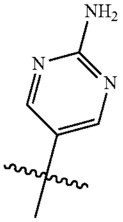 [SMILES: *c1cnc(N)nc1] | 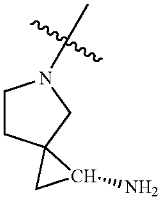 [SMILES: *N1CCC2(C[C@H]2N)C1] |
| 4.175 | 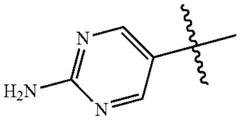 [SMILES: *c1cnc(N)nc1] | 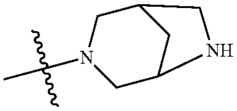 [SMILES: *N1CC2CNC(C2)C1] |
| 4.176 | 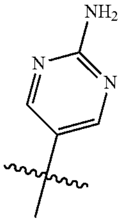 [SMILES: *c1cnc(N)nc1] | 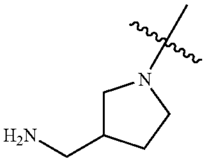 [SMILES: *N1CCC(CN)C1] |
| 4.177 | 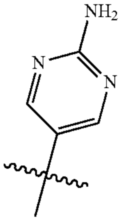 [SMILES: *c1cnc(N)nc1] | 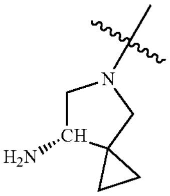 [SMILES: *N1C[C@@H](N)C2(CC2)C1] |
| 4.178 | 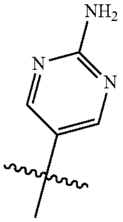 [SMILES: *c1cnc(N)nc1] | 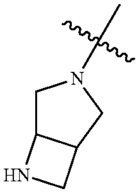 [SMILES: *N1CC2CNC2C1] |
| 4.179 | 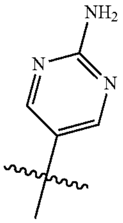 [SMILES: *c1cnc(N)nc1] | 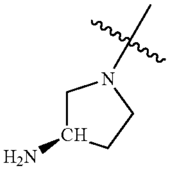 [SMILES: *N1CC[C@@H](N)C1] |

-continued
Table of Formula I Compounds Where L is O $R^x$, $R^z$ is CH, $R^y$ is F and $R^8$ is $NHCH_3$
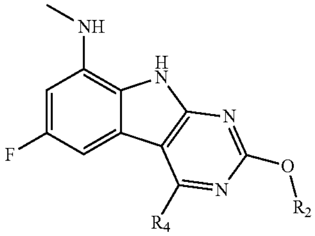
| | | |
|---|---|---|
| 4.180 | 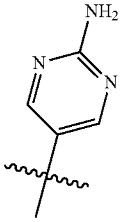 [SMILES: *c1cnc(N)nc1] | 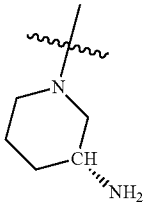 [SMILES: *N1CCC[C@@H](N)C1] |
| 4.181 | 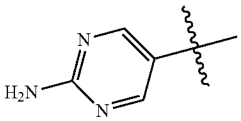 [SMILES: *c1cnc(N)nc1] | 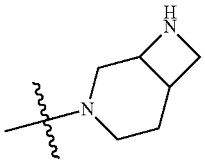 [SMILES: *N1CCC2CNC2C1] |
| 4.182 | 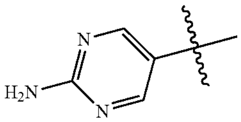 [SMILES: *c1cnc(N)nc1] | 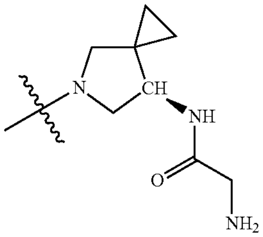 [SMILES: *N1C[C@H](NC(=O)CN)C2(CC2)C1] |
| 4.183 | 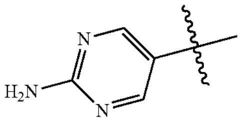 [SMILES: *c1cnc(N)nc1] | 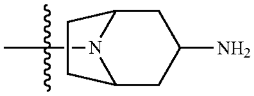 |
| 4.184 | 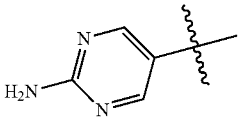 [SMILES: *c1cnc(N)nc1] | 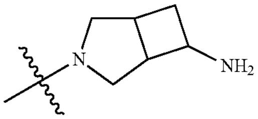 [SMILES: *N1CC2CC(N)C2C1] |
| 4.185 | 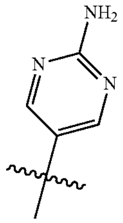 [SMILES: *c1cnc(N)nc1] | 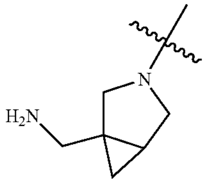 [SMILES: *N1CC2CC2(CN)C1] |
| 4.186 | 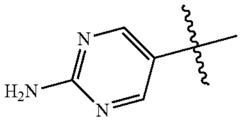 [SMILES: *c1cnc(N)nc1] | 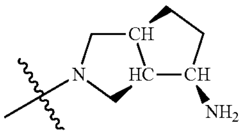 [SMILES: *N1C[C@H]2CC[C@@H](N)[C@H]2C1] |

-continued
Table of Formula I Compounds Where L is O $R^x$, $R^z$ is CH, $R^y$ is F and $R^8$ is $NHCH_3$
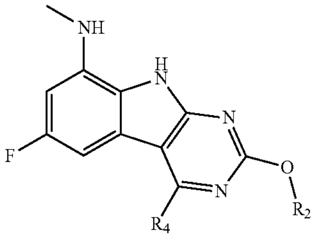
| | | |
|---|---|---|
| 4.187 | 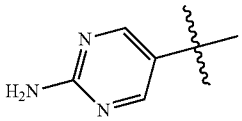 [SMILES: *c1cnc(N)nc1] | 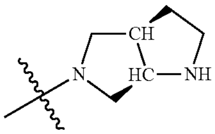 [SMILES: *N1C[C@H]2CCN[C@H]2C1] |
| 4.188 | 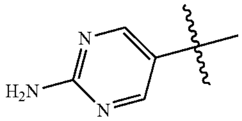 [SMILES: *c1cnc(N)nc1] | 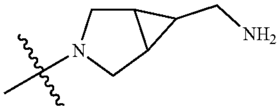 [SMILES: *N1CC2C(CN)C2C1] |
| 4.189 | 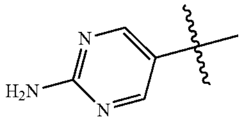 [SMILES: *c1cnc(N)nc1] | 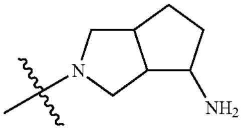 [SMILES: *N1CC2CCC(N)C2C1] |
| 4.190 | 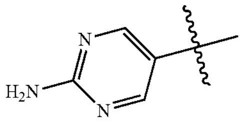 [SMILES: *c1cnc(N)nc1] | 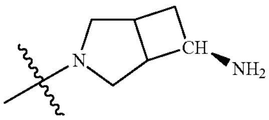 [SMILES: *N1CC2C[C@@H](N)C2C1] |
| 4.191 | 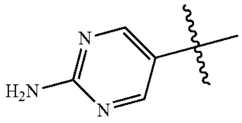 [SMILES: *c1cnc(N)nc1] | 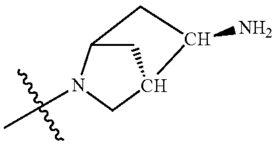 [SMILES: *N1C[C@H]2CC1C[C@H]2N] |
| 4.192 | 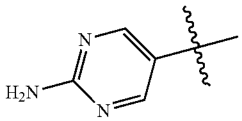 [SMILES: *c1cnc(N)nc1] | 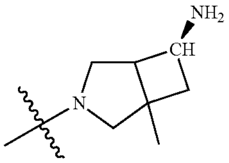 [SMILES: *N1CC2[C@@H](N)CC2(C)C1] |
| 4.193 | 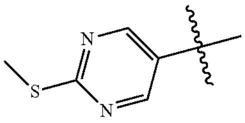 [SMILES: *c1cnc(SC)nc1] | 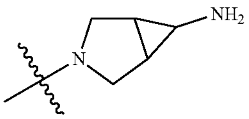 [SMILES: *N1CC2C(N)C2C1] |
| 4.194 | 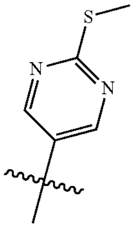 | 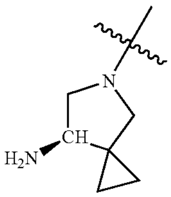 [SMILES: *N1C[C@H](N)C2(CC2)C1] |

-continued
Table of Formula I Compounds Where L is O $R^x$, $R^z$ is CH, $R^y$ is F and $R^8$ is $NHCH_3$
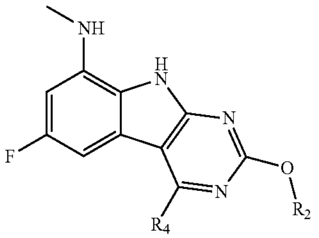
| | | |
|---|---|---|
| 4.195 | 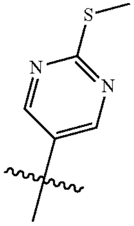 | 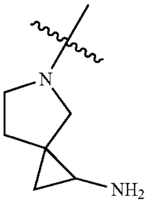 |
| 4.196 | 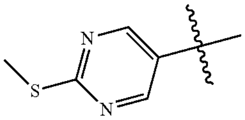 | 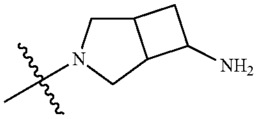 [SMILES: *N1CC2CC(N)C2C1] |
| 4.197 | 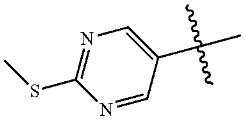 | 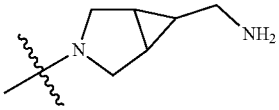 [SMILES: *N1CC2C(CN)C2C1] |
| 4.198 | 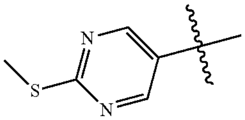 | 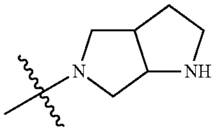 [SMILES: *N1CC2CCNC2C1] |
| 4.199 | 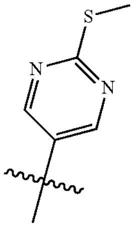 | 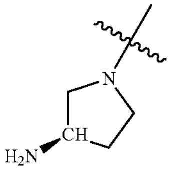 [SMILES: *N1CC[C@@H](N)C1] |
| 4.200 | 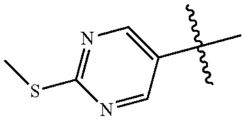 | 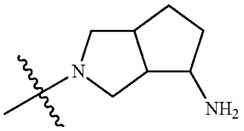 |
| 4.201 | 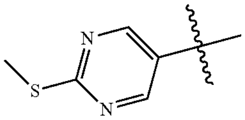 | 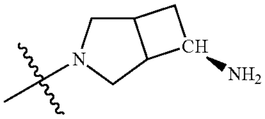 [SMILES: *N1CC2C[C@@H](N)C2C1] |
| 4.202 | 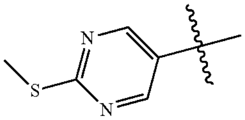 [SMILES: *c1cnc(SC)nc1] | 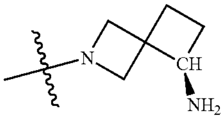 [SMILES: *N1CC2(CC[C@H]2N)C1] |

-continued
Table of Formula I Compounds Where L is O $R^x$, $R^z$ is CH, $R^y$ is F and $R^8$ is $NHCH_3$
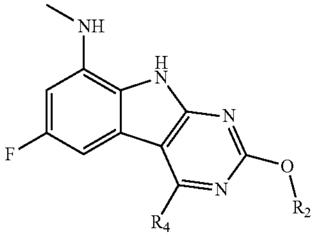
| | | |
|---|---|---|
| 4.203 | 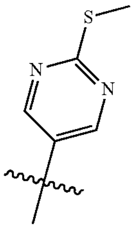 | 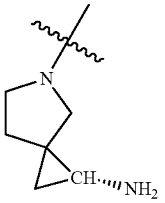 [SMILES: *N1CCC2(C[C@H]2N)C1] |
| 4.204 | 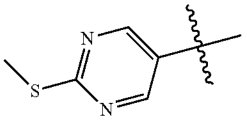 | 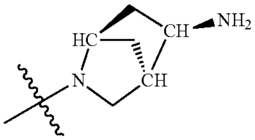 [SMILES: *N1C[C@H]2C[C@@H]1C[C@H]2N] |
| 4.205 | 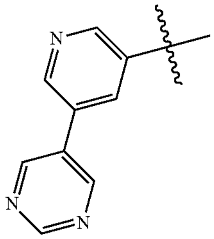 [SMILES: *c1cncc(-c2cncnc2)c1] | 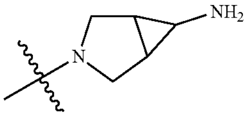 [SMILES: *N1CC2C(N)C2C1] |
| 4.206 | 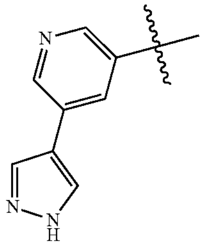 [SMILES: *c1cncc(-c2cn[nH]c2)c1] | 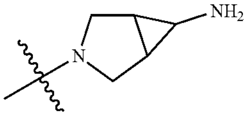 [SMILES: *N1CC2C(N)C2C1] |
| 4.207 | 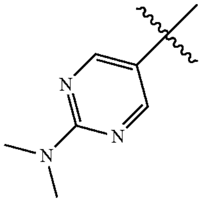 [SMILES: *c1cnc(N(C)C)nc1] | 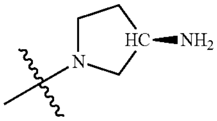 [SMILES: *N1CC[C@@H](N)C1] |
| 4.208 | 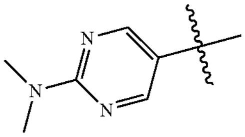 | 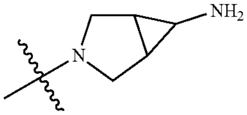 [SMILES: *N1CC2C(N)C2C1] |

-continued
| Table of Formula I Compounds Where L is O $R^x$, $R^z$ is CH, $R^y$ is F and $R^8$ is $NHCH_3$ | | |
|---|---|---|
| | 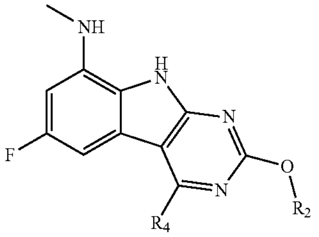 | |
| 4.209 | 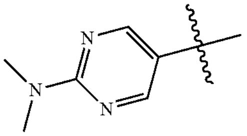 [SMILES: *c1cnc(N(C)C)nc1] | 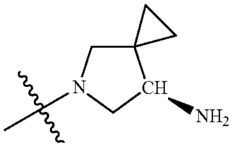 [SMILES: *N1C[C@H](N)C2(CC2)C1] |
| 4.210 | 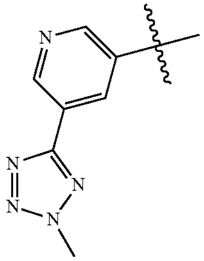 [SMILES: *c1cncc(-c2nnn(C)n2)c1] | 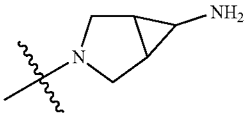 |
| 4.211 | 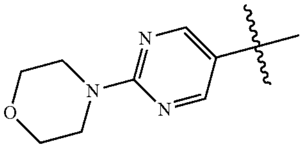 [SMILES: *c1cnc(N2CCOCC2)nc1] | 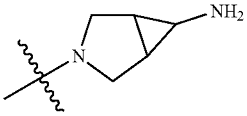 [SMILES: *N1CC2C(N)C2C1] |
| 4.212 | 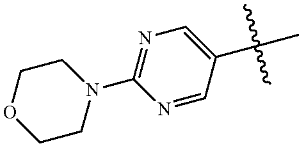 [SMILES: *c1cnc(N2CCOCC2)nc1] | 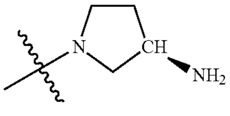 [SMILES: *N1CC[C@@H](N)C1] |
| 4.213 | 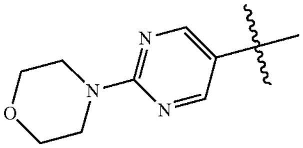 [SMILES: *c1cnc(N2CCOCC2)nc1] | 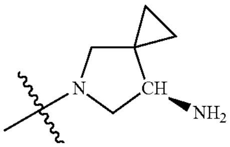 [SMILES: *N1C[C@H](N)C2(CC2)C1] |
| 4.214 | 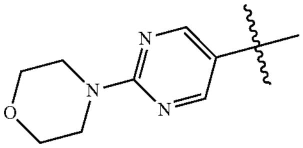 [SMILES: *c1cnc(N2CCOCC2)nc1] | 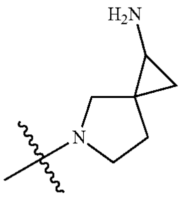 [SMILES: *N1CCC2(CC2N)C1] |
| 4.215 | 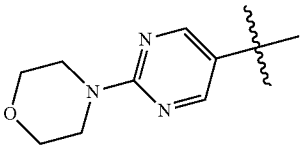 [SMILES: *c1cnc(N2CCOCC2)nc1] | 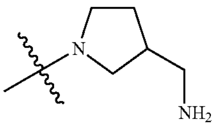 |

-continued
Table of Formula I Compounds Where L is O $R^x$, $R^z$ is CH, $R^y$ is F and $R^8$ is $NHCH_3$
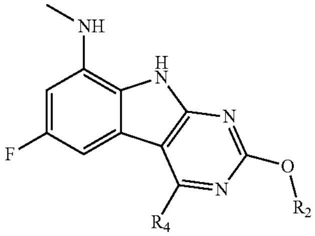
| | | |
|---|---|---|
| 4.216 | 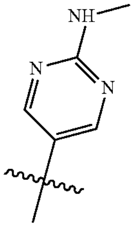 [SMILES: *c1cnc(NC)nc1] | 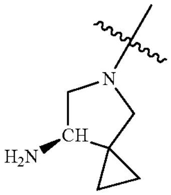 [SMILES: *N1C[C@H](N)C2(CC2)C1] |
| 4.217 | 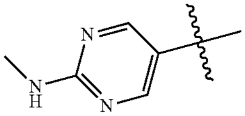 [SMILES: *c1cnc(NC)nc1] | 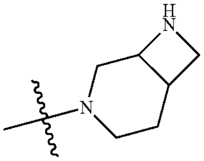 [SMILES: *N1CCC2CNC2C1] |
| 4.218 | 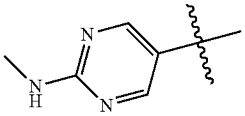 [SMILES: *c1cnc(NC)nc1] | 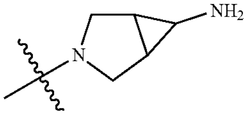 [SMILES: *N1CC2C(N)C2C1] |
| 4.219 | 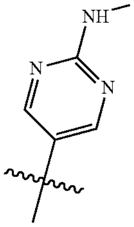 | 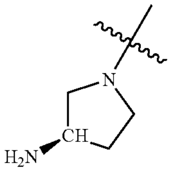 [SMILES: *N1CC[C@@H](N)C1] |
| 4.220 | 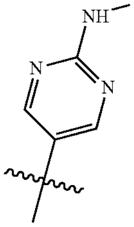 [SMILES: *c1cnc(NC)nc1] | 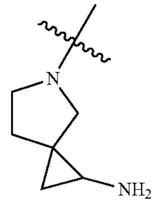 [SMILES: *N1CCC2(CC2N)C1] |
| 4.221 | 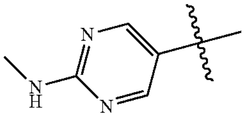 [SMILES: *c1cnc(NC)nc1] | 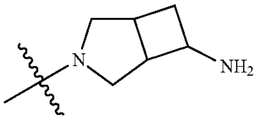 [SMILES: *N1CC2CC(N)C2C1] |
| 4.222 | 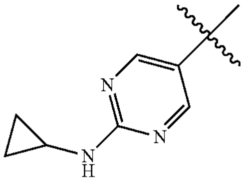 [SMILES: *c1cnc(NC2CC2)nc1] | 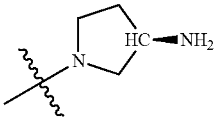 [SMILES: *N1CC[C@@H](N)C1] |

-continued
Table of Formula I Compounds Where L is O $R^x$, $R^z$ is CH, $R^y$ is F and $R^8$ is $NHCH_3$
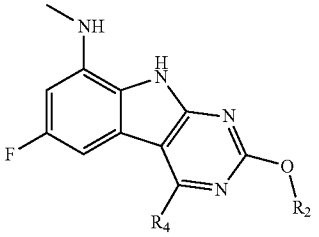
| | | |
|---|---|---|
| 4.223 | 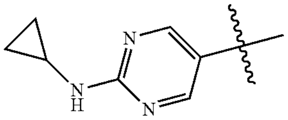 [SMILES: *c1cnc(NC2CC2)nc1] | 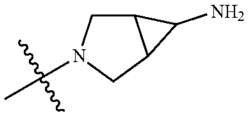 [SMILES: *N1CC2C(N)C2C1] |
| 4.224 | 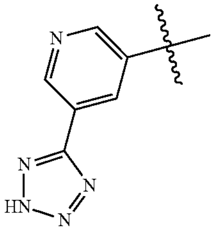 [SMILES: *c1cncc(-c2nn[nH]n2)c1] | 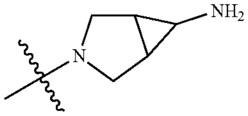 [SMILES: *N1CC2C(N)C2C1] |
| 4.225 | 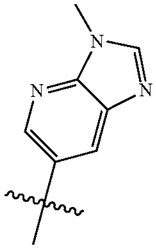 [SMILES: *c1cnc2c(c1)ncn2C] | 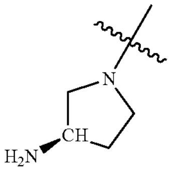 [SMILES: *N1CC[C@@H](N)C1] |
| 4.226 | 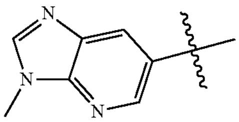 [SMILES: *c1cnc2c(c1)ncn2C] | 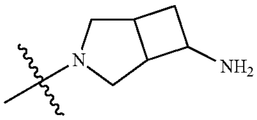 [SMILES: *N1CC2CC(N)C2C1] |
| 4.227 | 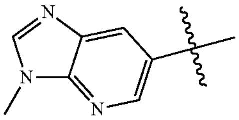 [SMILES: *c1cnc2c(c1)ncn2C] | 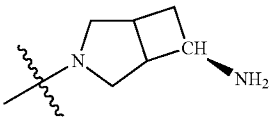 [SMILES: *N1CC2C[C@@H](N)C2C1] |
| 4.228 | 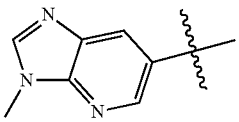 [SMILES: *c1cnc2c(c1)ncn2C] | 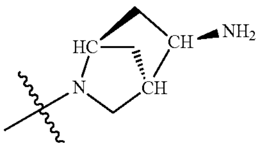 [SMILES: *N1C[C@H]2C[C@@H]1C[C@H]2N] |
| 4.229 | 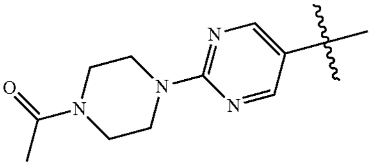 [SMILES: *c1cnc(N2CCN(C(C)=O)CC2)nc1] | 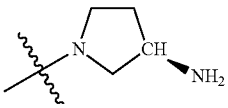 [SMILES: *N1CC[C@@H](N)C1] |

-continued
Table of Formula I Compounds Where L is O $R^x$, $R^z$ is CH, $R^y$ is F and $R^8$ is $NHCH_3$
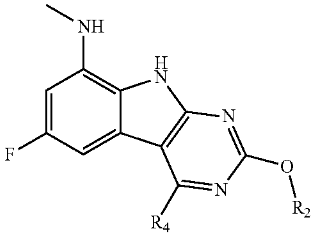
| | | |
|---|---|---|
| 4.230 | 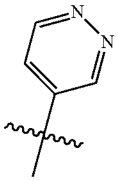 [SMILES: *c1ccnnc1] | 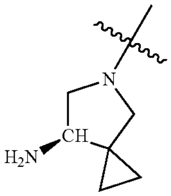 [SMILES: *N1C[C@H](N)C2(CC2)C1] |
| 4.231 | 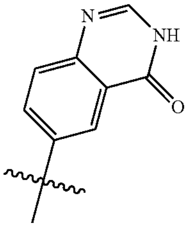 [SMILES: *c1ccc2nc[nH]c(=O)c2c1] | 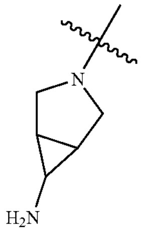 [SMILES: *N1CC2C(N)C2C1] |
| 4.232 | 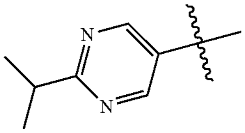 [SMILES: *c1cnc(C(C)C)nc1] | 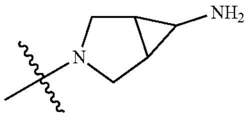 [SMILES: *N1CC2C(N)C2C1] |
| 4.233 | 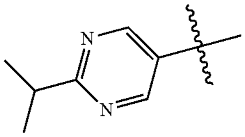 [SMILES: *c1cnc(C(C)C)nc1] | 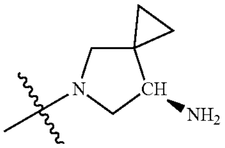 [SMILES: *N1C[C@H](N)C2(CC2)C1] |
| 4.234 | 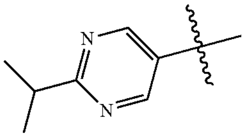 [SMILES: *c1cnc(C(C)C)nc1] | 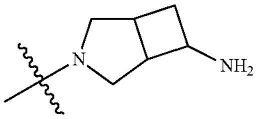 [SMILES: *N1CC2CC(N)C2C1] |
| 4.235 | 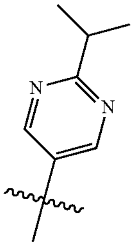 [SMILES: *c1cnc(C(C)C)nc1] | 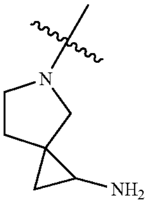 [SMILES: *N1CCC2(CC2N)C1] |

-continued
Table of Formula I Compounds Where L is O $R^x$, $R^z$ is CH, $R^y$ is F and $R^8$ is $NHCH_3$
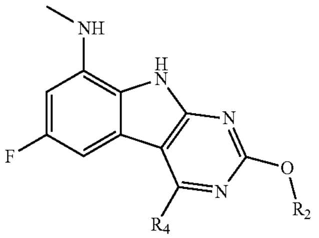
| | | |
|---|---|---|
| 4.236 | 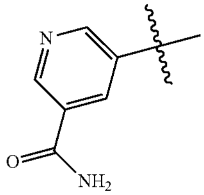 [SMILES: *c1cncc(C(N)=O)c1] | 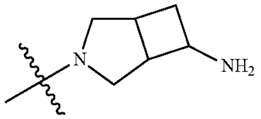 [SMILES: *N1CC2CC(N)C2C1] |
| 4.237 | 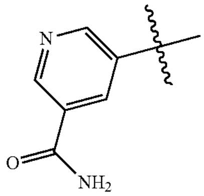 [SMILES: *c1cncc(C(N)=O)c1] | 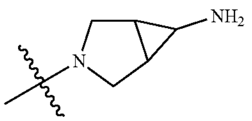 [SMILES: *N1CC2C(N)C2C1] |
| 4.238 | 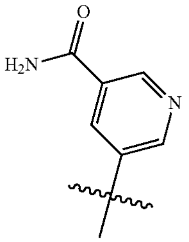 [SMILES: *c1cncc(C(N)=O)c1] | 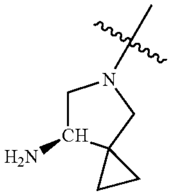 [SMILES: *N1C[C@H](N)C2(CC2)C1] |
| 4.239 | 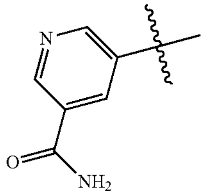 [SMILES: *c1cncc(C(N)=O)c1] | 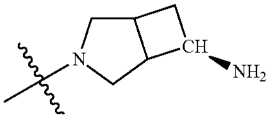 [SMILES: *N1CC2C[C@@H](N)C2C1] |
| 4.240 | 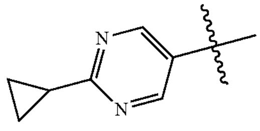 [SMILES: *c1cnc(C2CC2)nc1] | 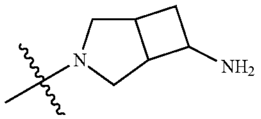 [SMILES: *N1CC2CC(N)C2C1] |
| 4.241 | 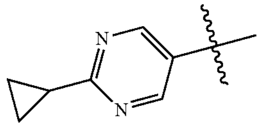 [SMILES: *c1cnc(C2CC2)nc1] | 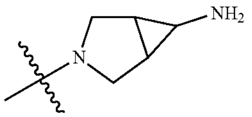 [SMILES: *N1CC2C(N)C2C1] |
| 4.242 | 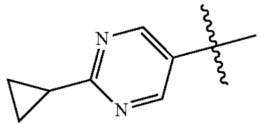 [SMILES: *c1cnc(C2CC2)nc1] | 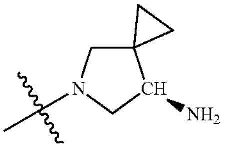 [SMILES: *N1C[C@H](N)C2(CC2)C1] |

-continued
Table of Formula I Compounds Where L is O $R^x$, $R^z$ is CH, $R^y$ is F and $R^8$ is $NHCH_3$
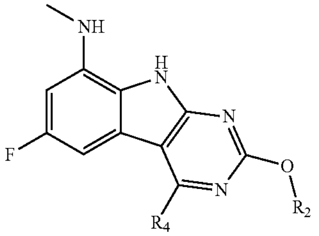
| | | |
|---|---|---|
| 4.243 | 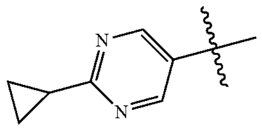 [SMILES: *c1cnc(C2CC2)nc1] | 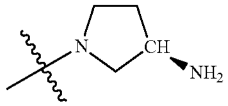 [SMILES: *N1CC[C@@H](N)C1] |
| 4.244 | 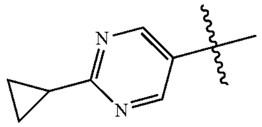 [SMILES: *c1cnc(C2CC2)nc1] | 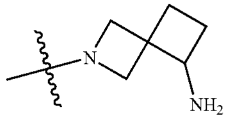 [SMILES: *N1CC2(CCC2N)C1] |
| 4.245 | 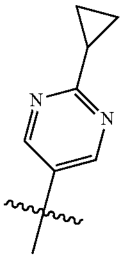 [SMILES: *c1cnc(C2CC2)nc1] | 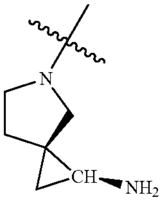 |
| 4.246 | 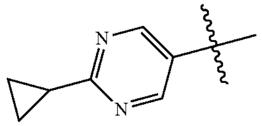 [SMILES: *c1cnc(C2CC2)nc1] | 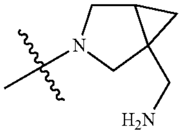 [SMILES: *N1CC2CC2(CN)C1] |
| 4.247 | 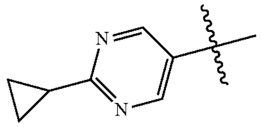 [SMILES: *c1cnc(C2CC2)nc1] | 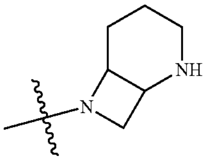 [SMILES: *N1CC2NCCCC21] |
| 4.248 | 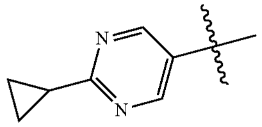 [SMILES: *c1cnc(C2CC2)nc1] | 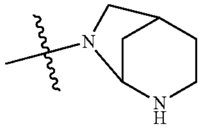 [SMILES: *N1CC2CCNC1C2] |
| 4.249 | 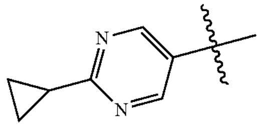 [SMILES: *c1cnc(C2CC2)nc1] | 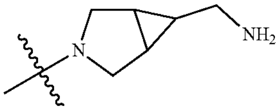 [SMILES: *N1CC2C(CN)C2C1] |
| 4.250 | 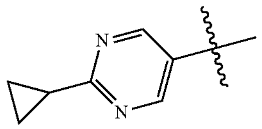 [SMILES: *c1cnc(C2CC2)nc1] | 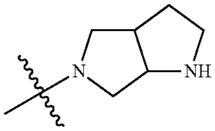 [SMILES: *N1CC2CCNC2C1] |

-continued
Table of Formula I Compounds Where L is O $R^x$, $R^z$ is CH, $R^y$ is F and $R^8$ is $NHCH_3$
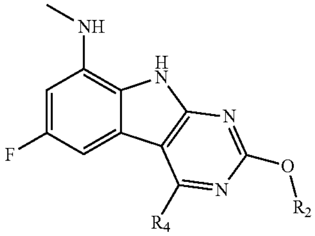
| | | |
|---|---|---|
| 4.251 | 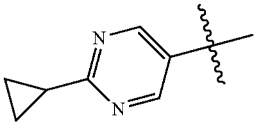 [SMILES: *c1cnc(C2CC2)nc1] | 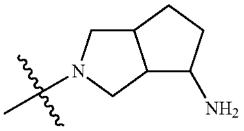 [SMILES: *N1CC2CCC(N)C2C1] |
| 4.252 | 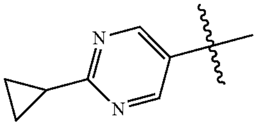 [SMILES: *c1cnc(C2CC2)nc1] | 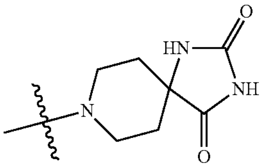 [SMILES: *N1CCC2(CC1)NC(=O)NC2=O] |
| 4.253 | 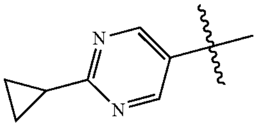 [SMILES: *c1cnc(C2CC2)nc1] | 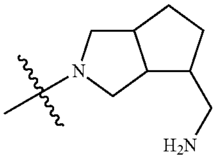 |
| 4.254 | 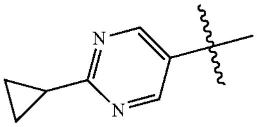 [SMILES: *c1cnc(C2CC2)nc1] | 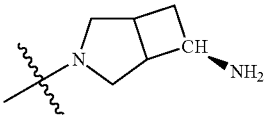 [SMILES: *N1CC2C[C@@H](N)C2C1] |
| 4.255 | 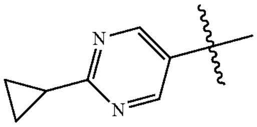 [SMILES: *c1cnc(C2CC2)nc1] | 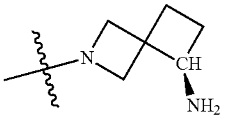 [SMILES: *N1CC2(CC[C@H]2N)C1] |
| 4.256 | 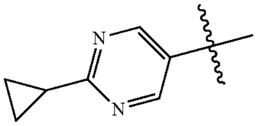 [SMILES: *c1cnc(C2CC2)nc1] | 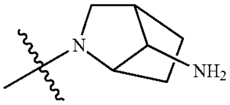 [SMILES: *N1CC2CCC1C2N] |
| 4.257 | 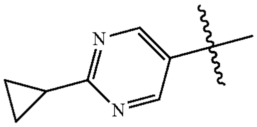 [SMILES: *c1cnc(C2CC2)nc1] | 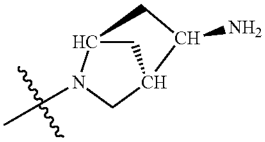 [SMILES: *N1C[C@H]2C[C@@H]1C[C@H]2N] |
| 4.258 | 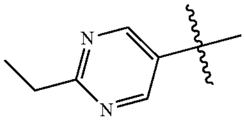 | 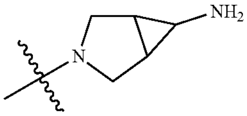 [SMILES: *N1CC2C(N)C2C1] |

-continued
Table of Formula I Compounds Where L is O $R^x$, $R^z$ is CH, $R^y$ is F and $R^8$ is $NHCH_3$
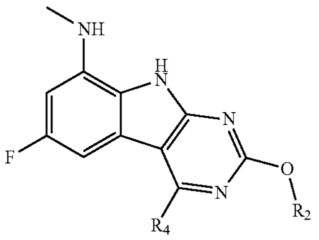
| | | |
|---|---|---|
| 4.259 | 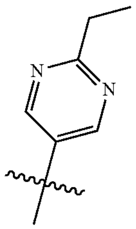 [SMILES: *c1cnc(CC)nc1] | 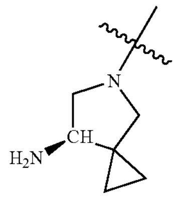 [SMILES: *N1C[C@H](N)C2(CC2)C1] |
| 4.260 | 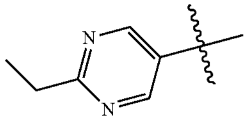 [SMILES: *c1cnc(CC)nc1] | 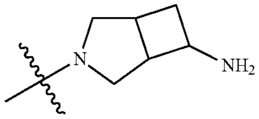 [SMILES: *N1CC2CC(N)C2C1] |
| 4.261 | 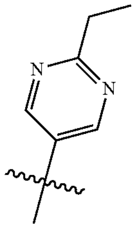 | 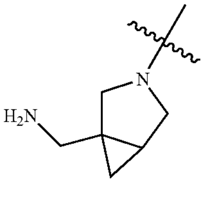 [SMILES: *N1CC2CC2(CN)C1] |
| 4.262 | 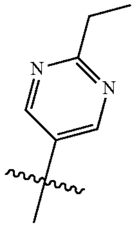 | 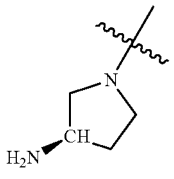 [SMILES: *N1CC[C@@H](N)C1] |
| 4.263 | 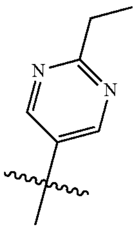 [SMILES: *c1cnc(CC)nc1] | 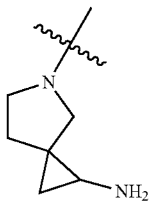 [SMILES: *N1CCC2(CC2N)C1] |
| 4.264 | 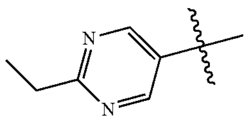 [SMILES: *c1cnc(CC)nc1] | 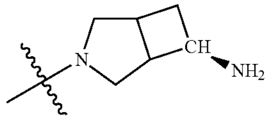 [SMILES: *N1CC2C[C@@H](N)C2C1] |

-continued
Table of Formula I Compounds Where L is O $R^x$, $R^z$ is CH, $R^y$ is F and $R^8$ is $NHCH_3$
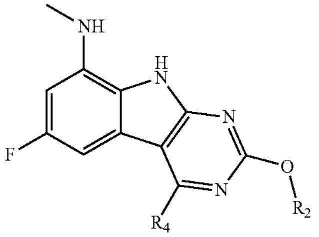
| | | |
|---|---|---|
| 4.265 | 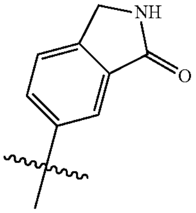 [SMILES: *c1ccc2c(c1)C(=O)NC2] | 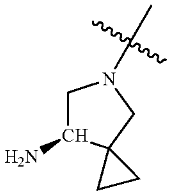 [SMILES: *N1C[C@H](N)C2(CC2)C1] |
| 4.266 | 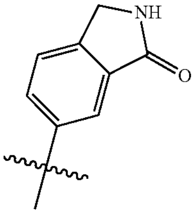 [SMILES: *c1ccc2c(c1)C(=O)NC2] | 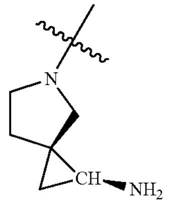 [SMILES: *N1CC[C@]2(C[C@@H]2N)C1] |
| 4.267 | 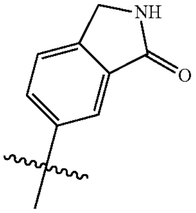 [SMILES: *c1ccc2c(c1)C(=O)NC2] | 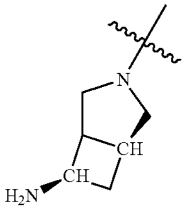 |
| 4.269 | 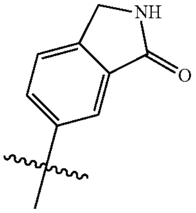 [SMILES: *c1ccc2c(c1)C(=O)NC2] | 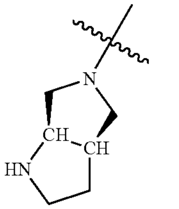 [SMILES: *N1C[C@H]2CCN[C@H]2C1] |
| 4.270 | 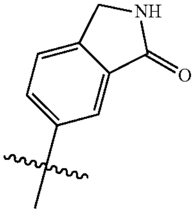 [SMILES: *c1ccc2c(c1)C(=O)NC2] | 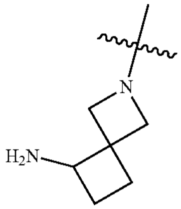 |
| 4.271 | 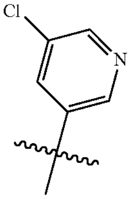 [SMILES: *c1cncc(Cl)c1] | 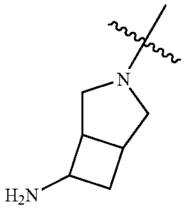 |

-continued
Table of Formula I Compounds Where L is O $R^x$, $R^z$ is CH, $R^y$ is F and $R^8$ is $NHCH_3$
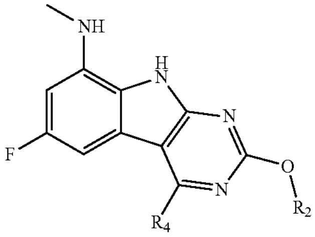
| | | |
|---|---|---|
| 4.272 | 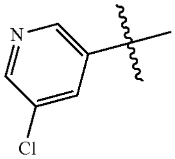 [SMILES: *c1cncc(Cl)c1] | 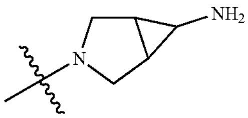 [SMILES: *N1CC2C(N)C2C1] |
| 4.273 | 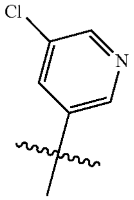 [SMILES: *c1cncc(Cl)c1] | 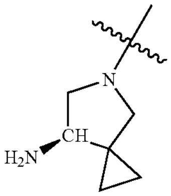 [SMILES: *N1C[C@H](N)C2(CC2)C1] |
| 4.274 | 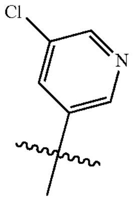 [SMILES: *c1cncc(Cl)c1] | 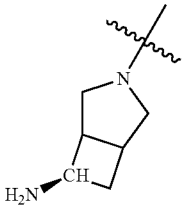 [SMILES: *N1CC2C[C@@H](N)C2C1] |
| 4.275 | 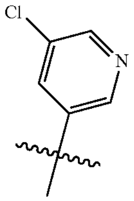 [SMILES: *c1cncc(Cl)c1] | 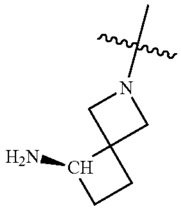 [SMILES: *N1CC2(CC[C@H]2N)C1] |
| 4.276 | 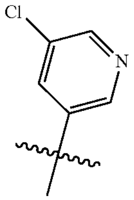 [SMILES: *c1cncc(Cl)c1] | 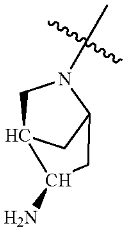 |
| 4.277 | 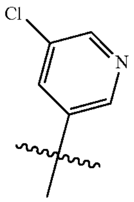 [SMILES: *c1cncc(Cl)c1] | 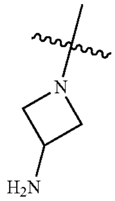 [SMILES: *N1CC(N)C1] |

-continued
| Table of Formula I Compounds Where L is O $R^x$, $R^z$ is CH, $R^y$ is F and $R^8$ is $NHCH_3$ | | |
|---|---|---|
| | 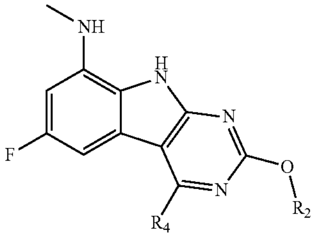 | |
| 4.278 | 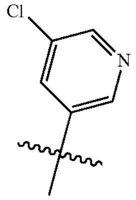 [SMILES: *c1cncc(Cl)c1] | 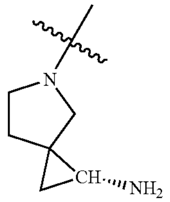 [SMILES: *N1CCC2(C[C@H]2N)C1] |
| 4.279 | 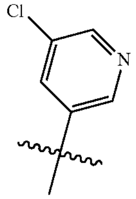 [SMILES: *c1cncc(Cl)c1] | 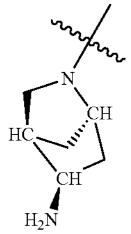 [SMILES: *N1C[C@H]2C[C@@H]1C[C@H]2N] |
| 4.280 | 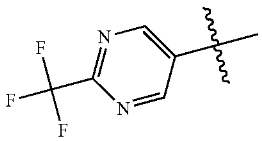 [SMILES: *c1cnc(C(F)(F)F)nc1] | 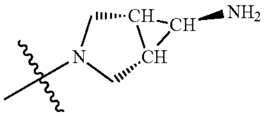 [SMILES: *N1C[C@@H]2[C@@H](N)[C@@H]2C1] |
| 4.281 | 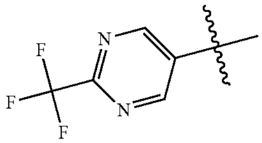 [SMILES: *c1cnc(C(F)(F)F)nc1] | 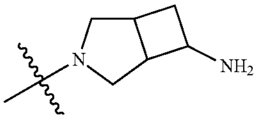 [SMILES: *N1CC2CC(N)C2C1] |
| 4.282 | 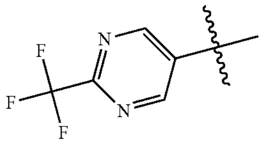 [SMILES: *c1cnc(C(F)(F)F)nc1] | 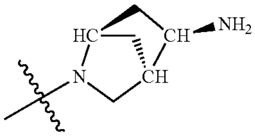 [SMILES: *N1C[C@H]2C[C@@H]1C[C@H]2N] |
| 4.283 | 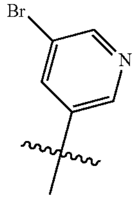 | 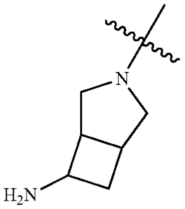 [SMILES: *N1CC2CC(N)C2C1] |

-continued
Table of Formula I Compounds Where L is O $R^x$, $R^z$ is CH, $R^y$ is F and $R^8$ is $NHCH_3$
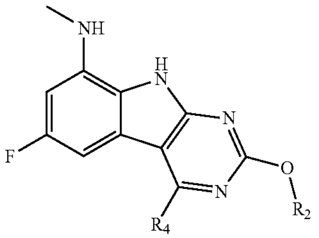
| | | |
|---|---|---|
| 4.284 | 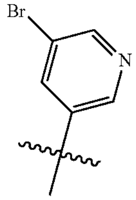 | 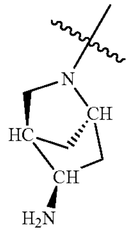 [SMILES: *N1C[C@H]2C[C@@H]1C[C@H]2N] |
| 4.285 | 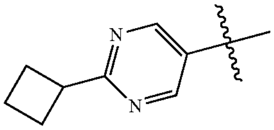 [SMILES: *c1cnc(C2CCC2)nc1] | 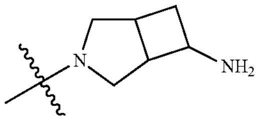 [SMILES: *N1CC2CC(N)C2C1] |
| 4.286 | 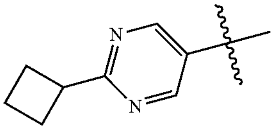 [SMILES: *c1cnc(C2CCC2)nc1] | 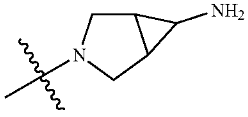 [SMILES: *N1CC2C(N)C2C1] |
| 4.287 | 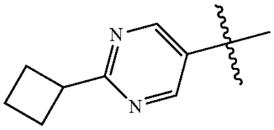 [SMILES: *c1cnc(C2CCC2)nc1] | 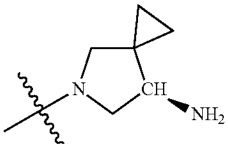 [SMILES: *N1C[C@H](N)C2(CC2)C1] |
| 4.288 | 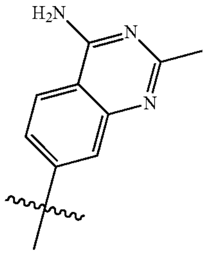 [SMILES: *c1ccc2c(N)nc(C)nc2c1] | 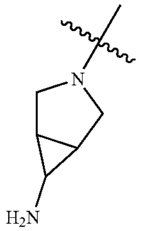 |
| 4.290 | 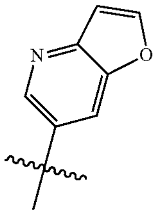 [SMILES: *c1cnc2ccoc2c1] | 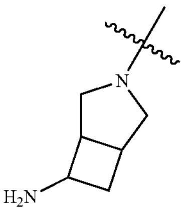 |
| 4.291 | 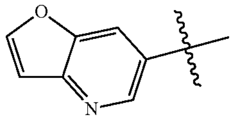 [SMILES: *c1cnc2ccoc2c1] | 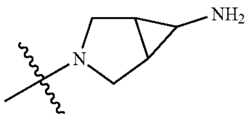 |

-continued
Table of Formula I Compounds Where L is O $R^x$, $R^z$ is CH, $R^y$ is F and $R^8$ is $NHCH_3$
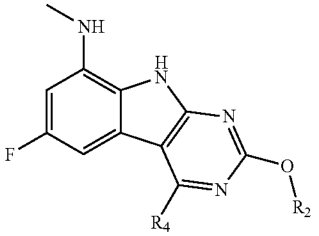
| | | |
|---|---|---|
| 4.292 | 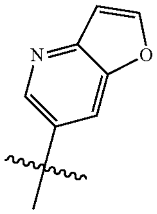 [SMILES: *c1cnc2ccoc2c1] | 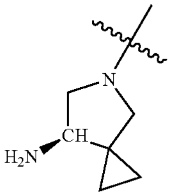 [SMILES: *N1C[C@H](N)C2(CC2)C1] |
| 4.293 | 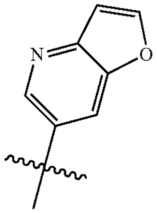 [SMILES: *c1cnc2ccoc2c1] | 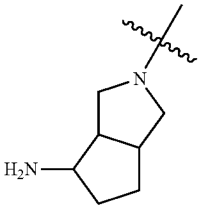 [SMILES: *N1CC2CCC(N)C2C1] |
| 4.294 | 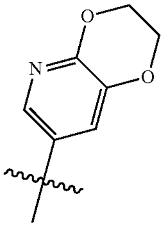 [SMILES: *c1cnc2c(c1)OCCO2] | 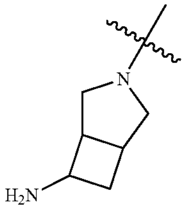 |
| 4.295 | 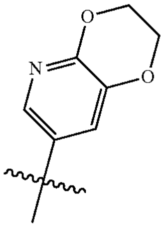 [SMILES: *c1cnc2c(c1)OCCO2] | 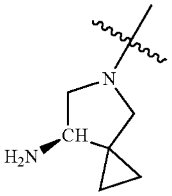 [SMILES: *N1C[C@H](N)C2(CC2)C1] |
| 4.296 | 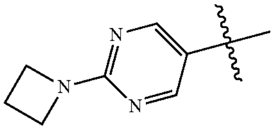 | 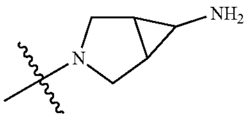 [SMILES: *N1CC2C(N)C2C1] |
| 4.297 | 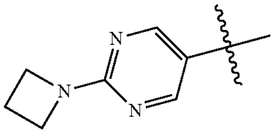 [SMILES: *c1cnc(N2CCC2)nc1] | 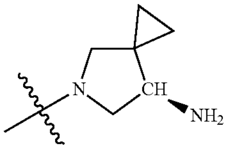 [SMILES: *N1C[C@H](N)C2(CC2)C1] |

-continued
| Table of Formula I Compounds Where L is O $R^x$, $R^z$ is CH, $R^y$ is F and $R^8$ is $NHCH_3$ | | |
|---|---|---|
| 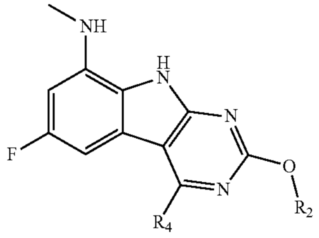 | | |
| 4.298 | 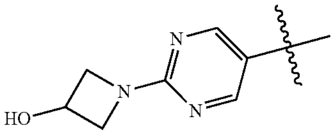 [SMILES: *c1cnc(N2CC(O)C2)nc1] | 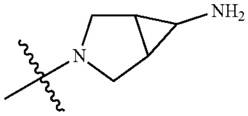 [SMILES: *N1CC2C(N)C2C1] |
| 4.299 | 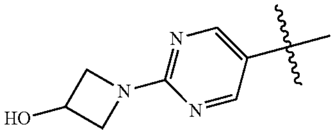 [SMILES: *c1cnc(N2CC(O)C2)nc1] | 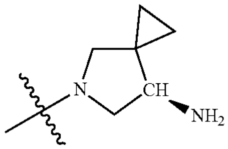 [SMILES: *N1C[C@H](N)C2(CC2)C1] |
| 4.300 | 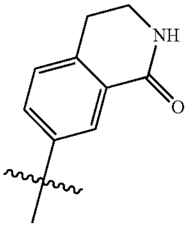 [SMILES: *c1ccc2c(c1)C(=O)NCC2] | 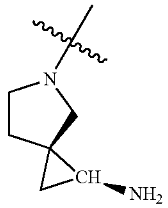 [SMILES: *N1CC[C@]2(C[C@@H]2N)C1] |
| 4.301 | 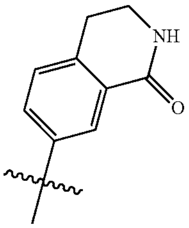 [SMILES: *c1ccc2c(c1)C(=O)NCC2] | 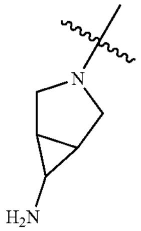 |
| 4.302 | 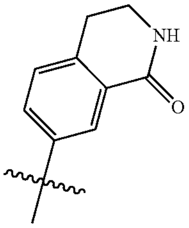 [SMILES: *c1ccc2c(c1)C(=O)NCC2] | 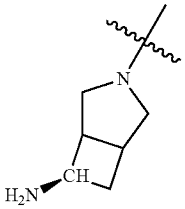 [SMILES: *N1CC2C[C@@H](N)C2C1] |
| 4.303 | 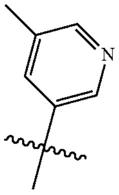 [SMILES: *c1cncc(C)c1] | 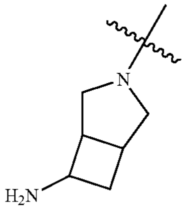 |

-continued
Table of Formula I Compounds Where L is O $R^x$, $R^z$ is CH, $R^y$ is F and $R^8$ is $NHCH_3$
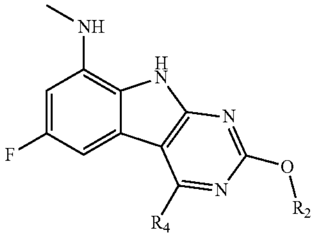
| | | |
|---|---|---|
| 4.304 | 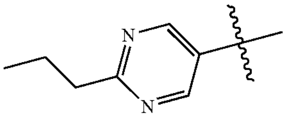 [SMILES: *c1cnc(CCC)nc1] | 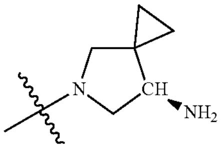 [SMILES: *N1C[C@H](N)C2(CC2)C1] |
| 4.305 | 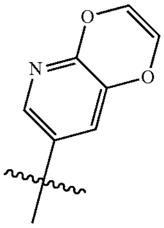 [SMILES: *c1cnc2c(c1)OC=CO2] | 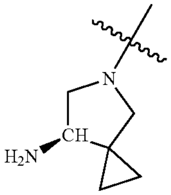 [SMILES: *N1C[C@H](N)C2(CC2)C1] |
| 4.309 | 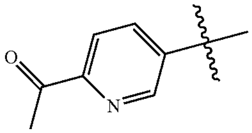 [SMILES: *c1ccc(C(C)=O)nc1] | 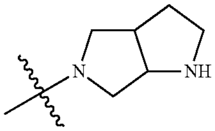 [SMILES: *N1CC2CCNC2C1] |
| 4.310 | 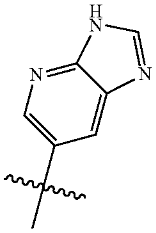 [SMILES: *c1cnc2[nH]cnc2c1] | 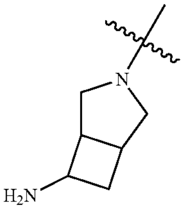 [SMILES: *N1CC2CC(N)C2C1] |
| 4.311 | 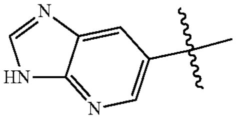 [SMILES: *c1cnc2[nH]cnc2c1] | 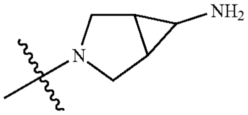 |
| 4.312 | 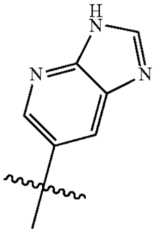 [SMILES: *c1cnc2[nH]cnc2c1] | 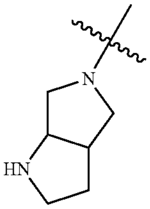 [SMILES: *N1CC2CCNC2C1] |

-continued
Table of Formula I Compounds Where L is O $R^x$, $R^z$ is CH, $R^y$ is F and $R^8$ is $NHCH_3$
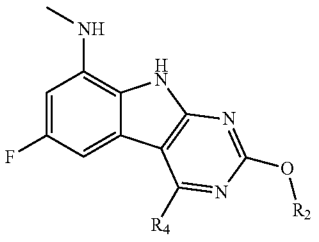
| | | |
|---|---|---|
| 4.313 | 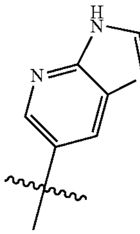 | 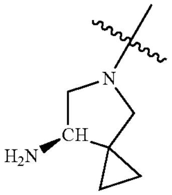 [SMILES: *N1C[C@H](N)C2(CC2)C1] |
| 4.314 | 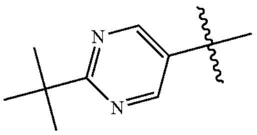 [SMILES: *c1cnc(C(C)(C)C)nc1] | 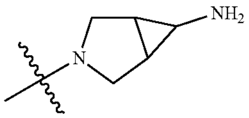 [SMILES: *N1CC2C(N)C2C1] |
| 4.315 | 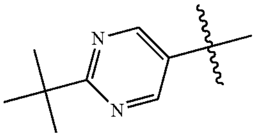 [SMILES: *c1cnc(C(C)(C)C)nc1] | 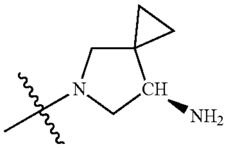 [SMILES: *N1C[C@H](N)C2(CC2)C1] |
| 4.316 | 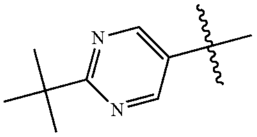 [SMILES: *c1cnc(C(C)(C)C)nc1] | 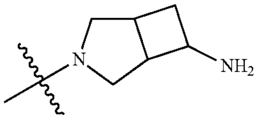 [SMILES: *N1CC2CC(N)C2C1] |
| 4.317 | 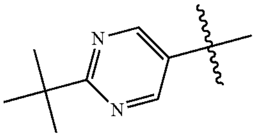 [SMILES: *c1cnc(C(C)(C)C)nc1] | 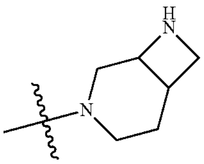 [SMILES: *N1CCC2CNC2C1] |
| 4.318 | 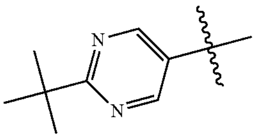 [SMILES: *c1cnc(C(C)(C)C)nc1] | 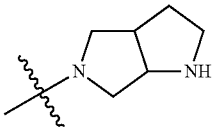 [SMILES: *N1CC2CCNC2C1] |
| 4.319 | 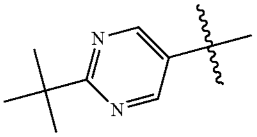 [SMILES: *c1cnc(C(C)(C)C)nc1] | 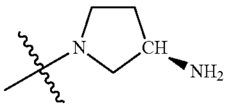 [SMILES: *N1CC[C@@H](N)C1] |

-continued
Table of Formula I Compounds Where L is O $R^x$, $R^z$ is CH, $R^y$ is F and $R^8$ is $NHCH_3$
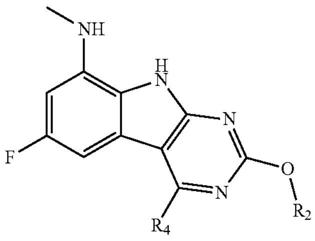
| | | |
|---|---|---|
| 4.320 | 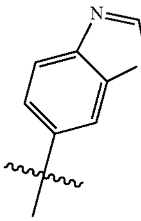 | 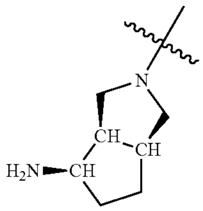 [SMILES: *N1C[C@H]2CC[C@@H](N)[C@H]2C1] |
| 4.321 | 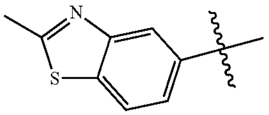 | 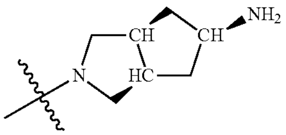 [SMILES: *N1C[C@H]2C[C@@H](N)C[C@H]2C1] |
| 4.322 | 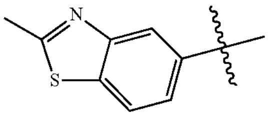 [SMILES: *c1ccc2sc(C)nc2c1] | 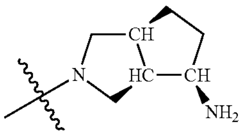 [SMILES: *N1C[C@H]2CC[C@@H](N)[C@H]2C1] |
| 4.323 | 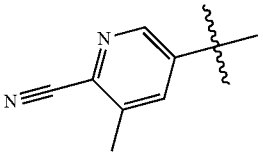 [SMILES: *c1cnc(C#N)c(C)c1] | 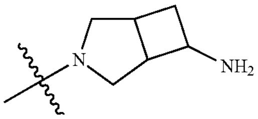 [SMILES: *N1CC2CC(N)C2C1] |
| 4.324 | 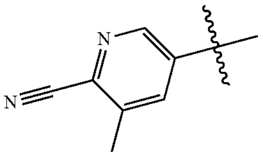 [SMILES: *c1cnc(C#N)c(C)c1] | 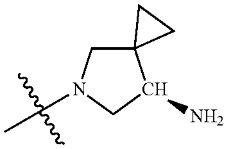 [SMILES: *N1C[C@H](N)C2(CC2)C1] |
| 4.325 | 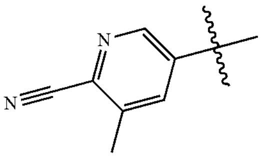 [SMILES: *c1cnc(C#N)c(C)c1] | 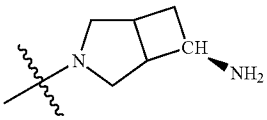 [SMILES: *N1CC2C[C@@H](N)C2C1] |
| 4.326 | 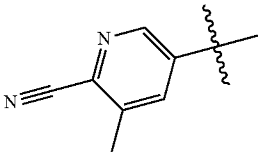 [SMILES: *c1cnc(C#N)c(C)c1] | 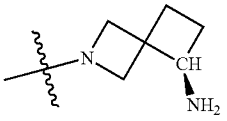 |

-continued
Table of Formula I Compounds Where L is O $R^x$, $R^z$ is CH, $R^y$ is F and $R^8$ is $NHCH_3$
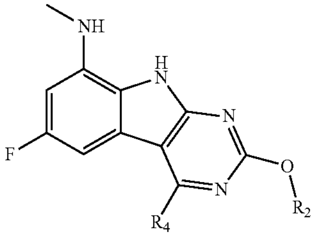
| | | |
|---|---|---|
| 4.327 | 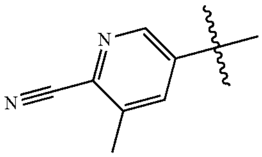 [SMILES: *c1cnc(C#N)c(C)c1] | 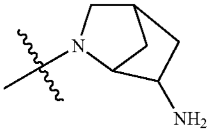 [SMILES: *N1CC2CC(N)C1C2] |
| 4.328 | 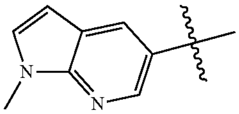 [SMILES: *c1cnc2c(ccn2C)c1] | 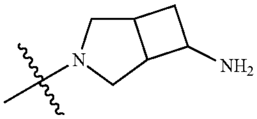 [SMILES: *N1CC2CC(N)C2C1] |
| 4.329 | 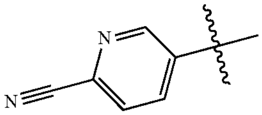 [SMILES: *c1ccc(C#N)nc1] | 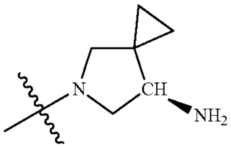 [SMILES: *N1C[C@H](N)C2(CC2)C1] |
| 4.330 | 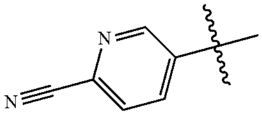 [SMILES: *c1ccc(C#N)nc1] | 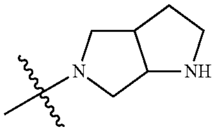 [SMILES: *N1CC2CCNC2C1] |
| 4.331 | 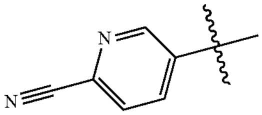 [SMILES: *c1ccc(C#N)nc1] | 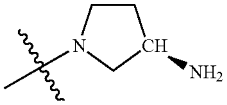 [SMILES: *N1CC[C@@H](N)C1] |
| 4.332 | 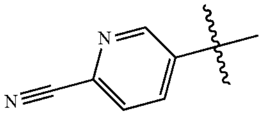 [SMILES: *c1ccc(C#N)nc1] | 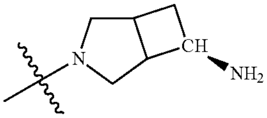 [SMILES: *N1CC2C[C@@H](N)C2C1] |
| 4.333 | 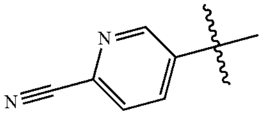 [SMILES: *c1ccc(C#N)nc1] | 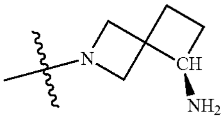 |
| 4.334 | 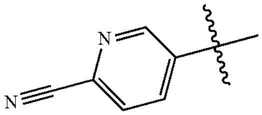 [SMILES: *c1ccc(C#N)nc1] | 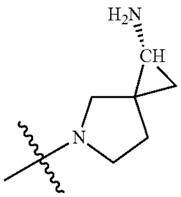 [SMILES: *N1CCC2(C[C@H]2N)C1] |

-continued
Table of Formula I Compounds Where L is O $R^x$, $R^z$ is CH, $R^y$ is F and $R^8$ is $NHCH_3$
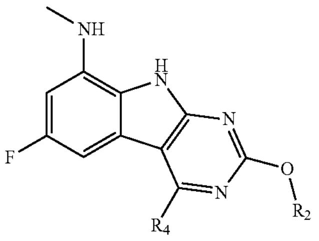
| | | |
|---|---|---|
| 4.335 | 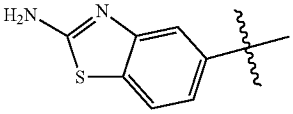 [SMILES: *c1ccc2sc(N)nc2c1] | 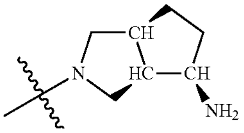 [SMILES: *N1C[C@H]2CC[C@@H](N)[C@H]2C1] |
| 4.336 | 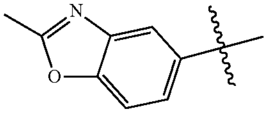 [SMILES: *c1ccc2oc(C)nc2c1] | 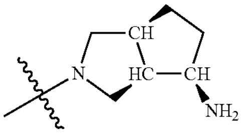 [SMILES: *N1C[C@H]2CC[C@@H](N)[C@H]2C1] |
| 4.337 | 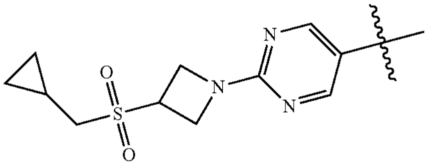 [SMILES: *c1cnc(N2CC(S(=O)(=O)CC3CC3)C2)nc1] | 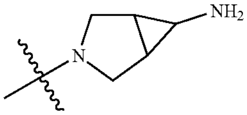 [SMILES: *N1CC2C(N)C2C1] |
| 4.338 | 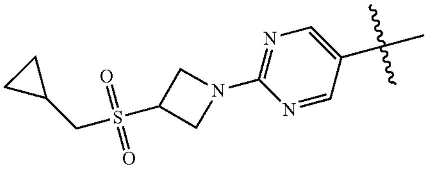 [SMILES: *c1cnc(N2CC(S(=O)(=O)CC3CC3)C2)nc1] | 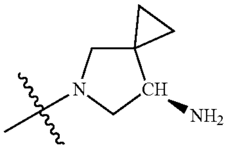 [SMILES: *N1C[C@H](N)C2(CC2)C1] |
| 4.339 | 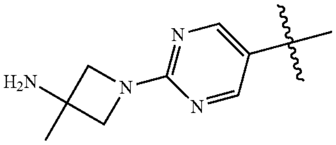 [SMILES: *c1cnc(N2CC(C)(N)C2)nc1] | 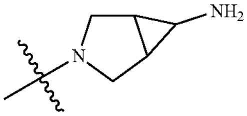 [SMILES: *N1CC2C(N)C2C1] |
| 4.340 | 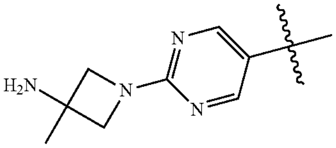 [SMILES: *c1cnc(N2CC(C)(N)C2)nc1] | 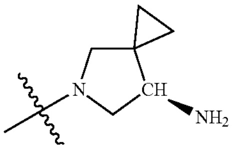 [SMILES: *N1C[C@H](N)C2(CC2)C1] |
| 4.341 | 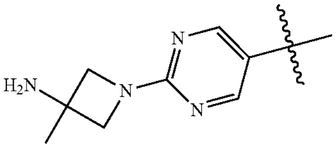 [SMILES: *c1cnc(N2CC(C)(N)C2)nc1] | 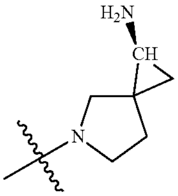 [SMILES: *N1CCC2(C[C@@H]2N)C1] |

-continued
| Table of Formula I Compounds Where L is O $R^x$, $R^z$ is CH, $R^y$ is F and $R^8$ is $NHCH_3$ | | |
|---|---|---|
| 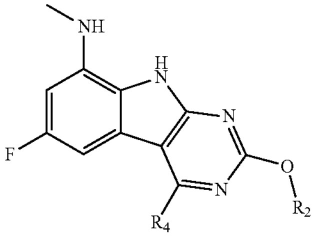 | | |
| 4.342 | 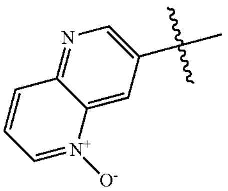 [SMILES: *c1cnc2ccc[n+]([O-])c2c1] | 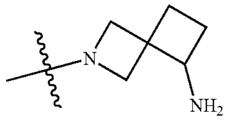 |
| 4.343 | 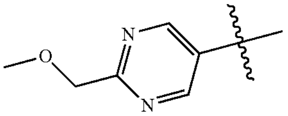 [SMILES: *c1cnc(COC)nc1] | 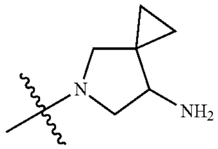 [SMILES: *N1CC(N)C2(CC2)C1] |
| 4.344 | 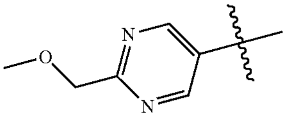 [SMILES: *c1cnc(COC)nc1] | 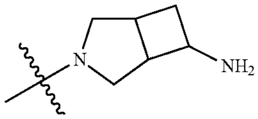 [SMILES: *N1CC2CC(N)C2C1] |
| 4.345 | 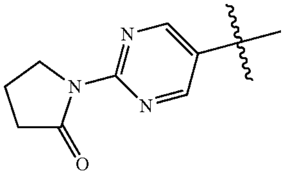 [SMILES: *c1cnc(N2CCCC2=O)nc1] | 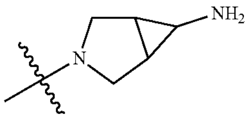 [SMILES: *N1CC2C(N)C2C1] |
| 4.346 | 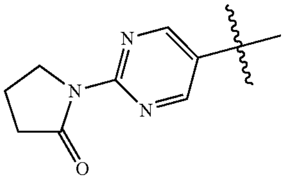 [SMILES: *c1cnc(N2CCCC2=O)nc1] | 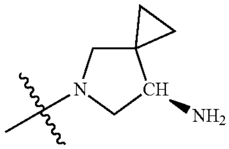 [SMILES: *N1C[C@H](N)C2(CC2)C1] |
| 4.347 | 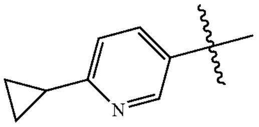 | 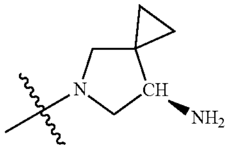 [SMILES: *N1C[C@H](N)C2(CC2)C1] |
| 4.348 | 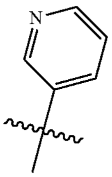 [SMILES: *c1cccnc1] | 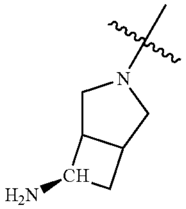 [SMILES: *N1CC2C[C@@H](N)C2C1] |

-continued
| Table of Formula I Compounds Where L is O $R^x$, $R^z$ is CH, $R^y$ is F and $R^8$ is $NHCH_3$ | | |
|---|---|---|
| 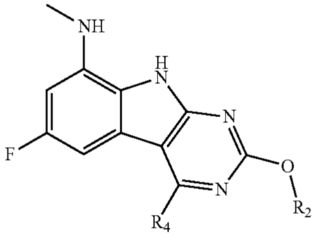 | | |
| 4.349 | 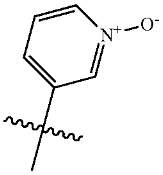 [SMILES: *c1ccc[n+]([O-])c1] | 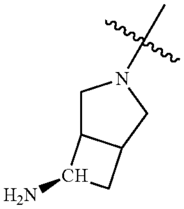 [SMILES: *N1CC2C[C@@H](N)C2C1] |
| 4.350 | 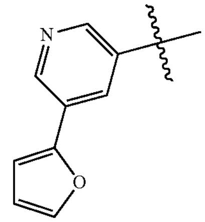 [SMILES: *c1cncc(-c2ccco2)c1] | 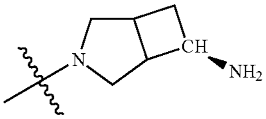 [SMILES: *N1CC2C[C@@H](N)C2C1] |
| 4.351 | 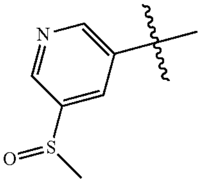 [SMILES: *c1cncc(S(C)=O)c1] | 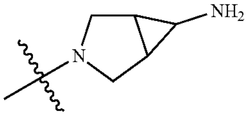 |
| 4.352 | 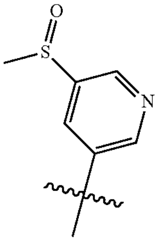 [SMILES: *c1cncc(S(C)=O)c1] | 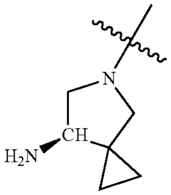 [SMILES: *N1C[C@H](N)C2(CC2)C1] |
| 4.353 | 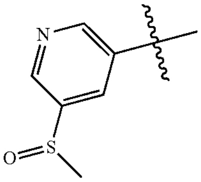 [SMILES: *c1cncc(S(C)=O)c1] | 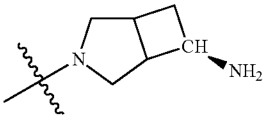 [SMILES: *N1CC2C[C@@H](N)C2C1] |
| 4.354 | 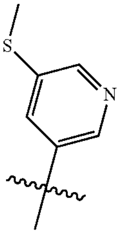 [SMILES: *c1cncc(SC)c1] | 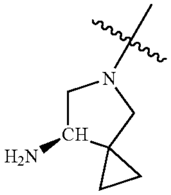 [SMILES: *N1C[C@H](N)C2(CC2)C1] |

-continued
Table of Formula I Compounds Where L is O $R^x$, $R^z$ is CH, $R^y$ is F and $R^8$ is $NHCH_3$
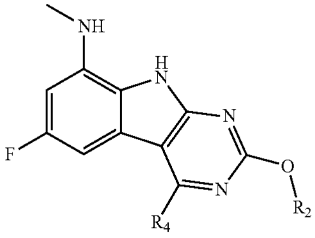
| | | |
|---|---|---|
| 4.355 | 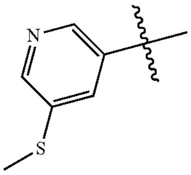 [SMILES: *c1cncc(SC)c1] | 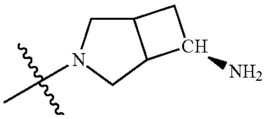 [SMILES: *N1CC2C[C@@H](N)C2C1] |
| 4.356 | 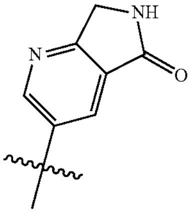 [SMILES: *c1cnc2c(c1)C(=O)NC2] | 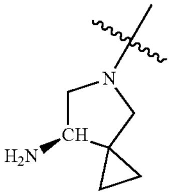 [SMILES: *N1C[C@H](N)C2(CC2)C1] |
| 4.357 | 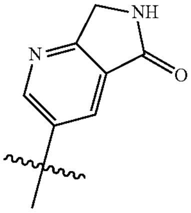 [SMILES: *c1cnc2c(c1)C(=O)NC2] | 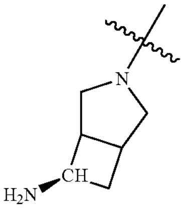 |
| 4.358 | 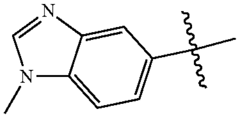 [SMILES: *c1ccc2c(c1)ncn2C] | 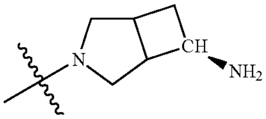 [SMILES: *N1CC2C[C@@H](N)C2C1] |
| 4.359 | 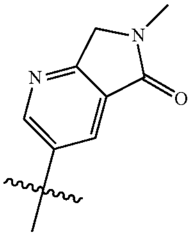 [SMILES: *c1cnc2c(c1)C(=O)N(C)C2] | 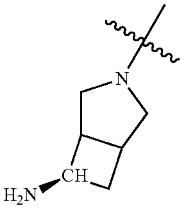 |
| 4.360 | 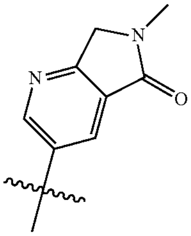 [SMILES: *c1cnc2c(c1)C(=O)N(C)C2] | 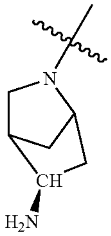 |

-continued
| Table of Formula I Compounds Where L is O $R^x$, $R^z$ is CH, $R^y$ is F and $R^8$ is $NHCH_3$ | | |
|---|---|---|
| 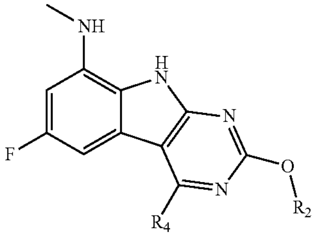 | | |
| 4.361 | 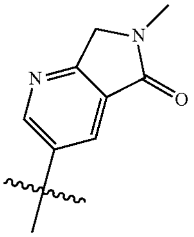 [SMILES: *c1cnc2c(c1)C(=O)N(C)C2] | 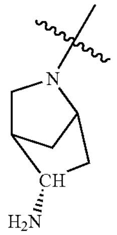 |
| 4.362 | 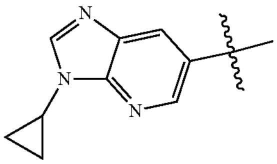 [SMILES: *c1cnc2c(c1)ncn2C1CC1] | 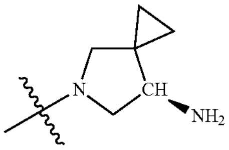 [SMILES: *N1C[C@H](N)C2(CC2)C1] |
| 4.363 | 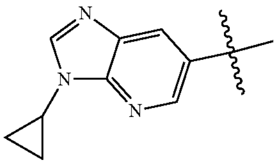 [SMILES: *c1cnc2c(c1)ncn2C1CC1] | 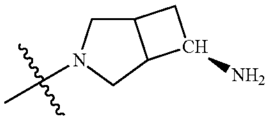 [SMILES: *N1CC2C[C@@H](N)C2C1] |
| 4.364 | 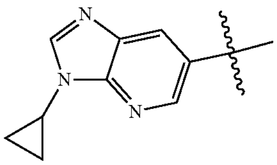 [SMILES: *c1cnc2c(c1)ncn2C1CC1] | 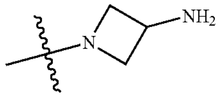 [SMILES: *N1CC(N)C1] |
| 4.365 | 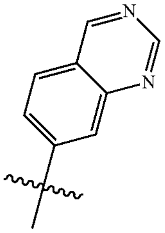 [SMILES: *c1ccc2cncnc2c1] | 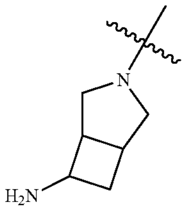 |
| 4.366 | 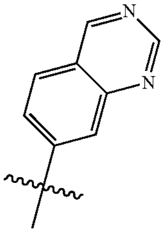 [SMILES: *c1ccc2cncnc2c1] | 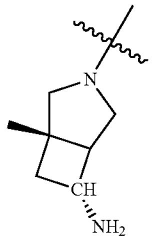 [SMILES: *N1CC2[C@H](N)C[C@]2(C)C1] |

-continued
Table of Formula I Compounds Where L is O $R^x$, $R^z$ is CH, $R^y$ is F and $R^8$ is $NHCH_3$
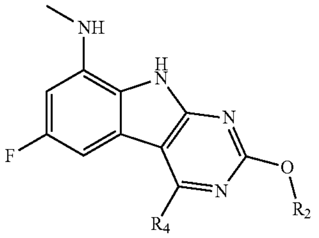
| | | |
|---|---|---|
| 4.367 | 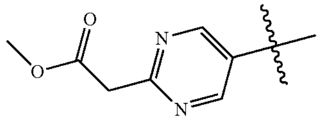 [SMILES: *c1cnc(CC(=O)OC)nc1] | 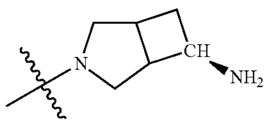 [SMILES: *N1CC2C[C@@H](N)C2C1] |
| 4.368 | 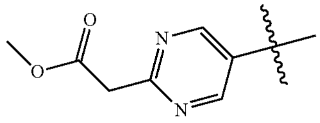 [SMILES: *c1cnc(CC(=O)OC)nc1] | 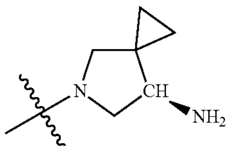 [SMILES: *N1C[C@H](N)C2(CC2)C1] |
| 4.369 | 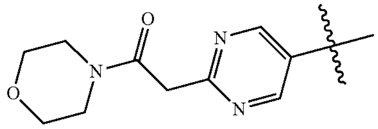 [SMILES: *c1cnc(CC(=O)N2CCOCC2)nc1] | 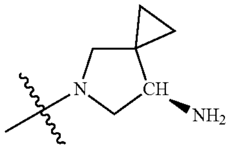 [SMILES: *N1C[C@H](N)C2(CC2)C1] |
| 4.370 | 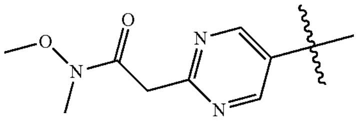 [SMILES: *c1cnc(CC(=O)N(C)OC)nc1] | 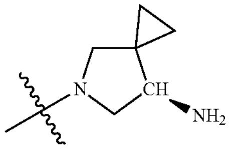 [SMILES: *N1C[C@H](N)C2(CC2)C1] |
| 4.371 | 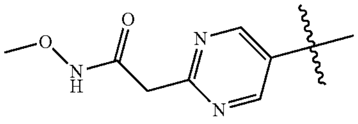 [SMILES: *c1cnc(CC(=O)NOC)nc1] | 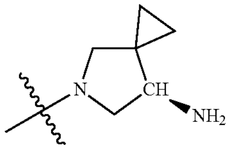 [SMILES: *N1C[C@H](N)C2(CC2)C1] |
| 4.372 | 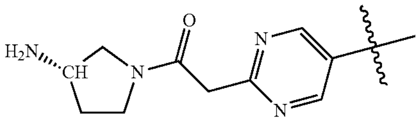 [SMILES: *c1cnc(CC(=O)N2CC[C@H](N)C2)nc1] | 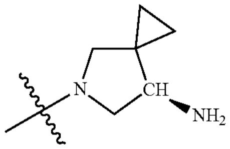 [SMILES: *N1C[C@H](N)C2(CC2)C1] |
| 4.373 | 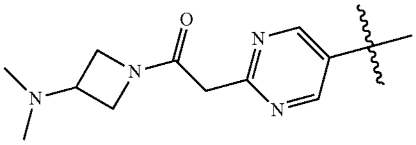 [SMILES: *c1cnc(CC(=O)N2CC(N(C)C)C2)nc1] | 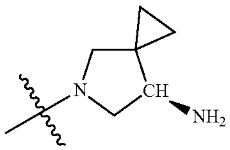 [SMILES: *N1C[C@H](N)C2(CC2)C1] |
| 4.374 | 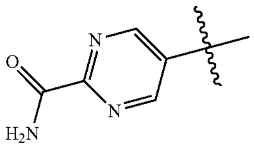 [SMILES: *c1cnc(C(N)=O)nc1] | 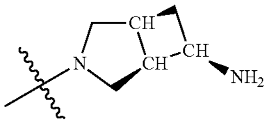 [SMILES: *N1C[C@H]2C[C@@H](N)[C@H]2C1] |

-continued
Table of Formula I Compounds Where L is O $R^x$, $R^z$ is CH, $R^y$ is F and $R^8$ is $NHCH_3$
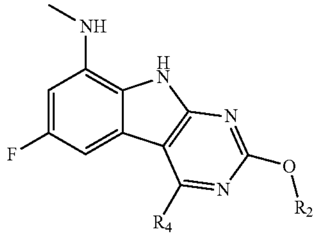
| | | |
|---|---|---|
| 4.375 | 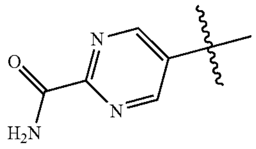 [SMILES: *c1cnc(C(N)=O)nc1] | 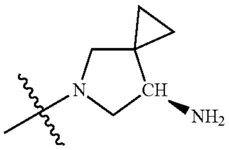 [SMILES: *N1C[C@H](N)C2(CC2)C1] |
| 4.376 | 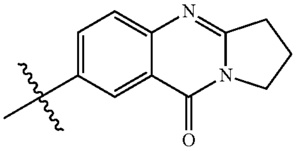 [SMILES: *c1ccc2nc3n(c(=O)c2c1)CCC3] | 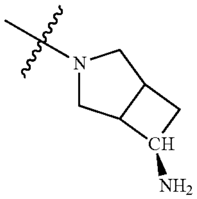 [SMILES: *N1CC2C[C@@H](N)C2C1] |
| 4.377 | 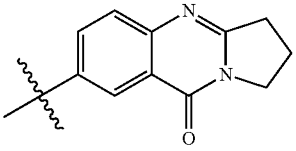 [SMILES: *c1ccc2nc3n(c(=O)c2c1)CCC3] | 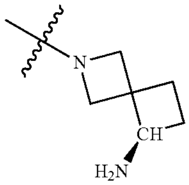 [SMILES: *N1CC2(CC[C@H]2N)C1] |
| 4.378 | 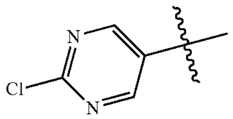 [SMILES: *c1cnc(Cl)nc1] | 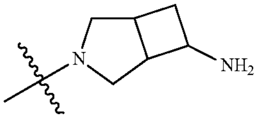 |
| 4.379 | 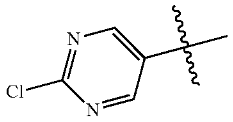 [SMILES: *c1cnc(Cl)nc1] | 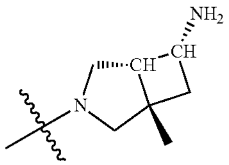 [SMILES: *N1C[C@@H]2[C@H](N)C[C@]2(C)C1] |
| 4.380 | 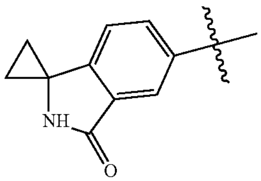 [SMILES: *c1ccc2c(c1)C(=O)NC21CC1] | 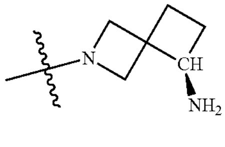 [SMILES: *N1CC2(CC[C@H]2N)C1] |
| 4.381 | 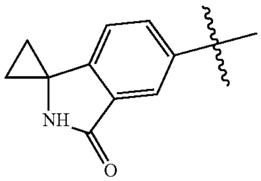 [SMILES: *c1ccc2c(c1)C(=O)NC21CC1] | 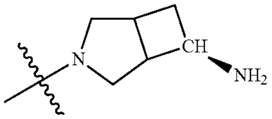 [SMILES: *N1CC2C[C@@H](N)C2C1] |

-continued
Table of Formula I Compounds Where L is O $R^x$, $R^z$ is CH, $R^y$ is F and $R^8$ is $NHCH_3$
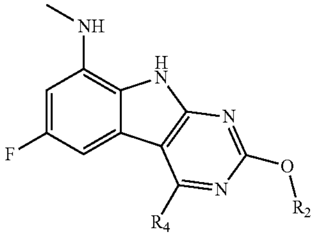
| | | |
|---|---|---|
| 4.382 | 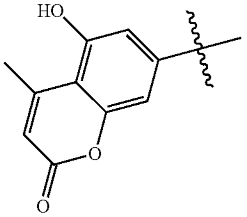 [SMILES: *c1cc(O)c2c(C)cc(=O)oc2c1] | 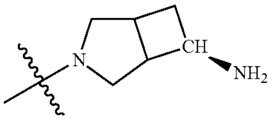 [SMILES: *N1CC2C[C@@H](N)C2C1] |
| 4.383 | 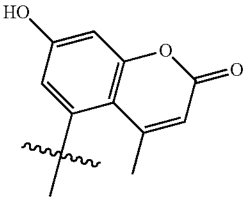 [SMILES: *c1cc(O)cc2oc(=O)cc(C)c12] | 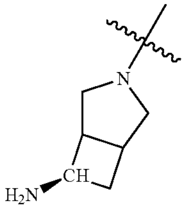 [SMILES: *N1CC2C[C@@H](N)C2C1] |
| 4.384 | 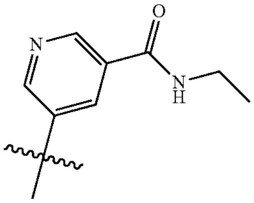 [SMILES: *c1cncc(C(=O)NCC)c1] | 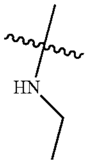 [SMILES: *NCC] |
| 4.385 | 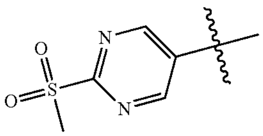 [SMILES: *c1cnc(S(C)(=O)=O)nc1] | 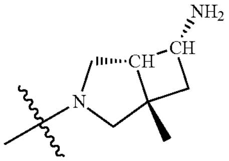 [SMILES: *N1C[C@@H]2[C@H](N)C[C@]2(C)C1] |
| 4.386 | 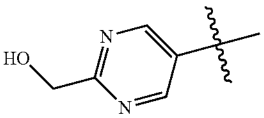 [SMILES: *c1cnc(CO)nc1] | 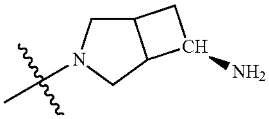 |
| 4.387 | 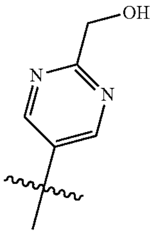 [SMILES: *c1cnc(CO)nc1] | 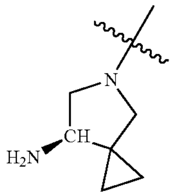 [SMILES: *N1C[C@H](N)C2(CC2)C1] |
| 4.388 | 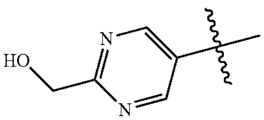 [SMILES: *c1cnc(CO)nc1] | 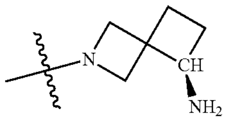 |

-continued
Table of Formula I Compounds Where L is O $R^x$, $R^z$ is CH, $R^y$ is F and $R^8$ is $NHCH_3$
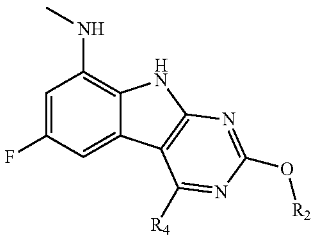
| | | |
|---|---|---|
| 4.389 | 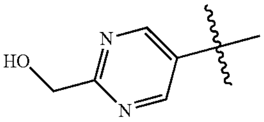 [SMILES: *c1cnc(CO)nc1] | 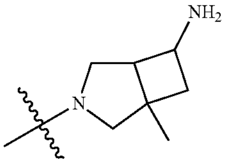 [SMILES: *N1CC2C(N)CC2(C)C1] |
| 4.390 | 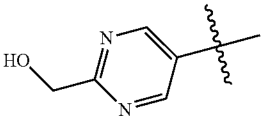 | 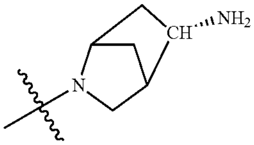 [SMILES: *N1CC2CC1C[C@@H]2N] |
| 4.391 | 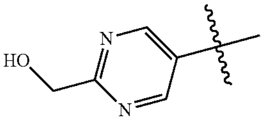 [SMILES: *c1cnc(CO)nc1] | 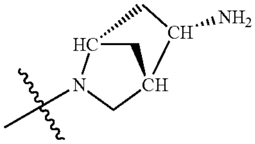 [SMILES: *N1C[C@@H]2C[C@H]1C[C@@H]2N] |
| 4.392 | 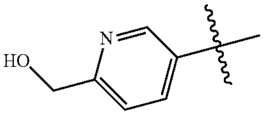 [SMILES: *c1ccc(CO)nc1] | 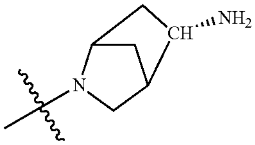 [SMILES: *N1CC2CC1C[C@@H]2N] |
| 4.393 | 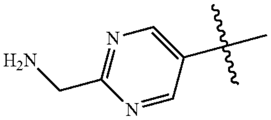 [SMILES: *c1cnc(CN)nc1] | 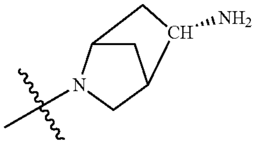 [SMILES: *N1CC2CC1C[C@@H]2N] |
| 4.394 | 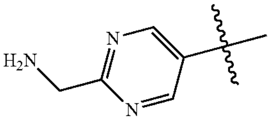 [SMILES: *c1cnc(CN)nc1] | 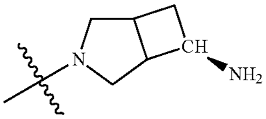 [SMILES: *N1CC2C[C@@H](N)C2C1] |
| 4.395 | 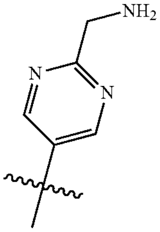 [SMILES: *c1cnc(CN)nc1] | 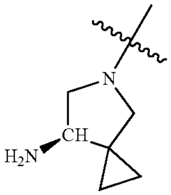 [SMILES: *N1C[C@H](N)C2(CC2)C1] |
| 4.396 | 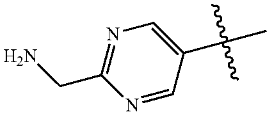 [SMILES: *c1cnc(CN)nc1] | 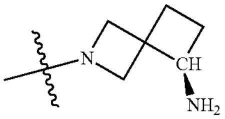 [SMILES: *N1CC2(CC[C@H]2N)C1] |

-continued
Table of Formula I Compounds Where L is O $R^x$, $R^z$ is CH, $R^y$ is F and $R^8$ is $NHCH_3$
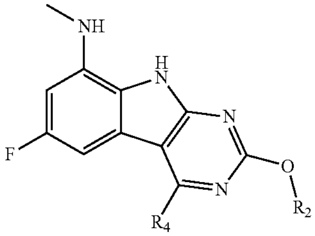
| | | |
|---|---|---|
| 4.397 | 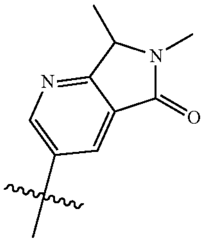 [SMILES: *c1cnc2c(c1)C(=O)N(C)C2C] | 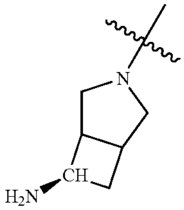 [SMILES: *N1CC2C[C@@H](N)C2C1] |
| 4.398 | 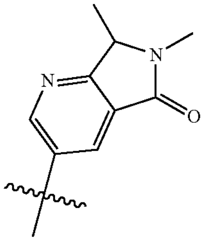 [SMILES: *c1cnc2c(c1)C(=O)N(C)C2C] | 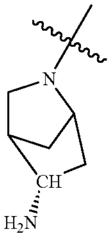 |
| 4.399 | 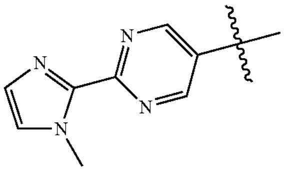 [SMILES: *c1cnc(-c2nccn2C)nc1] | 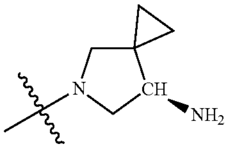 [SMILES: *N1C[C@H](N)C2(CC2)C1] |
| 4.400 | 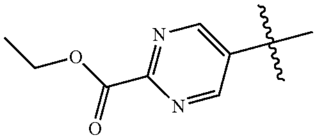 [SMILES: *c1cnc(C(=O)OCC)nc1] | 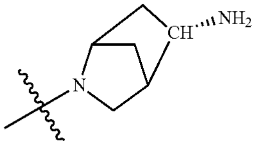 [SMILES: *N1CC2CC1C[C@@H]2N] |
| 4.401 | 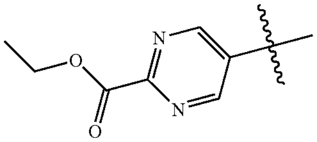 [SMILES: *c1cnc(C(=O)OCC)nc1] | 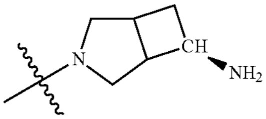 [SMILES: *N1CC2C[C@@H](N)C2C1] |
| 4.402 | 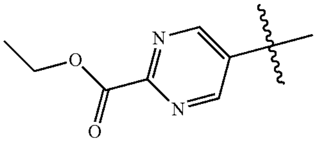 [SMILES: *c1cnc(C(=O)OCC)nc1] | 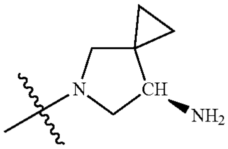 [SMILES: *N1C[C@H](N)C2(CC2)C1] |
| 4.403 | 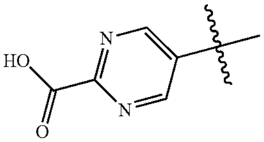 [SMILES: *c1cnc(C(=O)O)nc1] | 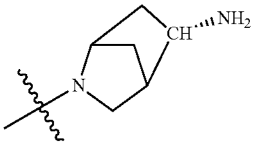 [SMILES: *N1CC2CC1C[C@@H]2N] |

-continued
Table of Formula I Compounds Where L is O $R^x$, $R^z$ is CH, $R^y$ is F and $R^8$ is $NHCH_3$
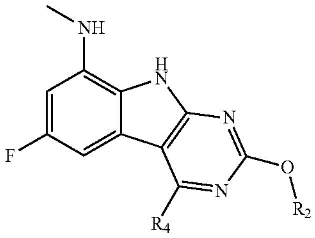
| | | |
|---|---|---|
| 4.404 | 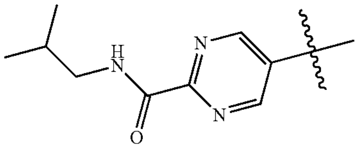 [SMILES: *c1cnc(C(=O)NCC(C)C)nc1] | 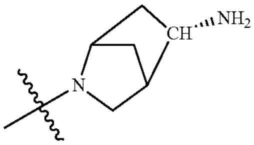 [SMILES: *N1CC2CC1C[C@@H]2N] |
| 4.405 | 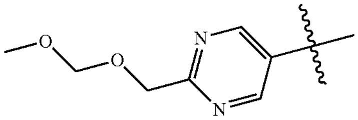 [SMILES: *c1cnc(COCOC)nc1] | 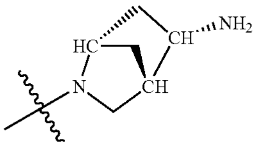 [SMILES: *N1C[C@@H]2C[C@H]1C[C@@H]2N] |
| 4.406 | 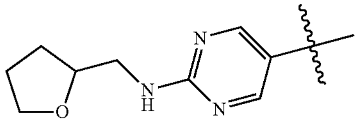 [SMILES: *c1cnc(NCC2CCCO2)nc1] | 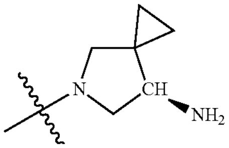 [SMILES: *N1C[C@H](N)C2(CC2)C1] |
| 4.407 | 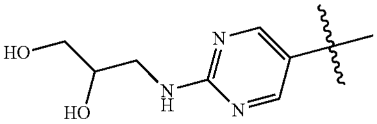 [SMILES: *c1cnc(NCC(O)CO)nc1] | 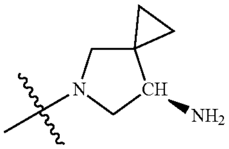 [SMILES: *N1C[C@H](N)C2(CC2)C1] |
| 4.408 | 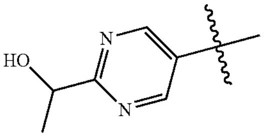 [SMILES: *c1cnc(C(C)O)nc1] | 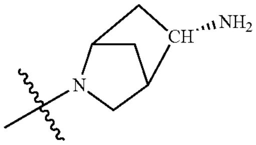 [SMILES: *N1CC2CC1C[C@@H]2N] |
| 4.409 | 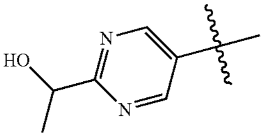 [SMILES: *c1cnc(C(C)O)nc1] | 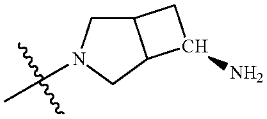 [SMILES: *N1CC2C[C@@H](N)C2C1] |
| 4.410 | 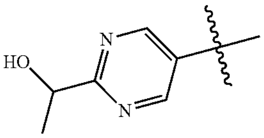 [SMILES: *c1cnc(C(C)O)nc1] | 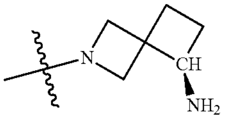 |
| 4.411 | 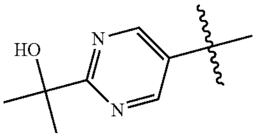 [SMILES: *c1cnc(C(C)(C)O)nc1] | 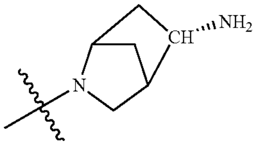 [SMILES: *N1CC2CC1C[C@@H]2N] |

-continued
Table of Formula I Compounds Where L is O $R^x$, $R^z$ is CH, $R^y$ is F and $R^8$ is $NHCH_3$
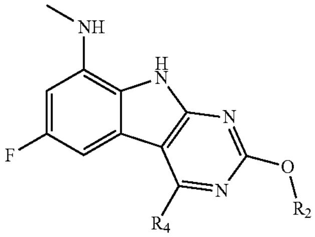
| | | |
|---|---|---|
| 4.412 | 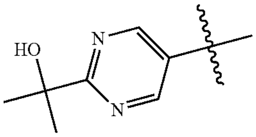 [SMILES: *c1cnc(C(C)(C)O)nc1] | 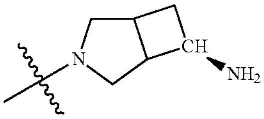 [SMILES: *N1CC2C[C@@H](N)C2C1] |
| 4.413 | 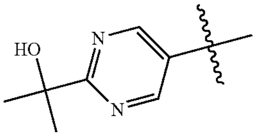 [SMILES: *c1cnc(C(C)(C)O)nc1] | 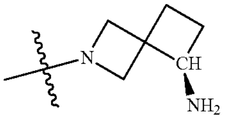 |
| 4.414 | 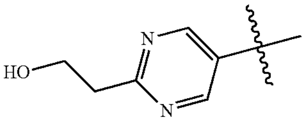 [SMILES: *c1cnc(CCO)nc1] | 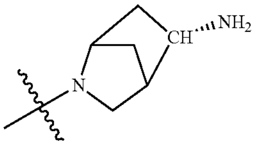 [SMILES: *N1CC2CC1C[C@@H]2N] |
| 4.415 | 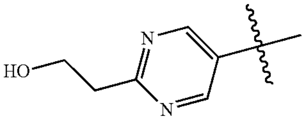 [SMILES: *c1cnc(CCO)nc1] | 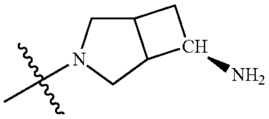 [SMILES: *N1CC2C[C@@H](N)C2C1] |
| 4.416 | 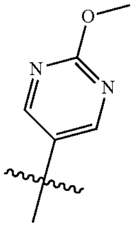 [SMILES: *c1cnc(OC)nc1] | 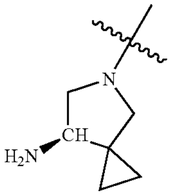 [SMILES: *N1C[C@H](N)C2(CC2)C1] |
| 4.417 | 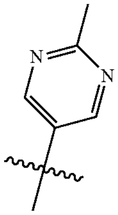 [SMILES: *c1cnc(C)nc1] | 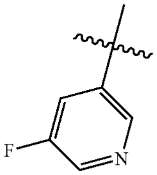 [SMILES: *c1cncc(F)c1] |
| 4.418 | 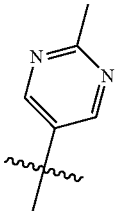 [SMILES: *c1cnc(C)nc1] | 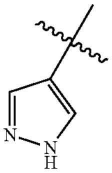 [SMILES: *c1cn[nH]c1] |

-continued
Table of Formula I Compounds Where L is O $R^x$, $R^z$ is CH, $R^y$ is F and $R^8$ is $NHCH_3$
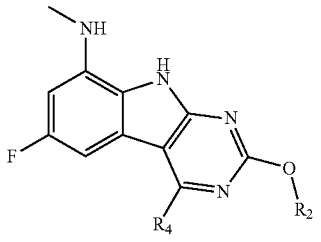
| | | |
|---|---|---|
| 4.419 | 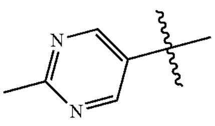 [SMILES: *c1cnc(C)nc1] | 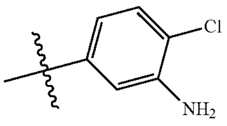 [SMILES: *c1ccc(Cl)c(N)c1] |
| 4.420 | 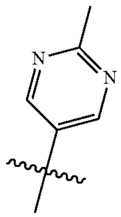 [SMILES: *c1cnc(C)nc1] | 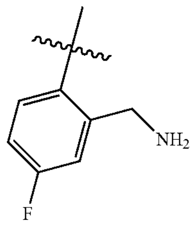 [SMILES: *c1ccc(F)cc1CN] |
| 4.421 | 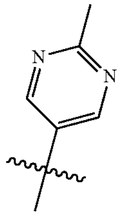 [SMILES: *c1cnc(C)nc1] | 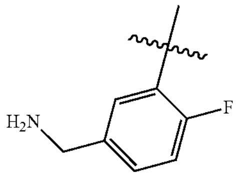 [SMILES: *c1cc(CN)ccc1F] |
| 4.422 | 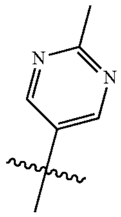 [SMILES: *c1cnc(C)nc1] | 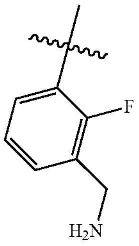 [SMILES: *c1cccc(CN)c1F] |
| Cmpd ID | |
|---|---|
| 4.423 | 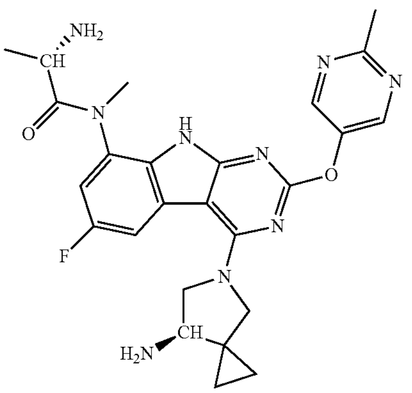 [SMILES: Cc1ncc(Oc2nc(N3C[C@H](N)C4(CC4)C3)c3c(n2)[nH]c2c(N(C)C(=O)[C@H](C)N)cc(F)cc23)cn1] |

-continued
| Table of Formula I Compounds Where L is O $R^x$, $R^z$ is CH, $R^y$ is F and $R^8$ is $NHCH_3$ |
| --- |
| 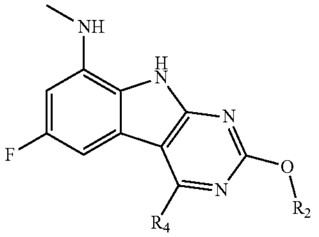 |
| | |
| --- | --- |
| 4.424 | 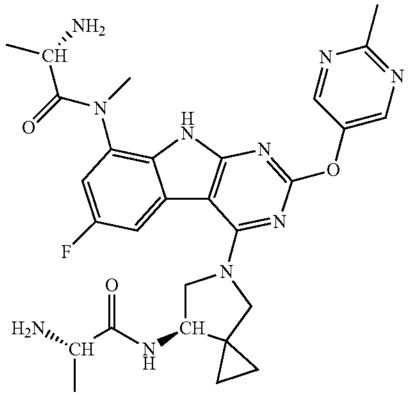 [SMILES: Cc1ncc(Oc2nc(N3C[C@H](NC(=O)[C@H](C)N)C4(CC4)C3)c3c(n2)[nH]c2c(N(C)C(=O)[C@H](C)N)cc(F)cc23)cn1] |
| 4.425 | 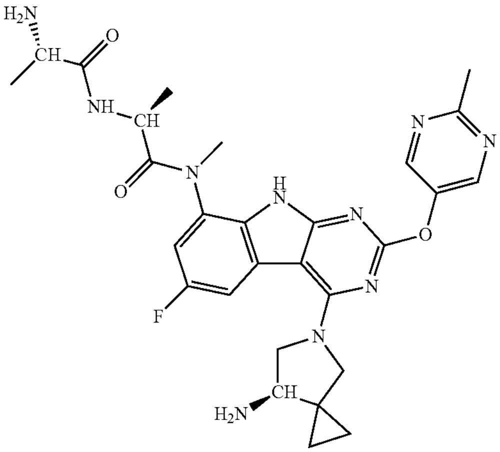 [SMILES: Cc1ncc(Oc2nc(N3C[C@H](N)C4(CC4)C3)c3c(n2)[nH]c2c(N(C)C(=O)[C@H](C)NC(=O)[C@H](C)N)cc(F)cc23)cn1] |
| 4.426 | 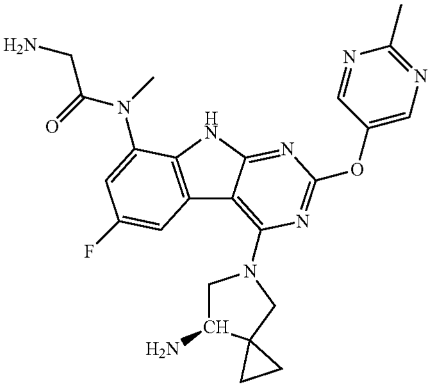 [SMILES: Cc1ncc(Oc2nc(N3C[C@H](N)C4(CC4)C3)c3c(n2)[nH]c2c(N(C)C(=O)CN)cc(F)cc23)cn1] |

-continued
Table of Formula I Compounds Where L is O $R^x$, $R^z$ is CH, $R^y$ is F and $R^8$ is $NHCH_3$
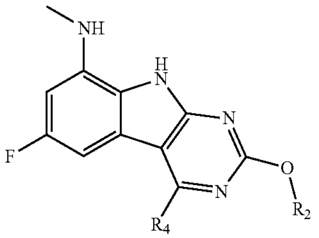
4.427
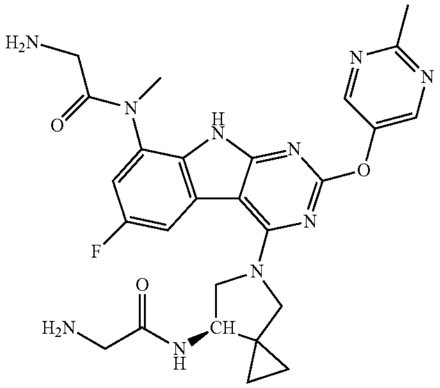 [SMILES: Cc1ncc(Oc2nc(N3C[C@H](NC(=O)CN)C4(CC4)C3)c3c(n2)[nH]c2c(N(C)C(=O)CN)cc(F)cc23)cn1]
4.428
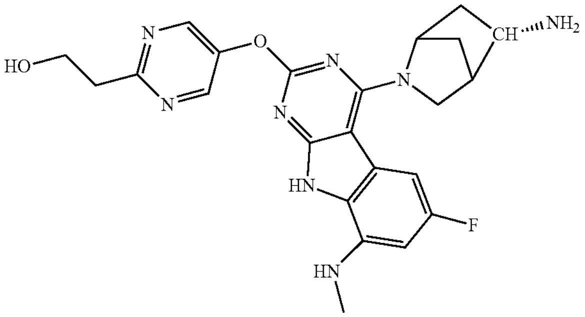 [SMILES: CNc1cc(F)cc2c1[nH]c1nc(Oc3cnc(CCO)nc3)nc(N3CC4CC3C[C@@H]4N)c12]
4.429
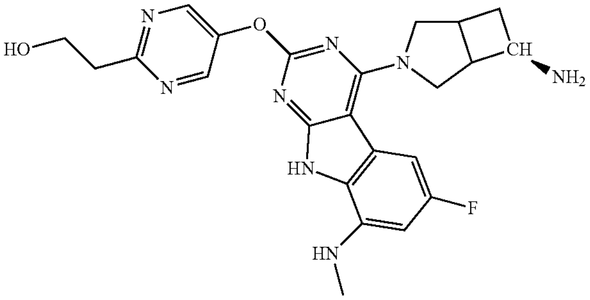 [SMILES: CNc1cc(F)cc2c1[nH]c1nc(Oc3cnc(CCO)nc3)nc(N3CC4C[C@@H](N)C4C3)c12]
4.430
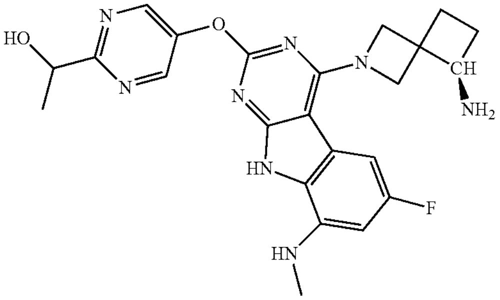 [SMILES: CNc1cc(F)cc2c1[nH]c1nc(Oc3cnc(C(C)O)nc3)nc(N3CC4(CC[C@H]4N)C3)c12]

-continued
Table of Formula I Compounds Where L is O $R^x$, $R^z$ is CH, $R^y$ is F and $R^8$ is $NHCH_3$
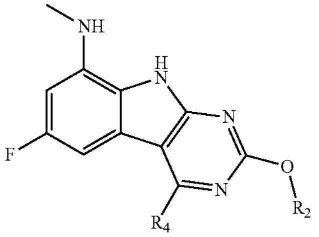
4.431
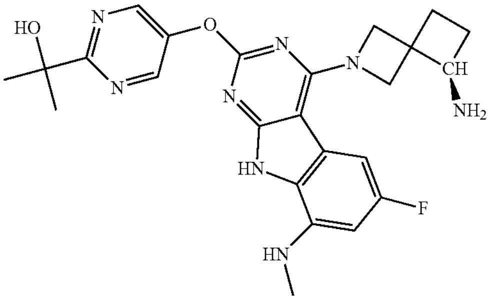 [SMILES: CNc1cc(F)cc2c1[nH]c1nc(Oc3cnc(C(C)(C)O)nc3)nc(N3CC4(CC[C@H]4N)C3)c12]
4.432
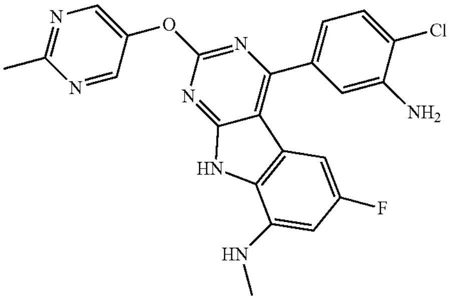 [SMILES: CNc1cc(F)cc2c1[nH]c1nc(Oc3cnc(C)nc3)nc(-c3ccc(Cl)c(N)c3)c12]
4.433
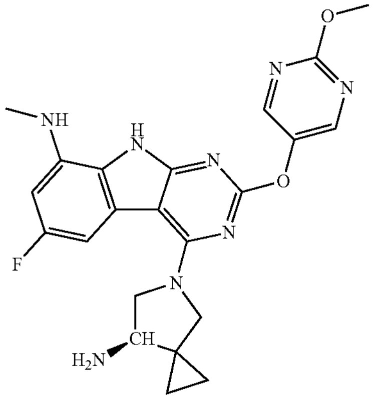
4.434
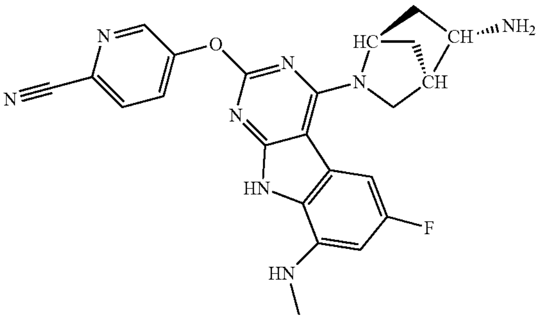 [SMILES: CNc1cc(F)cc2c1[nH]c1nc(Oc3ccc(C#N)nc3)nc(N3C[C@H]4C[C@@H]3C[C@@H]4N)c12]

-continued
Table of Formula I Compounds Where L is O $R^x$, $R^z$ is CH, $R^y$ is F and $R^8$ is $NHCH_3$
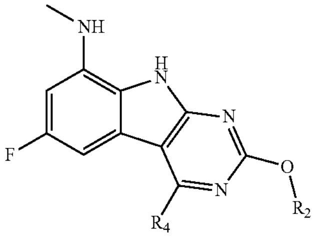
4.435
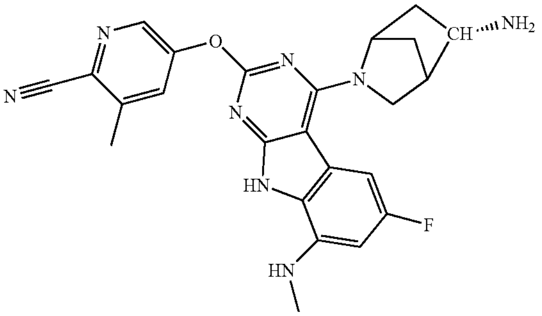 [SMILES: CNc1cc(F)cc2c1[nH]c1nc(Oc3cnc(C#N)c(C)c3)nc(N3CC4CC3C[C@@H]4N)c12]
4.436
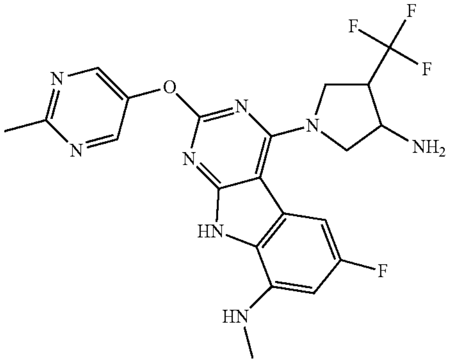 [SMILES: CNc1cc(F)cc2c1[nH]c1nc(Oc3cnc(C)nc3)nc(N3CC(N)C(C(F)(F)F)C3)c12]
4.437
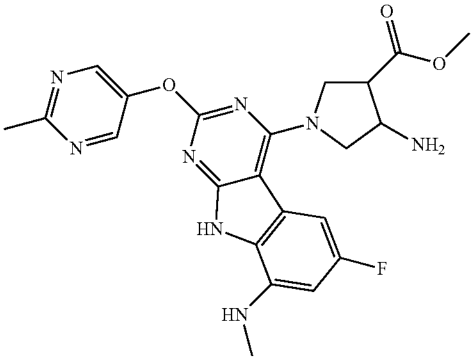

-continued
| Table of Formula I Compounds Where L is O $R^x$, $R^z$ is CH, $R^y$ is F and $R^8$ is $NHCH_3$ | |
|---|---|
| 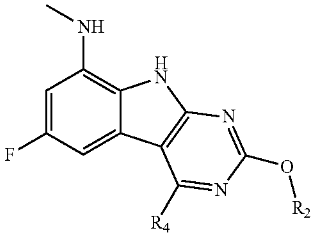 | |
| 4.438 | 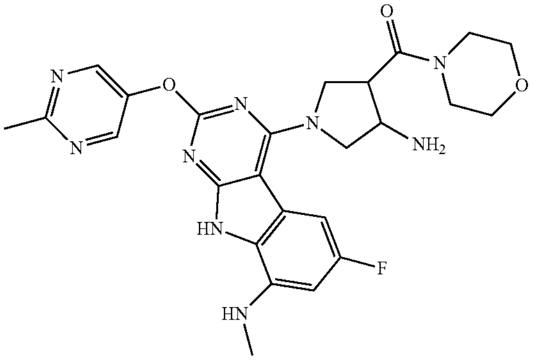 [SMILES: CNc1cc(F)cc2c1[nH]c1nc(Oc3cnc(C)nc3)nc(N3CC(N)C(C(=O)N4CCOCC4)C3)c12] |
| 4.439 | 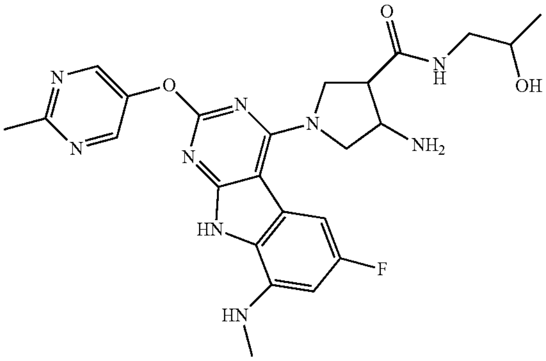 [SMILES: CNc1cc(F)cc2c1[nH]c1nc(Oc3cnc(C)nc3)nc(N3CC(N)C(C(=O)NCC(C)O)C3)c12] |
| 4.440 | 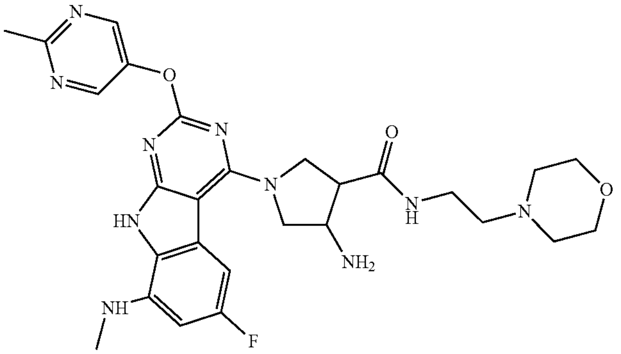 [SMILES: CNc1cc(F)cc2c1[nH]c1nc(Oc3cnc(C)nc3)nc(N3CC(N)C(C(=O)NCCN4CCOCC4)C3)c12] |

-continued
Table of Formula I Compounds Where L is O $R^x$, $R^z$ is CH, $R^y$ is F and $R^8$ is $NHCH_3$
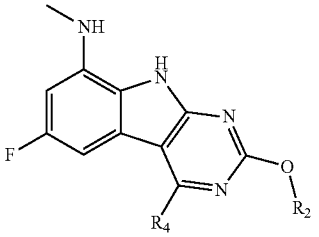
4.441
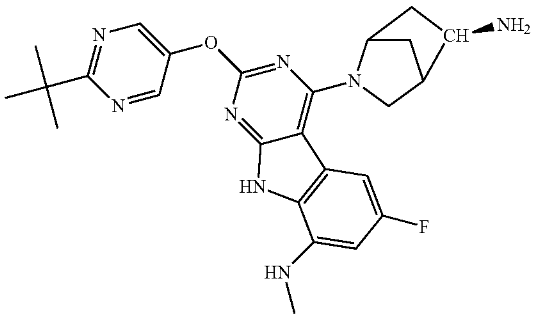 [SMILES: CNc1cc(F)cc2c1[nH]c1nc(Oc3cnc(C(C)(C)C)nc3)nc(N3CC4CC3C[C@H]4N)c12]
4.442
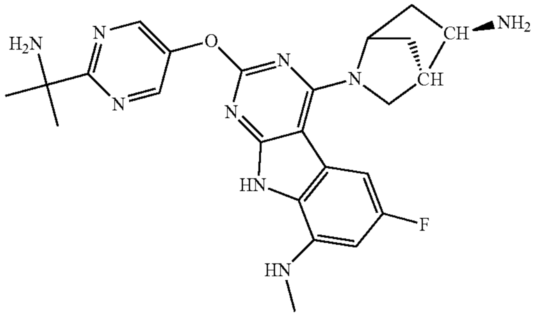 [SMILES: CNc1cc(F)cc2c1[nH]c1nc(Oc3cnc(C(C)(C)N)nc3)nc(N3C[C@H]4CC3C[C@H]4N)c12]
4.443
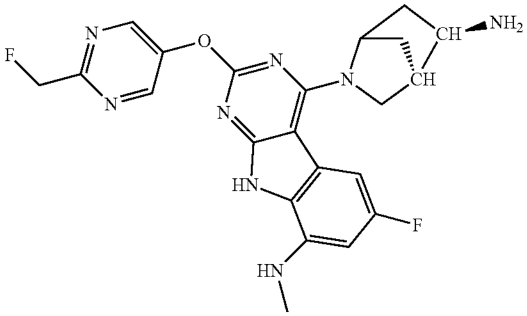 [SMILES: CNc1cc(F)cc2c1[nH]c1nc(Oc3cnc(CF)nc3)nc(N3C[C@H]4CC3C[C@H]4N)c12]

-continued
Table of Formula I Compounds Where L is O $R^x$, $R^z$ is CH, $R^y$ is F and $R^8$ is $NHCH_3$
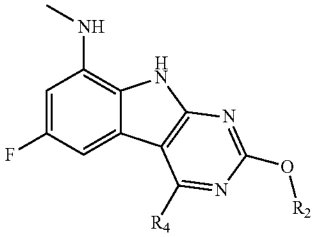
4.445
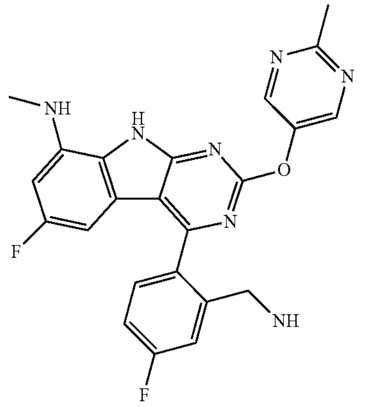 [SMILES: CNc1cc(F)cc2c1[nH]c1nc(Oc3cnc(C)nc3)nc(-c3ccc(F)cc3CN)c12]
4.446
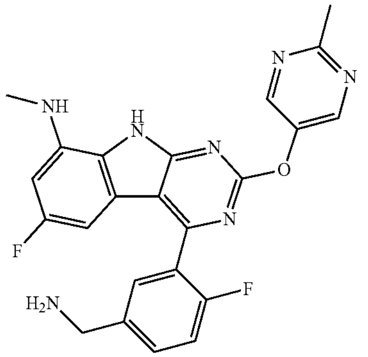 [SMILES: CNc1cc(F)cc2c1[nH]c1nc(Oc3cnc(C)nc3)nc(-c3cc(CN)ccc3F)c12]
4.447
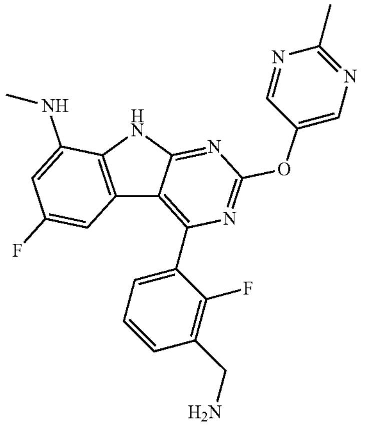 [SMILES: CNc1cc(F)cc2c1[nH]c1nc(Oc3cnc(C)nc3)nc(-c3cccc(CN)c3F)c12]

-continued
Table of Formula I Compounds Where L is O $R^x$, $R^z$ is CH, $R^y$ is F and $R^8$ is $NHCH_3$
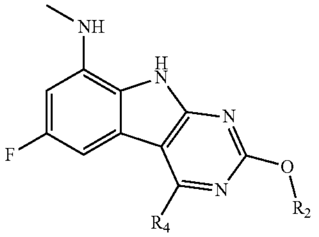
4.448
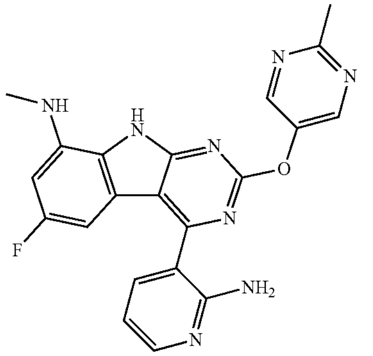 [SMILES: CNc1cc(F)cc2c1[nH]c1nc(Oc3cnc(C)nc3)nc(-c3cccnc3N)c12]
4.449
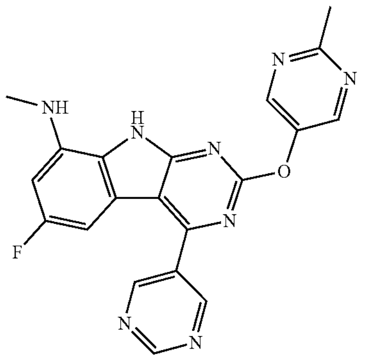 [SMILES: CNc1cc(F)cc2c1[nH]c1nc(Oc3cnc(C)nc3)nc(-c3cncnc3)c12]
4.450
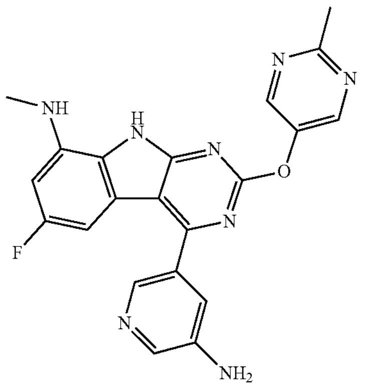 [SMILES: CNc1cc(F)cc2c1[nH]c1nc(Oc3cnc(C)nc3)nc(-c3cncc(N)c3)c12]

Difluorophenyl Analogs

Experimental

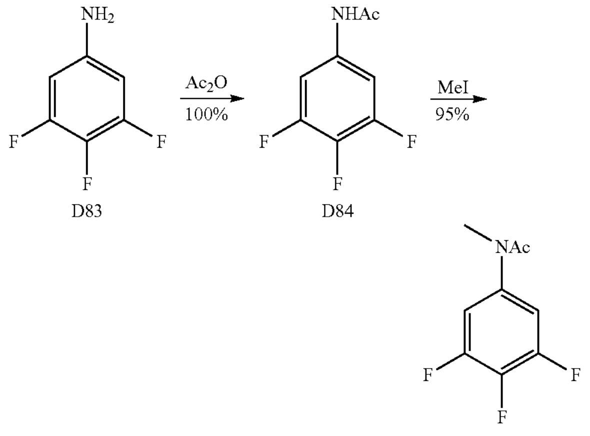

D83 D84 D85

Preparation of Compound D84:

Tri-frluo aniline (250 g) was portionly added into 500 ml acetic anhydride under the ice-water bath, after addition, the reaction was stirred vigorously for 4 hours, then poured into crashed ice, the precipitate (white granular solid) was collected and dry for next step (quantitive yield).

Preparation of Compound D85:

The above made acetyl aniline (126 g, 666 mmol) was portionly added into sodium hydride (40 g, 1 mmol, 60% in oil) solution in dry THF (1 L) under the ice water bath, then the solution was stirred for another 1 hours, then MeI (64 ml, 1 mol) in 100 ml THF was added dropwisely into the solution, the mixture was stirred for overnight (12 hours), and quenched with ice water. The aqueous solution was extracted with 3x500 ml ethyl acetate, the combined solution was dried and concentrated for next steps without purification.

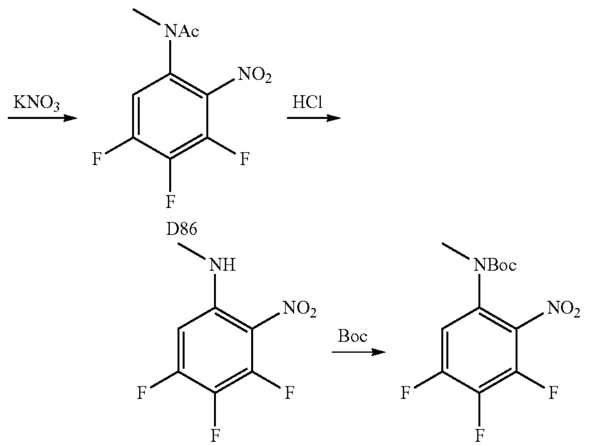

D86 D87 D88

Preparation of Compound D86:

The above crude compounds was dissolved into 1500 ml trifluoro acetice anydride under the ice-water bath, then $KNO_3$(168 g, 1.66 mol) was added portionly into the TFAA solution, keep the temperature under 35° C. by controlling the rate of $KNO_3$, after addition, the reaction was stirred for further 36 hours, then quenched the reaction with ice-water, the red solution was extracted with 3x500 ml ethyl acetate, the combined solution was dried and concentrated for next steps without purification.

Preparation of Compound D87:

The above sticky solid was dissolved into 1 L (2M HCl), the reaction solution was refluxed for 4 hours, TLC monitored the reaction, cooled down to room temperature when the starting material disappeared, the dark-red solution was extracted with 3x500 ml DCM, the combined solution was dried and concentrated. the residue was purified by flash chromatography, nice dark granular solids (105 g) was obtained with 75% yield.

Preparation of Compound D88:

The above N-methyl-aniline (21 g, 100 mmol) was portionly added into sodium hydride (40 g, 1 mmol, 60% in oil) solution in dry THF (1 L) under the ice water bath, then the solution was stirred for another 1 hours, then Boc anhydride (24 g, 110 mol) in 100 ml THF was added dropwisely into the solution, the mixture was stirred for overnight (12 hours), and quenched with 10% HOAc/ice water. the aqueous solution was extracted with 3x500 ml ethyl acetate, the combined solution was dried and concentrated to remove solvent, then the residue was purified by flash chromatography to gave 26 g desired products, 82% yield.

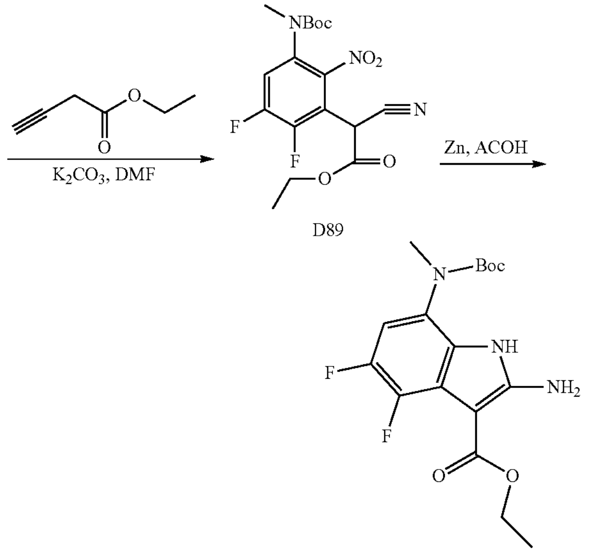

D89 D90

Preparation of Compound D89:

To a stirred suspension of $K_2CO_3$ (13.8 g, 0.1 mol) and ethyl cyanoacetate (11.2 g, 0.1 mol) in 200 mL DMF was added a solution of compound D88 (20.0 g, 066 mmol) in 100 mL DMF under $N_2$ protection. After addition, the reaction was stirred at room temperature for two days. TLC showed the SM was consumed, then the reaction mixture was diluted with ethyl acetate (400 mL) and water (1500 mL), the organic layer was separated, the aqueous layer extracted by ethyl acetate (200 mL). The combined organic layer was washed with brine (300 mLx3), dried over $Na_2SO_4$, filtered, and concentrated in vacuum. The crude product was purified by chromatography (pet. ether/EtOAc, 100/1 to 20/1, v/v) to give compound D89 as a pale yellow solid (12.0 g, 45% yield).

Preparation of Compound:

To a solution of compounds D89 (12 g, 30 mmol) in acetic acid (200 ml) was added portionly Zinc dust (13 g, 200 mmol). After addition, the reaction mixture was warmed to 50 degree, LCMS monitored the reaction process. The reaction was concentrated after the reaction completed (about 4 hours), and the residue was partitioned with H2O 2O (200 ml) and ethyl acetate (200 ml), the aqueous layer was extracted twice with ethyl acetate, the combined solvent was dried and concentrated, the residue was purified by flash chromatography to produce products D90 (9 g, 81% yield). %). LC-MS: M+1: 370.

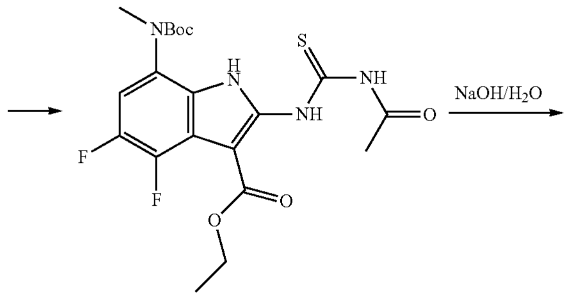

D91

Preparation of Compound D91:

To a stirred suspension of compound D90 (7.4 g, 20 mmol) in acetone (140 mL) was added dropwise a solution of acetyl thioisocynate (12 mL, 140 mmol) in acetone (50 mL) at room temperature. The reaction mixture was heated to reflux for 16 h. LCMS showed the reaction was completed. The reaction mixture was concentrated for next step without purification.

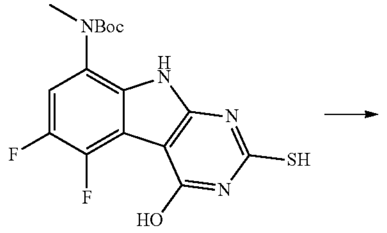

D92

Preparation of Compound D92:

Above residue was dissolved into 50 ml methanol and 50 ml H2O, then was added 10 ml 10% KOH solution, the mixture solution was heated to reflux for 30 minutes. When LCMS showed the reaction was completed the reaction was cooled to room temperature, acidified to pH 5 with 1M aq. HCl, and the precipitate collected by filtration to give compound D92 as a solid (5 g, 65.4% in two steps). LC-MS: M+1: 383.

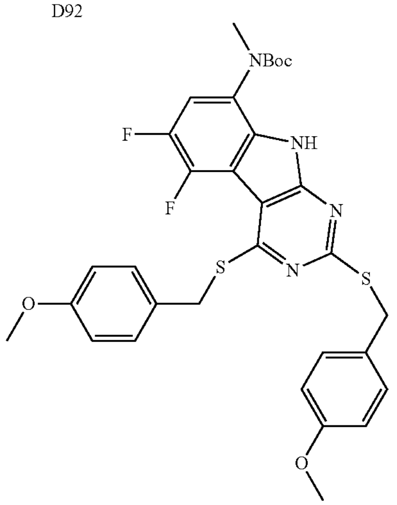

D93

Preparation of Compound D93:

To a stirred suspension of compound D92 (3.8 g, 10 mol) and $K_2CO_3$ (2.8 g, 20 mol) in 50 mL of NMP was added dropwise a solution of 1-(chloromethyl)-4-methoxybenzene (1.5 g, 9.6 mol) in 5 mL NMP at room temperature. LCMS showed the reaction was completed in 40 minutes. The reaction mixture was cooled to 0° C., BOP (4.86 g, 11 mmol) and $Et_3N$ (1.5 g, 15 mmol) were added. After 30 minutes, (4-methoxyphenyl)methanethiol (2 g, 12 mmol) was added to the reaction mixture, and was warmed to room temperature then heated to 40° C. for 1 h. The reaction mixture was diluted with ethyl acetate (200 mL) and water (500 mL), the organic layer was separated, the aqueous layer extracted by ethyl acetate (200 mL). The combined organic layer was washed with brine (100 mL×3), dried over $Na_2SO_4$, filtered, and concentrated in vacuum. The crude product was purified by chromatography (pet. ether/EtOAc, 100/1 to 20/1, v/v) to give compound D93 as a pale yellow solid (5.4 g, 84% yield). LC-MS: M+1: 639.

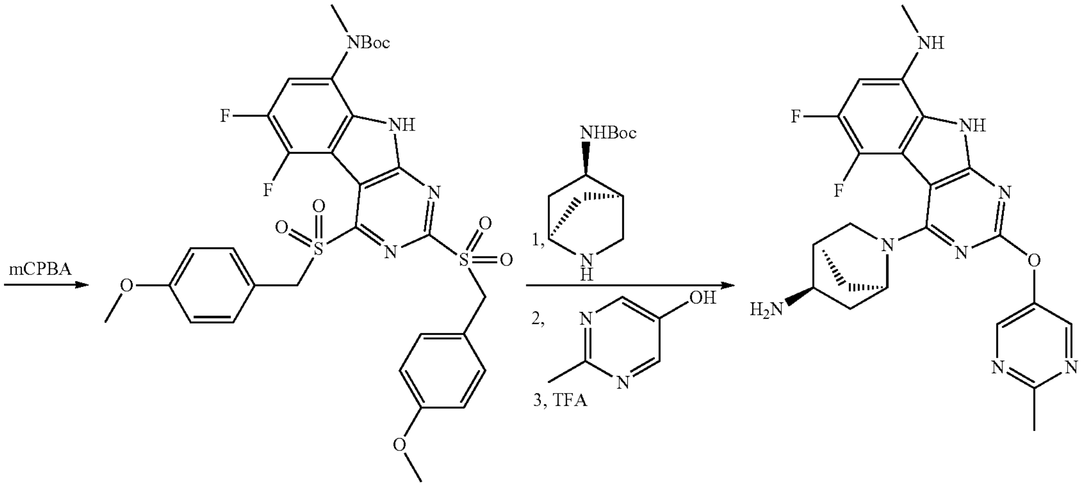

D94 D96 (5.13)

Preparation of Compound D94:

To a stirred suspension of compound D93 (2 g, 3.1 mmol) in 200 mL of $CH_2Cl_2$ at 0° C. was added MCPBA (2.8 g, 21 mmol) portion wise. The reaction mixture was stirred at room temperature for 16 h, 30 mL of saturated $Na_2S_2O_3$ was added. The reaction mixture was diluted with ethyl acetate (200 mL) and water (500 mL), the organic layer was separated, the aqueous layer extracted by ethyl acetate (100 mL). The combined organic layer was washed with 100 mL of saturated $Na_2CO_3$, brine (100 mL×3), dried over $Na_2SO_4$, filtered, and concentrated in vacuum. The crude product was purified by chromatography to give compound D94 as a yellow solid (1.4 g, 64%). LC-MS: M+1: 703.

Preparation of Compound D95:

The mixture of tert-butyl (1R,4R,5R)-2-azabicyclo[2.2.1]heptan-5-ylcarbamate (430 mg, 2 mmol), 7 (1.40 g, 2 mmol), and $K_2CO_3$ (280 mg, 2 mmol) in NMP (5 mL) was stirred for overnight at room temperature, then 2-methylpyrimidin-5-ol (330 mg, 3 mmol) was added and the resulting mixture was heated to 50° C. for overnight. The crude product was purified by HPLC to give compound D95 (the BOC protected D96) as a white solid (700 g, 54%). LC-MS: M+1: 653.

Preparation of Compound D96:

The above compound (700 mg, 1.1 mmol) was dissolved in 10 mL of TFA and stirred for 1 minute at room temperature. After removal of the solvents, the residue was redisolved into 10 ml methanol and 10 ml H2O, then 1N NaOH was added to neutralize the solution to PH 14, the basic solution then was diluted by another 100 ml H2O, and the solution was stirred vigorously for another 1 hour, collected the precipate, and dried to gave final compounds D96 as a white solid (400 mg, 80%). LC-MS: M+1: 453.20.

$^1$H NMR (300 MHz, DMSO) δ (ppm): 11.75 (s, 1H), 8.72 (s, 2H), 6.45 (dd, J=2.7, J=5.2, 1H), 5.37 (brm, 1H), 4.46 (s, 1H), 3.78 (m, 1H), 3.67 (m, 1H), 3.33 (brs, 1H), 2.83 (brs, 3H), 2.67 (s, 3H), 2.37 (brs, 1H), 2.01 (brt, 1H), 1.20 (brt, 1H).

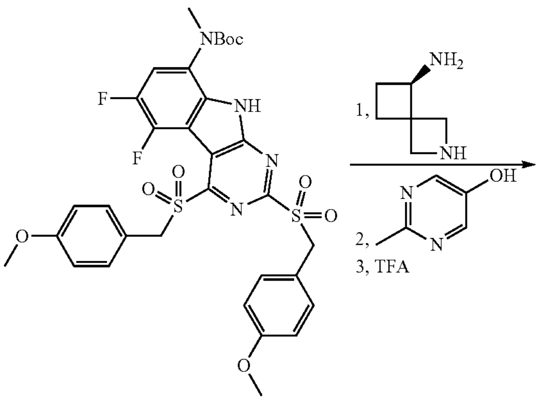

D94

-continued

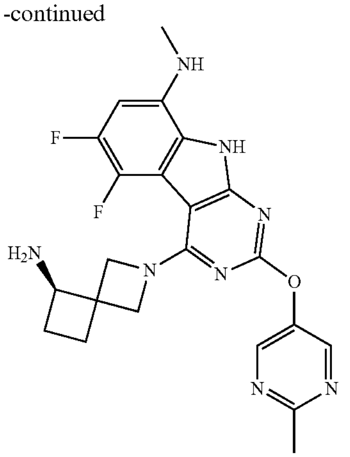

D97 (5.01)

Preparation of Compound D97:

The subtitle compound was synthesized using the same method described for the above compound starting with (R)-2-azaspiro[3.3]heptan-5-amine. LC-MS: M+1: 453.18.

$^1$H NMR (300 MHz, DMSO) δ (ppm): 11.75 (s, 1H), 8.72 (s, 2H), 6.37 (dd, J=2.7, J=5.2, 1H), 5.45 (brs, 1H), 4.63 (d, J=3, 1H), 4.12 (s, 3H), 3.20 (t, 1H), 2.83 (d, J=2, 3H), 2.67 (s, 3H), 1.75-2.01 (m, 7H), 1.39 (m, 1H).

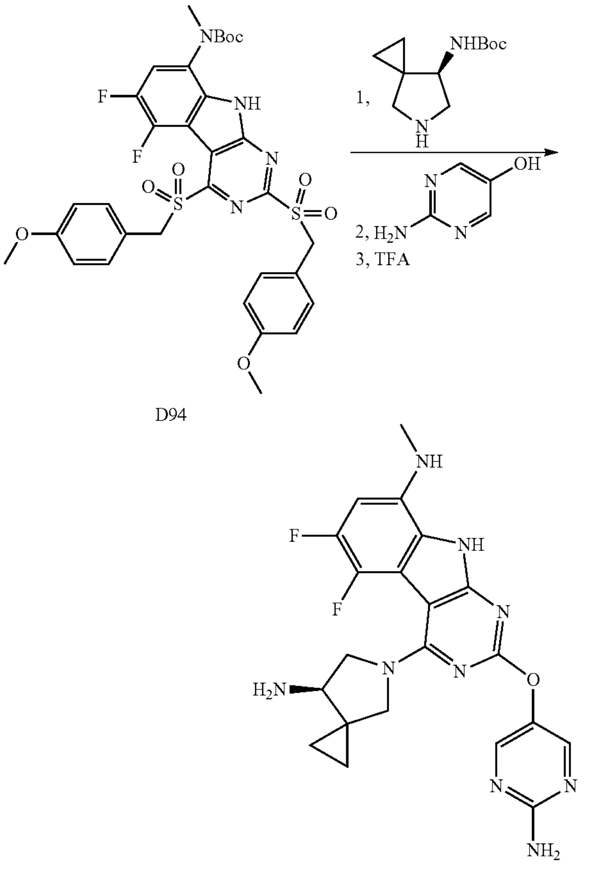

D94

D97 (5.11)

The subtitle compound D98 was synthesized using the same method described for the above compound starting with bis-sulfone, 2-aminopyrimidin-5-ol and (1R,4R,5R)-2-azabicyclo[2.2.1]heptan-5-amine (the diamine was prepared according patent procedure Eur. Pat. Appl. (1990), EP 357047 A1 19900307). LC-MS: M+1: 454.18.

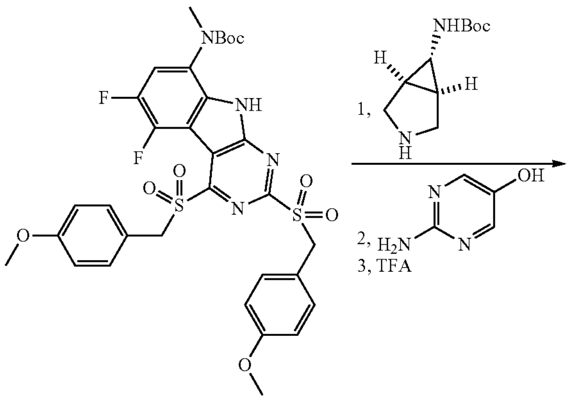

D94

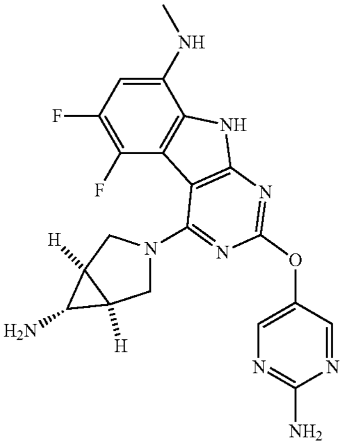

D99 (5.12)

The subtitle compound D99 was synthesized using the same method described for the above compound starting with bis-sulfone, 2-aminopyrimidin-5-ol and tert-butyl (1R, 5-azabicyclo[3.1.0]hexan-6-ylcarbamate. LC-MS: M+1: 440.15.

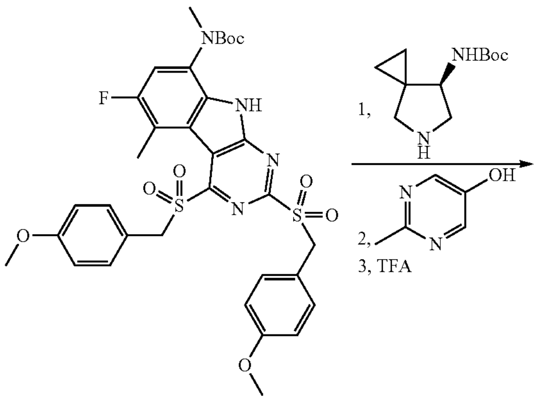

D100

-continued

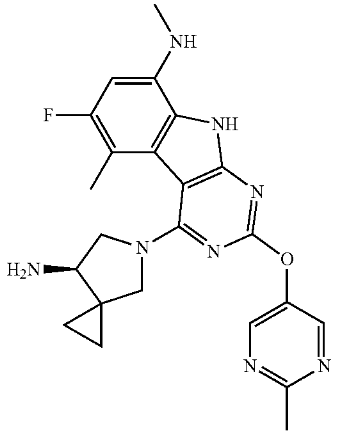

D101 (6.29)

The subtitle compound D101 was synthesized using the same method described for the above compound starting with bis-sulfone and (R)-tert-butyl 5-azaspiro[2.4]heptan-7-ylcarbamate. LC-MS: M+1: 449.24.

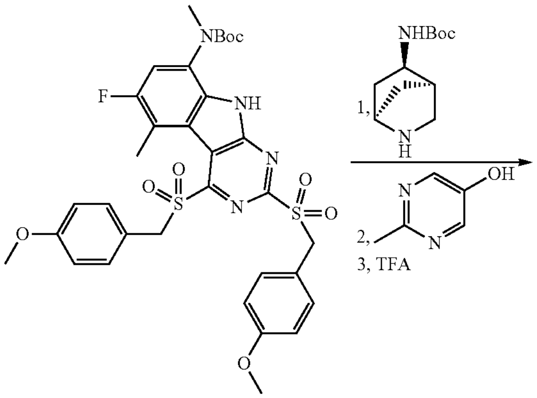

D100

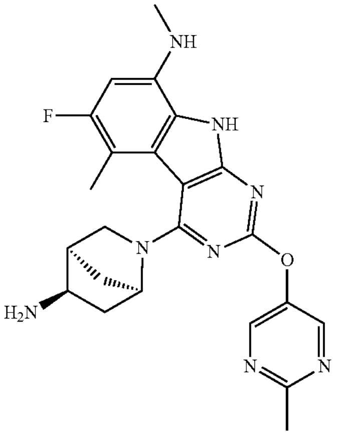

D102 (6.28)

The subtitle compound D102 was synthesized using the same method described for the above compound starting with bis-sulfone and tert-butyl (1R,4R,5R)-2-azabicyclo[2.2.1]heptan-5-ylcarbamate. LC-MS: M+1: 449.21.

Table of Formula I Compounds Where L is O, $R^x$, is CH, $R^y$ and $R^z$ are F and $R^8$ is $NHCH_3$
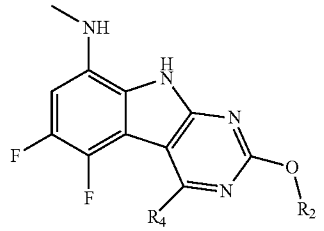
| Cmpd ID | R2 | R4 |
| --- | --- | --- |
| 5.01 | 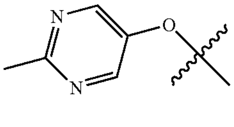 [SMILES: *Oc1cnc(C)nc1] | 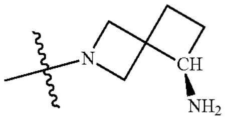 |
| 5.02 | 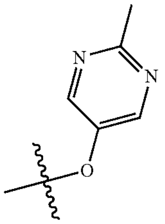 [SMILES: *Oc1cnc(C)nc1] | 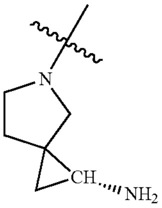 [SMILES: *N1CCC2(C[C@H]2N)C1] |
| 5.03 | 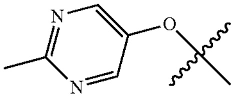 [SMILES: *Oc1cnc(C)nc1] | 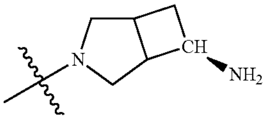 [SMILES: *N1CC2C[C@@H](N)C2C1] |
| 5.04 | 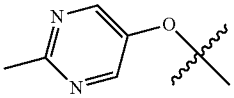 [SMILES: *Oc1cnc(C)nc1] | 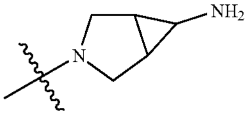 [SMILES: *N1CC2C(N)C2C1] |
| 5.05 | 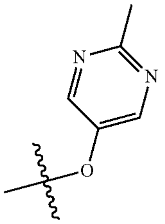 [SMILES: *Oc1cnc(C)nc1] | 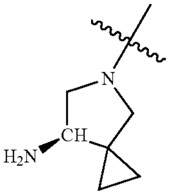 [SMILES: *N1C[C@H](N)C2(CC2)C1] |
| 5.06 | 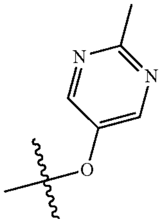 [SMILES: *Oc1cnc(C)nc1] | 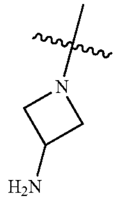 [SMILES: *N1CC(N)C1] |
| 5.07 | 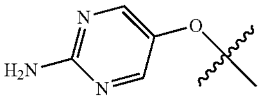 [SMILES: *Oc1cnc(N)nc1] | 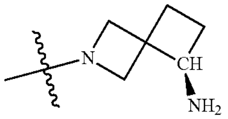 |

-continued
| Table of Formula I Compounds Where L is O, $R^x$, is CH, $R^y$ and $R^z$ are F and $R^8$ is $NHCH_3$ | | |
|---|---|---|
| 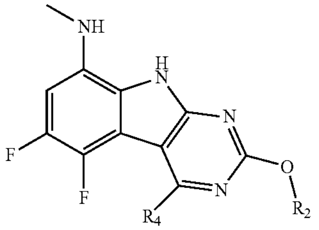 | | |
| 5.08 | 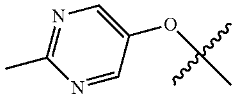 [SMILES: *Oc1cnc(C)nc1] | 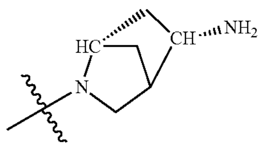 [SMILES: *N1CC2C[C@H]1C[C@@H]2N] |
| 5.09 | 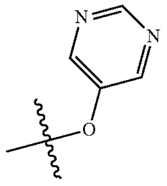 [SMILES: *Oc1cncnc1] | 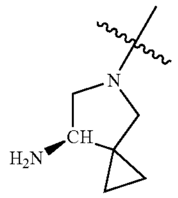 [SMILES: *N1C[C@H](N)C2(CC2)C1] |
| 5.1 | 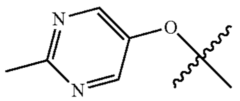 [SMILES: *Oc1cnc(C)nc1] | 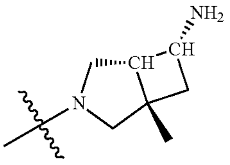 [SMILES: *N1C[C@@H]2[C@H](N)C[C@]2(C)C1] |
| 5.11 | 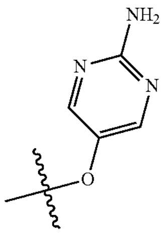 [SMILES: *Oc1cnc(N)nc1] | 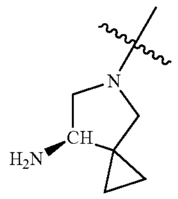 [SMILES: *N1C[C@H](N)C2(CC2)C1] |
| 5.12 | 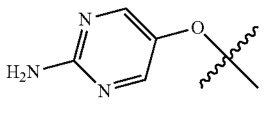 [SMILES: *Oc1cnc(N)nc1] | 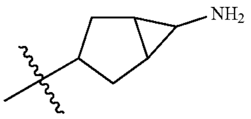 [SMILES: *C1CC2C(N)C2C1] |
| 5.13 | 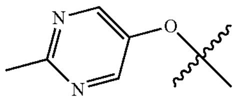 [SMILES: *Oc1cnc(C)nc1] | 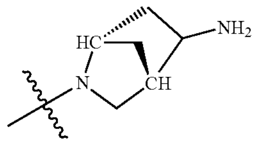 [SMILES: *N1C[C@@H]2C[C@H]1CC2N] |

-continued
Table of Formula I Compounds Where L is O, $R^x$, is CH, $R^y$ and $R^z$ are F and $R^8$ is $NHCH_3$
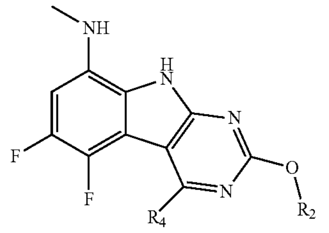
| Cmpd ID | |
|---|---|
| 5.14 | 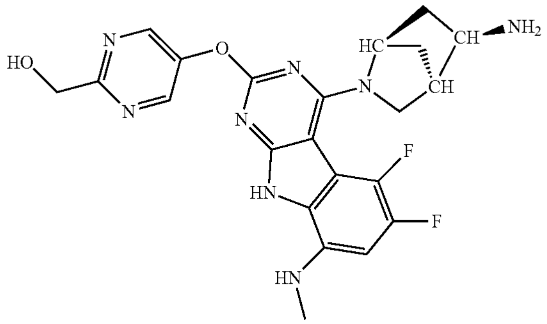 [SMILES: CNc1cc(F)c(F)c2c1[nH]c1nc(Oc3cnc(CO)nc3)nc(N3C[C@H]4C[C@@H]3C[C@H]4N)c12] |
| 5.15 | 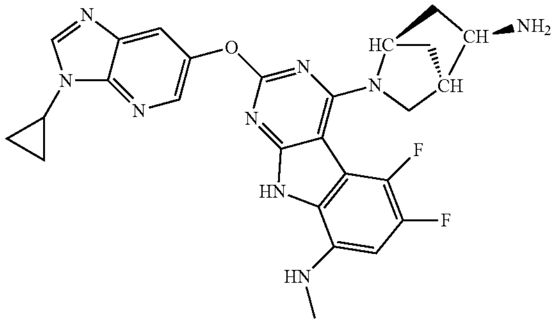 [SMILES: CNc1cc(F)c(F)c2c1[nH]c1nc(Oc3cnc4c(c3)ncn4C3CC3)nc(N3C[C@H]4C[C@@H]3C[C@H]4N)c12] |
Table of Formula I Compounds Where L is O, $R^8$ is $NHCH_3$ Alternative $R^x$ $R^y$, Rz combinations
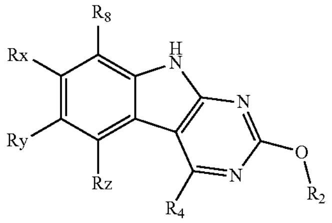
| Cmpd ID | R2 | R4 | Rz | Ry | Rx | R8 |
|---|---|---|---|---|---|---|
| 6.01 | 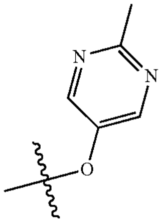 [SMILES: *Oc1cnc(C)nc1] | 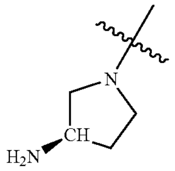 [SMILES: *N1CC[C@@H](N)C1] | H | H | F | NHMe |

-continued
Table of Formula I Compounds Where L is O, $R^8$ is $NHCH_3$ Alternative $R^x$ $R^y$, Rz combinations
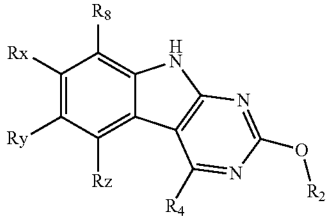
| | | | | | | |
|---|---|---|---|---|---|---|
| 6.02 | 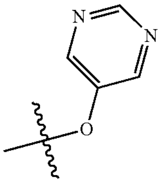 [SMILES: *Oc1cncnc1] | 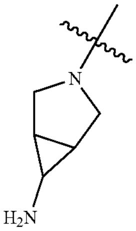 [SMILES: *N1CC2C(N)C2C1] | H | H | F | NHMe |
| 6.03 | 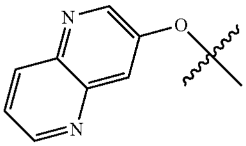 [SMILES: *Oc1cnc2cccnc2c1] | 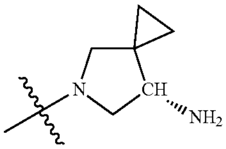 [SMILES: *N1C[C@@H](N)C2(CC2)C1] | H | H | F | NHMe |
| 6.04 | 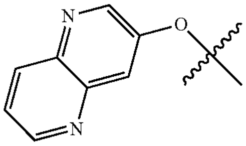 [SMILES: *Oc1cnc2cccnc2c1] | 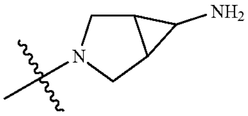 | H | H | F | NHMe |
| 6.05 | 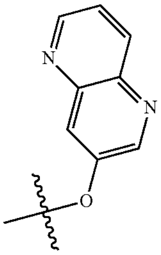 [SMILES: *Oc1cnc2cccnc2c1] | 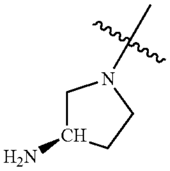 [SMILES: *N1CC[C@@H](N)C1] | H | H | F | NHMe |
| 6.06 | 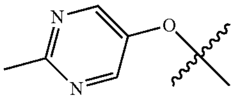 [SMILES: *Oc1cnc(C)nc1] | 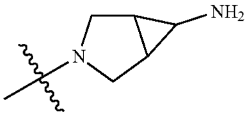 [SMILES: *N1CC2C(N)C2C1] | F | H | F | NHMe |
| 6.07 | 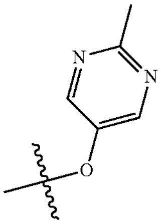 [SMILES: *Oc1cnc(C)nc1] | 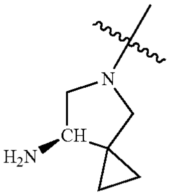 [SMILES: *N1C[C@H](N)C2(CC2)C1] | F | H | F | NHMe |

-continued
Table of Formula I Compounds Where L is O, $R^8$ is $NHCH_3$ Alternative $R^x$ $R^y$, Rz combinations
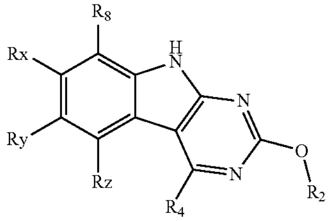
| | | | | | | |
|---|---|---|---|---|---|---|
| 6.08 | 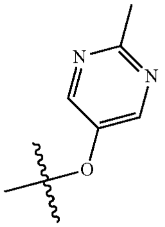 [SMILES: *Oc1cnc(C)nc1] | 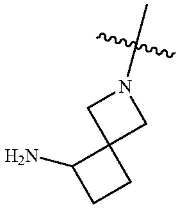 [SMILES: *N1CC2(CCC2N)C1] | F | H | F | NHMe |
| 6.09 | 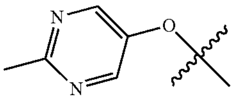 [SMILES: *Oc1cnc(C)nc1] | 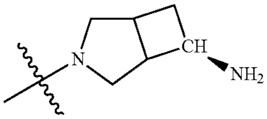 [SMILES: *N1CC2C[C@@H](N)C2C1] | F | H | F | NHMe |
| 6.10 | 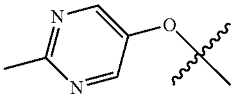 [SMILES: *Oc1cnc(C)nc1] | 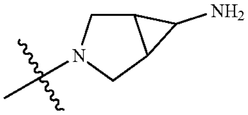 [SMILES: *N1CC2C(N)C2C1] | H | CF3 | H | NHMe |
| 6.11 | 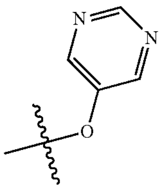 [SMILES: *Oc1cncnc1] | 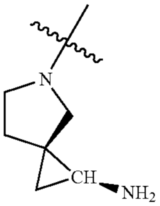 [SMILES: *N1CC[C@]2(C[C@@H]2N)C1] | H | Cl | H | NHMe |
| 6.12 | 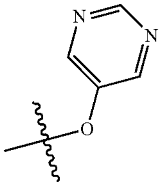 [SMILES: *Oc1cncnc1] | 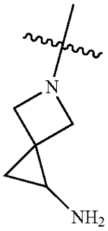 [SMILES: *N1CC2(CC2N)C1] | H | Cl | H | NHMe |
| 6.13 | 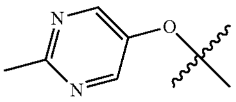 [SMILES: *Oc1cnc(C)nc1] | 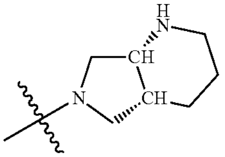 [SMILES: *N1C[C@H]2CCCN[C@H]2C1] | H | Cl | H | NHMe |
| 6.14 | 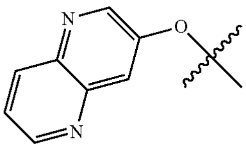 [SMILES: *Oc1cnc2cccnc2c1] | 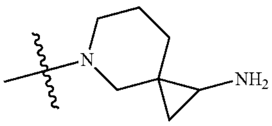 [SMILES: *N1CCCC2(CC2N)C1] | H | Cl | H | NHMe |

-continued
Table of Formula I Compounds Where L is O, $R^8$ is $NHCH_3$ Alternative $R^x$ $R^y$, Rz combinations
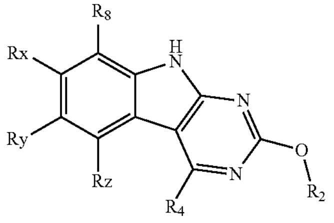
| | | | | | | |
|---|---|---|---|---|---|---|
| 6.15 | 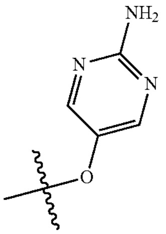 [SMILES: *Oc1cnc(N)nc1] | 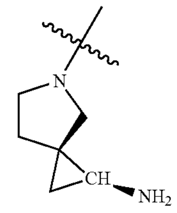 [SMILES: *N1CC[C@]2(C[C@@H]2N)C1] | H | Cl | H | NHMe |
| 6.16 | 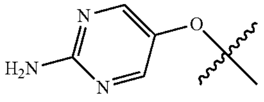 [SMILES: *Oc1cnc(N)nc1] | 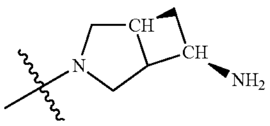 | H | Cl | H | NHMe |
| 6.17 | 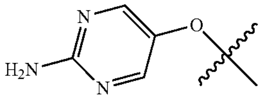 [SMILES: *Oc1cnc(N)nc1] | 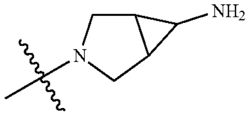 | H | Cl | H | NHMe |
| 6.18 | 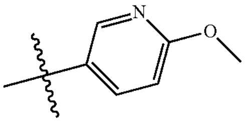 [SMILES: *c1ccc(OC)nc1] | 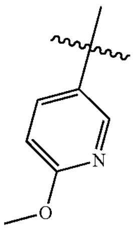 [SMILES: *c1ccc(OC)nc1] | H | F | H | NHMe |
| 6.19 | 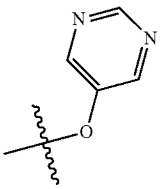 [SMILES: *Oc1cncnc1] | 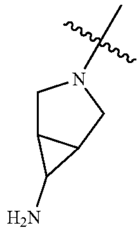 [SMILES: *N1CC2C(N)C2C1] | F | F | H | NHMe |
| 6.20 | 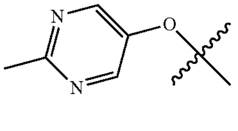 [SMILES: *Oc1cnc(C)nc1] | 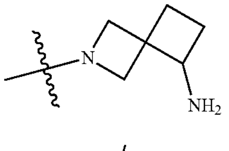 | Me | F | H | NHMe |
| 6.21 | 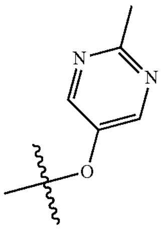 [SMILES: *Oc1cnc(C)nc1] | 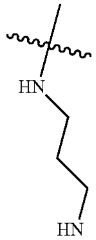 [SMILES: *NCCCN] | Me | F | H | NHMe |

-continued
Table of Formula I Compounds Where L is O, $R^8$ is $NHCH_3$ Alternative $R^x$ $R^y$, Rz combinations
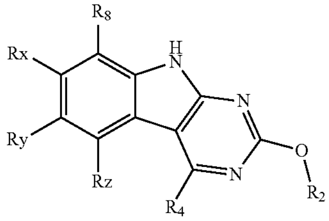
| | | | | | | |
|---|---|---|---|---|---|---|
| 6.22 | 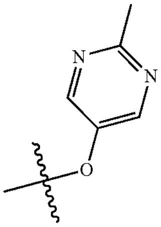 [SMILES: *Oc1cnc(C)nc1] | 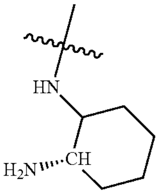 [SMILES: *NC1CCCC[C@@H]1N] | Me | F | H | NHMe |
| 6.23 | 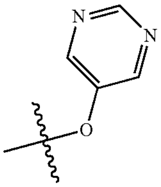 [SMILES: *Oc1cncnc1] | 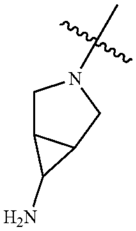 [SMILES: *N1CC2C(N)C2C1] | F | H | H | NHMe |
| 6.24 | 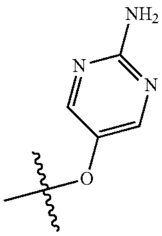 [SMILES: *Oc1cnc(N)nc1] | 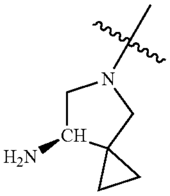 [SMILES: *N1C[C@H](N)C2(CC2)C1] | F | H | H | NHMe |
| 6.25 | 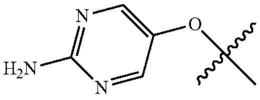 [SMILES: *Oc1cnc(N)nc1] | 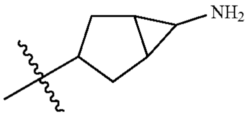 [SMILES: *C1CC2C(N)C2C1] | F | H | H | NHMe |
| 6.26 | 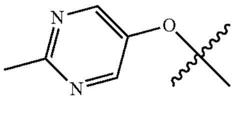 [SMILES: *Oc1cnc(C)nc1] | 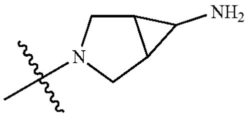 [SMILES: *N1CC2C(N)C2C1] | H | Me | H | NHMe |
| 6.27 | 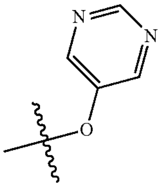 [SMILES: *Oc1cncnc1] | 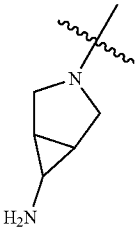 [SMILES: *N1CC2C(N)C2C1] | H | Me | H | NHMe |

-continued

Table of Formula I Compounds Where L is O, $R^8$ is $NHCH_3$ Alternative $R^x$ $R^y$, Rz combinations

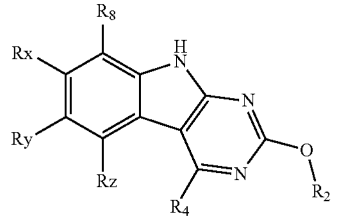

| Cmpd ID | |
|---|---|
| 6.28 | 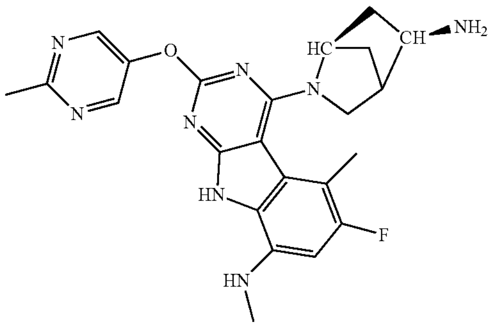 [SMILES: CNc1cc(F)c(C)c2c1[nH]c1nc(Oc3cnc(C)nc3)nc(N3CC4C[C@@H]3C[C@H]4N)c12] |
| 6.29 | 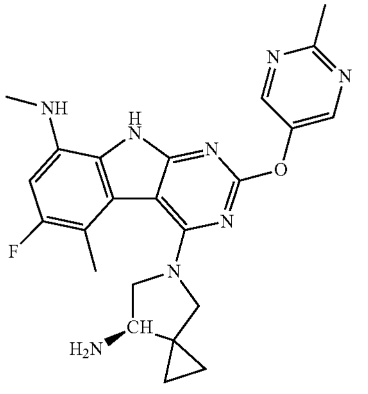 [SMILES: CNc1cc(F)c(C)c2c1[nH]c1nc(Oc3cnc(C)nc3)nc(N3C[C@H](N)C4(CC4)C3)c12] |

Synthesis of Analogs where Either X, Y or Z is N Pyrimidines

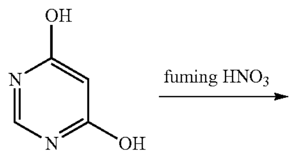

D103

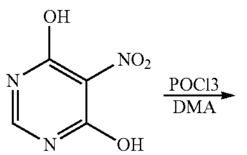

D104

-continued

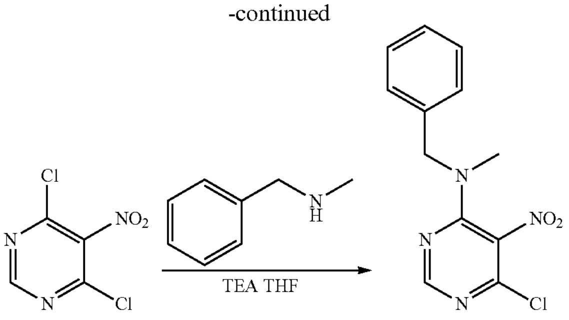

D105 D106

Preparation of Compound D104:

Compound D103 (280 g, 2.50 mol) was added to a solution of nitric acid (90%, 1120 ml) at −10° C. over 1 h and the whole was stirred at −10° C. for further 1.5 h, followed by warming to r.t. and stirred for 2 h. The mixture was poured into ice water and the yellow solid was collected by filtration, dried under reduced press to give D104 (200 g, 51% yield) as a yellow solid. LC-MS: M+1: 158

Preparation of Compound D105:

Compound D104 (200 g, 1.27 mol) was added to the mixture of $POCl_3$ (1300 ml) and DMA (255 ml) at r.t, and the whole was heated to reflux for 2-3 h and the reaction is monitored by TLC. The reaction mixture was poured into ice water, extracted with EtOAc (1 L*3), washed with sat. brine, dried ($Na_2SO_4$), and concentrated in vacuo to give crude product compound 1105 (170 g) as a black solid. It was used in next step directly without further purification. LC-MS: M+1: 194

Preparation of Compound D106:

To a mixture of compound D105 (170 g, 1.27 mol) obtained above and triethyl amine (107 g, 1.06 mol) in THF (500 ml) was added the solution of N-methyl(phenyl)methane amine (38.4 g, 316 mmol) in THF at −40° C. drop-wise, and the whole was stirred at that temperature. After the reaction was completed (monitored by TLC), the reaction mixture was diluted with $H_2O$ and extracted with EtOAc, washed with sat. NaCl, dried ($Na_2SO_4$) and concentrated in vacuo to give the crude product. It was purified by column chromatography to give the product of compound D106 (101 g, 41.4%) as an oil. LC-MS: M+1: 279.

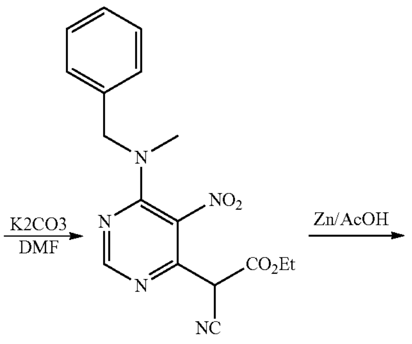

D107

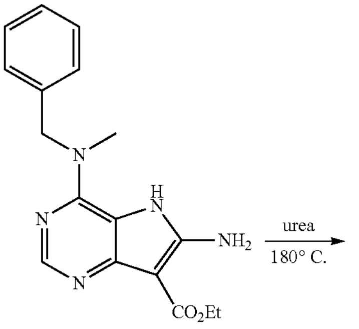

D108

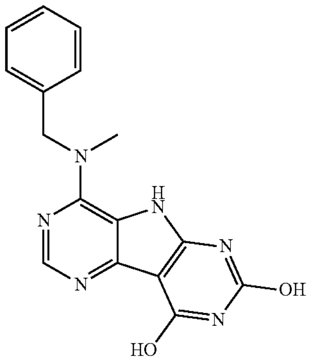

D109

Preparation of Compound D107:

To a mixture of compound D106 (5.0 g, 17.94 mmol) and $K_2CO_3$ (5.25 g, 35.89 mmol) in DMF (30 ml) was added ethyl 2-cyanoacetate (4.06 g, 35.89 mmol) at r.t., it was heated to 50° C. for 3 h and monitored by TLC. The reaction mixture was diluted with $H_2O$ and extracted with EtOAc. The organic layer was washed with sat. brine, dried ($Na_2SO_4$) and concentrated in vacuo to give the crude product. It was purified by column chromatography to give the product compound D107 (2.67 g, 42% yield) as a yellow solid. LC-MS: M+1: 356

Preparation of Compound D108:

To a mixture of compound D107 (39 g, 110 mmol) in acetic acid (300 ml) was added Zn (56 g, 858 mmol) at 80° C. over 0.5 h, and the whole was heated to 90° C. for further 3 h and the reaction was monitored by TLC. After the reaction was completed the mixture was cooled to r.t. and filtered to remove inorganic salts. The filtrate was concentrated in vacuo, and the residue was diluted with $H_2O$ and basified with $NaHCO_3$ to PH 7-8. Then it was extracted with EtOAc. The organic layer was washed with sat. brine, dried ($Na_2SO_4$), and concentrated in vacuo to give the product compound D108 (35 g, 98.0% yield) as a white solid. It was used in next step directly. LC-MS: M+1: 326.

Preparation of Compound D109:

The mixture of compound D108 (10.00 g, 30.73 mmol) and urea (50.0 g) was heated to 180° C. overnight, TLC and LCMS showed the reaction was completed. It was diluted with DMSO and heated to 180° C. for 10 min. After it was cooled to r,t, the insoluble material was filtered off and the filtrate was poured into $H_2O$. The solid precipitated put was collected by filtration. The solid was treated with $H_2O$, and the suspension was heated to reflux. It was filtered while hot. The collected solid was washed with hot water for 4 more times. Then it was washed with hot MeOH and EtOAc, dried in vacuo to give the pure enough product compound D109 (6.20 g, 62% yield) as a white sold. LC-MS: M+1: 323.

$^1$H-NMR (300 MHz, DMSO-d6) δ (ppm): 8.23 (1H, s), 7.25-7.36 (5H, m), 3.37 (2H, s), 2.51 (3H, s).

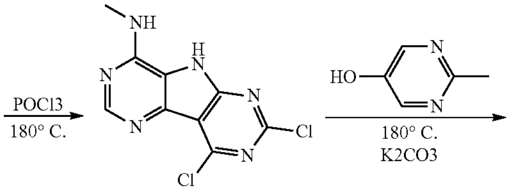

D110

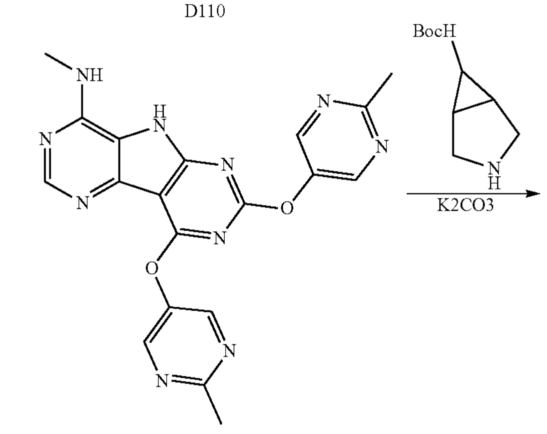

D111

-continued

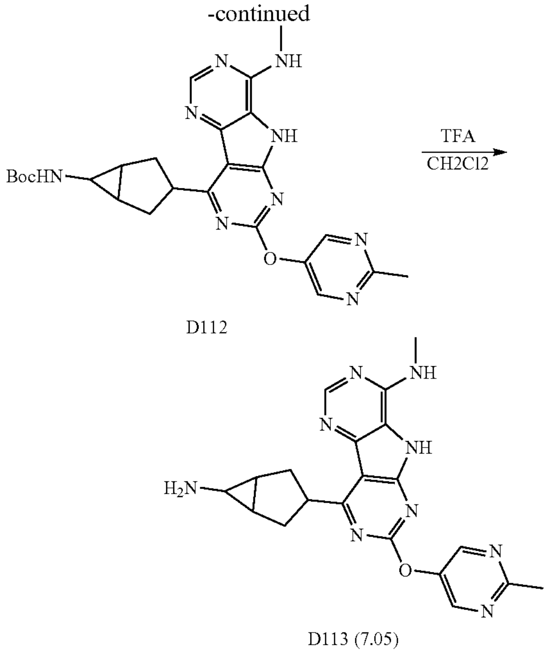

D112

D113 (7.05)

Pyridines

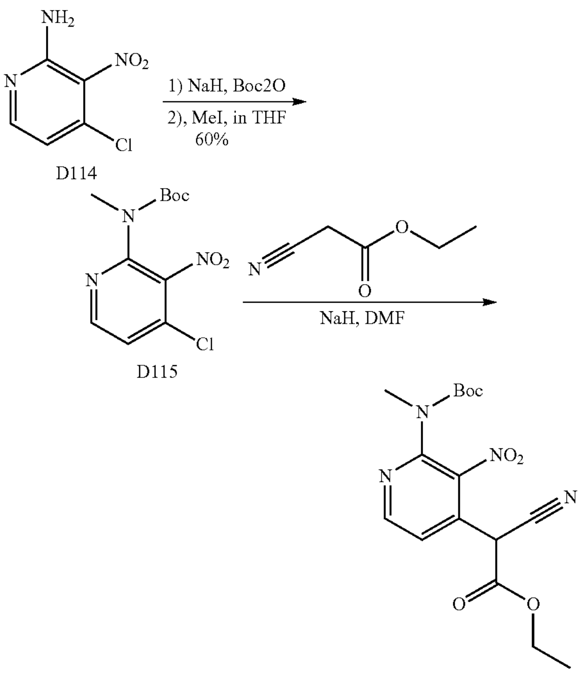

D114

D115

D116

Preparation of Compound D110:

Compound D109 (1.5 g, 4.64 mmol) was placed with a solution of $POCl_3$ (50 ml) in a pressure tube and few drops of N-ethyldiisopropyl amine. The reaction mixture was heated to at 185° C. under sealed condition over 10 h. The mixture was cooled and poured into ice water and the yellow solid was collected by filtration, dried under reduced press to give D110 (1.2 g, 98% yield) as a yellow solid. LC-MS: M+1: 270.

Preparation of Compound D111:

Compound D110 (100 mg, 0.37 mmol) was added to a solution of 2-methylpymiridin-5-ol (120 mg, 1.1 mmol) and $K_2CO_3$ (15 mg, 1.0 mmol) in NMP (4 mL) in a microwave tube. The reaction mixture was sealed and placed in Microwave at 150° C. for 10 minutes. The desired product was obtained by HPLC purification to give D111 (100 mg, 75%) as a white solid. LC-MS: M+1: 417.

Preparation of Compound D112:

To a stirred solution of compound D111 (50 mg, 0.12 mmol) in 2 mL of NMP at 110° C. was added tert-butyl 3-azabicyclo[3.1.0]hexan-6-ylcarbamate (27 mg, 0.1 mmol) and $K_2CO_3$ (2 mg, 0.05 mmol). After the completion of the reaction in 10 minutes, the reaction mixture was purified by HPLC to give the product D112 (38 mg, 63%) as a white solid. LC-MS: M+1: 505.

Preparation of Compound D113:

To a stirred solution of compound D112 (38 mg, 0.07 mmol) in 5 mL of acetonitrile at room temperature was added 2 mL of TFA. After the completion of the reaction in 20 minutes. The reaction mixture was concentrated and purified by HPLC to give the product D113 (28 mg, 95%) as a white solid. LC-MS: M+1: 405.

$^1$H-NMR (300 MHz, DMSO-d6) δ (ppm): 8.23 (1H, s), 7.26 (2H, s), 2.51 (3H, s), 2.55 (3H, s), 2.88 (2H, m), 2.63 (2H, m), 1.22 (1H, m), 0.66 (2H, m).

4-chloro-3-nitropyridin-2-amine (1.73 g, 10 mmol) in 10 ml THF was portionly added into sodium hydride (2 g, 50 mmol, 60% in oil) solution in dry THF (200 ml) under the ice water bath, then the solution was stirred for another 1 hours, then Boc2O (2.4 g, 11 mol) in 10 ml THF was added dropwisely into the solution, the solution was stirred for 4 hours at room temperature, then MeI (2.8 g, 20 mol) in 10 ml THF was added dropwisely into the solution, the mixture was stirred for overnight (12 hours), and quenched with ice water. The aqueous solution was extracted with 3×100 ml ethyl acetate, the combined organic solution was dried and concentrated. The residue was purified by flash chromatography to give 2.1 g desired products D115 with 73% yield.

To the mixture of NaH (0.8 g, 20 mmol, 60% in oil) and ethyl 2-cyanoacetate (2.2 g, 20 mmol) in dry DMF (100 ml) at room temperature was added tert-butyl (4-chloro-3-nitropyridin-2-yl)(methyl)carbamate (2 g, 7 mmol), the mixture was stirred for overnight at 100° C. for 12 hours, then the reaction mixture was carefully quenched by water, then the solution was partitioned by water and ethyl acetate (100 ml+100 ml), then organic layer was dried and concentrated. The residue was purified by flash chromatography to give 2.4 g desired products D116 with 66% yield. LC-MS: M+1: 365.15.

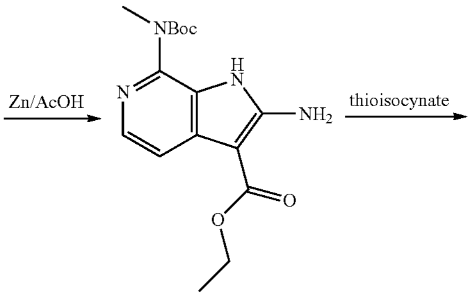

D117

-continued

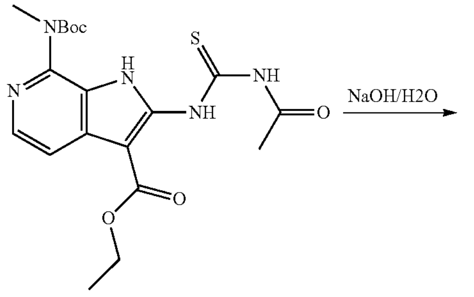

D118

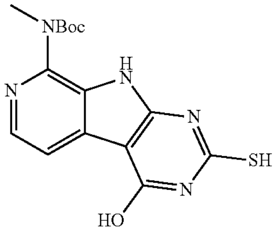

D119

To a stirred suspension of compound ethyl 2-amino-7-((tert-butoxycarbonyl)(methyl)amino)-1H-pyrrolo[2,3-c] pyridine-3-carboxylate (500 mg, 1.5 mmol) in acetone (20 mL) was added dropwise a solution of acetyl isothiocyanate (0.24 mL, 3 mmol) in acetone (5 mL) at room temperature. The reaction mixture was heated to reflux for 16 h. LCMS showed the reaction was completed. The reaction mixture was concentrated for next step without purification.

Above residue was dissolved into 20 ml methanol and 20 ml H2O, and then added 5 ml 10% KOH solution, the mixture solution was heated to reflux for 30 minutes. When LCMS showed the reaction was completed the reaction was cooled to room temperature, acidified to pH 5 with 1M aq. HCl, and the precipitate collected by filtration to give desired compound tert-butyl (4-hydroxy-2-mercapto-9H-pyrido[4',3': 4,5]pyrrolo[2,3-d]pyrimidin-8-yl)(methyl)carbamate D119 as a solid (340 mg, 65.4% in two steps). LC-MS: M+1: 348.

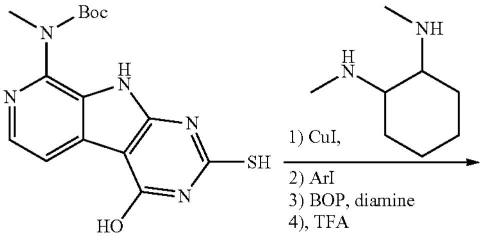

-continued

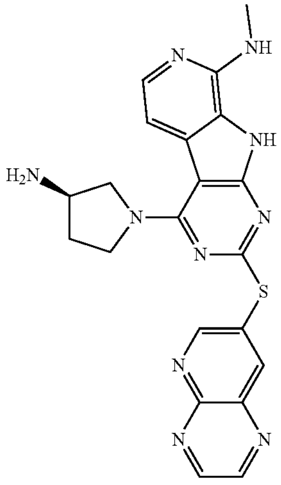

D121 (7.01)

The solution of CuI (67 mg, 0.35 mmol), N,N'-dimethylcyclohexane-1,2-diamine (100 mg, 0.70 mmol) in 9 mL of NMP was added to a stirring suspension tert-butyl (4-hydroxy-2-mercapto-9H-pyrido[4',3': 4,5]pyrrolo[2,3-d]pyrimidin-8-yl)(methyl)carbamate (350 mg, 1.0 mmol), a proper I—Ar (1.17 mmol), $K_2C0_3$ (324 mg, 2.35 mmol) and $PPh_3$ (400 mg, 1.53 mmol) in NMP (9 mL). The mixture was heated to 130° C. for 2 to 12 hrs monitored by LC-MS for the completion of the reaction. When the reaction completed, the mixture was cooled to 0° C., BOP (621 mg, 1.40 mmol) and $Et_3N$ (0.41 mL, 2.93 mmol) was added, stirred for 30 minutes at 0° C., then warmed up to room temperature, a suitable Boc-protected diamine (2.34 mmol) was added. The reaction mixture was heated to 50° C. for 30 minutes. LC-MS indicated the completed reaction. After completed the reaction, the mixture was partitioned with ethyl acetate and water, the aqueous layer was extracted by ethyl acetate twice, the combined organic layer was dried and purified by flash chromatography to give products compound D120 as a solid (420 mg, 65% in two steps). LC-MS: M+1: 644.

The above compound (420 mg, 0.64 mmol) was dissolved in 10 mL of TFA and stirred for 30 minute at room temperature. After removal of the solvents, the residue was re-dissolved into 10 ml methanol and 10 ml H2O, then 1N NaOH was added to neutralize the solution to PH 14, the basic solution then was diluted by another 100 ml H2O, and the solution was stirred vigorously for another 1 hour, collected the precipitate, and dried to gave final compound D121 as a white solid (200 mg, 70%). LC-MS: M+1: 444.

Table of Formula I Compounds Where L is O, where one or more $R^x$, $R^y$, $R^z$ is N and $R^8$ is $NHCH_3$
| Cmpd ID | Structure |
|---|---|
| 7.01 | 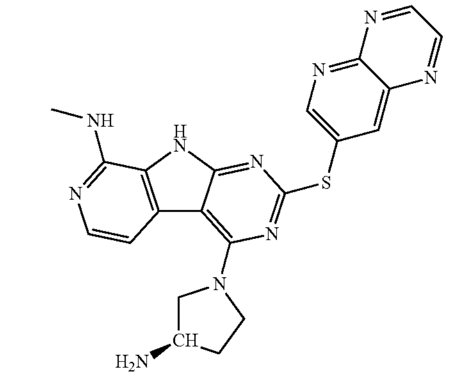 [SMILES: CNc1nccc2c1[nH]c1nc(Sc3cnc4nccnc4c3)nc(N3CC[C@@H](N)C3)c12] |
| 7.02 | 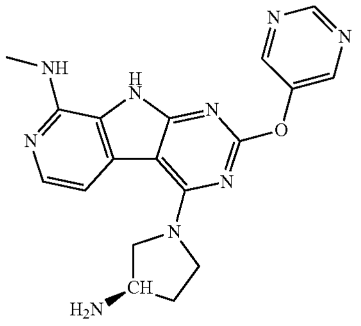 [SMILES: CNc1nccc2c1[nH]c1nc(Oc3cncnc3)nc(N3CC[C@@H](N)C3)c12] |
| 7.03 | 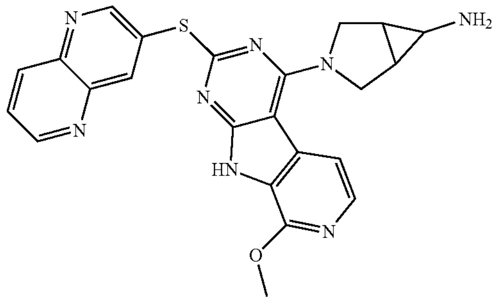 [SMILES: COc1nccc2c1[nH]c1nc(Sc3cnc4cccnc4c3)nc(N3CC4C(N)C4C3)c12] |
| 7.04 | 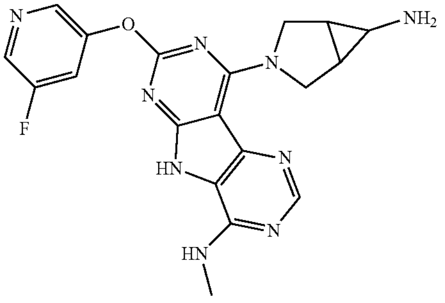 [SMILES: CNc1ncnc2c1[nH]c1nc(Oc3cncc(F)c3)nc(N3CC4C(N)C4C3)c12] |
-continued
Table of Formula I Compounds Where L is O, where one or more $R^x$, $R^y$, $R^z$ is N and $R^8$ is $NHCH_3$
| Cmpd ID | Structure |
|---|---|
| 7.05 | 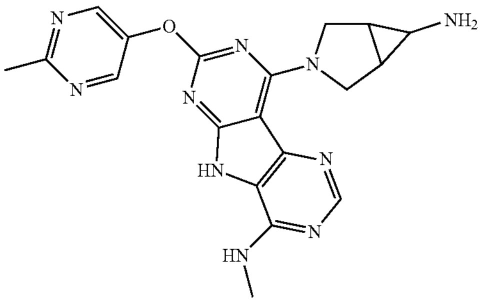 [SMILES: CNc1ncnc2c1[nH]c1nc(Oc3cnc(C)nc3)nc(N3CC4C(N)C4C3)c12] |
| 7.06 | 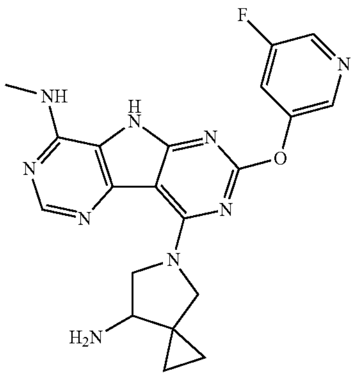 [SMILES: CNc1ncnc2c1[nH]c1nc(Oc3cncc(F)c3)nc(N3CC(N)C4(CC4)C3)c12] |
| 7.07 | 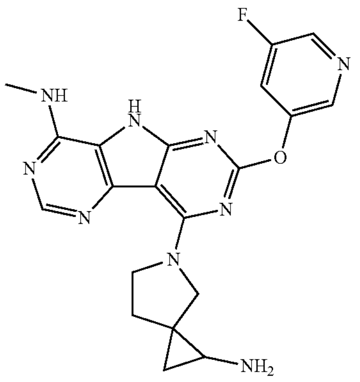 [SMILES: CNc1ncnc2c1[nH]c1nc(Oc3cncc(F)c3)nc(N3CCC4(CC4N)C3)c12] |
| 7.08 | 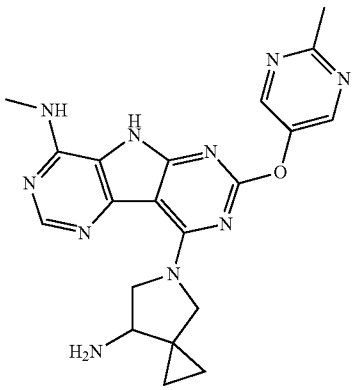 [SMILES: CNc1ncnc2c1[nH]c1nc(Oc3cnc(C)nc3)nc(N3CC(N)C4(CC4)C3)c12] |

-continued

Table of Formula I Compounds Where L is O, where one or more $R^x$, $R^y$, $R^z$ is N and $R^8$ is $NHCH_3$

| Cmpd ID | Structure |
|---|---|
| 7.09 | 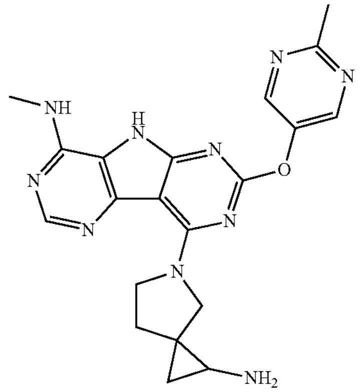 [SMILES: CNc1ncnc2c1[nH]c1nc(Oc3cnc(C)nc3)nc(N3CCC4(CC4N)C3)c12] |
| 7.10 | 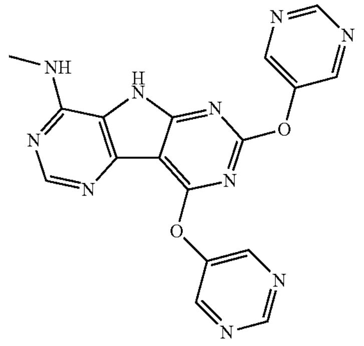 [SMILES: CNc1ncnc2c1[nH]c1nc(Oc3cncnc3)nc(Oc3cncnc3)c12] |
| 7.11 | 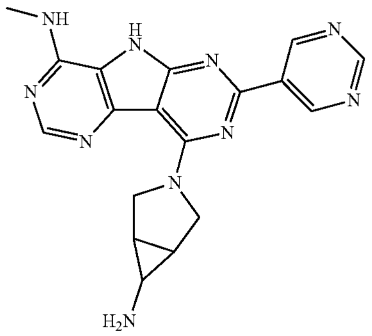 [SMILES: CNc1ncnc2c1[nH]c1nc(-c3cncnc3)nc(N3CC4C(N)C4C3)c12] |
| 7.12 | 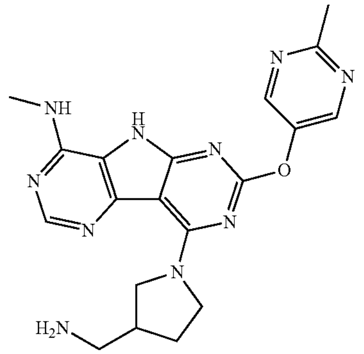 [SMILES: CNc1ncnc2c1[nH]c1nc(Oc3cnc(C)nc3)nc(N3CCC(CN)C3)c12] |

Bis Aryloxys

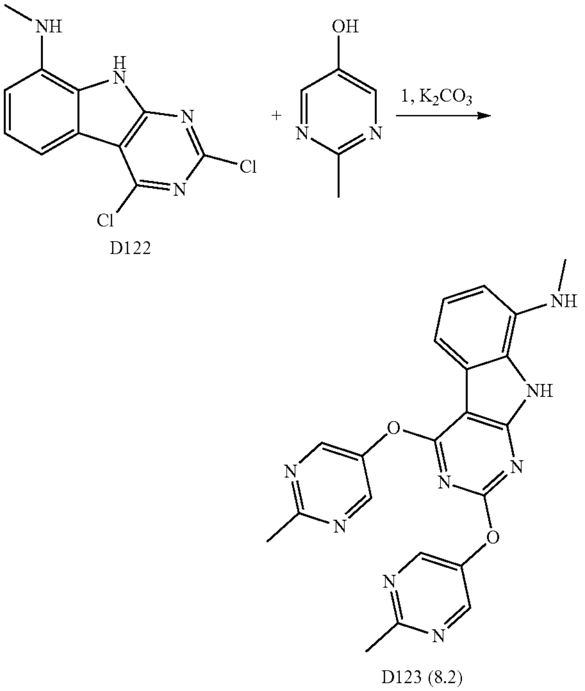

N-methyl-2,4-bis(2-methylpyrimidin-5-yloxy)-9H-pyrimido[4,5-b]indol-8-amine

To the solution of compound (D122)(100 mg, 0.37 mmol) in NMP (5 ml) was added 2-methylpyrimidine-5-ol (100 mg, 0.9 mmol) and potassium carbonate (43.6 mg, 0.31 mmol). It was then heated at 180° C. under microwave condition for 15 minutes. The mixture was then purified through HPLC to afford the title compound D123 as yellow solid (80 mg, 52%). LC-MS: M+1: 415.15.

$^1H$ NMR (300 MHz, DMSO) δ (ppm): 14.01 (S, 1H), 11.71 (s, 1H), 8.98 (s, 2H), 8.78 (s, 2H), 7.84 (d, J=7.5, 1H), 7.47 (m, 1H), 6.90 (d, J=9.7, 1H), 4.18 (s, 1H), 3.10 (s, 3H), 2.65 (s, 3H), 2.64 (s, 3H).

Table of Formula I Compounds Where $R^4$ is OR

| Cmpd ID | Structure |
|---|---|
| 8.1 | 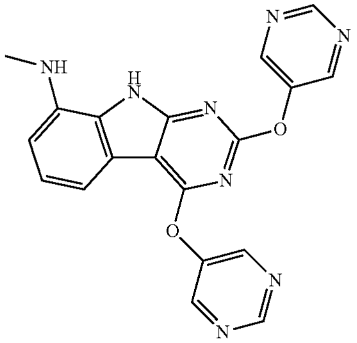 [SMILES: CNc1cccc2c1[nH]c1nc(Oc3cncnc3)nc(Oc3cncnc3)c12] |

-continued
Table of Formula I Compounds Where $R^4$ is OR
| Cmpd ID | Structure |
|---|---|
| 8.2 | 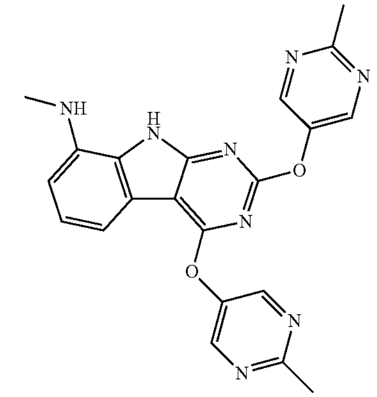 [SMILES: CNc1cccc2c1[nH]c1nc(Oc3cnc(C)nc3)nc(Oc3cnc(C)nc3)c12] |
| 8.3 | 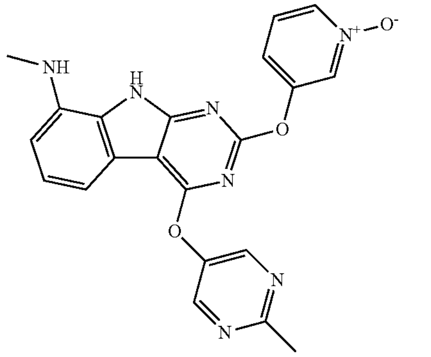 [SMILES: CNc1cccc2c1[nH]c1nc(Oc3ccc[n+]([O-])c3)nc(Oc3cnc(C)nc3)c12] |
| 8.4 | 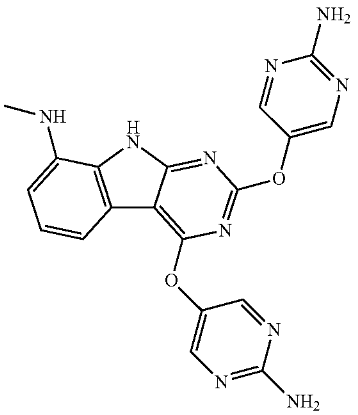 [SMILES: CNc1cccc2c1[nH]c1nc(Oc3cnc(N)nc3)nc(Oc3cnc(N)nc3)c12] |
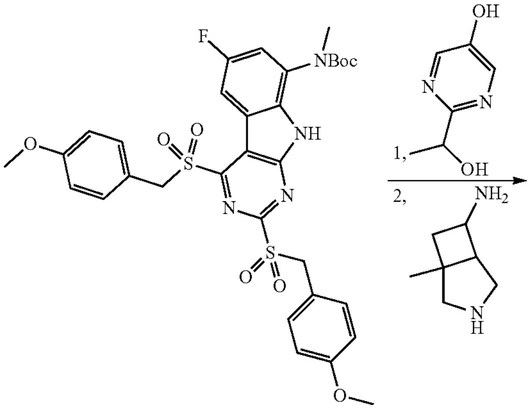
D16
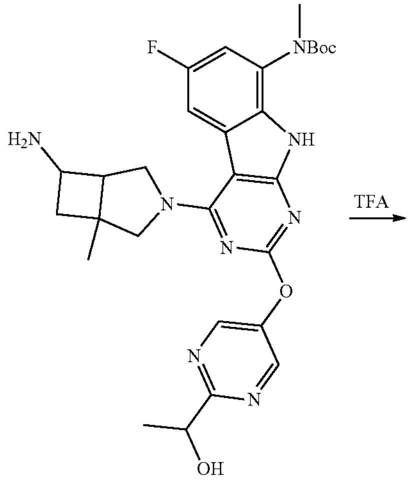
D124
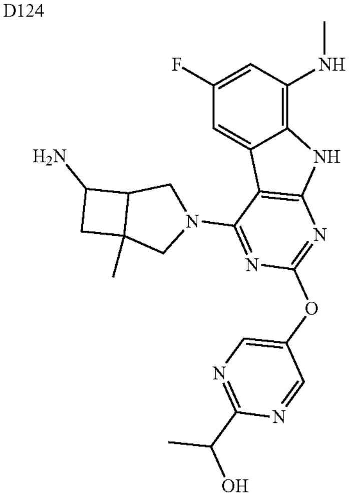
D125 (4.451)
The subtitle compound D125 was synthesized using the same method described for the above compound starting with bis-sulfone, 2-(1-hydroxyethyl)pyrimidin-5-ol and 1-methyl-3-azabicyclo[3.2.0]heptan-6-amine (the diamine was prepared in accordance with the procedure described in PCT Int. Appl. (1994), WO 9415933 A1 19940721). LC-MS: M+1: 479.25.

Determination of Anti-Bacterial Efficacy

Colonies of *H. influenzae, E. coli, S. aureus, A. baumannii, S. pneumoniae, P. aeruginosa*, and *B. thailandensis* were picked from overnight plates and resuspended in 3 mL DPBS solution. Absorbance was read at 600 nM and suspensions were diluted to an OD of 0.1.

Inocula were added to appropriate growth medium, and 98 μL of the mixture were plated into columns 1-11 of a 96 well flat-bottomed cell-culture plate. Column 12 was plated with medium only.

| | | Resuspended Cells | Medium | Incubation |
|---|---|---|---|---|
| *S. aureus* | ATCC 13709 | 50 uL | 20 mL Mueller Hinton cationic adjusted | Ambient 18 h |
| SA + serum | ATCC 13709 | 50 uL | 16 mL MHCA + 4 mL mouse serum | Ambient 18 h |
| *S. pneumoniae* | ATCC 51916 | 100 uL | 20 mL MHCA + 3% Laked Horse Blood | 5% $CO_2$ 18 h |
| *E. coli* | ATCC 25922 | 100 uL | 20 mL MHCA | Ambient 18 h |
| EC + serum | ATCC 25922 | 100 uL | 16 mL MHCA + 4 mL mouse serum | Ambient 18 h |
| *E. coli* | MX1313 | 100 uL | 20 mL MHCA | Ambient 18 h |
| *E. coli* imp | Benson BAS849 | 100 uL | 20 mL MHCA | Ambient 18 h |
| *E. coli* Δtolc | BW25113 Δtolc | 100 uL | 20 mL MHCA | Ambient 18 h |
| *P. aeruginosa* | ATCC 15692 | 100 uL | 20 mL MHCA | Ambient 18 h |
| *A. baumannii* | ATCC 19606 | 100 uL | 20 mL MHCA | Ambient 18 h |
| *A. baumannii* | MX2585 | 100 uL | 20 mL MHCA | Ambient 18 h |
| *K. pneumoniae* | ATCC 700603 | 100 uL | 20 mL MHCA | Ambient 18 h |
| *S. enteritidis* | ATCC 53000 | 100 uL | 20 mL MHCA | Ambient 18 h |
| *S. typhi* | ATCC 33459 | 100 uL | 20 mL MHCA | Ambient 18 h |
| *S. typhimurium* | ATCC 14028 | 100 uL | 20 mL MHCA | Ambient 18 h |
| *S. dysenteriae* | ATCC 13313 | 100 uL | 20 mL MHCA | Ambient 18 h |
| *Y. pestis* | CO92 pgm- | 100 uL | 20 mL MHCA | Ambient 42 h |
| *B. thailandensis* | ATCC E264 | 100 uL | 20 mL MHCA | Ambient 18 h |
| *C. jejuni* | ATCC 33560 | 100 uL | 20 mL MHCA | GasPak EZ Campy Container System 42 h |
| *F. tularensis* | *holarctica* LVS | 100 uL | 20 mL MHCA with Isovitalex | Ambient 42 h |
| *F. tularensis* | *novicida* Utah 112 | 100 uL | 20 mL MHCA with Isovitalex | Ambient 42 h |

2 μL of compound dilution series in 100% DMSO were added to columns 1-10. Plates were agitated in a plate-shaker for 1 min.

Mixtures of cells and media were diluted 1000× in DPBS and 100 μL, were plated onto appropriate media and incubated overnight in order to count CFUs.

Plates were incubated overnight at 35° C. *H. influenzae* and *S. pneumoniae* plates were incubated with 5% $CO_2$.

10 μL of Alamar Blue (Invitrogen) were added to plates, and plates were agitated for 1 min in a plate-shaker. Plates were incubated at 35° C. for 1 h. Plates were read visually, with any change in color from blue read as alive.

TABLE 9

MIC data for Compounds in Tables 1-8 (Concentration in μg/mL)

| Cmpd ID | Sa | Ec |
|---|---|---|
| 1.01 | 4 | 64 |
| 1.02 | 32 | >64 |
| 1.03 | 32 | >64 |
| 1.04 | 32 | 64 |
| 1.05 | >64 | >64 |
| 1.06 | 32 | >64 |
| 1.07 | 4 | >32 |
| 1.08 | 64 | >64 |
| 1.09 | 64 | >64 |
| 1.10 | ≤0.5 | 4 |
| 1.11 | ≤0.5 | 8 |

TABLE 9-continued

MIC data for Compounds in Tables 1-8 (Concentration in μg/mL)

| Cmpd ID | Sa | Ec |
|---|---|---|
| 1.12 | ≤0.5 | 1 |
| 1.13 | ≤0.5 | ≤0.5 |
| 1.14 | ≤0.5 | 1 |
| 1.15 | 1 | 2 |
| 1.16 | ≤0.5 | 1 |

TABLE 9-continued

MIC data for Compounds in Tables 1-8 (Concentration in μg/mL)

| Cmpd ID | Sa | Ec |
|---|---|---|
| 1.17 | ≤0.5 | >64 |
| 1.18 | ≤0.5 | 2 |
| 1.19 | >64 | >64 |
| 1.20 | 4 | 16 |
| 1.21 | ≤0.5 | >64 |
| 1.22 | 1 | 8 |
| 1.23 | ≤0.5 | ≤0.5 |
| 1.24 | ≤0.5 | 1 |
| 1.25 | ≤0.5 | 4 |
| 1.26 | ≤0.5 | 1 |
| 1.27 | ≤0.5 | 1 |
| 1.28 | 4 | 16 |
| 1.29 | 1 | >64 |
| 1.30 | 16 | >64 |
| 1.31 | ≤0.5 | ≤0.5 |
| 1.32 | ≤0.5 | 4 |
| 1.33 | ≤0.5 | 4 |
| 1.34 | 1 | 4 |
| 1.35 | ≤0.5 | 2 |
| 1.36 | 2 | 4 |
| 1.37 | 1 | 4 |
| 1.38 | ≤0.5 | 2 |
| 1.39 | ≤0.5 | 1 |
| 1.40 | ≤0.5 | 1 |
| 1.41 | 4 | 8 |
| 1.42 | 8 | 32 |
| 1.43 | 2 | 8 |

TABLE 9-continued

| MIC data for Compounds in Tables 1-8 (Concentration in μg/mL) | | |
|---|---|---|
| Cmpd ID | Sa | Ec |
| 1.44 | 1 | 2 |
| 1.45 | 1 | 4 |
| 1.46 | 2 | 4 |
| 1.47 | ≤0.5 | 2 |
| 1.48 | ≤0.5 | 2 |
| 1.49 | ≤0.5 | ≤0.5 |
| 1.50 | ≤0.5 | ≤0.5 |
| 1.51 | ≤0.5 | ≤0.5 |
| 1.52 | 1 | 16 |
| 1.53 | ≤0.5 | 8 |
| 1.54 | ≤0.5 | >64 |
| 1.55 | 1 | 8 |
| 1.56 | 4 | 32 |
| 1.57 | >32 | >32 |
| 1.58 | ≤0.5 | 8 |
| 1.59 | 1 | 4 |
| 1.60 | 0.5 | 2 |
| 1.61 | 8 | 64 |
| 1.62 | ≤0.5 | ≤0.5 |
| 1.63 | ≤0.5 | ≤0.5 |
| 1.64 | ≤0.5 | ≤0.5 |
| 1.65 | ≤0.5 | ≤0.5 |
| 1.66 | <0.13 | ≤0.5 |
| 1.67 | ≤0.5 | >64 |
| 1.68 | 16 | 32 |
| 1.69 | ≤0.5 | 8 |
| 1.70 | 1 | >32 |
| 1.71 | ≤0.5 | ≤0.5 |
| 1.72 | ≤0.5 | 1 |
| 1.73 | ≤0.5 | 8 |
| 1.74 | 4 | >64 |
| 1.75 | ≤0.5 | >64 |
| 1.76 | 1 | >64 |
| 1.77 | 2 | >64 |
| 1.78 | ≤0.5 | 64 |
| 2.01 | ≤0.5 | >16 |
| 2.02 | 2 | 4 |
| 2.03 | 1 | 16 |
| 2.04 | ≤0.5 | 1 |
| 20.5 | ≤0.5 | 2 |
| 2.06 | 1 | 16 |
| 2.07 | 4 | >16 |
| 2.08 | 16 | >64 |
| 2.09 | 16 | 16 |
| 2.10 | 2 | 32 |
| 2.11 | 4 | >64 |
| 2.12 | 16 | >64 |
| 2.13 | 2 | 64 |
| 2.14 | 1 | >64 |
| 2.15 | 1 | >32 |
| 2.16 | 8 | 16 |
| 3.01 | 1 | 4 |
| 3.02 | 4 | 16 |
| 3.03 | 0.5 | 1 |
| 3.04 | 0.5 | ≤0.5 |
| 3.05 | 0.25 | ≤0.5 |
| 3.06 | 0.5 | 1 |
| 3.07 | 1 | 4 |
| 3.08 | 16 | >64 |
| 3.09 | 2 | 32 |
| 3.10 | 32 | >64 |
| 3.11 | ≤0.5 | 2 |
| 3.12 | 1 | 8 |
| 3.13 | ≤0.5 | 1 |
| 3.14 | ≤0.5 | 2 |
| 3.15 | 1 | 8 |
| 3.16 | 4 | 4 |
| 3.17 | 2 | >16 |
| 3.18 | 4 | >16 |
| 3.19 | 8 | 32 |
| 3.20 | >8 | >8 |
| 3.21 | ≤0.5 | 1 |
| 3.22 | 16 | 64 |
| 3.23 | ≤0.5 | 2 |
| 3.24 | 2 | 8 |
| 3.26 | >16 | >16 |

TABLE 9-continued

| MIC data for Compounds in Tables 1-8 (Concentration in μg/mL) | | |
|---|---|---|
| Cmpd ID | Sa | Ec |
| 3.27 | 1 | 4 |
| 3.28 | 1 | 2 |
| 3.29 | ≤0.5 | ≤0.5 |
| 3.30 | 16 | 16 |
| 3.31 | 2 | 8 |
| 3.32 | ≤0.5 | 2 |
| 3.33 | ≤0.5 | 1 |
| 3.34 | ≤0.5 | ≤0.5 |
| 3.35 | ≤0.5 | 1 |
| 3.36 | ≤0.5 | 2 |
| 3.37 | 2 | >64 |
| 3.38 | 1 | >32 |
| 3.39 | 2 | 64 |
| 3.40 | ≤0.5 | 1 |
| 3.41 | ≤0.5 | ≤0.5 |
| 3.42 | ≤0.5 | 2 |
| 3.43 | ≤0.5 | 1 |
| 3.44 | 8 | 16 |
| 3.45 | ≤0.5 | ≤0.5 |
| 3.46 | 2 | 4 |
| 3.47 | ≤0.5 | ≤0.5 |
| 3.48 | 2 | 8 |
| 3.49 | ≤0.5 | ≤0.5 |
| 3.50 | ≤0.5 | 2 |
| 3.51 | 8 | 32 |
| 3.52 | ≤0.5 | ≤0.5 |
| 3.53 | 8 | >64 |
| 3.54 | 8 | >32 |
| 3.55 | 64 | >64 |
| 3.56 | >64 | >64 |
| 3.57 | 1 | 8 |
| 3.58 | 32 | >64 |
| 3.59 | 4 | >64 |
| 3.60 | 8 | >64 |
| 3.61 | 4 | 16 |
| 3.62 | ≤0.5 | 8 |
| 3.63 | ≤0.5 | 8 |
| 3.64 | 16 | 64 |
| 3.65 | 8 | 64 |
| 3.66 | 8 | >32 |
| 3.67 | 16 | 64 |
| 4.001 | ≤0.5 | ≤0.5 |
| 4.002 | ≤0.5 | ≤0.5 |
| 4.003 | ≤0.5 | ≤0.5 |
| 4.004 | ≤0.5 | 2 |
| 4.005 | ≤0.5 | ≤0.5 |
| 4.006 | ≤0.5 | 1 |
| 4.007 | ≤0.5 | ≤0.5 |
| 4.008 | ≤0.5 | ≤0.5 |
| 4.009 | ≤0.5 | >64 |
| 4.010 | ≤0.5 | ≤0.5 |
| 4.011 | ≤0.5 | ≤0.5 |
| 4.012 | ≤0.5 | ≤0.5 |
| 4.013 | ≤0.5 | ≤0.5 |
| 4.014 | ≤0.5 | 1 |
| 4.015 | ≤0.5 | 1 |
| 4.016 | ≤0.5 | 1 |
| 4.017 | ≤0.5 | ≤0.5 |
| 4.018 | ≤0.5 | ≤0.5 |
| 4.019 | 2 | 16 |
| 4.020 | ≤0.5 | ≤0.5 |
| 4.021 | ≤0.5 | 2 |
| 4.022 | 8 | 16 |
| 4.023 | ≤0.5 | 1 |
| 4.024 | ≤0.5 | 2 |
| 4.025 | ≤0.5 | 2 |
| 4.026 | ≤0.5 | ≤0.5 |
| 4.027 | ≤0.5 | 1 |
| 4.028 | ≤0.5 | ≤0.5 |
| 4.029 | 4 | 16 |
| 4.030 | 2 | 16 |
| 4.031 | 2 | >16 |
| 4.032 | ≤0.5 | 2 |
| 4.033 | ≤0.5 | 4 |
| 4.034 | ≤0.5 | ≤0.5 |
| 4.035 | ≤0.5 | ≤0.5 |

TABLE 9-continued

| MIC data for Compounds in Tables 1-8 (Concentration in μg/mL) | | |
|---|---|---|
| Cmpd ID | Sa | Ec |
| 4.036 | ≤0.5 | ≤0.5 |
| 4.037 | ≤0.5 | ≤0.5 |
| 4.038 | ≤0.5 | ≤0.5 |
| 4.039 | ≤0.5 | 2 |
| 4.040 | ≤0.5 | ≤0.5 |
| 4.041 | ≤0.5 | 1 |
| 4.042 | ≤0.5 | ≤0.5 |
| 4.043 | ≤0.5 | ≤0.5 |
| 4.044 | ≤0.5 | ≤0.5 |
| 4.045 | ≤0.5 | ≤0.5 |
| 4.046 | ≤0.5 | 1 |
| 4.047 | ≤0.5 | ≤0.5 |
| 4.048 | ≤0.5 | 1 |
| 4.049 | ≤0.5 | 2 |
| 4.050 | ≤0.5 | ≤0.5 |
| 4.051 | ≤0.5 | 2 |
| 4.052 | ≤0.5 | ≤0.5 |
| 4.053 | ≤0.5 | ≤0.5 |
| 4.054 | ≤0.5 | ≤0.5 |
| 4.055 | ≤0.5 | ≤0.5 |
| 4.056 | ≤0.5 | ≤0.5 |
| 4.057 | ≤0.5 | ≤0.5 |
| 4.058 | ≤0.5 | ≤0.5 |
| 4.059 | ≤0.5 | 1 |
| 4.060 | ≤0.5 | ≤0.5 |
| 4.061 | ≤0.5 | ≤0.5 |
| 4.062 | ≤0.5 | ≤0.5 |
| 4.063 | 1 | 8 |
| 4.064 | ≤0.5 | ≤0.5 |
| 4.065 | ≤0.5 | ≤0.5 |
| 4.066 | ≤0.5 | ≤0.5 |
| 4.067 | ≤0.5 | ≤0.5 |
| 4.068 | ≤0.5 | ≤0.5 |
| 4.069 | ≤0.5 | ≤0.5 |
| 4.070 | ≤0.5 | 1 |
| 4.071 | ≤0.5 | 2 |
| 4.072 | ≤0.5 | 1 |
| 4.073 | ≤0.5 | ≤0.5 |
| 4.074 | ≤0.5 | ≤0.5 |
| 4.075 | ≤0.5 | ≤0.5 |
| 4.076 | ≤0.5 | ≤0.5 |
| 4.077 | ≤0.5 | ≤0.5 |
| 4.078 | ≤0.5 | 8 |
| 4.079 | ≤0.5 | ≤0.5 |
| 4.080 | ≤0.5 | 1 |
| 4.081 | ≤0.5 | 1 |
| 4.082 | 1 | 8 |
| 4.083 | ≤0.5 | ≤0.5 |
| 4.084 | ≤0.5 | ≤0.5 |
| 4.085 | ≤0.5 | 2 |
| 4.086 | ≤0.5 | 2 |
| 4.087 | ≤0.5 | 1 |
| 4.088 | ≤0.5 | 1 |
| 4.089 | ≤0.5 | ≤0.5 |
| 4.090 | ≤0.5 | 4 |
| 4.091 | ≤0.5 | 1 |
| 4.092 | ≤0.5 | 2 |
| 4.093 | ≤0.5 | 4 |
| 4.094 | ≤0.5 | ≤0.5 |
| 4.095 | 2 | 8 |
| 4.096 | ≤0.5 | ≤0.5 |
| 4.097 | ≤0.5 | 2 |
| 4.098 | ≤0.5 | 1 |
| 4.099 | ≤0.5 | 4 |
| 4.100 | ≤0.5 | ≤0.5 |
| 4.101 | ≤0.5 | ≤0.5 |
| 4.102 | ≤0.5 | 2 |
| 4.103 | ≤0.5 | ≤0.5 |
| 4.104 | ≤0.5 | ≤0.5 |
| 4.105 | ≤0.5 | ≤0.5 |
| 4.106 | ≤0.5 | 2 |
| 4.107 | >16 | >16 |
| 4.108 | 4 | >16 |
| 4.109 | ≤0.5 | 1 |
| 4.110 | ≤0.5 | ≤0.5 |
| 4.111 | ≤0.5 | ≤0.5 |

TABLE 9-continued

| MIC data for Compounds in Tables 1-8 (Concentration in μg/mL) | | |
|---|---|---|
| Cmpd ID | Sa | Ec |
| 4.112 | ≤0.5 | 1 |
| 4.113 | ≤0.5 | 4 |
| 4.114 | ≤0.5 | 2 |
| 4.115 | 1 | 8 |
| 4.116 | ≤0.5 | ≤0.5 |
| 4.117 | ≤0.5 | ≤0.5 |
| 4.118 | ≤0.5 | ≤0.5 |
| 4.119 | ≤0.5 | 2 |
| 4.120 | ≤0.5 | 1 |
| 4.121 | 1 | 8 |
| 4.122 | ≤0.5 | 1 |
| 4.123 | 16 | >16 |
| 4.124 | ≤0.5 | 8 |
| 4.125 | ≤0.5 | 4 |
| 4.126 | ≤0.5 | 2 |
| 4.127 | 8 | >16 |
| 4.128 | ≤0.5 | 4 |
| 4.129 | ≤0.5 | ≤0.5 |
| 4.130 | ≤0.5 | ≤0.5 |
| 4.131 | ≤0.5 | ≤0.5 |
| 4.132 | ≤0.5 | 2 |
| 4.133 | >16 | >16 |
| 4.134 | >16 | >16 |
| 4.135 | ≤0.5 | 1 |
| 4.136 | 2 | 8 |
| 4.137 | ≤0.5 | 1 |
| 4.138 | ≤0.5 | ≤0.5 |
| 4.139 | ≤0.5 | ≤0.5 |
| 4.140 | ≤0.5 | 2 |
| 4.141 | ≤0.5 | ≤0.5 |
| 4.142 | ≤0.5 | 1 |
| 4.143 | ≤0.5 | 2 |
| 4.144 | ≤0.5 | 1 |
| 4.145 | 1 | 8 |
| 4.146 | ≤0.5 | ≤0.5 |
| 4.147 | ≤0.5 | 1 |
| 4.148 | ≤0.5 | 4 |
| 4.149 | ≤0.5 | 2 |
| 4.150 | ≤0.5 | 1 |
| 4.151 | ≤0.5 | ≤0.5 |
| 4.152 | ≤0.5 | 1 |
| 4.153 | ≤0.5 | 2 |
| 4.154 | 2 | 16 |
| 4.155 | 2 | >16 |
| 4.156 | ≤0.5 | ≤0.5 |
| 4.157 | ≤0.5 | ≤0.5 |
| 4.158 | ≤0.5 | 4 |
| 4.159 | ≤0.5 | ≤0.5 |
| 4.160 | ≤0.5 | 2 |
| 4.161 | ≤0.5 | ≤0.5 |
| 4.162 | 8 | >16 |
| 4.163 | ≤0.5 | ≤0.5 |
| 4.164 | ≤0.5 | 1 |
| 4.165 | ≤0.5 | 1 |
| 4.166 | ≤0.5 | 2 |
| 4.167 | ≤0.5 | ≤0.5 |
| 4.168 | ≤0.5 | 2 |
| 4.169 | 2 | 8 |
| 4.170 | 2 | >16 |
| 4.171 | ≤0.5 | 4 |
| 4.172 | ≤0.5 | ≤0.5 |
| 4.173 | ≤0.5 | 1 |
| 4.174 | ≤0.5 | ≤0.5 |
| 4.175 | ≤0.5 | 8 |
| 4.176 | ≤0.5 | 1 |
| 4.177 | ≤0.5 | ≤0.5 |
| 4.178 | ≤0.5 | 8 |
| 4.179 | ≤0.5 | 1 |
| 4.180 | 1 | 8 |
| 4.181 | ≤0.5 | 8 |
| 4.182 | 2 | 16 |
| 4.183 | 1 | 8 |
| 4.184 | ≤0.5 | 1 |
| 4.185 | ≤0.5 | 8 |
| 4.186 | ≤0.5 | 2 |
| 4.187 | ≤0.5 | 2 |

TABLE 9-continued

MIC data for Compounds in Tables 1-8 (Concentration in μg/mL)

| Cmpd ID | Sa | Ec |
| --- | --- | --- |
| 4.188 | ≤0.5 | 8 |
| 4.189 | ≤0.5 | 2 |
| 4.190 | ≤0.5 | 1 |
| 4.191 | ≤0.5 | 2 |
| 4.192 | ≤0.5 | 4 |
| 4.193 | ≤0.5 | ≤0.5 |
| 4.194 | ≤0.5 | ≤0.5 |
| 4.195 | ≤0.5 | 1 |
| 4.196 | ≤0.5 | ≤0.5 |
| 4.197 | ≤0.5 | ≤0.5 |
| 4.198 | ≤0.5 | ≤0.5 |
| 4.199 | ≤0.5 | ≤0.5 |
| 4.200 | ≤0.5 | ≤0.5 |
| 4.201 | ≤0.5 | ≤0.5 |
| 4.202 | ≤0.5 | ≤0.5 |
| 4.203 | ≤0.5 | ≤0.5 |
| 4.204 | ≤0.5 | ≤0.5 |
| 4.205 | ≤0.5 | ≤0.5 |
| 4.206 | ≤0.5 | 4 |
| 4.207 | ≤0.5 | ≤0.5 |
| 4.208 | ≤0.5 | ≤0.5 |
| 4.209 | ≤0.5 | ≤0.5 |
| 4.210 | ≤0.5 | 1 |
| 4.211 | 16 | >16 |
| 4.212 | ≤0.5 | ≤0.5 |
| 4.213 | ≤0.5 | 1 |
| 4.214 | ≤0.5 | 2 |
| 4.215 | ≤0.5 | 4 |
| 4.216 | ≤0.5 | ≤0.5 |
| 4.217 | ≤0.5 | 4 |
| 4.218 | ≤0.5 | ≤0.5 |
| 4.219 | ≤0.5 | ≤0.5 |
| 4.220 | ≤0.5 | ≤0.5 |
| 4.221 | ≤0.5 | 2 |
| 4.222 | ≤0.5 | ≤0.5 |
| 4.223 | ≤0.5 | ≤0.5 |
| 4.224 | 1 | >16 |
| 4.225 | ≤0.5 | 2 |
| 4.226 | ≤0.5 | 2 |
| 4.227 | ≤0.5 | 1 |
| 4.228 | ≤0.5 | 1 |
| 4.229 | ≤0.5 | 2 |
| 4.230 | 32 | >16 |
| 4.231 | ≤0.5 | 2 |
| 4.232 | ≤0.5 | ≤0.5 |
| 4.233 | ≤0.5 | 1 |
| 4.234 | ≤0.5 | 1 |
| 4.235 | ≤0.5 | ≤0.5 |
| 4.236 | ≤0.5 | ≤0.5 |
| 4.237 | ≤0.5 | 2 |
| 4.238 | 2 | >16 |
| 4.239 | ≤0.5 | 8 |
| 4.240 | ≤0.5 | ≤0.5 |
| 4.241 | ≤0.5 | ≤0.5 |
| 4.242 | ≤0.5 | ≤0.5 |
| 4.243 | ≤0.5 | ≤0.5 |
| 4.244 | ≤0.5 | ≤0.5 |
| 4.245 | ≤0.5 | ≤0.5 |
| 4.246 | ≤0.5 | ≤0.5 |
| 4.247 | 1 | 8 |
| 4.248 | ≤0.5 | ≤0.5 |
| 4.249 | ≤0.5 | ≤0.5 |
| 4.250 | ≤0.5 | ≤0.5 |
| 4.251 | ≤0.5 | ≤0.5 |
| 4.252 | >16 | >16 |
| 4.253 | ≤0.5 | ≤0.5 |
| 4.254 | ≤0.5 | ≤0.5 |
| 4.255 | ≤0.5 | ≤0.5 |
| 4.256 | ≤0.5 | ≤0.5 |
| 4.257 | ≤0.5 | ≤0.5 |
| 4.258 | ≤0.5 | ≤0.5 |
| 4.259 | ≤0.5 | ≤0.5 |
| 4.260 | ≤0.5 | ≤0.5 |
| 4.261 | ≤0.5 | 1 |
| 4.262 | ≤0.5 | ≤0.5 |
| 4.263 | ≤0.5 | ≤0.5 |

TABLE 9-continued

MIC data for Compounds in Tables 1-8 (Concentration in μg/mL)

| Cmpd ID | Sa | Ec |
| --- | --- | --- |
| 4.264 | ≤0.5 | ≤0.5 |
| 4.265 | ≤0.5 | 4 |
| 4.266 | ≤0.5 | 1 |
| 4.267 | ≤0.5 | 4 |
| 4.269 | ≤0.5 | 4 |
| 4.270 | ≤0.5 | 2 |
| 4.271 | ≤0.5 | ≤0.5 |
| 4.272 | ≤0.5 | ≤0.5 |
| 4.273 | ≤0.5 | 2 |
| 4.274 | ≤0.5 | ≤0.5 |
| 4.275 | ≤0.5 | ≤0.5 |
| 4.276 | ≤0.5 | 8 |
| 4.277 | ≤0.5 | ≤0.5 |
| 4.278 | ≤0.5 | ≤0.5 |
| 4.279 | ≤0.5 | ≤0.5 |
| 4.280 | ≤0.5 | ≤0.5 |
| 4.281 | ≤0.5 | ≤0.5 |
| 4.282 | ≤0.5 | ≤0.5 |
| 4.283 | ≤0.5 | ≤0.5 |
| 4.284 | ≤0.5 | ≤0.5 |
| 4.285 | ≤0.5 | ≤0.5 |
| 4.286 | ≤0.5 | ≤0.5 |
| 4.287 | ≤0.5 | ≤0.5 |
| 4.288 | 4 | >16 |
| 4.290 | ≤0.5 | ≤0.5 |
| 4.291 | ≤0.5 | ≤0.5 |
| 4.292 | ≤0.5 | ≤0.5 |
| 4.293 | ≤0.5 | 1 |
| 4.294 | ≤0.5 | 1 |
| 4.295 | ≤0.5 | ≤0.5 |
| 4.296 | ≤0.5 | ≤0.5 |
| 4.297 | ≤0.5 | ≤0.5 |
| 4.298 | ≤0.5 | 2 |
| 4.299 | ≤0.5 | 4 |
| 4.300 | ≤0.5 | ≤0.5 |
| 4.301 | ≤0.5 | 1 |
| 4.302 | ≤0.5 | 2 |
| 4.303 | ≤0.5 | ≤0.5 |
| 4.304 | ≤0.5 | ≤0.5 |
| 4.305 | ≤0.5 | 1 |
| 4.309 | ≤0.5 | ≤0.5 |
| 4.310 | 8 | >16 |
| 4.311 | 4 | >16 |
| 4.312 | 16 | >16 |
| 4.313 | 8 | >16 |
| 4.314 | ≤0.5 | ≤0.5 |
| 4.315 | ≤0.5 | ≤0.5 |
| 4.316 | ≤0.5 | 1 |
| 4.317 | ≤0.5 | 2 |
| 4.318 | ≤0.5 | 8 |
| 4.319 | ≤0.5 | ≤0.5 |
| 4.320 | ≤0.5 | 1 |
| 4.321 | ≤0.5 | 1 |
| 4.322 | ≤0.5 | ≤0.5 |
| 4.323 | ≤0.5 | 1 |
| 4.324 | ≤0.5 | ≤0.5 |
| 4.325 | ≤0.5 | ≤0.5 |
| 4.326 | ≤0.5 | ≤0.5 |
| 4.327 | ≤0.5 | 8 |
| 4.328 | ≤0.5 | 1 |
| 4.329 | ≤0.5 | ≤0.5 |
| 4.330 | ≤0.5 | ≤0.5 |
| 4.331 | ≤0.5 | ≤0.5 |
| 4.332 | ≤0.5 | ≤0.5 |
| 4.333 | ≤0.5 | ≤0.5 |
| 4.334 | ≤0.5 | 8 |
| 4.335 | ≤0.5 | 4 |
| 4.336 | ≤0.5 | 1 |
| 4.337 | ≤0.5 | 1 |
| 4.338 | ≤0.5 | 2 |
| 4.339 | ≤0.5 | 1 |
| 4.340 | 1 | 2 |
| 4.341 | ≤0.5 | 1 |
| 4.342 | ≤0.5 | 4 |
| 4.343 | ≤0.5 | ≤0.5 |
| 4.344 | ≤0.5 | 2 |

TABLE 9-continued

| MIC data for Compounds in Tables 1-8 (Concentration in μg/mL) | | |
|---|---|---|
| Cmpd ID | Sa | Ec |
| 4.345 | ≤0.5 | 2 |
| 4.346 | ≤0.5 | 4 |
| 4.347 | ≤0.5 | 1 |
| 4.348 | ≤0.5 | ≤0.5 |
| 4.349 | ≤0.5 | 1 |
| 4.350 | ≤0.5 | 4 |
| 4.351 | ≤0.5 | 2 |
| 4.352 | ≤0.5 | 4 |
| 4.353 | ≤0.5 | 2 |
| 4.354 | ≤0.5 | 1 |
| 4.355 | ≤0.5 | ≤0.5 |
| 4.356 | ≤0.5 | 4 |
| 4.357 | ≤0.5 | 4 |
| 4.358 | ≤0.5 | 4 |
| 4.359 | ≤0.5 | ≤0.5 |
| 4.360 | ≤0.5 | 2 |
| 4.361 | ≤0.5 | 1 |
| 4.362 | ≤0.5 | 1 |
| 4.363 | ≤0.5 | 1 |
| 4.364 | ≤0.5 | 4 |
| 4.365 | ≤0.5 | ≤0.5 |
| 4.366 | ≤0.5 | 1 |
| 4.367 | ≤0.5 | ≤0.5 |
| 4.368 | ≤0.5 | ≤0.5 |
| 4.369 | ≤0.5 | 1 |
| 4.370 | ≤0.5 | 1 |
| 4.371 | 1 | 16 |
| 4.372 | 4 | 16 |
| 4.373 | 2 | 8 |
| 4.374 | ≤0.5 | 4 |
| 4.375 | ≤0.5 | 4 |
| 4.376 | >16 | >16 |
| 4.377 | 4 | 16 |
| 4.378 | ≤0.5 | ≤0.5 |
| 4.379 | ≤0.5 | ≤0.5 |
| 4.380 | 4 | 16 |
| 4.381 | 4 | 16 |
| 4.382 | 1 | 16 |
| 4.383 | 4 | >16 |
| 4.384 | 1 | >16 |
| 4.385 | ≤0.5 | ≤0.5 |
| 4.386 | ≤0.5 | ≤0.5 |
| 4.387 | ≤0.5 | ≤0.5 |
| 4.388 | ≤0.5 | ≤0.5 |
| 4.389 | ≤0.5 | ≤0.5 |
| 4.390 | ≤0.5 | ≤0.5 |
| 4.391 | ≤0.5 | ≤0.5 |
| 4.392 | 16 | >16 |
| 4.393 | ≤0.5 | 1 |
| 4.394 | ≤0.5 | ≤0.5 |
| 4.395 | 1 | 1 |
| 4.396 | ≤0.5 | 2 |
| 4.397 | ≤0.5 | ≤0.5 |
| 4.398 | ≤0.5 | ≤0.5 |
| 4.399 | ≤0.5 | 2 |
| 4.400 | ≤0.5 | ≤0.5 |
| 4.401 | ≤0.5 | ≤0.5 |
| 4.402 | ≤0.5 | ≤0.5 |
| 4.403 | 4 | >16 |
| 4.404 | ≤0.5 | 1 |
| 4.405 | ≤0.5 | ≤0.5 |
| 4.406 | ≤0.5 | 1 |
| 4.407 | 2 | >16 |
| 4.408 | ≤0.5 | ≤0.5 |
| 4.409 | ≤0.5 | ≤0.5 |
| 4.410 | ≤0.5 | ≤0.5 |
| 4.411 | ≤0.5 | ≤0.5 |
| 4.412 | ≤0.5 | ≤0.5 |
| 4.413 | ≤0.5 | ≤0.5 |
| 4.414 | ≤0.5 | 2 |
| 4.415 | ≤0.5 | 1 |
| 4.416 | ≤0.5 | ≤0.5 |
| 4.417 | ≤0.5 | 1 |
| 4.418 | ≤0.5 | 1 |
| 4.419 | ≤0.5 | >16 |
| 4.420 | 2 | >16 |

TABLE 9-continued

| MIC data for Compounds in Tables 1-8 (Concentration in μg/mL) | | |
|---|---|---|
| Cmpd ID | Sa | Ec |
| 4.421 | 2 | 8 |
| 4.422 | 4 | 16 |
| 4.423 | >16 | >16 |
| 4.424 | >16 | >16 |
| 4.425 | >16 | >16 |
| 4.426 | 8 | >16 |
| 4.427 | >16 | >16 |
| 4.428 | ≤0.5 | 2 |
| 4.429 | ≤0.5 | 1 |
| 4.430 | ≤0.5 | ≤0.5 |
| 4.431 | ≤0.5 | ≤0.5 |
| 4.432 | ≤0.5 | >16 |
| 4.433 | ≤0.5 | ≤0.5 |
| 4.434 | ≤0.5 | ≤0.5 |
| 4.435 | ≤0.5 | ≤0.5 |
| 4.436 | ≤0.5 | >16 |
| 4.437 | ≤0.5 | 1 |
| 4.438 | 1 | 16 |
| 4.439 | 8 | >16 |
| 4.440 | 16 | >16 |
| 4.441 | ≤0.5 | ≤0.5 |
| 4.442 | 1 | 2 |
| 4.443 | ≤0.5 | ≤0.5 |
| 4.445 | 2 | >16 |
| 4.446 | 2 | 8 |
| 4.447 | 4 | 16 |
| 4.448 | ≤0.5 | 1 |
| 4.449 | ≤0.5 | >16 |
| 4.450 | ≤0.5 | 2 |
| 4.451 | ≤0.5 | ≤0.5 |
| 5.01 | ≤0.5 | ≤0.5 |
| 5.02 | ≤0.5 | ≤0.5 |
| 5.03 | ≤0.5 | ≤0.5 |
| 5.04 | ≤0.5 | ≤0.5 |
| 5.05 | ≤0.5 | ≤0.5 |
| 5.06 | ≤0.5 | ≤0.5 |
| 5.07 | ≤0.5 | 1 |
| 5.08 | ≤0.5 | ≤0.5 |
| 5.09 | ≤0.5 | ≤0.5 |
| 5.10 | ≤0.5 | ≤0.5 |
| 5.11 | ≤0.5 | ≤0.5 |
| 5.12 | ≤0.5 | ≤0.5 |
| 5.13 | ≤0.5 | ≤0.5 |
| 5.14 | ≤0.5 | ≤0.5 |
| 5.15 | ≤0.5 | 1 |
| 6.01 | ≤0.5 | 1 |
| 6.02 | ≤0.5 | ≤0.5 |
| 6.03 | ≤0.5 | ≤0.5 |
| 6.04 | ≤0.5 | ≤0.5 |
| 6.05 | ≤0.5 | ≤0.5 |
| 6.06 | ≤0.5 | ≤0.5 |
| 6.07 | ≤0.5 | ≤0.5 |
| 6.08 | ≤0.5 | ≤0.5 |
| 6.09 | ≤0.5 | 1 |
| 6.10 | ≤0.5 | ≤0.5 |
| 6.11 | ≤0.5 | ≤0.5 |
| 6.12 | ≤0.5 | ≤0.5 |
| 6.13 | ≤0.5 | ≤0.5 |
| 6.14 | ≤0.5 | 1 |
| 6.15 | ≤0.5 | ≤0.5 |
| 6.16 | ≤0.5 | 1 |
| 6.17 | ≤0.5 | ≤0.5 |
| 6.18 | >64 | >64 |
| 6.19 | >16 | >16 |
| 6.20 | 4 | >16 |
| 6.21 | >16 | >16 |
| 6.22 | >16 | >16 |
| 6.23 | ≤0.5 | ≤0.5 |
| 6.24 | ≤0.5 | 1 |
| 6.25 | ≤0.5 | ≤0.5 |
| 6.26 | ≤0.5 | 1 |
| 6.27 | ≤0.5 | 1 |
| 6.28 | ≤0.5 | ≤0.5 |
| 6.29 | ≤0.5 | ≤0.5 |
| 7.01 | 8 | >64 |
| 7.02 | >64 | 32 |

TABLE 9-continued

| MIC data for Compounds in Tables 1-8 (Concentration in μg/mL) | | |
|---|---|---|
| Cmpd ID | Sa | Ec |
| 7.03 | 2 | >64 |
| 7.04 | 8 | 32 |
| 7.05 | 8 | 64 |
| 7.06 | 8 | 64 |
| 7.07 | 16 | >64 |
| 7.08 | 16 | >64 |
| 7.09 | 8 | >64 |
| 7.10 | >64 | >64 |
| 7.11 | >64 | >64 |
| 7.12 | >64 | >64 |
| 8.1 | 2 | >64 |
| 8.2 | 1 | >32 |
| 8.3 | 2 | 64 |
| 8.4 | 8 | >64 |

TABLE 10

MIC data for Select Formula 1 Compounds versus a Broad Bacterial Panel

| Cmpd. # | Sa | Spn | Ec | Ab | Kpn | Pa | Bt | Ft | Yp |
|---|---|---|---|---|---|---|---|---|---|
| | | | | MIC (μg/mL) | | | | | |
| 4.035 | ≤0.5 | ≤0.5 | ≤0.5 | ≤0.5 | 2 | 4 | ≤0.5 | 1 | ≤0.5 |
| 4.045 | ≤0.5 | ≤0.5 | ≤0.5 | ≤0.5 | 8 | 4 | 1 | 2 | ≤0.5 |
| 4.066 | ≤0.5 | ≤0.5 | ≤0.5 | ≤0.5 | 2 | 2 | ≤0.5 | 1 | ≤0.5 |
| 4.069 | ≤0.5 | ≤0.5 | ≤0.5 | ≤0.5 | 2 | 4 | ≤0.5 | 2 | ≤0.5 |
| 4.073 | ≤0.5 | ≤0.5 | ≤0.5 | ≤0.5 | 2 | 4 | ≤0.5 | 1 | ≤0.5 |
| 4.076 | ≤0.5 | ≤0.5 | ≤0.5 | ≤0.5 | 4 | 4 | 1 | 2 | ≤0.5 |
| 4.079 | ≤0.5 | ≤0.5 | ≤0.5 | ≤0.5 | 8 | 4 | 1 | 4 | ≤0.5 |
| 4.084 | ≤0.5 | ≤0.5 | ≤0.5 | ≤0.5 | 4 | 1 | ≤0.5 | ≤0.5 | ≤0.5 |
| 4.103 | ≤0.5 | ≤0.5 | ≤0.5 | ≤0.5 | 2 | 2 | ≤0.5 | 1 | ≤0.5 |
| 4.105 | ≤0.5 | ≤0.5 | ≤0.5 | ≤0.5 | 2 | 1 | ≤0.5 | 1 | ≤0.5 |
| 4.117 | ≤0.5 | ≤0.5 | ≤0.5 | ≤0.5 | 2 | 1 | ≤0.5 | 1 | ≤0.5 |
| 4.131 | ≤0.5 | ≤0.5 | ≤0.5 | ≤0.5 | 2 | 1 | ≤0.5 | ≤0.5 | ≤0.5 |
| 4.151 | ≤0.5 | ≤0.5 | ≤0.5 | ≤0.5 | 1 | 1 | | | |
| 4.157 | ≤0.5 | ≤0.5 | ≤0.5 | ≤0.5 | 4 | 8 | | | |
| 4.160 | ≤0.5 | ≤0.5 | 2 | >16 | >16 | >16 | | | |
| 4.365 | ≤0.5 | ≤0.5 | ≤0.5 | ≤0.5 | 4 | 1 | ≤0.5 | 1 | ≤0.5 |
| 4.409 | ≤0.5 | ≤0.5 | ≤0.5 | 1 | 4 | 1 | | | |
| 4.410 | ≤0.5 | ≤0.5 | ≤0.5 | 2 | 2 | 1 | | | |
| 4.434 | ≤0.5 | ≤0.5 | ≤0.5 | ≤0.5 | 1 | 1 | | | |
| 4.451 | ≤0.5 | ≤0.5 | ≤0.5 | ≤0.5 | 1 | 2 | | | |
| 5.010 | ≤0.5 | ≤0.5 | ≤0.5 | ≤0.5 | 1 | ≤0.5 | | | |
| 5.110 | ≤0.5 | ≤0.5 | ≤0.5 | 2 | 4 | 4 | | | |
| 5.120 | ≤0.5 | ≤0.5 | ≤0.5 | ≤0.5 | 1 | 4 | | | |
| 5.130 | ≤0.5 | ≤0.5 | ≤0.5 | ≤0.5 | 1 | ≤0.5 | | | |
| 6.280 | ≤0.5 | ≤0.5 | ≤0.5 | ≤0.5 | 2 | 1 | | | |
| 6.290 | ≤0.5 | ≤0.5 | ≤0.5 | ≤0.5 | 2 | 2 | | | |

Sa = *S. aureus*,
Spn = *S. pneumoniae*,
Ec = *E. coli*,
Ab = *A. baumannii*,
Kpn = *K. pneumoniae*,
Pa = *P. aeruginosa*,
Bt = *B. thailandensis*,
Ft = *F. tularensis*,
Yp = *Y. pestis*

What is claimed is:

1. An intermediate compound having the structure:

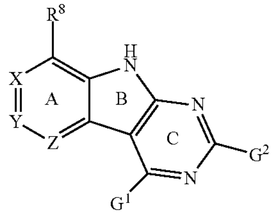

wherein $G^1$ and $G^2$ are leaving groups independently selected from the group consisting of SH, OH, Cl, Br, F, I, SR, SOR, $SO_2R$, $OSO_2R$, tosylate, triflate and OAr;

R is C1-8 alkyl, aryl, or heteroaryl;

Ar is aryl or heteroaryl containing 0-5 O, S, or N atoms optionally substituted with C1-C4 alkyl, C1-C4 alkoxy, halo or $NO_2$;

$R^8$ is (a) an interacting substituent selected from the group consisting of Cl, F, Br, $NH_2$, 1-3C alkyl, amino-1-3C alkyl, aminocyclopropyl, $OCH_3$, $OCH_2CH_3$, cyclopropyl, $CH_2$cyclopropyl, $CH_2Cl$, $CHCl_2$, $CH_2F$, $CHF_2$, $CF_3$, $CH_2CH_2F$, $CH_2CHF_2$, $CH_2CF_3$, $NHNH_2$, NHOH, $NHNHCH_3$, $NHOCH_3$, $NHCD_3$, $SCH_3$, and NHCOH; or (b) an amine protected with a protecting group, wherein the protecting group is selected from the group consisting of carbobenzyloxy (Cbz) and BOC; and X, Y and Z are independently selected from the group consisting of N, $CR^X$, $CR^Y$, and $CR^Z$ respectively, provided that no more than two of X, Y and Z are N, wherein $R^X$ is H or an interacting substituent selected from the group consisting of $CH_3$, Cl, Br, and F;

wherein $R^Y$ is H or an interacting substituent selected from the group consisting of $CH_3$, $CHF_2$, $CF_3CN$, $CH_2CH_3$, Cl, Br, and F;

wherein $R^Z$ is H or an interacting substituent selected from the group consisting of $CH_3$, Cl, Br, and F;

with a proviso wherein $R^8$ is not $CH_3$.

2. The intermediate compound of claim 1 wherein $R^8$ is an amine protected with carbobenzyloxy (Cbz) or BOC.

3. The intermediate compound of claim 2, wherein the $G^1$ and $G^2$ are leaving groups independently selected from the group consisting of mesylate, triflate, O-pyrimidine, O-phenyl and O-pyridine.

4. The intermediate compound of claim 1, wherein the OAr for $G^1$ and $G^2$ is OBt, wherein Bt is benzotriazole.

5. The intermediate compound of claim 2, wherein the amine is selected from the group consisting of $NHCD_3$, $NHCH_3$, $NHCH_2CH_3$, and $NH_2$ and is protected with Cbz or BOC.

* * * * *

UNITED STATES PATENT AND TRADEMARK OFFICE

CERTIFICATE OF CORRECTION

PATENT NO. : 9,732,083 B2
APPLICATION NO. : 13/496188
DATED : August 15, 2017
INVENTOR(S) : Daniel Bensen It is certified that error appears in the above-identified patent and that said Letters Patent is hereby corrected as shown below:

In the Specification

At Column 1, Line number 28, please add the following after "TC02128.0.":
-The United States Government has rights in this application pursuant to Contract No. DE-AC52-07NA27344 between the United States Department of Energy and Lawrence Livermore National Security, LLC for the operation of Lawrence Livermore National Laboratory.-

Signed and Sealed this
Twenty-sixth Day of November, 2019

Andrei Iancu
*Director of the United States Patent and Trademark Office*